(12) United States Patent
Arrieumerlou et al.

(10) Patent No.: US 12,091,670 B2
(45) Date of Patent: *Sep. 17, 2024

(54) BACTERIA-BASED PROTEIN DELIVERY

(71) Applicant: Universitaet Basel, Basel (CH)

(72) Inventors: Cécile Arrieumerlou, Issy les Moulineaux (FR); Simon Ittig, Basel (CH)

(73) Assignee: Universitaet Basel, Basel (CH)

( * ) Notice: Subject to any disclaimer, the term of this patent is extended or adjusted under 35 U.S.C. 154(b) by 690 days.

This patent is subject to a terminal disclaimer.

(21) Appl. No.: 17/111,332

(22) Filed: Dec. 3, 2020

(65) Prior Publication Data
US 2021/0155942 A1    May 27, 2021

Related U.S. Application Data

(63) Continuation of application No. 15/311,424, filed as application No. PCT/EP2015/061086 on May 20, 2015, now Pat. No. 10,889,823.

(30) Foreign Application Priority Data

May 21, 2014   (EP) .................................... 14169335

(51) Int. Cl.
*C12N 15/74* (2006.01)
*A61K 48/00* (2006.01)
(Continued)

(52) U.S. Cl.
CPC ............ *C12N 15/74* (2013.01); *C07K 14/195* (2013.01); *C07K 14/24* (2013.01); *C12N 15/70* (2013.01);
(Continued)

(58) Field of Classification Search
CPC ........ C12N 15/74; C12N 15/70; C12N 15/62; C07K 14/195; C07K 14/24;
(Continued)

(56) References Cited

U.S. PATENT DOCUMENTS 5,965,381 A * 10/1999 van der Bruggen .... A61P 37/04
435/69.3
7,763,420 B2  7/2010 Stritzker et al.
(Continued)

FOREIGN PATENT DOCUMENTS

WO    WO 1999045098    9/1999
WO    WO 200002996     1/2000
(Continued)

OTHER PUBLICATIONS

Roschitzki-Voser, et al. Human caspases in vitro: Expression, purification and kinetic characterization, Protein Expression and Purification, 84 (2012) 236-246) (Year: 2012).*

(Continued)

*Primary Examiner* — Jeremy C Flinders
*Assistant Examiner* — Thomas R. Amick
(74) *Attorney, Agent, or Firm* — Bozicevic, Field & Francis LLP; Shweta Chandra

(57) ABSTRACT

The present invention relates to recombinant Gram-negative bacterial strains and the use thereof for delivery of heterologous proteins into eukaryotic cells.

11 Claims, 36 Drawing Sheets

Figure 1:
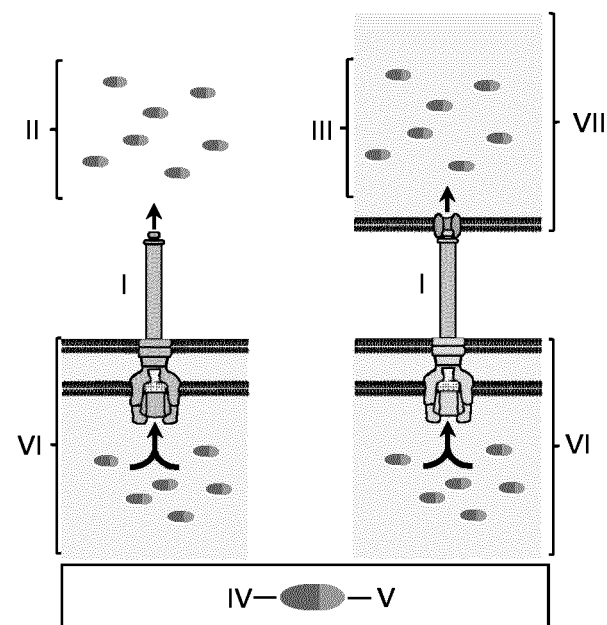
Figure 1:
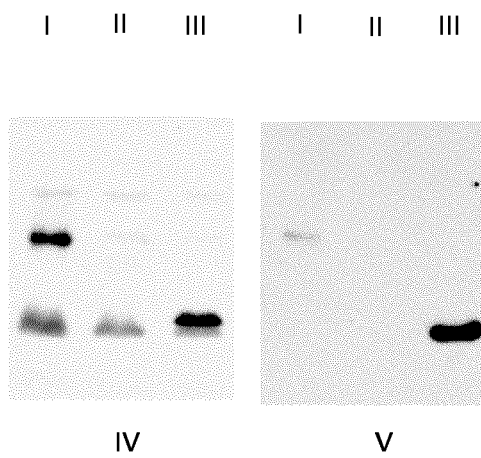
Figure 2:
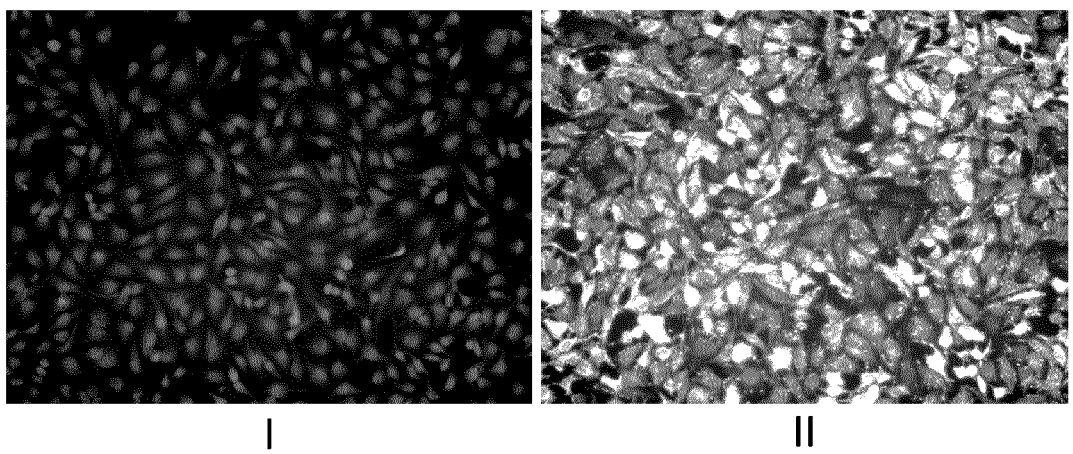
Figure 2:
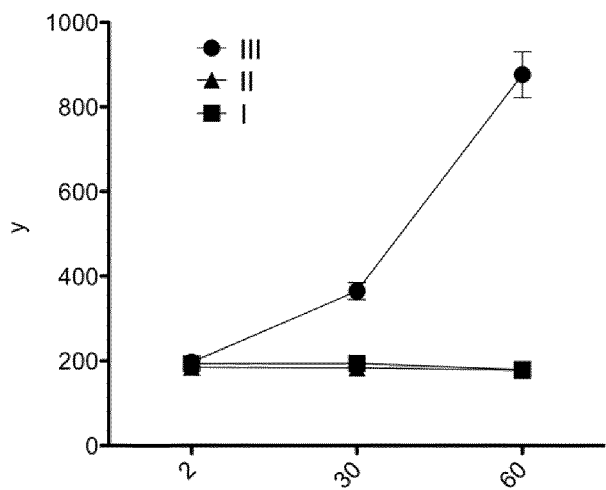
Figure 2:
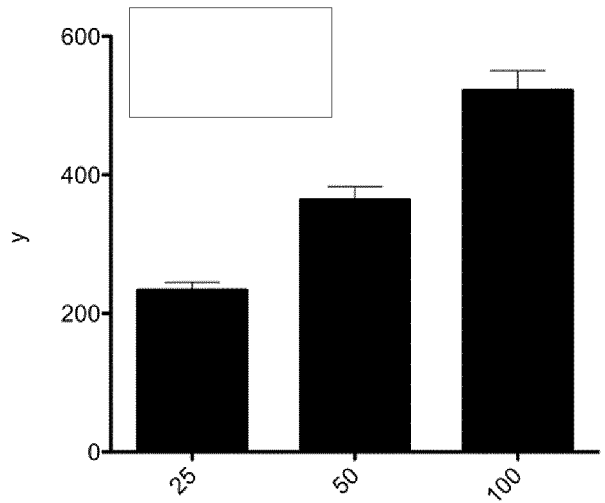
Figure 3:
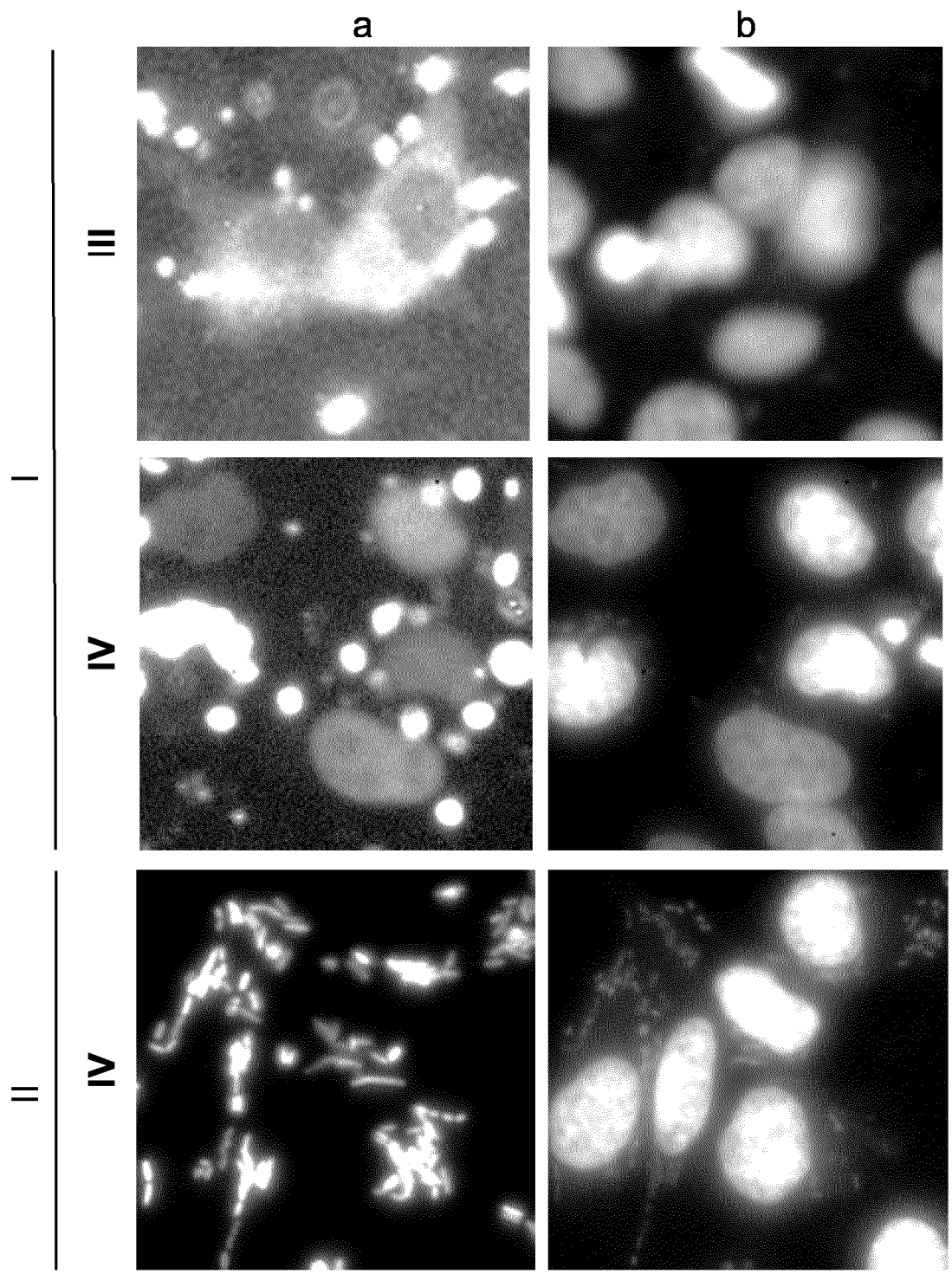

Specification includes a Sequence Listing.

(51) Int. Cl.
C07K 14/195 (2006.01)
C07K 14/24 (2006.01)
C12N 15/70 (2006.01)
C12Q 1/02 (2006.01)

(52) U.S. Cl.
CPC .............. *C12Q 1/025* (2013.01); *A61K 48/00* (2013.01); *C07K 2319/035* (2013.01); *C07K 2319/50* (2013.01); *G01N 2333/24* (2013.01); *G01N 2333/245* (2013.01); *G01N 2333/255* (2013.01); *G01N 2500/10* (2013.01)

(58) Field of Classification Search
CPC .......... C07K 2319/035; C07K 2319/50; C12Q 1/025; A61K 48/00; G01N 2333/24; G01N 2333/245; G01N 2333/255; G01N 2500/10; A61P 37/00; Y02A 50/30
See application file for complete search history.

(56) References Cited

U.S. PATENT DOCUMENTS

| 10,889,823 | B2 | 1/2021 | Arrieumerlou et al. |
| 2004/0147719 | A1 | 7/2004 | Cornelis |
| 2008/0187520 | A1 | 8/2008 | Polack et al. |
| 2011/0183908 | A1 | 7/2011 | Rüter et al. |
| 2015/0140037 | A1 | 5/2015 | Galan et al. |
| 2017/0198297 | A1 | 7/2017 | Ittig et al. |
| 2019/0015497 | A1 | 1/2019 | Ittig et al. |
| 2019/0194670 | A1 | 6/2019 | Ittig et al. |
| 2020/0123207 | A1 | 4/2020 | Ittig et al. |

FOREIGN PATENT DOCUMENTS

| WO | WO 2002026819 | 4/2002 |
| WO | WO 2002077249 | 10/2002 |
| WO | WO 2007044406 | 4/2007 |
| WO | WO 2008019183 | 2/2008 |
| WO | WO 2009115531 | 9/2009 |
| WO | WO 2015042705 | 4/2015 |
| WO | WO 2015177197 | 11/2015 |
| WO | WO 2018115140 | 6/2018 |

OTHER PUBLICATIONS

Pan et al. Pan, N., Goguen, J., Lee, C. (2007). High Throughput Screening for Small-Molecule Inhibitors of Type III Secretion in Yersinia pestis. In: Perry, R.D., Fetherston, J.D. (eds) The Genus *Yersinia*. Advances In Experimental Medicine And Biology, vol. 603. (Year: 2007).*

Coburn et al. (Coburn B, Sekirov I, Finlay BB. Type III secretion systems and disease. Clin Microbiol Rev. Oct. 2007;20(4):535-49.). (Year: 2007).*

Kim KJ, Kim HE, Lee KH, Han W, Yi MJ, Jeong J, Oh BH. Two-promoter vector is highly efficient for overproduction of protein complexes. Protein Sci. Jun. 2004;13(6):1698-703 (Year: 2004).*

Bos JL. p21ras: an oncoprotein functioning in growth factor-induced signal transduction. Eur J Cancer. Jul.-Aug. 1995;31A(7-8): 1051-4) (Year: 1995).*

Ahmed Kamal et al., (2014) "Apoptosi s-inducing agents: a patent review (2010-2013)", Expert Opinion On Therapeutic Patents, 1(3):339-354.

Akeda, Y &, Galan J.E. (2005) "Chaperone release and unfolding of substrates in type III secretion"; Nature 437; pp. 911-915.

Bohme et al., (2012) "Concerted Actions of a Thermo-labile Regulator and a Unique Intergenic RNA Thermosensor Control Yersinia Virulence", Plos Pathogens, 8(2): e1002518, XP055365892.

Boyd AP, et al (2000) "Yersinia enterocolitica can deliver Yop proteins into a wide range of cell types: development of a delivery system for heterologous proteins"; Eur J Cell Biol.79(10); pp. 659-671.

Briones et al., (2006) "Cre Reporter System To Monitor the Translocation of Type III Secreted Proteins into Host Cells", Infection and Immunity, 1084-1090.

Burdette et al., (2018) "Developing Gram-negative bacteria for the secretion of heterologous proteins", Microb Cell Fact, 17(196):1-16.

Cardenal-Munoz, and Ramos-Morales (2011) "Analysis of the Expression, Secretion and Translocation of the *Salmonella enterica* Type III Secretion System Effector SteA"; PLOS ONE 6(10); pp. 1-13.

Chamekh et al., (2008) "Delivery of 1 Biologically Active Anti-Inflammatory Cytokines IL-10 and IL-1ra In Vivo by the Shigella Type III Secretion Apparatus", The Journal of Immunology, 180(6): 4292-4298.

Chen, Li-Mei, et al., (2006) "Optimization of the Delivery of Heterologous Proteins by the *Salmonella enterica* Serovar Typhimurium Type III Secretion System for Vaccine Development", Infection and Immunity, 74(10):5826-5833.

Corrales et al., (2014) "Direct activation of STING in the tumor microenvironment with synthetic cyclic dinucleotide derivatives leads to potent and systemic tumor-specific immunity", Journal for Immunotherapy of Cancer, 2(3):010, XP021202342.

Culliton, Barbara J. (1986) "NIH considers major change in definition of recombinant DNA"; Science 2344773); pp. 146.

De et al., (2009) "Determinants for the Activation and Autoinhibition of the Diguanylate Cyclase Response Regulator WspR", Journal of Molecular Biology, 393(3):619-633, XP026676221.

Feldman M. et al. (2002) "SycE allows secretion of YopE-DHFR hybrids by the Yersinia enterocolitica type III Ysc system"; Molecular Microbiology 46(4); pp. 1183-1197.

Fensterle J et al, (2008) "Cancer immunotherapy based on recombinant *Salmonella enterica* serovar Typhimurium aroA strains secreting prostate-specific antigen and cholera toxin subunit B", Cancer Gene Therapy, Appleton & Lange, GB, 15(2):85-93.

Garcia, Julie Torruellas, et al., (2006) "Measurement of Effector Protein Injection by Type III and Type IV Secretion Systems by Using a 13-Residue Phosphorylatable Glycogen Synthase Kinase Tag", Infection and Immunity, 74(10):5645-5657.

Gentschev Ivaylo et al., (2005) "Use of a recombinant *Salmonella enterica* serovar Typhimurium strain expressing C-Raf for protection against C-Raf induced lung adenoma in mice", BMC Cancer, Biomed Central, London, GB, 5(1):1-9.

Gosh P. (2004) "Process of Protein Transport by the Type III Secretion System", Microbiology and Molecular Biology Reviews 68(4); pp. 771-795.

Iriarte, Maite, et al., (1998) "TyeA, a protein involved in control of Yop release and in translocation of Yersinia Yop effectors", The EMBO Journal, 17(7):1907-1918.

Ittig et al., (2015) "A bacterial type III secretion-based protein delivery tool for broad applications in cell biology", The Journal of Cell Biology : JCB, 211(4):913-931.

Jacobi, C. A. et al. (1998) "In vitro and in vivo expression studies of yopE from Yeresinia enterocolitica using the gfp reporter gene"; Molecular microbiology 30(4); pp. 865-882.

Karavolos et al. (2015) "Type III Secretion of the *Salmonella effector* Protein SopE Is Mediated via an N-Terminal Amino Acid Signal and Not an mRNA Sequence"; Journal Of Bacteriology 187(5); pp. 1559-1567.

Lee, V. T. & Schneewind, O. (2002) "Yop Fusions to Tightly Folded Protein Domains and Their Effects on Yersinia enterocolitica Type III Secretion"; Journal Of Bacteriology, vol. 184, No. 13; pp. 3740-3745.

Li et al., (2014) "Tumor suppressor activity of RIG-I", Molecular & Celluar Oncology, 1(4):e968016, XP055366048.

Lloyd et al.(2001) "Yersinian YopE is targeted for Type III secretion by N-terminal, not mRNA, signals"; Molecular Microbiology 39(2); pp. 520-531.

Mota and Cornelis (2005) "The bacterial injection kit: type III secretion systems"; Ann Med.37(4); pp. 234-249.

Russmann et al., (2001) "Protection Against Murine Listeriosis by Oral Vaccination with Recombinant *Salmonella* Expressing Hybrid Yersinia Type III Proteins", The Journal of Immunology, 167(1):357-365.

(56) References Cited

OTHER PUBLICATIONS

Stadler et al., (2014) "The use of a neutral peptide aptamer scaffold to anchor BH3 peptides constitutes a viable approach to studying their function", Cell Death and Disease, 5(1):1-9.
Viboud et al., (2005) "Yersinia Outer Proteins: Role in Modulation of Host Cell Signaling Responses and Pathogensis", Annu. Rev. Microbial, 59:69-89.
Wiedig, et al. (2005) "Induction of CD8+ T cell responses by Yersinia vaccine carrier strains"; Vaccine.23(42); pp. 4984-4998.
Wu et al., (2014) "Innate Immune Sensing and Signaling of Cytosolic Nucleic Acids", Annual Review of Immunology, 32(1):461-488, XP055366371.
Y. Zhang et al., (2011) "Type III Secretion System-Dependent Translocation of Ectopically Expressed Yop Effectors into Macrophages by Intracellular Yersinia pseudotuberculosis", Infection and Immunity, 79(11):4322-4331.
Blanco-Toribio et al., (2010) "Direct Injection of Functional Single-Domain Antibodies from E. coli into Human Cells.", PLOS One, 5(12):1-12, e15227.
Reed et al., (2004) "The Domains of Apoptosis: A Genomics Perspective.", Science STKE, 2004(239):re9.
Li et al., (2006) "Ankyrin repeat: a unique motif mediating protein-protein interactions.", Biochemistry,45:15168-15178.
Le Rouzic and Benichou, (2005) "The Vpr protein from HIV-1: distinct roles along the viral life cycle.", Retrovirology, 2(11):1-14.
Colussi et al., (1998) "Conversion of Procaspase-3 to an Autoactivating Caspase by Fusion to the Caspase-2 Prodomain.", Journal of Biological Chemistry, 273(41):26566-26570.
Schweizer et al., (2003) "Crystal Structure of Caspase-2, Apical Initiator of the Intrinsic Apoptotic Pathway.", Journal of Biological Chemistry, 278(43):42441-42447.
Park et al., (2018) "Structure of TRAF Family: Current Understanding of Receptor Recognition.", Frontiers in Immunology, 9(1999):1-7.
Letzelter, (2006) The discovery of SycO reveals a new function for Type Three Secretion Effector Chaperones (dissertation).
Addgene Vector Database, pUCP20. Retrieved from internet https://www.addgene.org/vector-database/4537/, [retrieved Apr. 3, 2022] (Year: 2022).
Addgene Vector Database, pACYCDuet-1. Retrieved from internet https://www.addgene.org/vector-database/1680/, [retrieved Apr. 4, 2022] (Year: 2022).
Bichsel et al. (2011) "Bacterial Delivery of Nuclear Proteins into Pluripotent and Differentiated Cells," PLOS ONE, vol. 6, No. 1, e16465, pp. 1-9.
Bowie et al., (1990) "Deciphering the Message in Protein Sequences: Tolerance to Amino Acid Substitutions", Science, vol. 247, pp. 1306-1310.
Boyd et al., (2000) "Competition between the Yaps of Yersinia enterocolitica for Delivery into Eukaryotic Cells: Role of the SycE Chaperone Binding Domain of YopE," Journal of Bacteriology, vol. 182, No. 17, pp. 4811-4821.
Burgess et al., (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" The Journal of Cell Biology, vol. 111, pp. 2129-2138.
Dittmann et al., (2007) "The Yersinia enterocolitica type three secretion chaperone SycO is integrated into the Yop regulatory network and binds to the Yop secretion protein YscMI", BMC Microbiology, vol. 7, No. 67, pp. 1-10.
Goldsmith et al., (2006) BH3 peptidomimetics potently activate apoptosis and demonstrate single agent efficacy in neuroblastoma Oncogene (2006), 25: 4525-4533 (Year: 2006).
Höppner, (2002) "Clinical Impact of Molecular Diagnostics in Endocrinology", Harm Research, vol. 58, Suppl. 3, pp. 7-15.
Lazar et al., (1988) Transforming Growth Factor α: Mutation of Aspartic Acid 47 and Leucine 48 Results in Different Biological Activities, Molecular and Cellular Biology, vol. 8, pp. 1247-1252.
Radics et al., (2013) "Structure of a pathogenic type 3 secretion system in action," Nature Structural and Molecular Biology, vol. 21, No. 1, pp. 82-87 and Supplemental Materials (Year: 2013).
Shangary et al., (2002) "Peptides Derived from BH3 Domains of Bcl-2 Family Members: A Comparative v Analysis of Inhibition of Bcl-2, Bel-$x_L$ and Bax Oligomerization, Induction of cytochrome c Release, and Activation of Cell Death," Biochemistry (2002), 41: 9485-9495 (Year: 2002).
Sory et al., (1995) "Identification of the YopE and YopH domains required for secretion and internalization into the cytosol of macrophages, using the cyaA gene fusion approach," PNAS, vol. 92, No. 26, p. 11998-12002.
Van Den Berg et al., (2006) "Improved solubility of TEV protease by directed evolution", Journal of Bioecology, vol. 121, pp. 291-298.
Wertz and Dixit, (2010) "Regulation of death receptor signaling by the ubiquitin system," Cell Death and Differentiation, vol. 17, pp. 14-24.
Xu et al., (2014) "Structural basis for the prion-like MAVS filaments in antiviral innate immunity", eLife, vol. 3, e01489, pp. 1-25.

* cited by examiner

A

B

A

I a b c

II a b c

B

A

B

B

YopE1-138    XhoI    XbaI    BstBI

GTTCGCCACG CTCGAGTCTA GATTCGAA
HindIII                                   *myc* epitope

AAGCTTGGGC CGAACAAAA ACTCATCTCA

GAAGAGGATCTGAATAGCGC CGTCGACCAT
    6x His - tag        ***

CATCATCATC ATCATTGAGT TTAAACGGTC

TCCAGCTTGG CTGTTTTGG C

A

B

A

B

Figure 15A

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT | Y. enterocolitica ΔyopH,O,P,E,M,T | MRS40 pIML421 [yopHΔ1-352, yopOΔ65-558, yopP23, yopE21, yopM23, yopT135] | | | | | Nal | Iriarte and Cornelis, 1998 |
| ΔHOPEMT asd yopB | Y. enterocolitica ΔyopH,O,P,E,M,T ΔyopB | MRS40 pIML421 [yopBΔ89-217, yopHΔ1-352, yopOΔ65-558, yopP23, yopE21, yopM23, yopT135] | | | | | Nal Kan | |
| ΔHOPEMT asd | Y. enterocolitica ΔyopH,O,P,E,M,T Δasd | MRS40 asdΔ292-610 pIML421 [yopHΔ1-352, yopOΔ65-558, yopP23, yopE21, yopM23, yopT135] | | | | | Nal | Kudryashev et al., 2013 |
| ΔHOPEMT asd inv | Y. enterocolitica ΔyopH,O,P,E,M,T Δasd ΔinvA | MRS40 asdΔ292-610 invAΔ352-2225::aphA-3 pIML421 [yopHΔ1-352, yopOΔ65-558, yopP23, yopE21, yopM23, yopT135] | | | | 445/446, 447/448, 449/450 | Nal Kan | |
| ΔHOPEMT asd inv yadA | Y. enterocolitica ΔyopH,O,P,E,M,T Δasd ΔinvA ΔyadA | MRS40 asdΔ292-610 invAΔ587-836 (vector cointegration) yadAΔ89-354::aphA3 pIML421 [yopHΔ1-352, yopOΔ65-558, yopP23, yopE21, yopM23, yopT135] | | | | 352/353, 354/355, 356/

Figure 15B

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pBad_Si1 | Y. enterocolitica ΔyopH,O,P,E,M,T Δasd | EGFP (Arabinose inducible), SycE-YopE1-138-MycHis fragment | | pBad-MycHisA (Invitrogen) | pBad_Si_1 | 285/286 (EGFP), 287/288 (sycE-YopE1-138) | Nal Amp | |
| ΔHOPEMT asd pBad_Si2 | Y. enterocolitica ΔyopH,O,P,E,M,T Δasd | SycE-YopE1-138-MycHis fragment | YopE1-138-MycHis | pBad-MycHisA (Invitrogen) | pBad_Si_2 | 287/288 (sycE-YopE1-138) | Nal Amp | |
| ΔHOPEMT asd pSi_16 | Y. enterocolitica ΔyopH,O,P,E,M,T Δasd | | YopE1-138-IpgB1 | pBad_Si_2 | pSi_16 | 292/293 | Nal Amp | |
| ΔHOPEMT asd pSi_20 | Y. enterocolitica ΔyopH,O,P,E,M,T Δasd | | YopE1-138-SopE | pBad_Si_2 | pSi_20 | 296/297 | Nal Amp | |
| ΔHOPEMT asd pSi_22 | Y. enterocolitica ΔyopH,O,P,E,M,T Δasd | | YopE1-138-Rac1 Q61L | pBad_Si_2 | pSi_22 | 299/300 | Nal Amp | |
| ΔHOPEMT asd pSi_24 | Y. enterocolitica ΔyopH,O,P,E,M,T Δasd | | YopE1-138-RhoA Q61E | pBad_Si_2 | pSi_24 | 301/302 | Nal Amp | |

Figure 15C

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_28 | Y. enterocolitica ΔyopH,O,P,E,M,T Δasd | | YopE1-138-SopE-MycHis | pBad_Si_2 | pSi_28 | 296/306 | Nal Amp | |
| ΔHOPEMT yopB asd pSi_28 | Y. enterocolitica ΔyopH,O,P,E,M,T ΔyopB Δasd | | YopE1-138-SopE-MycHis | pBad_Si_2 | pSi_28 | 296/306 | Nal Amp | |
| ΔHOPEMT asd pSi_30 | Y. enterocolitica ΔyopH,O,P,E,M,T Δasd | | YopE1-138-SopB | pBad_Si_2 | pSi_30 | 307/308 | Nal Amp | |
| ΔHOPEMT asd pSi_37 | Y. enterocolitica ΔyopH,O,P,E,M,T Δasd | | YopE1-138-FADD | pBad_Si_2 | pSi_37 | 367/386 | Nal Amp | |
| ΔHOPEMT asd pSi_38 | Y. enterocolitica ΔyopH,O,P,E,M,T Δasd | | YopE1-138-OspF | pBad_Si_2 | pSi_38 | 317/318 | Nal Amp | |
| ΔHOPEMT asd pSi_43 | Y. enterocolitica ΔyopH,O,P,E,M,T Δasd | | YopE1-138-BepG 715-end | pBad_Si_2 | pSi_43 | 324/351 | Nal Amp | |

Figure 15D

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_51 | Y. enterocolitica ΔyopH,O,P,E,M,T Δasd | | YopE1-138-Rac1 Q61L-MycHis | pBad_Si_2 | pSi_51 | 299/339 | Nal Amp | |
| ΔHOPEMT asd yopB asd pSi_51 | Y. enterocolitica ΔyopH,O,P,E,M,T ΔyopB Δasd | | YopE1-138-Rac1 Q61L-MycHis | pBad_Si_2 | pSi_51 | 299/339 | Nal Amp | |
| ΔHOPEMT asd pSi_53 | Y. enterocolitica ΔyopH,O,P,E,M,T Δasd | | YopE1-138-Slmb1-VhH4 | pBad_Si_2 | pSi_53 | 341/342 | Nal Amp | |
| ΔHOPEMT asd pSi_57 | Y. enterocolitica ΔyopH,O,P,E,M,T Δasd | | YopE1-138-Bad | pBad_Si_2 | pSi_57 | 346/347 | Nal Amp | |
| ΔHOPEMT asd pSi_64 | Y. enterocolitica ΔyopH,O,P,E,M,T Δasd | | YopE1-138-SptP | pBad_Si_2 | pSi_64 | 364/365 | Nal Amp | |
| ΔHOPEMT asd pSi_70 | Y. enterocolitica ΔyopH,O,P,E,M,T Δasd | | YopE1-138-NLS-Slmb1-VhH4 | pBad_Si_2 | pSi_70 | 369/342 | Nal Amp | |

Figure 15E

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_85 | Y. enterocolitica ΔyopH,O,P,E,M,T Δasd | | YopE1-138-Bid | pBad_Si_2 | pSi_85 | 387/391 | Nal Amp | |
| ΔHOPEMT asd pSi_87 | Y. enterocolitica ΔyopH,O,P,E,M,T Δasd | | YopE1-138-t-Bid | pBad_Si_2 | pSi_87 | 389/391 | Nal Amp | |
| ΔHOPEMT asd pSi_97 | Y. enterocolitica ΔyopH,O,P,E,M,T Δasd | | YopE1-138-Caspase3 p17 | pBad_Si_2 | pSi_97 | 403/406 | Nal Amp | |
| ΔHOPEMT asd pSi_103 | Y. enterocolitica ΔyopH,O,P,E,M,T Δasd | | YopE1-138-GPCR GNA12 | pBad_Si_2 | pSi_103 | 410/413 | Nal Amp | |
| ΔHOPEMT asd pSi_106 | Y. enterocolitica ΔyopH,O,P,E,M,T Δasd | | YopE1-138-Caspase3 p10/12 | pBad_Si_2 | pSi_106 | 417/420 | Nal Amp | |
| ΔHOPEMT asd pSi_111 | Y. enterocolitica ΔyopH,O,P,E,M,T Δasd | | YopE1-138-IpgD | pBad_Si_2 | pSi_111 | 423/424 | Nal Amp | |
| ΔHOPEMT asd pSi_112 | Y. enterocolitica ΔyopH,O,P,E,M,T Δasd | | YopE1-138-Slmb1-VhH4-NLS | pBad_Si_2 | pSi_112 | 341/425 | Nal Amp | |

Figure 15F

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_116 | Y. enterocolitica ΔyopH,O,P,E,M, T Δasd | | YopE1-138-z-Bid | pBad_Si_2 | pSi_116 | 428/430 | Nal Amp | |
| ΔHOPEMT asd pSi_117 | Y. enterocolitica ΔyopH,O,P,E,M, T Δasd | | YopE1-138-z-t-Bid | pBad_Si_2 | pSi_117 | 429/430 | Nal Amp | |
| ΔHOPEMT asd pSi_118 | Y. enterocolitica ΔyopH,O,P,E,M, T Δasd | | YopE1-138-BepA E305-end | pBad_Si_2 | pSi_118 | 433/435 | Nal Amp | |
| ΔHOPEMT asd pSi_119 | Y. enterocolitica ΔyopH,O,P,E,M, T Δasd | | YopE1-138-BepA | pBad_Si_2 | pSi_119 | 434/435 | Nal Amp | |
| ΔHOPEMT asd pSi_120 | Y. enterocolitica ΔyopH,O,P,E,M, T Δasd | | YopE1-138-ET1 | pBad_Si_2 | pSi_120 | 436/437 | Nal Amp | |
| ΔHOPEMT asd pSi_121 | Y. enterocolitica ΔyopH,O,P,E,M, T Δasd | | YopE1-138-z-BIM | pbad_Si_1 | pSi_121 | 438/439 | Nal Amp | |
| ΔHOPEMT asd pSi_124 | Y. enterocolitica ΔyopH,O,P,E,M, T Δasd | | YopE1-138-VhH4 nanobody recognizing EGFP | pBad_Si_2 | pSi_124 | 451/373 | Nal Amp | |

Figure 15G

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_132 | Y. enterocolitica ΔyopH,O,P,E,M, T Δasd | | YopE1-138-TEV protease S219V | pBad_Si_2 | pSi_132 | 463/464 | Nal Amp | |
| ΔHOPEMT asd pSi_140 | Y. enterocolitica ΔyopH,O,P,E,M, T Δasd | | YopE1-138-EGFP | pBad_Si_2 | pSi_140 | 477/476 | Nal Amp | |
| ΔHOPEMT asd pSi_143 | Y. enterocolitica ΔyopH,O,P,E,M, T Δasd | | YopE1-138-Cdk1 | pBad_Si_2 | pSi_143 | 478/479 | Nal Amp | |
| ΔHOPEMT asd pSi_145 | Y. enterocolitica ΔyopH,O,P,E,M, T Δasd | | YopE1-138-Mad2 | pBad_Si_2 | pSi_145 | 482/483 | Nal Amp | |
| ΔHOPEMT asd pSi_147 | Y. enterocolitica ΔyopH,O,P,E,M, T Δasd | | YopE1-138-Ink4A | pBad_Si_2 | pSi_147 | 486/487 | Nal Amp | |
| ΔHOPEMT asd pSi_150 | Y. enterocolitica ΔyopH,O,P,E,M, T Δasd | | YopE1-138-Ink4B | pBad_Si_2 | pSi_150 | 492/493 | Nal Amp | |
| ΔHOPEMT asd pSi_151 | Y. enterocolitica ΔyopH,O,P,E,M, T Δasd | | YopE1-138-Ink4C | pBad_Si_2 | pSi_151 | 494/495 | Nal Amp | |

Figure 15H

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_153 | Y. enterocolitica ΔyopH,O,P,E,M,T Δasd | | YopE1-138-TIFA | pBad_Si_2 | pSi_153 | 558/559 | Nal Amp | |
| ΔHOPEMT asd pSi_156 | Y. enterocolitica ΔyopH,O,P,E,M,T Δasd | | YopE1-138-2x TEVsite - ET1 | pBad_Si_2 | pSi_156 | 504/505 | Nal Amp | |
| ΔHOPEMT asd pSi_159 | Y. enterocolitica ΔyopH,O,P,E,M,T Δasd | | YopE1-138-2xTEVsite - EGFP - NLS | pBad_Si_2 | pSi_159 | 511/513 | Nal Amp | |
| ΔHOPEMT asd pSi_160 | Y. enterocolitica ΔyopH,O,P,E,M,T Δasd | | YopE1-138-2xTEVsite - NLS - EGFP | pBad_Si_2 | pSi_160 | 512/476 | Nal Amp | |
| ΔHOPEMT asd pSi_161 | Y. enterocolitica ΔyopH,O,P,E,M,T Δasd | | YopE1-138-2x TEVsite - INK4C | pBad_Si_2 | pSi_161 | 508/509 | Nal Amp | |
| ΔHOPEMT asd pSi_164 | Y. enterocolitica ΔyopH,O,P,E,M,T Δasd | | YopE1-138-2x TEVsite - Flag - INK4C | pBad_Si_2 | pSi_164 | 515/509 | Nal Amp | |
| ΔHOPEMT asd pSi_166 | Y. enterocolitica ΔyopH,O,P,E,M,T Δasd | | YopE1-138-murine Traf6 | pBad_Si_2 | pSi_166 | 561/562 | Nal Amp | |

Figure 15I

| Strain Name | Background strain | Insert/relevant characteristics | Protein to be delivered by T3SS | Backbone plasmid | Resulting plasmid name | Primers. Si_Nr.: | resistances | Reference |
|---|---|---|---|---|---|---|---|---|
| ΔHOPEMT asd pSi_318 | Y. enterocolitica ΔyopH,O,P,E,M,T Δasd | | YopE1-138-Y. enterocolitica codon optimized murine tBid B

Figure 15J

| Strain Name | Background strain | Insert/relevant characteristics | Protein to be delivred by T3SS | Backbone plasmid | Resulting plasmid name | Primers. Si_Nr.: | resistances | References |
|---|---|---|---|---|---|---|---|---|
| S. enterica ΔaroA pSi_268 | S. enterica SL1344 ΔaroA | | SopE1-80 | pBad-MycHisA (Invitrogen) | pSi_268 | 614/615 | Amp | |
| S. enterica ΔaroA pSi_269 | S. enterica SL1344 ΔaroA | | SopE1-104 | pBad-MycHisA (Invitrogen) | pSi_269 | 614/616 | Amp | |
| S. enterica ΔaroA pSi_270 | S. enterica SL1344 ΔaroA | | SteA1-20-S. enterica codon optimized murine tBid | pSi_266 | pSi_270 | synthetic construct | Amp | |
| S. enterica ΔaroA pSi_271 | S. enterica SL1344 ΔaroA | | SteA-S. enterica codon optimized murine tBid | pSi_267 | pSi_271 | synthetic construct | Amp | |
| S. enterica ΔaroA pSi_272 | S. enterica SL1344 ΔaroA | | SopE1-80-S. enterica codon optimized murine tBid | pSi_268 | pSi_272 | synthetic construct | Amp | |
| S. enterica ΔaroA pSi_273 | S. enterica SL1344 ΔaroA | | SopE1-104-S. enterica codon optimized murine tBid | pSi_269 | pSi_273 | synthetic construct | Amp | |

Figure 15K

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_362 | Y. enterocolitica ΔyopH,O,P,E,M,T Δasd | | YopE1-138-Y. enterocolitica codon optimized Ink4A 84-103 | pBad_Si_2 | pSi_362 | 745/746 | Nal Amp | |
| ΔHOPEMT asd pSi_363 | Y. enterocolitica ΔyopH,O,P,E,M,T Δasd | | YopE1-138-Y. enterocolitica codon optimized Cdk2/cyclin inhibitory peptide I | pBad_Si_2 | pSi_363 | 747/748 | Nal Amp | |
| ΔHOPEMT asd pSi_364 | Y. enterocolitica ΔyopH,O,P,E,M,T Δasd | | YopE1-138-Y. enterocolitica codon optimized p21 peptide 10 (DtoA) | pBad_Si_2 | pSi_364 | 749/750 | Nal Amp | |
| ΔHOPEMT asd pSi_366 | Y. enterocolitica ΔyopH,O,P,E,M,T Δasd | | YopE1-138-Y. enterocolitica codon optimized p21 core of peptide 10 and 11 | pBad_Si_2 | pSi_366 | 753/754 | Nal Amp | |
| ΔHOPEMT asd pSi_367 | Y. enterocolitica ΔyopH,O,P,E,M,T Δasd | | YopE1-138-Y. enterocolitica codon optimized p21 peptide 17-33 | pBad_Si_2 | pSi_367 | 755/756 | Nal Amp | |

Figure 15L

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| ΔHOPEMT asd pSi_368 | Y. enterocolitica ΔyopH,O,P,E,M,T Δasd | | YopE1-138-Y. enterocolitica codon optimized pep5 of G1/S cyclin D2 | pBad_Si_2 | pSi_368 | 757/758 | Nal Amp | |
| S. enterica ΔaroA pSi_333 | S. enterica SL1344 ΔaroA | | SteA-Ink4a-MycHis | pSi_267 | pSi_333 | 703/704 | Amp | |
| S. enterica ΔaroA pSi_334 | S. enterica SL1344 ΔaroA | | SopE1-104-Ink4a-MycHis | pSi_269 | pSi_334 | 703/704 | Amp | |
| S. enterica ΔaroA pSi_335 | S. enterica SL1344 ΔaroA | | SteA-Ink4c-MycHis | pSi_267 | pSi_335 | 705/706; 707/708; 705/708 | Amp | |
| S. enterica ΔaroA pSi_336 | S. enterica SL1344 ΔaroA | | SopE1-104-Ink4c-MycHis | pSi_269 | pSi_336 | 705/706; 707/708; 705/708 | Amp | |
| S. enterica ΔaroA pSi_337 | S. enterica SL1344 ΔaroA | | SteA-Mad2-MycHis | pSi_267 | pSi_337 | 709/710 | Amp | |

Figure 15M

| Strain Name | Background strain | Insert/relevant characteristics | Protein to be delivred by T3SS | Backbone plasmid | Resulting plasmid name | Primers. Si_Nr.: | resistances | Reference |
|---|---|---|---|---|---|---|---|---|
| S. enterica ΔaroA pSi_338 | S. enterica SL1344 ΔaroA | | SopE1-104-Mad2-MycHis | pSi_269 | pSi_338 | 709/710 | Amp | |
| S. enterica ΔaroA pSi_339 | S. enterica SL1344 ΔaroA | | SteA-Cdk1-MycHis | pSi_267 | pSi_339 | 711/712 | Amp | |
| S. enterica ΔaroA pSi_340 | S. enterica SL1344 ΔaroA | | SopE1-104-Cdk1-MycHis | pSi_269 | pSi_340 | 711/712 | Amp | |
| ΔHOPEMT asd pSi_315 | Y. enterocolitica ΔyopH,O,P,E,M,T Δasd | | YopE1-138-Y. enterocolitica codon optimized murine tBid | pBad_Si_2 | pSi_315 | synthetic construct | Nal Amp | |
| ΔHOPEMT asd pSi_236 | Y. enterocolitica ΔyopH,O,P,E,M,T Δasd | | YopE1-138-Ubiquitin | pBad_Si_2 | pSi_236 | 585/586 | Nal Amp | |
| ΔHOPEMT asd pSi_237_II | Y. enterocolitica ΔyopH,O,P,E,M,T Δasd | | YopE1-138-Ubiquitin-Flag-INK4C-MycHis | pSi_236 | pSI_237_II | 588/509 | Nal Amp | |

A

B

BACTERIA-BASED PROTEIN DELIVERY

CROSS REFERENCE TO RELATED APPLICATIONS

This application is a continuation of U.S. application Ser. No. 15/311,424 filed on Nov. 15, 2016, which is a national phase application under 35 USC § 371 of International Patent Application No. PCT/EP2015/061086, filed May 20, 2015, which application claims priority from European Patent Application No 14169335.8 filed on May 21, 2014, the content of which is incorporated herein by reference.

THE FIELD OF THE INVENTION

The present invention relates to recombinant Gram-negative bacterial strains and the use thereof for delivery of heterologous proteins into eukaryotic cells.

BACKGROUND OF THE INVENTION

Transient transfection techniques have been applied in cell biological research over many years to address protein functions. These methods generally result in a massive overrepresentation of the protein under study, which might lead to oversimplified models of signalling [1]. For proteins controlling short-lived signalling processes, the protein of interest is present for far longer as the signalling event it controls [2]. Even more, DNA transfection based transient over-expression leads to a heterogenous and unsynchronized cell population, which complicates functional studies and hampers-omics approaches. Besides this, the upscaling of such assays to a larger scale is very expensive. Some of the above mentioned points are covered by existing techniques as microinjection or proteo-fection of purified proteins, the inducible translocation strategy to rapidly target plasmid born small GTPases to the cell membrane [2] or the addition of purified proteins fused to cell-permeable bacterial toxins [3]. But these techniques are all time-consuming and cumbersome and to our knowledge none fulfils all mentioned criteria.

Bacteria have evolved different mechanisms to directly inject proteins into target cells [4]. The type III secretion system (T3SS) used by bacteria like Yersinia, Shigella and Salmonella [5] functions like a nano-syringe that injects so-called bacterial effector proteins into host cells. Bacterial proteins to be secreted via the T3SS, called effectors, harbour a short N-terminal secretion signal [6]. Inside bacteria, some effectors are bound by chaperones. Chaperones might mask toxic domains [7], they contribute to exposition of the secretion signal [8, 9] and keep the substrates in a secretion-competent conformation [10], therefore facilitating secretion. Upon induction of secretion, an ATPase adjacent to the T3SS removes the chaperones [1 1] and the effectors travel unfolded or only partially folded through the needle [10], and refold once in the host cytoplasm.

T3S has been exploited to deliver hybrid peptides and proteins into target cells. Heterologous bacterial T3SS effectors have been delivered in case the bacterium under study is hardly accessible by genetics (like Chlamydia trachomatis; [12]). Often reporter proteins were fused to possible T3SS secretion signals as to study requirements for T3SS dependent protein delivery, such as the Bordetella pertussis adenylate cyclase [13], murine DHFR [10] or a phosphorylatable tag [14]. Peptide delivery was mainly conducted with the aim of vaccination. This includes viral epitopes [15, 16], bacterial epitopes (listeriolysin O, [17]) as well as peptides representing epitopes of human cancer cells [1 8]. In few cases functional eukaryotic proteins have been delivered to modulate the host cell, as done with nanobodies [1 9], nuclear proteins (Cre-recombinase, MyoD) [20, 21] or 1110 and IL1ra [22]. None of the above-mentioned systems allows single-protein delivery as in each case one or multiple endogenous effector proteins are still encoded. Furthermore, the vectors used have not been designed in a way allowing simple cloning of other DNA fragments encoding proteins of choice, hindering broad application of the system.

Therefore, a cheap and simple method allowing scalable, rapid, synchronized, homogenous and tuneable delivery of a protein of interest at physiological concentrations would be of great benefit for many cell biologists.

SUMMARY OF THE INVENTION

The present invention relates generally to recombinant Gram-negative bacterial strains and the use thereof for delivery of heterologous proteins into eukaryotic cells. The present invention provides Gram-negative bacterial strains and the use thereof, which allows the translocation of various type III effectors, but also of type IV effectors, of viral proteins and most importantly of functional eukaryotic proteins. Means for fluorescent tracking of delivery, for relocalization to the nucleus and notably for removal of the bacterial appendage after delivery to the host cell are provided. This allows for the first time delivery of almost native proteins into eukaryotic cells using only a T3SS. The presented T3SS based system results in scalable, rapid, synchronized, homogenous and tunable delivery of a protein of interest. The delivery system of the present invention is suitable to inject eukaryotic proteins in living animals and can be used for therapeutic purposes.

In a first aspect the present invention relates to a recombinant Gram-negative bacterial strain selected from the group consisting of the genera Yersinia, Escherichia, Salmonella and Pseudomonas, wherein said Gram-negative bacterial strain is transformed with a vector which comprises in the 5' to 3' direction:
  a promoter;
  a first DNA sequence encoding a delivery signal from a bacterial T3SS effector protein, operably linked to said promoter; and
  a second DNA sequence encoding a heterologous protein fused in frame to the 3'end of said first DNA sequence, wherein the heterologous protein is selected from the group consisting of proteins involved in apoptosis or apoptosis regulation.

In a further aspect, the present invention relates to a recombinant Gram-negative bacterial strain transformed with a vector, which comprises in the 5' to 3' direction: a promoter;
  a first DNA sequence encoding a delivery signal from a bacterial T3SS effector protein, operably linked to said promoter;
  a second DNA sequence encoding a heterologous protein fused in frame to the 3'end of said first DNA sequence; and
  a third DNA sequence encoding a protease cleavage site, wherein the third DNA sequence is located between the 3'end of said first DNA sequence and the 5'end of said second DNA sequence.

In a further aspect the present invention relates to a recombinant Gram-negative bacterial strain, wherein the recombinant Gram-negative bacterial strain is a Yersinia strain and wherein said Yersinia strain is wild type or deficient in the production of at least one T3SS effector protein and is transformed with a vector which comprises in the 5' to 3' direction: a promoter;
  a first DNA sequence encoding a delivery signal from a bacterial T3SS effector protein wherein the delivery signal from the bacterial T3SS effector protein comprises the N-terminal 138 amino acids of the *Y. enterocolitica* YopE effector protein, operably linked to said promoter; and
  a second DNA sequence encoding a heterologous protein fused in frame to the 3'end of said first DNA sequence.

In a further aspect the present invention relates to a recombinant Gram-negative bacterial strain, wherein the recombinant Gram-negative bacterial strain is a *Salmonella* strain and wherein said *Salmonella* strain is wild type or deficient in the production of at least one T3SS effector protein and is transformed with a vector which comprises in the 5' to 3' direction:

a promoter;

a first DNA sequence encoding a delivery signal from a bacterial T3SS effector protein wherein the delivery signal from the bacterial T3SS effector protein comprises the *S. enterica* SteA effector protein or the N-terminal 81 or 105 amino acids of the *S. enterica* SopE effector protein, operably linked to said promoter; and a second DNA sequence encoding a heterologous protein fused in frame to the 3'end of said first DNA sequence.

In a further aspect the present invention relates to a vector which comprises in the 5' to 3' direction:

a promoter;

a first DNA sequence encoding a delivery signal from a bacterial T3SS effector protein, operably linked to said promoter;

a second DNA sequence encoding a heterologous protein fused in frame to the 3'end of said first DNA sequence; and a third DNA sequence encoding a protease cleavage site, wherein the third DNA sequence is located between the 3'end of said first DNA sequence and the 5'end of said second DNA sequence.

The present invention further relates to a method for delivering a heterologous protein into a eukaryotic cell comprising the following steps:

i) culturing a Gram-negative bacterial strain; and ii) contacting a eukaryotic cell with the Gram-negative bacterial strain of i) wherein a fusion protein which comprises a delivery signal from a bacterial T3SS effector protein and the heterologous protein is expressed by the Gram-negative bacterial strain and is translocated into the eukaryotic cell.

The present invention further relates to a method for delivering a heterologous protein into a eukaryotic cell comprising the following steps:

i) culturing a Gram-negative bacterial strain;

ii) contacting a eukaryotic cell with the Gram-negative bacterial strain of i) wherein a fusion protein which comprises a delivery signal from a bacterial T3SS effector protein and the heterologous protein is expressed by the Gram-negative bacterial strain and is translocated into the eukaryotic cell; and iii) cleaving the fusion protein so that the heterologous protein is cleaved from the delivery signal from the bacterial T3SS effector protein.

The present invention further relates to a method of purifying a heterologous protein comprising culturing a Gram-negative bacterial strain so that a fusion protein which comprises a delivery signal from a bacterial T3SS effector protein and the heterologous protein is expressed and secreted into the supernatant of the culture.

In a further aspect the present invention relates to a library of Gram-negative bacterial strains, wherein the heterologous protein encoded by the second DNA sequence of the expression vector of the Gram-negative bacterial strains is a human or murine protein and, wherein each human or murine expressed by a Gram-negative bacterial strain is different in amino acid sequence.

BRIEF DESCRIPTION OF THE FIGURES

FIG. 1: Characterization of T3SS protein delivery. (A) Schematic representation of T3SS dependent protein secretion into the surrounding medium (in-vitro secretion)(left side) or into eukaryotic cells (right side). I: shows the type 3 secretion system. II indicates proteins secreted into the surrounding medium, III proteins translocated through the membrane into the cytosol of eukaryotic cells (VII). VI shows a stretch of the two bacterial membranes in which the T3SS is inserted and the bacterial cytosol underneath. IV is a fusion protein attached to the YopEi_i38N-terminal fragment (V) (B) In-vitro secretion of I: *Y. enterocolitica* E40 wild type, II: *Y. enterocolitica* ΔHOPEMT asd or III: *Y. enterocolitica* ΔHOPEMT asd+pBadSi_2 as revealed by Western blotting on total bacterial lysates (IV) and precipitated culture supernatants (V) using an anti-YopE antibody.

FIG. 2: Characterization of T3SS protein delivery into epithelial cells. (A) Anti-Myc immunofluorescence staining on HeLa cells infected at an MOI of 100 for 1 h with I: *Y. enterocolitica* ΔHOPEMT asd or II: *Y. enterocolitica* ΔHOPEMT asd+pBad_Si2. (B) Quantification of anti-Myc immunofluorescence staining intensity from (A) within HeLa cells. Data were combined from n=20 sites, error bars indicated are standard error of the mean. I: uninfected, II: *Y. enterocolitica* ΔHOPEMT asd or III: *Y. enterocolitica* ΔHOPEMT asd+pBad_Si2. Y-axis indicates anti-Myc staining intensity [arbitrary unit], x-axis indicates time of infection in minutes (C) Quantification of Anti-Myc immunofluorescence staining intensity within cells. HeLa cells were infected for 1 h with *Y. enterocolitica* ΔHOPEMT asd+pBad_Si2 at an MOI indicated on the x-axis. Data were combined from n=20 sites, error bars indicated are standard error of the mean. Y-axis indicates anti-Myc staining intensity [a.u.].

FIG. 3: Modifications of the T3SS based protein delivery allow nuclear localization of a YopEi.138 fusion protein (EGFP). EGFP signal in HeLa cells infected with I: *Y. enterocolitica* ΔHOPEMT asd or II: *Y. enterocolitica* ΔHOPEMT asd ΔyopB carrying the plasmids III: +YopEi_i38-EGFP or IV: +YopEi_$i_{38}$-EGFP-NLS at an MOI of 100. EGFP signal is shown in "a", for localization comparison nuclei were stained in "b".

FIG. 4: Modifications of the T3SS based protein delivery allow removal of the YopEi.i$3_s$ appendage. HeLa cells are infected with two different *Y. enterocolitica* strains at the same time, which is reached by simple mixing of the two bacterial suspensions. One strain is delivering the TEV protease fused to YopEi_$i_{38}$, while the other strain delivers a protein of interest fused to YopEi_$i_{38}$ with a linker containing a double TEV protease cleavage site. After protein delivery into the eukaryotic cell, the TEV protease will cleave the YopEi_$i_{38}$ appendage from the protein of interest (A) Digitonin lysed HeLa cells uninfected (II) or after infection (MOI of 100) for 2 h with I: *Y. enterocolitica* ΔHOPEMT asd and III: +pBadSi_2, IV: +YopEi_$i_{38}$-2x TEV cleavage site-Flag-INK4C, V: +YopEi_i$_{38}$-2x TEV cleavage site-Flag-INK4C and further overnight treatment with purified TEV protease and VI: +YopEi_i$_{38}$-2x TEV cleavage site-Flag-INK4C and a second strain+YopEi_i$_{38}$-TEV were analyzed by Western blotting anti-INK4C (shown in "a") for the presence of YopEi_i$_{38}$-2x TEV cleavage site -Flag-INK4C or its cleaved form Flag-INK4C. As a loading control western blotting anti-Actin was performed (shown in "b"). In one case (V) the lysed cells were incubated overnight with purified TEV protease. (B) Actin normalized quantification of anti-INK4C staining intensity (shown as [a.u.] on the y-axis) from (A) at the size of full length YopEi_i$_{3_8}$-2x TEV cleavage site-Flag-INK4C, where sample IV is set to 100%. I: *Y. enterocolitica* ΔHOPEMT asd and IV: +YopEi_i$_{3_8}$-2x TEV cleavage site-Flag-INK4C, V: +YopEi_i$_{3_8}$-2x TEV cleavage site-Flag-INK4C and further overnight treatment with purified TEV protease and VI: +YopEi_i$_{3_8}$-2x TEV cleavage site-Flag-INK4C and a second strain+YopEi_i$_{3_8}$-TEV. Data were combined from n=2 independent experiments, error bars indicated are standard error of the mean (C) Digitonin lysed HeLa cells uninfected (II) or after infection (MOI of 100) for 2 h with I: *Y. enterocolitica* ΔHOPEMT asd and III: +pBadSi_2, IV: +YopEi_i$_{3_8}$-2x TEV cleavage site-ET1-Myc, V: +YopEi_i$_{38}$-2x TEV cleavage site-ET1-Myc and further overnight treatment with purified TEV protease and VI: +YopEi_i$_{38}$-2x TEV cleavage site-ET1-Myc and a second strain+YopEi_i$_{38}$-TEV were analyzed by Western blotting anti-Myc (shown in "a") for the presence of YopEi_i$_{38}$-2x TEV cleavage site-ET1-Myc or its cleaved form ET1-Myc. As a loading control western blotting anti-Actin was performed (shown in "b") In one case (V) the lysed cells were incubated overnight with purified TEV protease.

Figure 5:
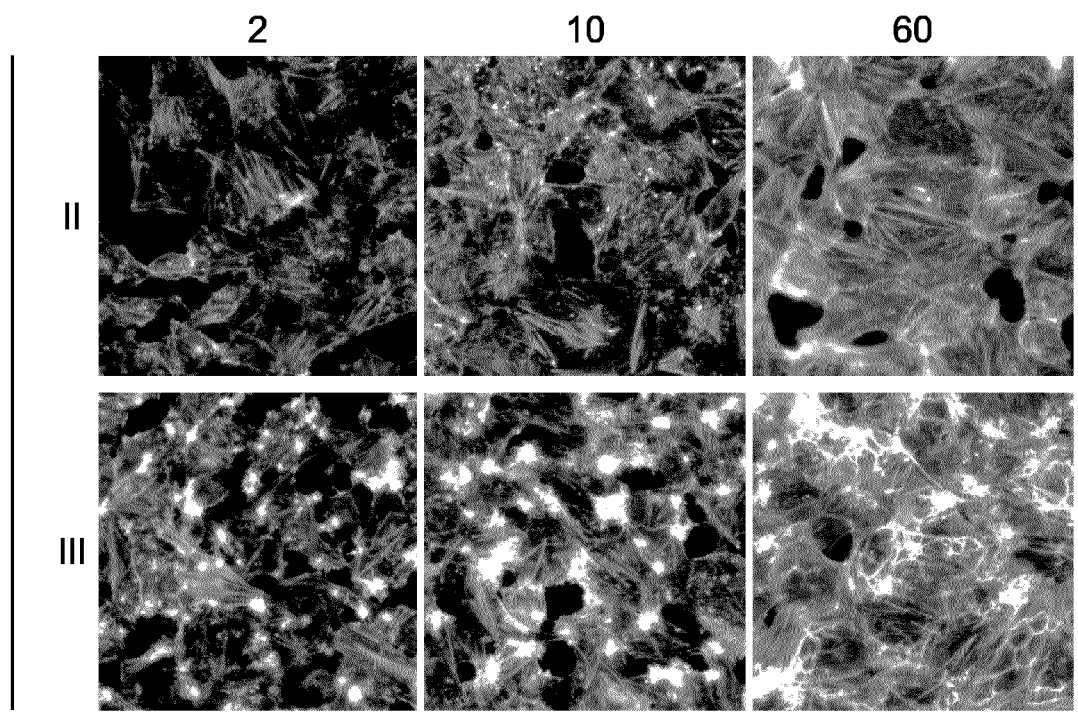
Figure 5:
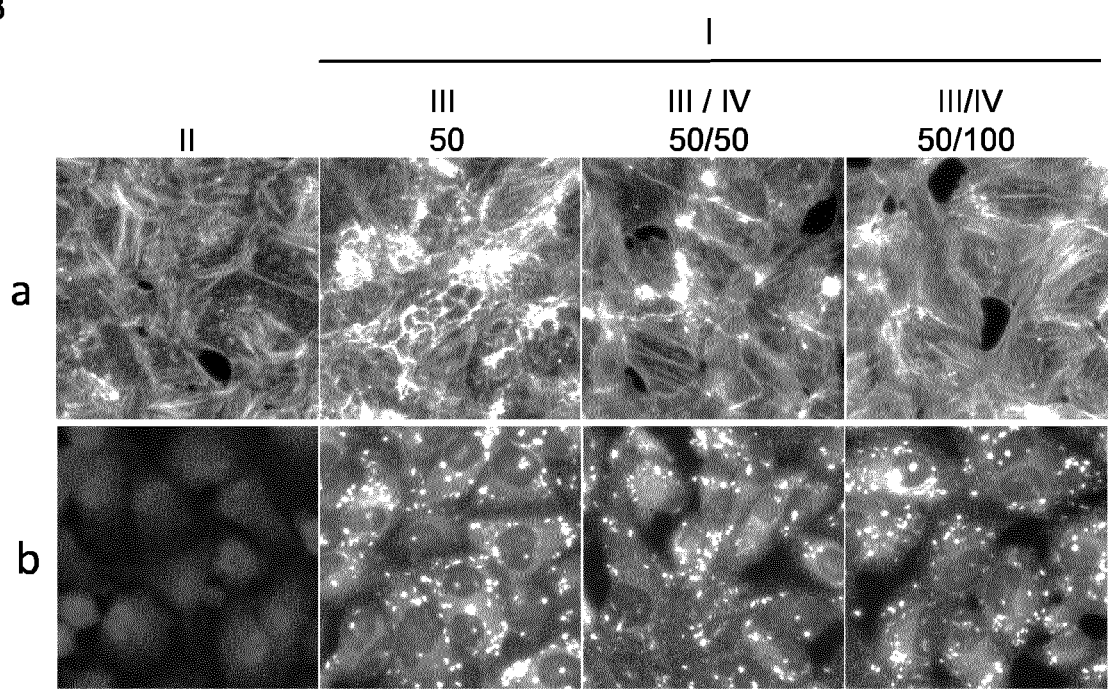

FIG. 5: Delivery of bacterial effector proteins into eukaryotic cells (A) HeLa cells were infected with I: *Y. enterocolitica* ΔHOPEMT asd carrying II: pBad_Si2 or III: YopEi_i$_{38}$-SopE at an MOI of 100 for the time indicated above the images (2, 10 or 60 minutes). After fixation cells were stained for the actin cytoskeleton (B) HeLa cells were left uninfected (II) or infected with I: *Y. enterocolitica* ΔHOPEMT asd carrying III: YopEi_i$_{38}$-SopE-Myc and in some cases coinfected with IV: YopEi_i$_{38}$-SptP at the MOI indicated below the strain (MOI 50; MOI50:MOI50 or MOI50:MOI100) for 1 h. After fixation cells were stained for the actin cytoskeleton (shown in "a") and the presence of the YopEi_i$_{38}$-SopE-Myc fusion protein was followed via staining anti-Myc (shown in "b").

Figure 6:
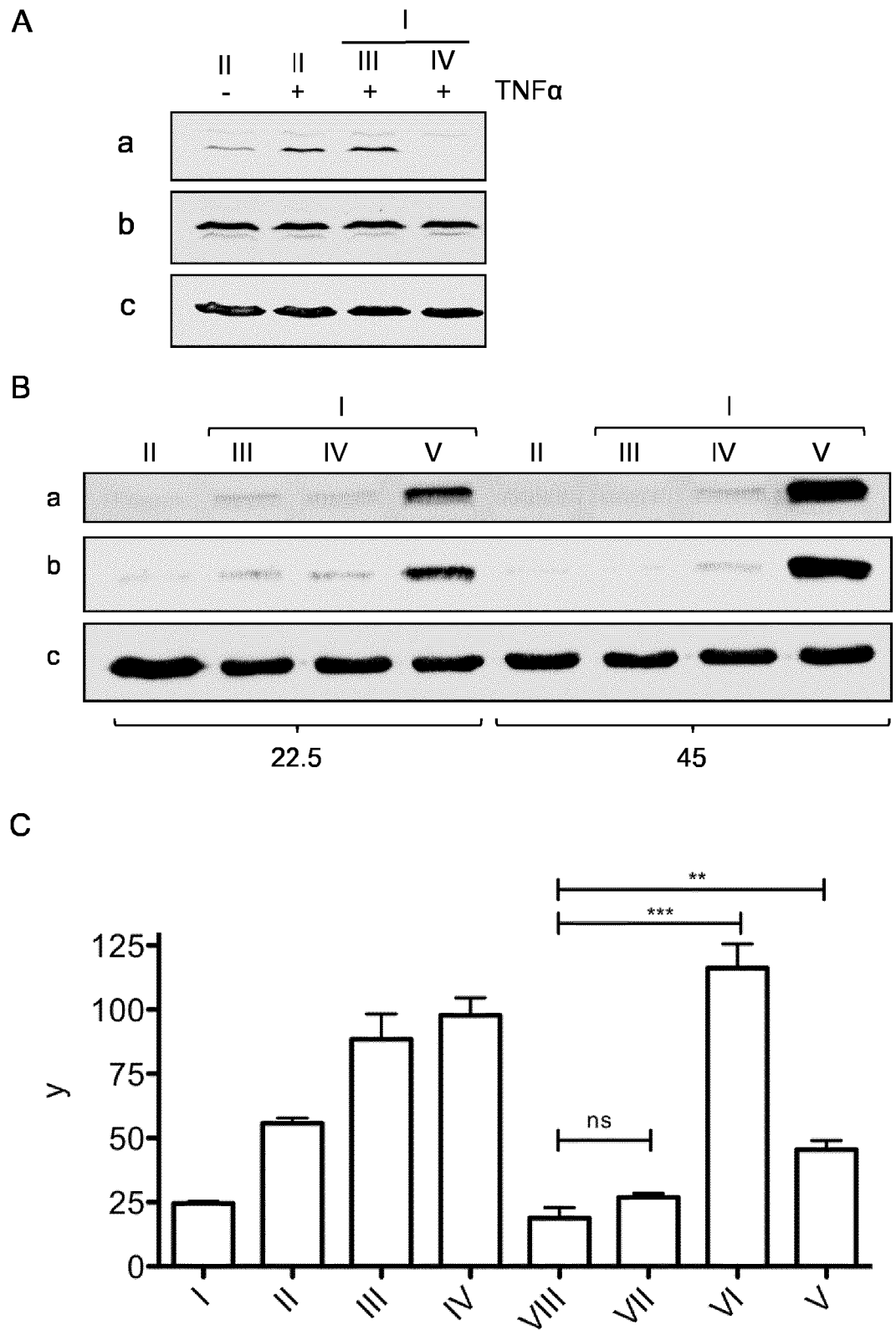

FIG. 6: Delivery of bacterial effector proteins into eukaryotic cells (A) Phospho-p38 ("a"), total p38 ("b") and actin ("c") western blot analysis on HeLa cells left untreated (II) or infected for 75 min with I: *Y. enterocolitica* ΔHOPEMT asd carrying III: pBad_Si2 or IV: YopEi_i$_{38}$-OspF at an MOI of 100. Cells were stimulated with TNFa for the last 30 min of the infection as indicated (+ stands for addition of TNFa, – represent no treatment with TNFa) (B) Phospho-Akt T308 ("a") and S473 ("b") and actin ("c") western blot analysis on HeLa cells left untreated (II) or infected for 22.5 or 45 min (indicated below the blots) with I: *Y. enterocolitica* ΔHOPEMT asd carrying III: pBad_Si2, IV: YopEi_i$_{38}$-SopE or V: YopEi_i$_{38}$-SopB at an MOI of 100 (C) cAMP levels (in fmol/well shown on y-axis) in HeLa cells left untreated (I) or infected for 2.5 h with V: *Y. enterocolitica* ΔHOPEMT asd+YopEi_i$_{3_8}$-BepA, VI: *Y. enterocolitica* ΔHOPEMT asd+YopEi_i3$_8$-BepA$_{E305\text{-}end}$, VII: *Y. enterocolitica* ΔHOPEMT asd+YopEi_i$_{38}$-BepG$_{Bid}$ or VIII: *Y. enterocolitica* ΔHOPEMT asd+pBad_Si2 at an MOI of 100. Cholera toxin (CT) was added for 1 h as positive control to samples II (1 μg/ηιl), III (25 μg/ηιl) or IV (50 μg/ηιl) Data were combined from n=3 independent experiments, error bars indicated are standard error of the mean. Statistical analysis was performed using an unpaired two-tailed t-test (ns indicates a non significant change,  indicates a p value<0.01, * indicates a p value<0.001).

Figure 7:
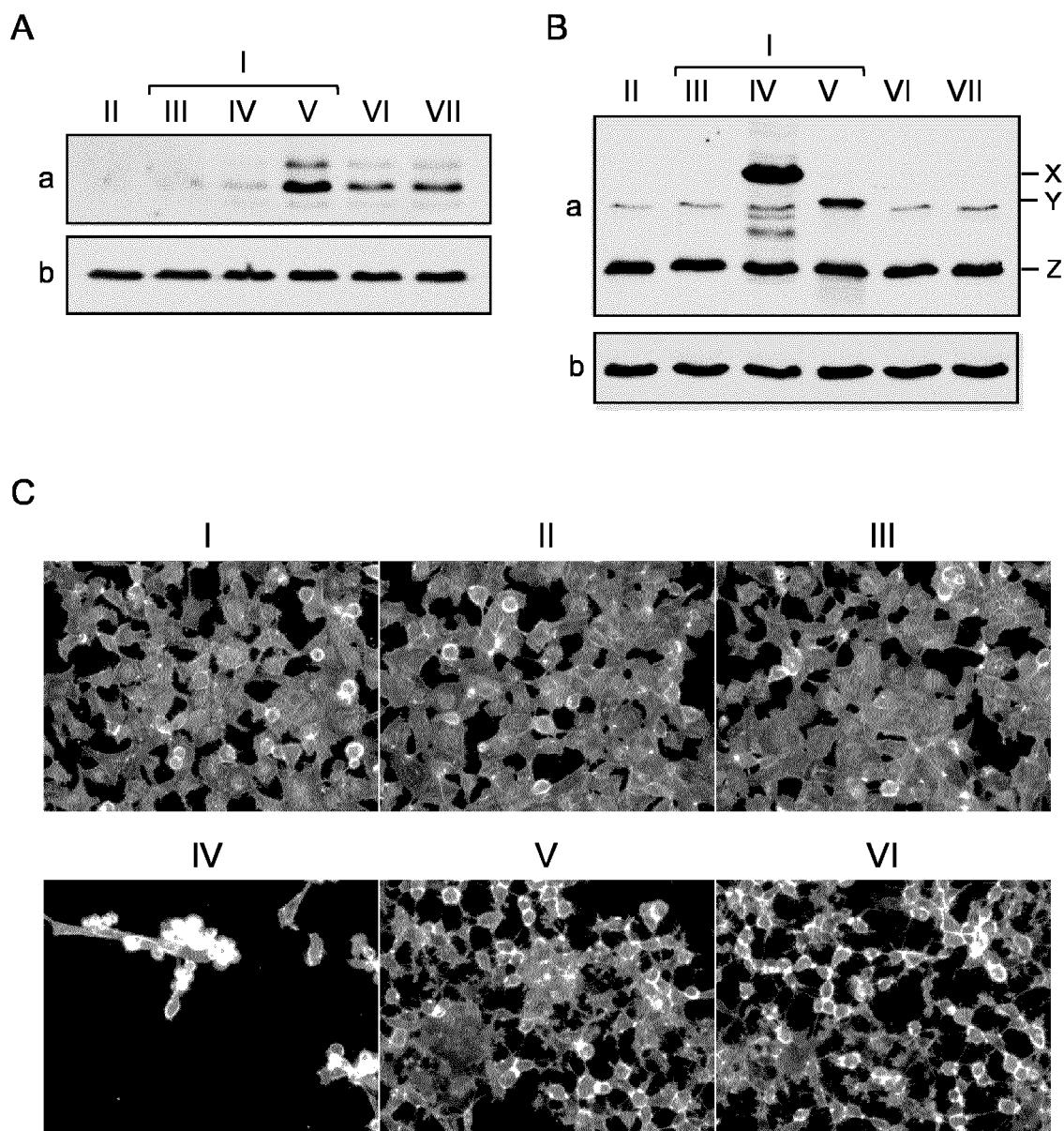

FIG. 7: Delivery of human tBid into eukaryotic cells induces massive apoptosis. (A) Cleaved Caspase 3 p17 ("a") and actin ("b") western blot analysis on HeLa cells left untreated (II) or infected for 60 min with I: *Y. enterocolitica* ΔHOPEMT asd carrying III: pBad_Si2, IV: YopEi_i38-Bid or V: YopEi_i$_{3_8}$-t-Bid at an MOI of 100. In some cases, cells were treated with VI: 0.5 μM Staurosporine or VII: 1 μM Staurosporine (B) Digitonin lysed HeLa cells left untreated (II) or after infection for 1 h with I: *Y. enterocolitica* ΔHOPEMT asd carrying III: pBad_Si2, IV: YopEi_i$_{38}$-Bid or V: YopEi_i$_{38}$-t-Bid at an MOI of 100 were analyzed by Western blotting anti-Bid ("a") allowing comparison of endogenous Bid levels (marked Z) to translocated YopEi_i$_{38}$-Bid (marked X) or YopEi_i$_{38}$-tBid (marked Y) levels. As a loading control western blotting anti-Actin was performed (shown in "b"). In some cases, cells were treated with VI: 0.5 μM Staurosporine or VII: 1 μM Staurosporine (C) HeLa cells were left untreated (I) or infected at an MOI of 100 for 1 h with II: *Y. enterocolitica* ΔHOPEMT asd+pBad_Si2, III: *Y. enterocolitica* ΔHOPEMT asd+YopEi_i$_{38}$-Bid, IV: *Y. enterocolitica* ΔHOPEMT asd+YopEi_i$_{38}$-tBid. In some cases, cells were treated with V: 0.5 μM Staurosporine or VI: 1 μM Staurosporine. After fixation cells were stained for the actin cytoskeleton (gray).

Figure 8:
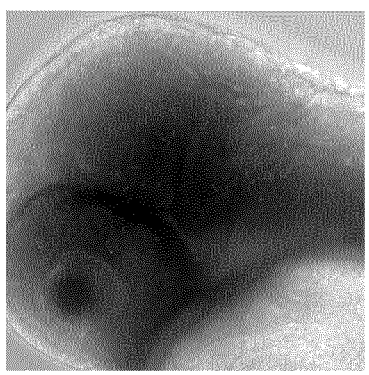
Figure 8:
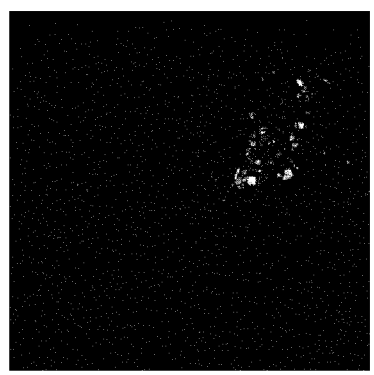
Figure 8:
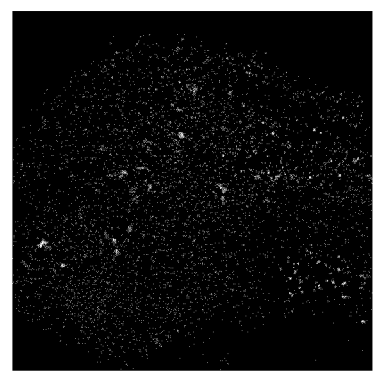
Figure 8:
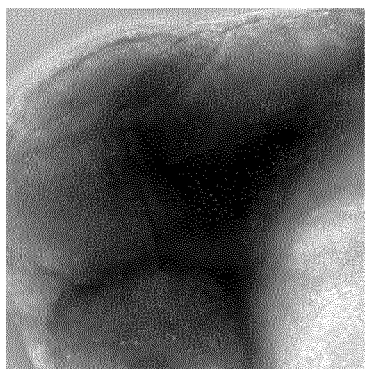
Figure 8:
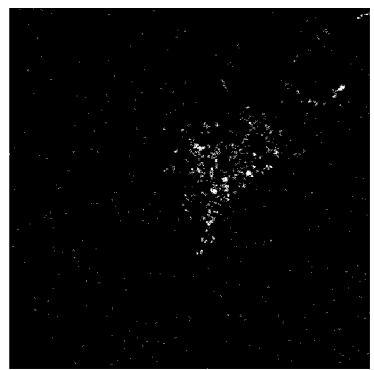
Figure 8:
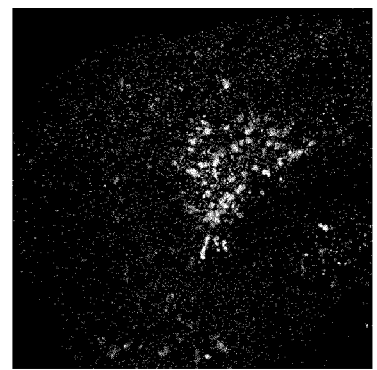
Figure 8:
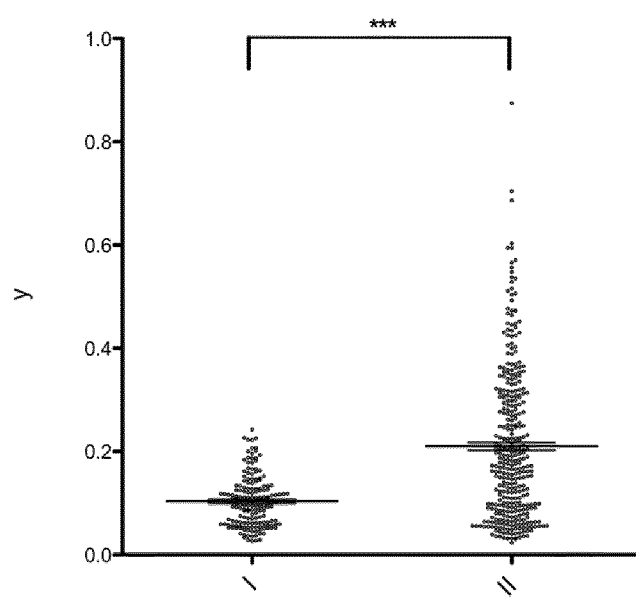

FIG. 8: T3SS dependent delivery of zebrafish BIM induces apoptosis in zebrafish embryos. (A) 2 dpf zebrafish embryos were infected with the EGFP expressing *Y. enterocolitica* ΔHOPEMT asd+pBad_Sil control strain (I) or zBIM translocating strain (II: *Y. enterocolitica* ΔHOPEMT asd+YopEi_i$_{38}$-zBIM) by injection of about 400 bacteria into the hindbrain region. After 5.5 h the embryos were fixed, stained for activated Caspase 3 (cleaved Caspase 3, p17; shown in "c") and analyzed for presence of bacteria (EGFP signal, shown in "b"). Maximum intensity z projections are shown for fluorescent images. Bright-field z projection are shown in "a" (B) Automated image analysis on maximum intensity z projections of recorded z-stack images of (A). Briefly, bacteria were detected via the GFP channel. Around each area of a bacterial spot a circle with a radius of 10 pixels was created. Overlapping regions were separated equally among the connecting members. In those areas closely surrounding bacteria, the Caspase 3 p17 staining intensity was measured and is plotted on the y-axis (as [a.u.]). Statistical analysis was performed using a Mann-Whitney test (*** indicates a p value<0.001). Data were combined from n=14 for *Y. enterocolitica* ΔHOPEMT asd+pBad_Sil control strain (I) or n=19 for II: *Y. enterocolitica* ΔHOPEMT asd+YopEi_i38-zBIM infected animals, error bars indicated are standard error of the mean.

Figure 9:
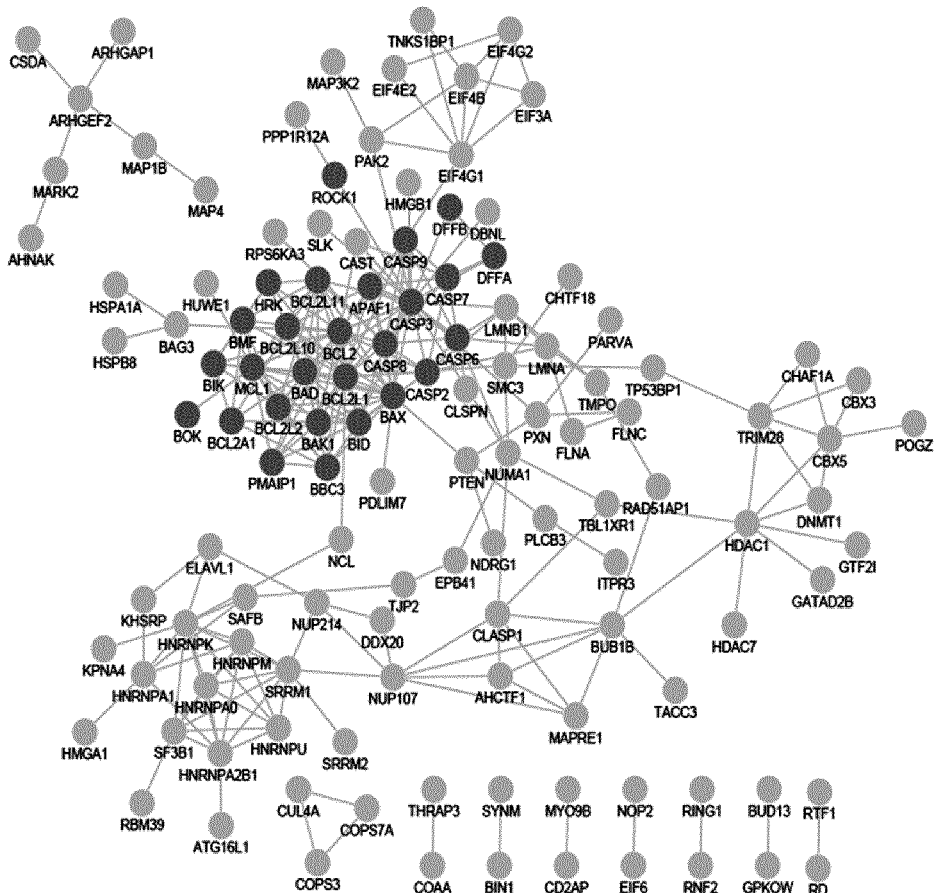
Figure 9:
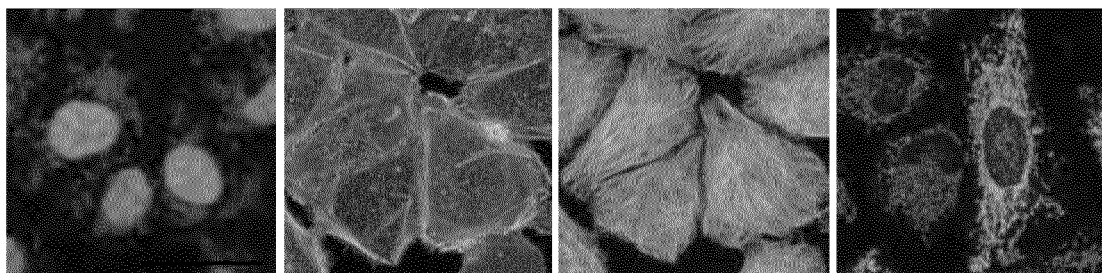
Figure 9:
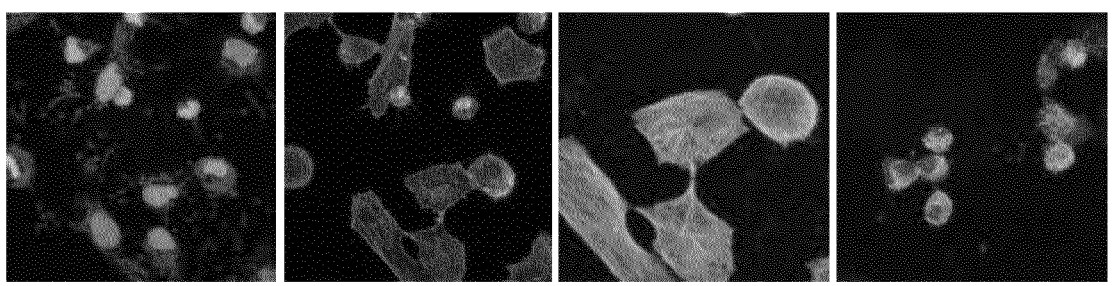

FIG. 9: tBiD dependent phosphoproteome: HeLa cells were infected for 30 min with *Y. enterocolitica* ΔHOPEMT asd+YopEi_i$_{3_8}$-t-Bid at an MOI of 100 and as a control with *Y. enterocolitica* ΔHOPEMT asd+pBad_Si2. (A) Graphical representation of the tBID phosphoproteome. Proteins containing phosphopeptides that were significantly regulated in a tBid dependent manner (gray) (q-value<0.01) as well as known apoptosis related proteins (dark gray) are represented in a STRING network of known and predicted protein-protein interactions (high-confidence, score 0.7). Only proteins with at least one connection in STRING are represented. (B) Confocal images of HeLa cells infected with either *Y. enterocolitica* ΔHOPEMT asd+pBad_Si2 (I) or *Y. enterocolitica* ΔHOPEMT asd+YopEi$_{-138}$-t-Bid (II) reveal the induction of an apoptotic phenotype upon tBid delivery. Cells were stained for the nuclei with Hoechst ("a"), for F-actin with phalloidin ("b"), for tubulin with an anti-tubulin antibody ("c") and for mitochondria with mitotracker ("d"). Scale bar represents 40μm.

Figure 10:
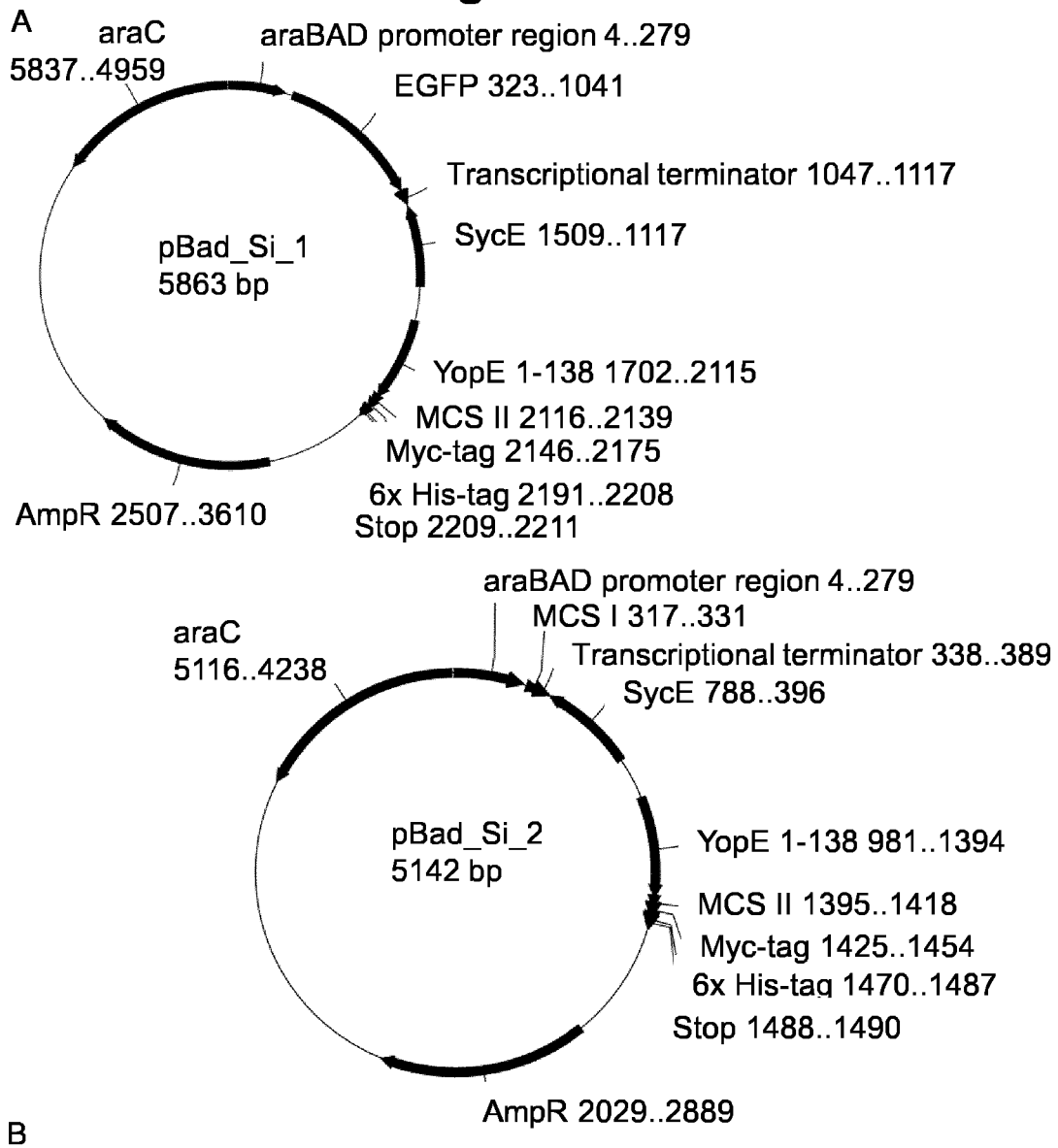

FIG. 10: Description of the type III secretion-based delivery toolbox. (A) Vector maps of the cloning plasmids pBad_Si1 and pBad_Si2 used to generate fusion constructs with YopEi_138- The chaperone SycE and the YopEi_i3$_8$- fusion are under the native *Y. enterocolitica* promoter. The two plasmids only differ in presence of an arabinose inducible EGFP present on pBad_Si1 (B) Multiple cloning site directly following the yopEi_i$_{38}$ fragment on pBad_Si1 and pBad_Si2 plasmids.

Figure 11:
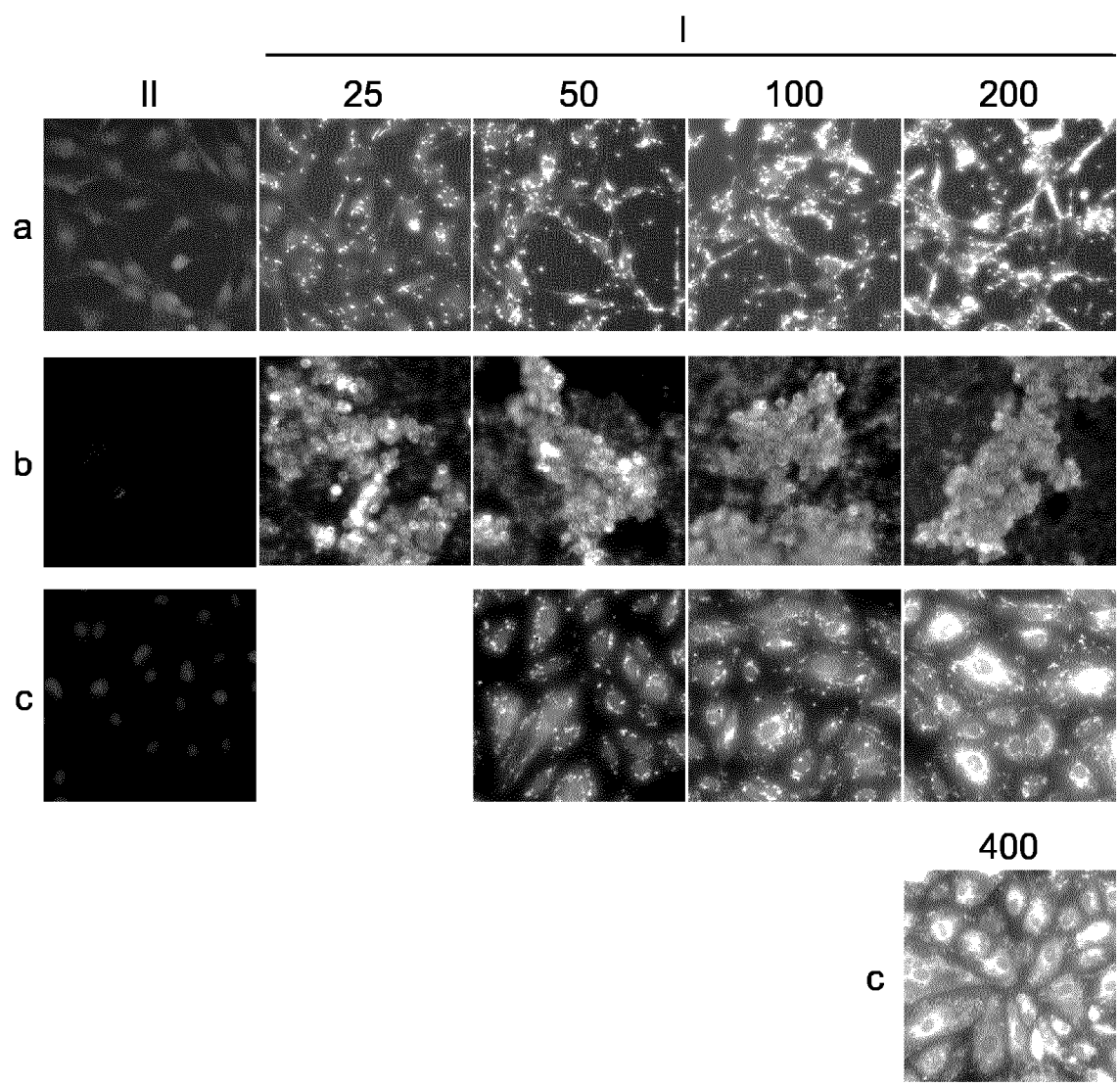

FIG. 11: Characterization of T3SS protein delivery into various cell lines. Anti-Myc immunofluorescence staining on Swiss 3T3 fibroblasts ("a"), Jurkat cells ("b") and HUVEC cells ("c") left untreated (II) or infected with *Y. enterocolitica* ΔHOPEMT asd+pBad_Si2 (I) at the MOI indicated above the images (MOI 25, 50, 100, 200 and 400 for HUVECs) for 1 h.

Figure 12:
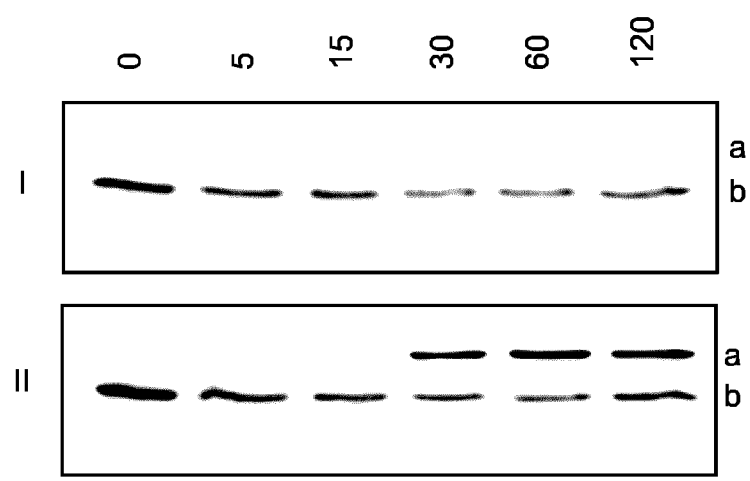

FIG. 12: T3SS dependency of delivery of bacterial effector proteins into eukaryotic cell. Digitonin lysed HeLa cells after infection at an MOI of 100 for time indicated above the blots (0, 5, 15, 10, 60 and 120 minutes) with *Y. enterocolitica* ΔHOPEMT asd ΔyopB+YopEi_i$_{38}$-SopE-Myc (I) or *Y. enterocolitica* ΔHOPEMT asd+YopEi_i$_{3_8}$-SopE-Myc (II) were analyzed by Western blotting anti-Myc. The size corresponding to YopEi_i$_{3_8}$-SopE-Myc is marked with "a", while the size of the endogenous c-Myc protein is marked with "b".

Figure 13:
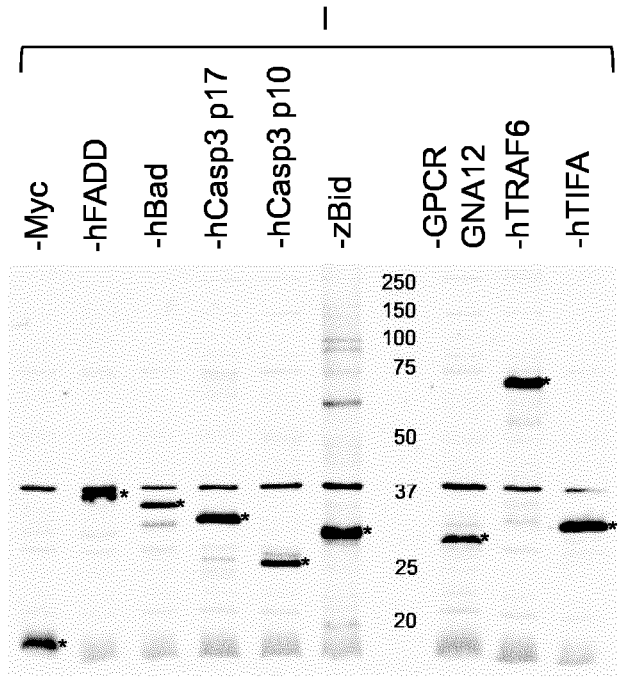
Figure 13:
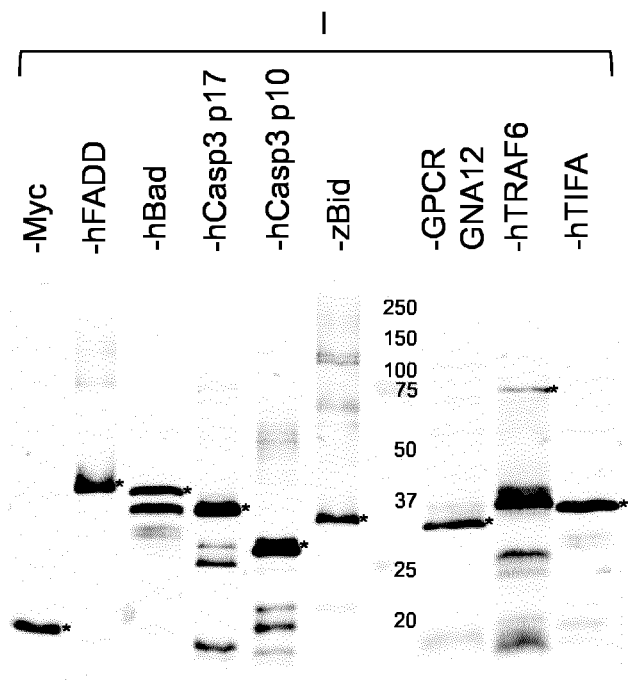
Figure 14:
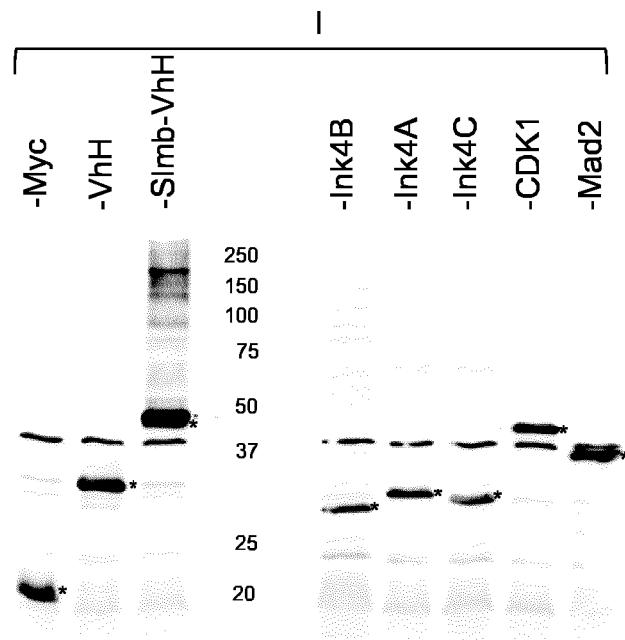
Figure 14:
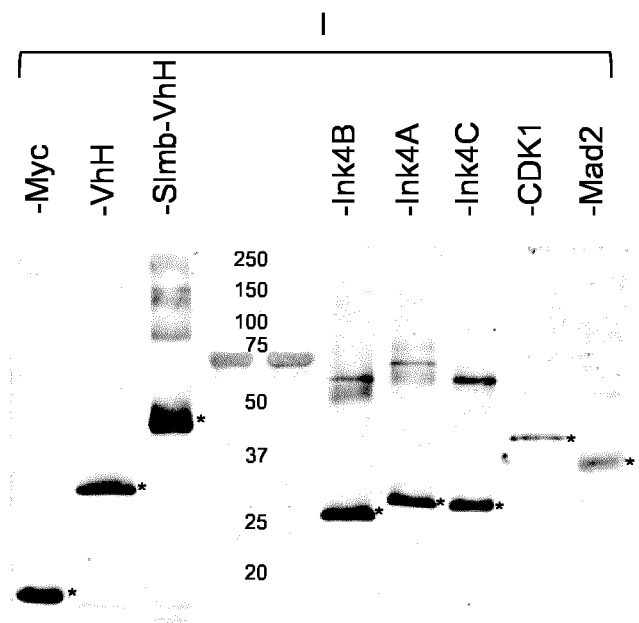

FIGS. 13 and 14: T3SS dependent secretion of various other proteins into the culture supernatant. In-vitro secretion experiment of I: *Y. enterocolitica* ΔHOPEMT asd+YopEi$_{-138}$ fused to the protein as indicated. Protein content of total bacterial lysates ("A") and precipitated culture supernatants ("B") was analyzed by Western blotting using an anti-YopE antibody. Numbers written indicate molecular weight in kDa at the corresponding height.

FIGS. 15A to M: *Y. enterocolitica* and *S. enterica* strains used in this study. List of *Y. enterocolitica* and *S. enterica* strains used in this study providing information on background strains, plasmids and proteins for T3SS dependent delivery encoded on corresponding plasmids. Further, information on oligonucleotides used for construction of the corresponding plasmid, the backbone plasmid and antibiotic resistances is provided.

Figure 16:
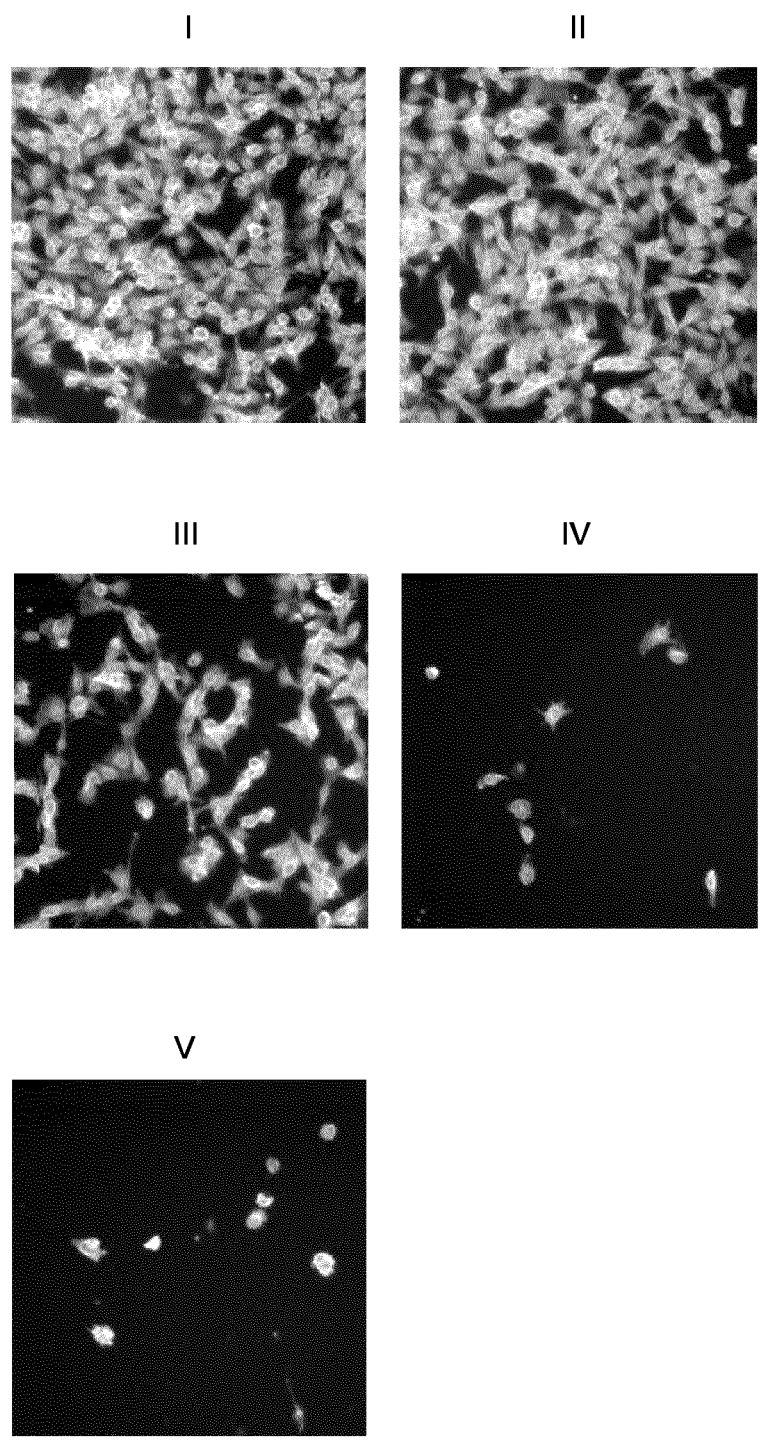

FIG. 16: Delivery of murine tBid, murine Bid BH3 and murine Bax BH3 into B16F10 cells induces massive apoptosis. B16F10 cells uninfected (I) or after infection (MOI of 50) for 2.5 h with *Y. enterocolitica* ΔHOPEMT asd and II: +pBadSi_2, III: +YopEi_i$_{38}$-7. *enterocolitica* codon optimized murine tBid, IV: +YopEi_i$_{38}$-7. *enterocolitica* codon optimized murine Bid BH3 or V: +YopEi_i$_{38}$-7. *enterocolitica* codon optimized murine Bax BH3. After fixation cells were stained for the actin cytoskeleton and nuclei (both in gray).

Figure 17:
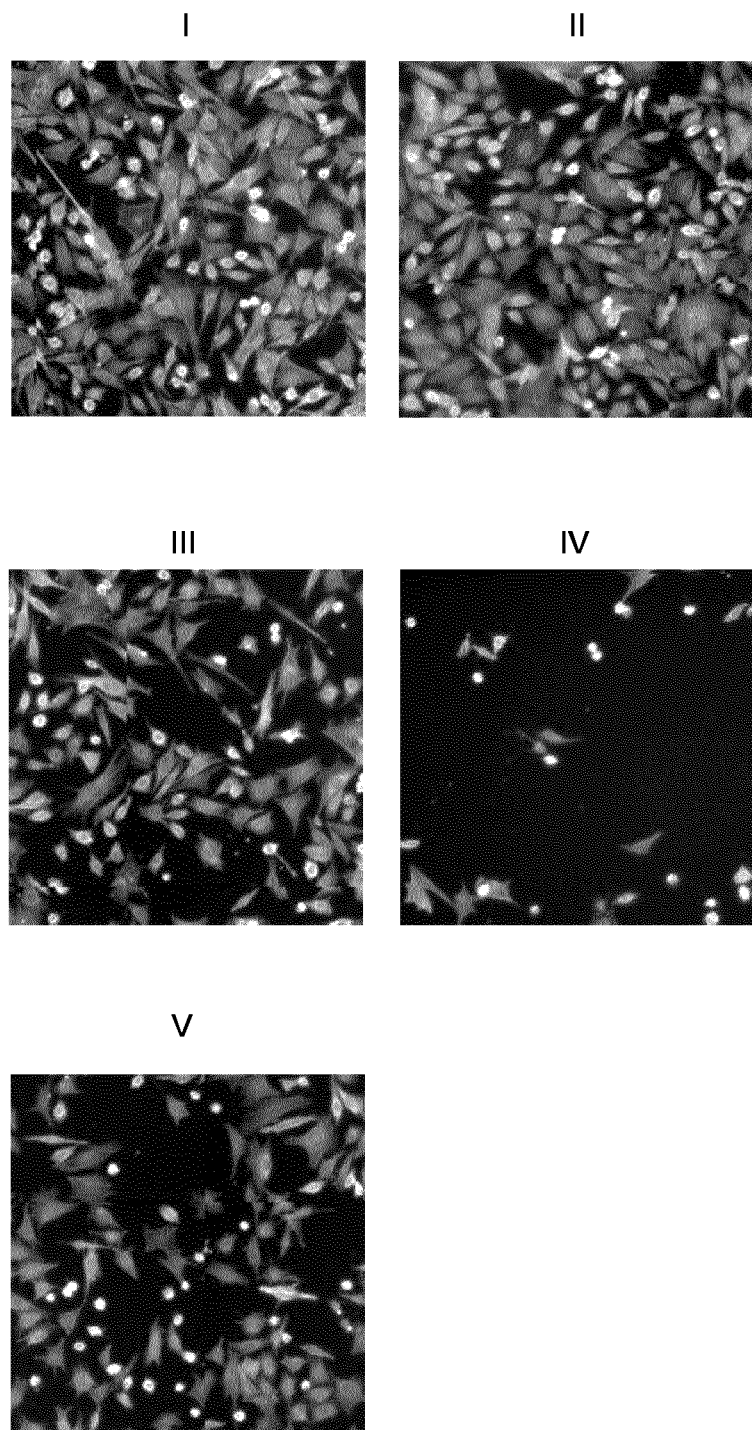

FIG. 17: Delivery of murine tBid, murine Bid BH3 and murine Bax BH3 into D2A1 cells induces massive apoptosis. D2A1 cells uninfected (I) or after infection (MOI of 50) for 2.5 h with *Y. enterocolitica* ΔHOPEMT asd and II: +pBadSi_2, III: +YopEi_i$_{38}$-7. *enterocolitica* codon optimized murine tBid, IV: +YopEi_i$_{38}$-7. *enterocolitica* codon optimized murine Bid BH3 or V: +YopEi_i$_{38}$-7. *enterocolitica* codon optimized murine Bax BH3. After fixation cells were stained for the actin cytoskeleton and nuclei (both in gray).

Figure 18:
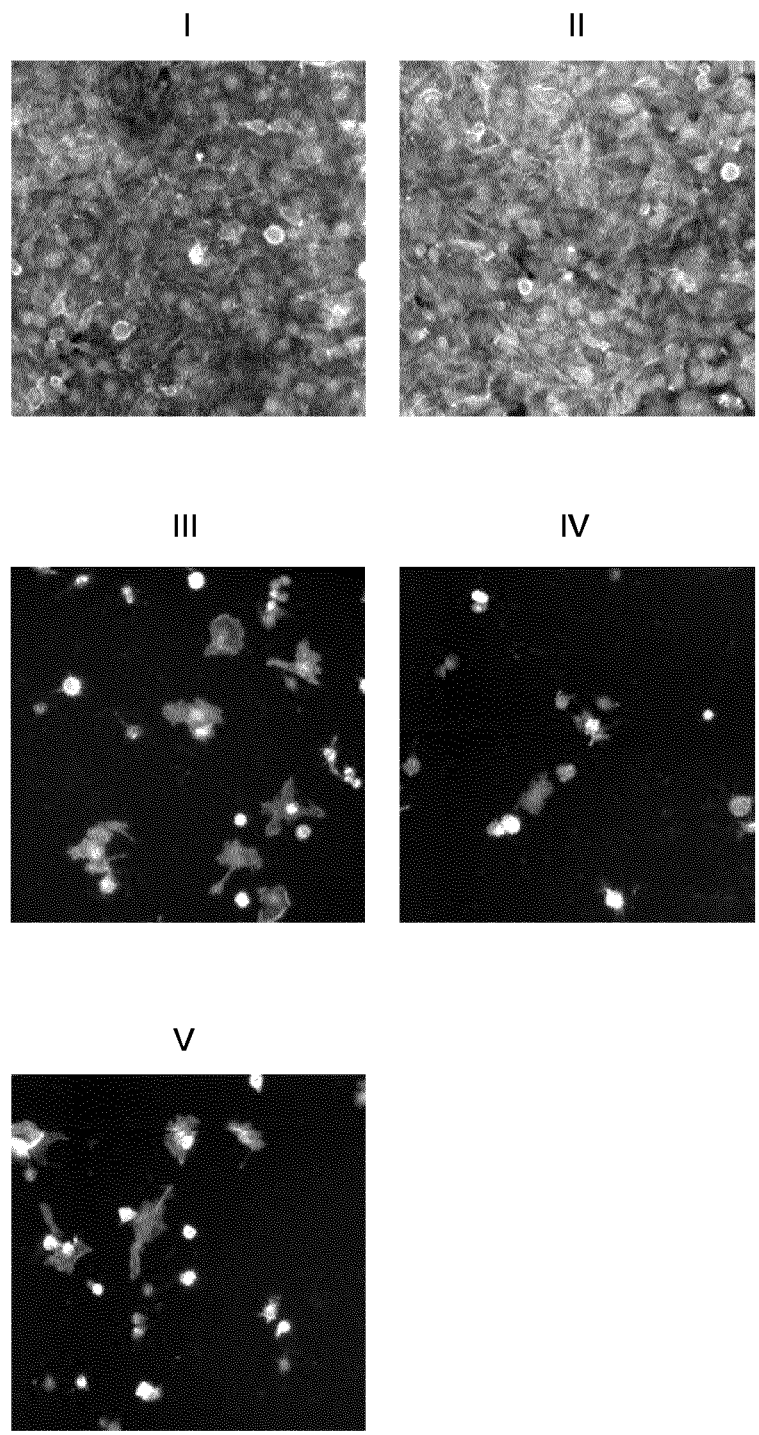

FIG. 18: Delivery of murine tBid, murine Bid BH3 and murine Bax BH3 into HeLa cells induces massive apoptosis. HeLa cells uninfected (I) or after infection (MOI of 50) for 2.5 h with *Y. enterocolitica* ΔHOPEMT asd and II: +pBadSi_2, III: +YopEi_i$_{38}$-7. *enterocolitica* codon optimized murine tBid, IV: +YopEi_i$_{38}$-7. *enterocolitica* codon optimized murine Bid BH3 or V: +YopEi_i$_{38}$-7. *enterocolitica* codon optimized murine Bax BH3. After fixation cells were stained for the actin cytoskeleton and nuclei (both in gray).

Figure 19:
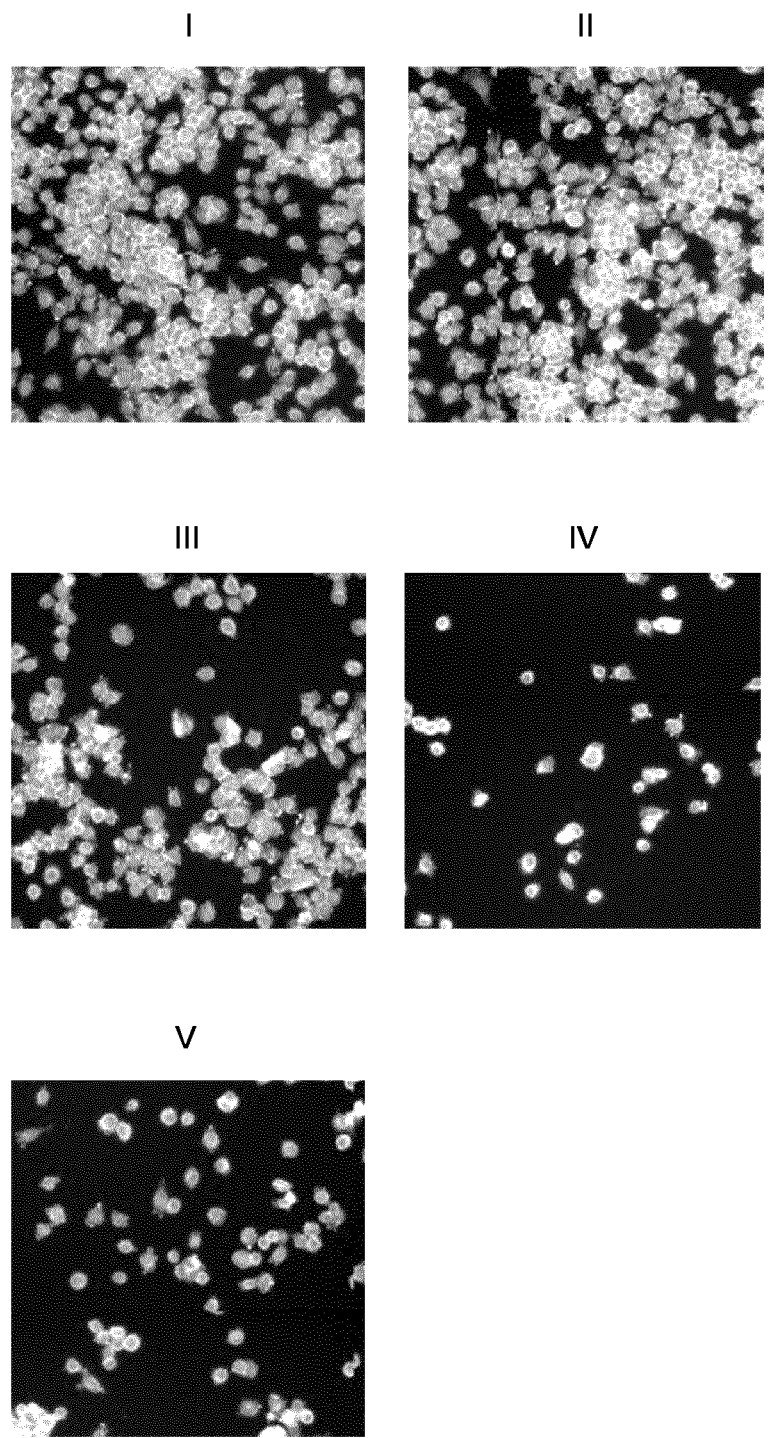

FIG. 19: Delivery of murine tBid, murine Bid BH3 and murine Bax BH3 into 4T1 cells induces massive apoptosis. 4T1 cells uninfected (I) or after infection (MOI of 50) for 2.5 h with *Y. enterocolitica* ΔHOPEMT asd and II: +pBadSi_2, III: +YopEi_i$_{38}$-7. *enterocolitica* codon optimized murine tBid, IV: +YopEi_i$_{38}$-7. *enterocolitica* codon optimized murine Bid BH3 or V: +YopEi_i$_{38}$-7. *enterocolitica* codon optimized murine Bax BH3. After fixation cells were stained for the actin cytoskeleton and nuclei (both in gray).

Figure 20:
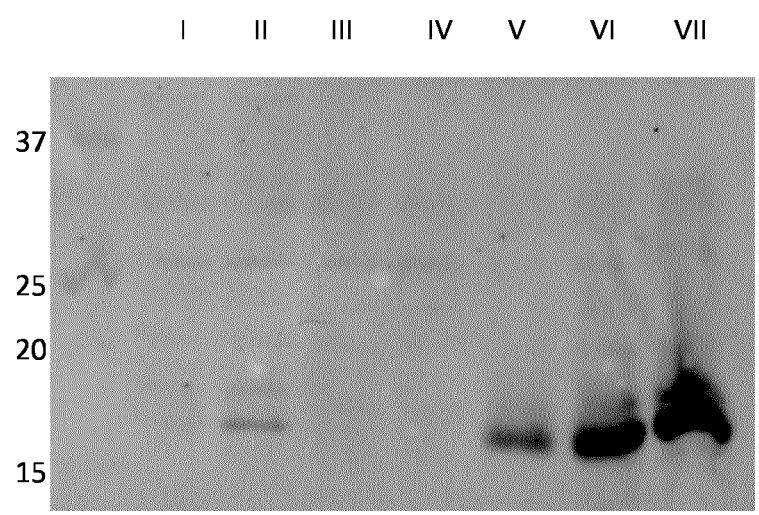

FIG. 20: Delivery of murine tBid by *S. enterica* grown under SPI-1 T3SS inducing conditions into eukaryotic cells induces apoptosis. Cleaved Caspase 3 p17 western blot analysis on HeLa cells left untreated (I) or infected for 4 h with III: *S. enterica* aroA carrying IV: SteAi$_{-20}$-t-Bid, V: SteA$_{FL}$-Bid, VI: SopEi$_{-8^i}$-t-Bid or VII: SopEi_i$_{05}$-t-Bid at an MOI of 100. For this experiment, all *S. enterica* aroA strains were grown under SPI-1 T3SS inducing conditions. In some cases, cells were treated with II: 1 μM Staurosporine. Numbers written indicate molecular weight in kDa at the corresponding height.

Figure 21:
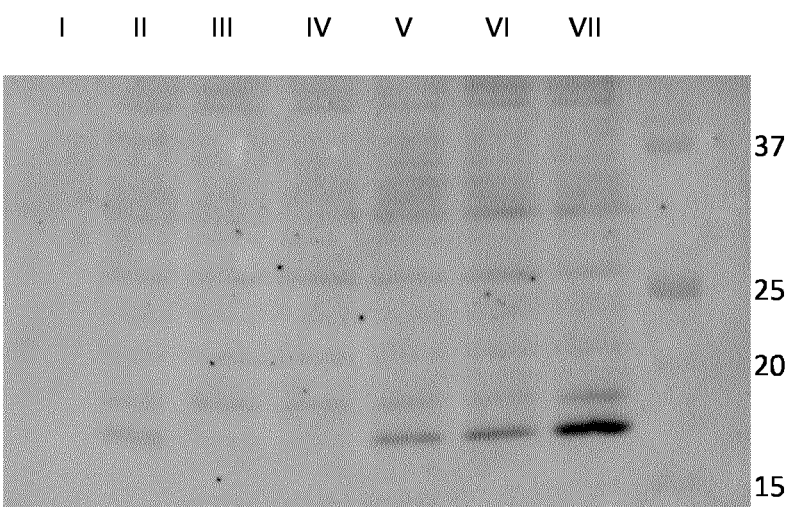

FIG. 21: Delivery of murine tBid by *S. enterica* grown under SPI-2 T3SS inducing conditions into eukaryotic cells induces apoptosis. Cleaved Caspase 3 p17 western blot analysis on HeLa cells left untreated (I) or infected for 4 h with III: *S. enterica* aroA carrying IV: SteAi$_{-20}$-t-Bid, V: SteA$_{FL}$-Bid, VI: SopEi$_{-8^i}$-t-Bid or VII: SopEi_i$_{05}$-t-Bid at an MOI of 100. For this experiment, all *S. enterica* aroA strains were grown under SPI-2 T3SS inducing conditions. In some cases, cells were treated with II: 1 μM Staurosporine. Numbers written indicate molecular weight in kDa at the corresponding height.

Figure 22:
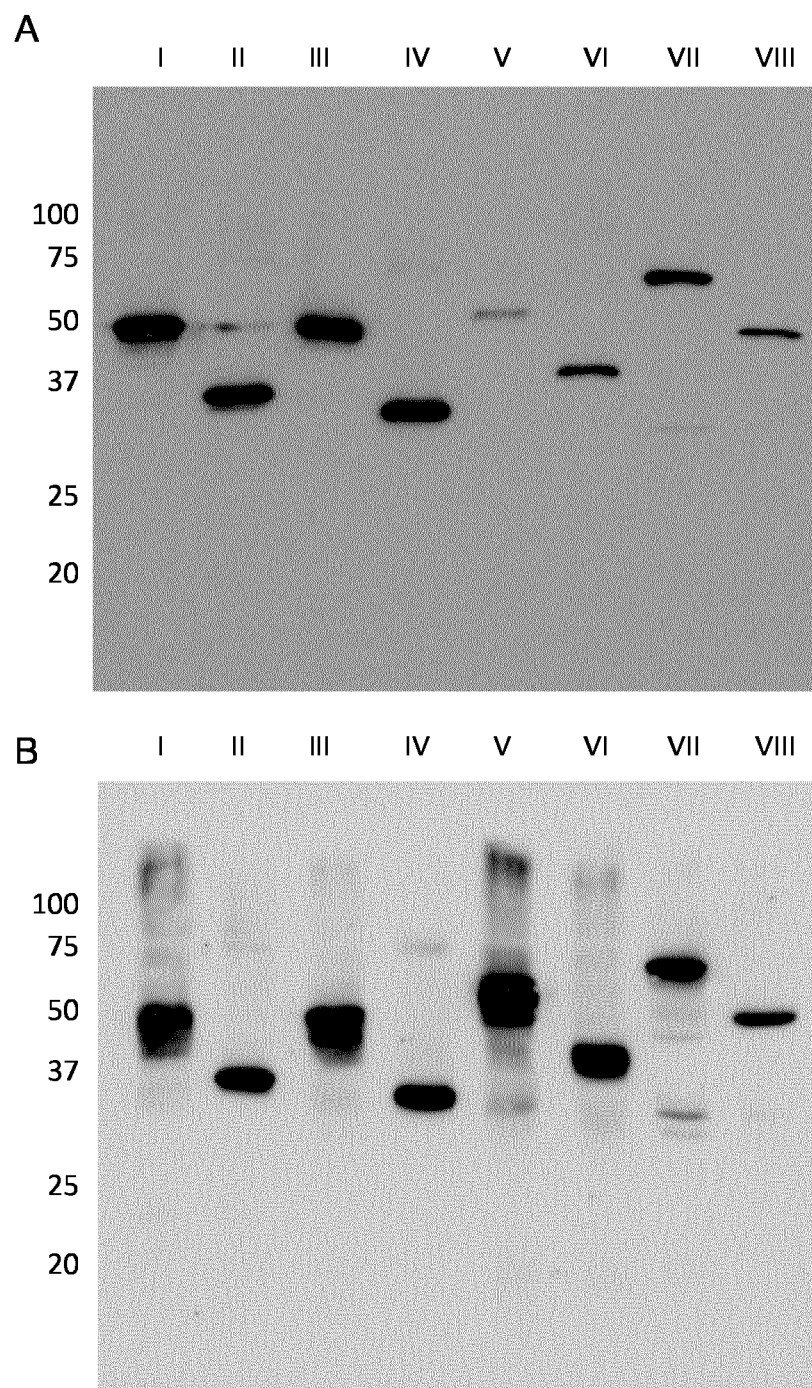

FIG. 22: *S. enterica* T3SS dependent secretion of various cell cycle proteins into the culture supernatant. In-vitro secretion experiment of *S. enterica* aroA+either SteA$_{FL}$ (I, III, V, VII) or SopEi_i$_{05}$ (II, IV, VI, VIII) fused to proteins as listed following. I and II: Ink4a-MycHis; III and IV: Ink4c-MycHis; V and VI: Mad2-MycHis; VII and VIII: Cdkl-MycHis. Protein content of precipitated culture supernatants ("A") and total bacterial lysates ("B") was analyzed by Western blotting using an anti-myc antibody. Numbers written indicate molecular weight in kDa at the corresponding height.

Figure 23:
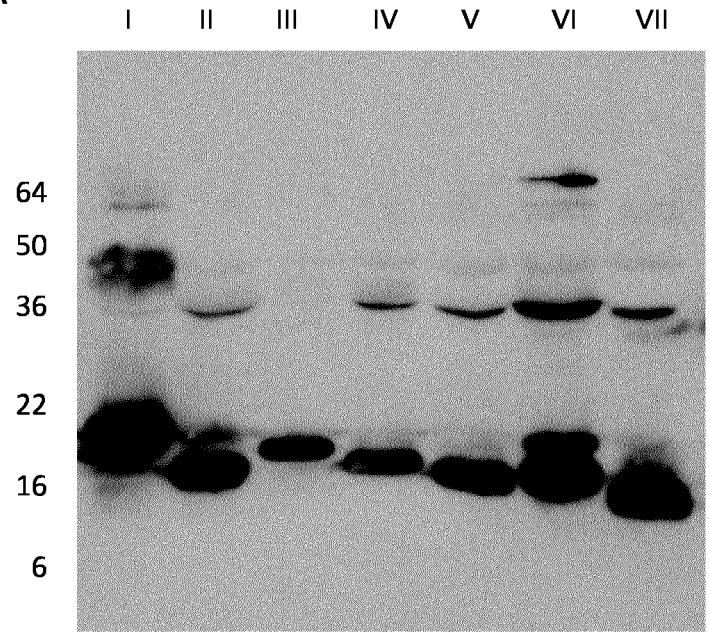
Figure 23:
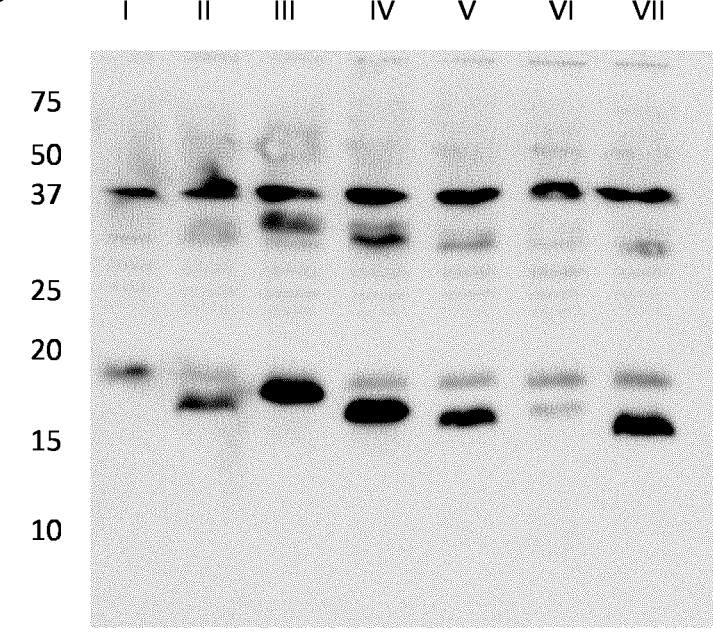

FIG. 23: T3SS dependent secretion of various known cell cycle interfering peptides into the culture supernatant. In-vitro secretion experiment of I: *Y. enterocolitica* ΔHOPEMT asd+pBad_Si2. II-VII: *Y. enterocolitica* ΔHOPEMT asd+ YopEi_i$_{38}$ fused to peptides as listed following: II: Ink4 A$_{84}{}^{-i\alpha3}$, III: p107/RBL1$_{657-662}$, IV: p21$_{141-160D149A}$, V: p21$_{145-160D149A}$, VI: p2i$_{7-33}$; VII: cyclin D2i$_{39-i_{47}}$. Protein content of precipitated culture supernatants ("A") and total bacterial lysates ("B") was analyzed by Western blotting using an anti-YopE antibody. Numbers written indicate molecular weight in kDa at the corresponding height.

Figure 24:
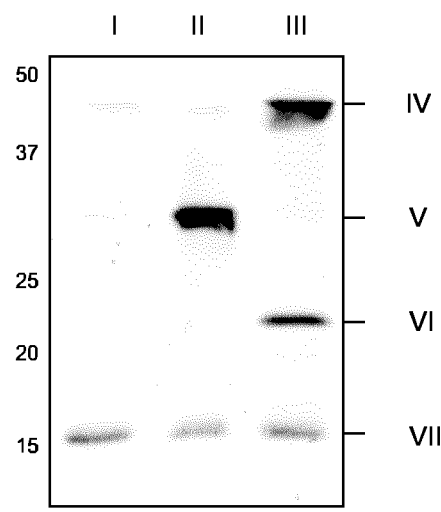

FIG. 24: Fusion of the T3SS delivered protein to Ubiquitin allows removal of the YopEi_$i_{138}$ appendage. HeLa cells are infected with a strain delivering a protein of interest fused to YopEi_i38 with a directly fused Ubiquitin (YopEi_$i_{38}$-Ubi). After protein delivery into the eukaryotic cell, endogenous Ubiquitin specific proteases will cleave the YopEi_$i_{38}$-Ubi appendage from the protein of interest. Digitonin lysed HeLa cells uninfected (I) or after infection (MOI of 100) for 1 h with II: *Y. enterocolitica* ΔHOPEMT asd+ YopEi_$i_{38}$-Flag-INK4C-MycHis or III: +YopEi_$i_{38}$-Flag-Ubiquitin-INK4C-MycHis were analyzed by Western blotting anti-INK4C for the presence of IV: YopEi_$i_{38}$-Flag-Ubiquitin-INK4C-MycHis or V: YopEi_$i_{38}$-Flag-INK4C-MycHis, the cleaved form VI: INK4C-MycHis and VII: the endogenous INK4C.

DETAILED DESCRIPTION OF THE INVENTION

The present invention provides recombinant Gram-negative bacterial strains and the use thereof for delivery of heterologous proteins into eukaryotic cells.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The term "Gram-negative bacterial strain" as used herein includes the following bacteria: *Aeromonas salmonicida, Aeromonas hydrophila, Aeromonas veronii, Anaeromyxobacter dehalogenans, Bordetella bronchiseptica, Bordetella bronchiseptica, Bordetella parapertussis, Bordetella pertussis, Bradyrhizobium japonicum, Burkholderia cenocepacia, Burkholderia cepacia, Burkholderia mallei, Burkholderia pseudomallei, Chlamydia muridarum, Chlamydia trachmoatis, Chlamydophila abortus, Chlamydophila pneumoniae, Chromobacterium violaceum, Citrobacter rodentium, Desulfovibrio vulgaris, Edwardsiella tarda, Endozoicomonas elysicola, Erwinia amylovora, Escherichia albertii, Escherichia coli, Lawsonia intracellularis, Mesorhizobium loti, Myxococcus xanthus, Pantoea agglomerans, Photobacterium damselae, Photorhabdus luminescens, Photorabdus temperate, Pseudoalteromonas spongiae, Pseudomonas aeruginosa, Pseudomonas plecoglossicida, Pseudomonas syringae, Ralstonia solanacearum, Rhizobium sp, Salmonella enterica* and other *Salmonella sp, Shigella flexneri* and other *Shigella sp, Sodalis glossinidius, Vibrio alginolyticus, Vibrio azureus, Vibrio campellii, Vibrio caribbenthicus, Vibrio harvey, Vibrio parahaemolyticus, Vibrio tasmaniensis, Vibrio tubiashii, Xanthomonas axonopodis, Xanthomonas campestris, Xanthomonas oryzae, Yersinia enterocolitica, Yersinia pestis, Yersinia pseudotuberculosis*. Preferred Gram-negative bacterial strains of the invention are Gram-negative bacterial strains comprised by the family of Enterobacteriaceae and Pseudomonadaceae. The Gram-negative bacterial strain of the present invention is normally used for delivery of heterologous proteins by the bacterial T3SS into eukaryotic cells in vitro and in vivo.

The term "recombinant Gram-negative bacterial strain" used herein refers to a Gram-negative bacterial strain genetically transformed with a vector. A useful vector of the present invention is e.g an expression vector, a vector for chromosomal or virulence plasmid insertion or a DNA fragment for chromosomal or virulence plasmid insertion.

The terms "Gram-negative bacterial strain deficient to produce an amino acid essential for growth" and "auxotroph mutant" are used herein interchangeably and refer to Gram-negative bacterial strains which can not grow in the absence of at least one exogenously provided essential amino acid or a precursor thereof. The amino acid the strain is deficient to produce is e.g. aspartate, meso-2,6-diaminopimelic acid, aromatic amino acids or leucine-arginine [23]. Such a strain can be generated by e.g. deletion of the aspartate-beta-semialdehyde dehydrogenase gene (Aasd). Such an auxotroph mutant cannot grow in absence of exogenous meso-2,6-diaminopimelic acid [24]. The mutation, e.g. deletion of the aspartate-beta-semialdehyde dehydrogenase gene is preferred herein for a Gram-negative bacterial strain deficient to produce an amino acid essential for growth of the present invention.

The term "Gram-negative bacterial strain deficient to produce adhesion proteins binding to the eukaryotic cell surface or extracellular matrix" refers to mutant Gram-negative bacterial strains which do not express at least one adhesion protein compared to the adhesion proteins expressed by the corresponding wild type strain. Adhesion proteins may include e.g. extended polymeric adhesion molecules like pili/fimbriae or non-fimbrial adhesins. Fimbrial adhesins include type-1 pili (such as *E. coli* Fim-pili with the FimH adhesin), P-pili (such as Pap-pili with the PapG adhesin from *E. coli*), type 4 pili (as pilin protein from e.g. *P. aeruginosa*) or curli (Csg proteins with the CsgA adhesin from *S. enterica*). Non-fimbrial adhesions include trimeric autotransporter adhesins such as YadA from *Y. enterocolitica*, BpaA (*B. pseudomallei*), Hia (*H. influenzae*), BadA (*B. henselae*), NadA (*N. meningitidis*) or UspA1 (*M. catarrhalis*) as well as other autotransporter adhesins such as AIDA-1 (*E. coli*) as well as other adhesins/invasins such as InvA from *Y. enterocolitica* or Intimin (*E. coli*) or members of the Dr-family or Afa-family (*E. coli*). The terms YadA and InvA as used herein refer to proteins from *Y. enterocolitica*. The autotransporter YadA [25, 26] binds to different froms of collagen as well as fibronectin, while the invasin InvA [27-29] binds to β-integrins in the eukaryotic cell membrane. If the Gram-negative bacterial strain is a *Y. enterocolitica* strain the strain is preferably deficient in InvA and/or YadA.

As used herein, the term "family of Enterobacteriaceae" comprises a family of gram-negative, rod-shaped, facultatively anaerobic bacteria found in soil, water, plants, and animals, which frequently occur as pathogens in vertebrates. The bacteria of this family share a similar physiology and demonstrate a conservation within functional elements and genes of the respective genomes. As well as being oxidase negative, all members of this family are glucose fermenters and most are nitrate reducers.

Enterobacteriaceae bacteria of the invention may be any bacteria from that family, and specifically includes, but is not limited to, bacteria of the following genera: *Escherichia, Shigella, Edwardsiella, Salmonella, Citrobacter, Klebsiella, Enterobacter, Serratia, Proteus, Erwinia, Morganella, Providencia*, or *Yersinia*. In more specific embodiments, the bacterium is of the *Escherichia coli, Escherichia blattae, Escherichia fergusonii, Escherichia hermanii, Escherichia vuneris, Salmonella enterica, Salmonella bongori, Shigella dysenteriae, Shigella flexneri, Shigella boydii, Shigella sonnei, Enterobacter aerogenes, Enterobacter gergoviae, Enterobacter sakazakii, Enterobacter cloacae, Enterobacter agglomerans, Klebsiella pneumoniae, Klebsiella oxytoca, Serratia marcescens, Yersinia pseudotuberculosis, Yersinia pestis, Yersinia enterocolitica, Erwinia amylovora, Proteus mirabilis, Proteus vulgaris, Proteus penneri, Proteus hauseri, Providencia alcalifaciens*, or *Morganella morganii* species. Preferably the Gram-negative bacterial strain is selected from the group consisting of the genera *Yersinia, Escherichia, Salmonella, Shigella, Pseudomonas, Chlamydia, Erwinia, Pantoea, Vibrio, Burkholderia, Ralstonia, Xanthomonas,* Chromobacterium, Sodalis, *Citrobacter, Edwardsiella, Rhizobiae, Aeromonas, Photorhabdus, Bordetella* and *Desulfovibrio,* more preferably from the group consisting of the genera *Yersinia, Escherichia, Salmonella,* and *Pseudomonas,* most preferably from the group consisting of the genera *Yersinia* and *Salmonella.*

The term "*Yersinia*" as used herein includes all species of *Yersinia,* including *Yersinia enterocolitica, Yersinia pseudotuberculosis* and *Yersiniapestis.* Preferred is *Yersinia enterocolitica.*

The term "*Salmonella*" as used herein includes all species of *Salmonella,* including *Salmonella enterica* and *S. bongori.* Preferred is *Salmonella enterica.*

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. Within the promoter region will be found a transcription initiation site (conveniently defined by mapping with nuclease SI), as well as protein binding domains (consensus sequences) responsible for the binding of RNA polymerase such as the putative −35 region and the Pribnow box. The term "operably linked" when describing the relationship between two DNA regions simply means that they are functionally related to each other and they are located on the same nucleic acid fragment. A promoter is operably linked to a structural gene if it controls the transcription of the gene and it is located on the same nucleic acid fragment as the gene. Usually the promoter is functional in said Gram-negative bacterial strain, i.e. the promoter is capable of expressing the fusion protein of the present invention, i.e. the promoter is capable of expressing the fusion protein of the present invention without further genetic engineering or expression of further proteins. Furthermore, a functional promoter must not be naturally counter-regulated to the bacterial T3SS.

The term "delivery" used herein refers to the transportation of a protein from a recombinant Gram-negative bacterial strain to a eukaryotic cell, including the steps of expressing the heterologous protein in the recombinant Gram-negative bacterial strain, secreting the expressed protein(s) from such Gram-negative bacterial strain and translocating the secreted protein(s) by such Gram-negative bacterial strain into the cytosol of the eukaryotic cell. Accordingly, the terms "delivery signal" or "secretion signal" which are used interchangeably herein refer to a polypeptide sequence which can be recognized by the secretion and translocation system of the Gram-negative bacterial strain and directs the delivery of a protein from the Gram-negative bacterial strain to eukaryotic cells.

As used herein, the "secretion" of a protein refers to the transportation of a heterologous protein outward across the cell membrane of a recombinant Gram-negative bacterial strain. The "translocation" of a protein refers to the transportation of a heterologous protein from a recombinant Gram-negative bacterial strain across the plasma membrane of a eukaryotic cell into the cytosol of such eukaryotic cell.

The term "eukaryotic cells" as used herein includes e.g. the following eukaryotic cells: Hi-5, HeLa, Hek, HUVECs, 3T3, CHO, Jurkat, Sf-9, HepG2, Vera, MDCK, Mefs, THP-1, J774, RAW, Caco2, NCI60, DU145, Lncap, MCF-7, MDA-MB-438, PC3, T47D, A549, U87, SHSY5Y, Ea.Hy926, Saos-2, 4T1, D2A1, B16F10, and primary human hepatocytes. "Eukaryotic cells" as used herein, are also referred to as "target cells" or "target eukaryotic cells".

The term "T3SS effector protein" as used herein refers to proteins which are naturally injected by T3S systems into the cytosol of eukaryotic cells and to proteins which are naturally secreted by T3S systems that might e.g form the translocation pore into the eukaryotic membrane (including pore-forming tranlocators (as *Yersinia* YopB and YopD) and tip-proteins like *Yersinia* LcrV). Preferably proteins which are naturally injected by T3S systems into the cytosol of eukaryotic cells are used. These virulence factors will paralyze or reprogram the eukaryotic cell to the benefit of the pathogen. T3S effectors display a large repertoire of biochemical activities and modulate the function of crucial host regulatory molecules [5, 30] and include AvrA, AvrB, AvrBs2, AvrBS3, AvrBsT, AvrD, AvrDl, AvrPphB, AvrPphC, AvrPphEPto, AvrPpiBPto, AvrPto, AvrPtoB, AvrRpml, AvrRpt2, AvrXv3, CigR, EspF, EspG, EspH, EspZ, ExoS, ExoT, GogB, GtgA, GtgE, GALA family of proteins, HopAB2, HopAOl, Hopll, HopMl, HopNl, HopPtoD2, HopPtoE, HopPtoF, HopPtoN, HopUl, HsvB, IcsB, IpaA, IpaB, IpaC, IpaH, IpaH7.8, IpaH9.8, IpgBl, IpgB2, IpgD, LcrV, Map, OspCl, OspE2, OspF, OspG, Ospl, PipB, PipB2, PopB, PopP2, PthXol, PthXo6, PthXo7, SifA, SifB, SipA/ SspA, SipB, SipC/SspC, SipD/SspD, SlrP, SopA, SopB/ SigD, SopD, SopE, SopE2, SpiC/SsaB, SptP, SpvB, SpvC, SrfH, SrfJ, Sse, SseB, SseC, SseD, SseF, SseG, Ssel/SrfH, SseJ, SseKl, SseK2, SseK3, SseL, SspHl, SspH2, SteA, SteB, SteC, SteD, SteE, TccP2, Tir, VirA, VirPphA, VopF, XopD, YopB, YopD YopE, YopH, YopJ, YopM, YopO, YopP, YopT, YpkA.

T3SS effector genes of *Yersinia* have been cloned from e.g. *Y. enterocolitica* which are YopE, YopH, YopM, YopO, YopP/Y opJ, and YopT [31]. The respective effector genes can be cloned from *Shigellaflexneri* (e.g. OspF, IpgD, IpgBl), *Salmonella enterica* (e.g. SopE, SopB, SptP), *P. aeruginosa* (e.g ExoS, ExoT, ExoU, ExoY) or *E. coli* (e.g. Tir, Map, EspF, EspG, EspH, EspZ). The nucleic acid sequences of these genes are available to those skilled in the art, e.g., in the Genebank Database (yopH, yopO, yopE, yopP, yopM, yopT from NC_002120 GL10955536; *S flexneri* effector proteins from AF386526.1 GL18462515; *S enterica* effectors from NC_0168 10.1 GL378697983 or FQ312003.1 GL301 156631; *P. aeruginosa* effectors from AE00409 1.2 GI:1 10227054 or CP000438.1 GI:1 15583796 and *E. coli* effector proteins from NC_011601.1 GL215485161).

For the purpose of the present invention, genes are denoted by letters of lower case and italicised to be distinguished from proteins. In case the genes (denoted by letters of lower case and italicised) are following a bacterial species name (like *E. coli*), they refer to a mutation of the corresponding gene in the corresponding bacterial species. For example, YopE refers to the effector protein encoded by the yopE gene. *Y. enterocolitica* yopE represents a *Y. enterocolitica* having a mutation in the yopE gene.

As used herein, the terms "polypeptide", "peptide", "protein", "polypeptidic" and "peptidic" are used interchangeably to designate a series of amino acid residues connected to each other by peptide bonds between the alpha-amino and carboxy groups of adjacent residues. Preferred are proteins which have an amino acid sequence comprising at least 10 amino acids, more preferably at least 20 amino acids.

According to the present invention, "a heterologous protein" includes naturally occurring proteins or parts thereof and also includes artificially engineered proteins or parts thereof. As used herein, the term "heterologous protein"

refers to a protein or a part thereof other than the T3SS effector protein or N-terminal fragment thereof to which it can be fused. In particular the heterologous protein as used herein refers to a protein or a part thereof, which do not belong to the proteome, i.e. the entire natural protein complement of the specific recombinant Gram-negative bacterial strain provided and used by the invention, e.g. which do not belong to the proteome, i.e. the entire natural protein complement of a specific bacterial strain of the genera *Yersinia, Escherichia, Salmonella* or *Pseudomonas*. Usually the heterologous protein is of animal origin including human origin. Preferably the heterologous protein is a human protein. More preferably the heterologous protein is selected from the group consisting of proteins involved in apoptosis or apoptosis regulation, cell cycle regulators, ankyrin repeat proteins, cell signaling proteins, reporter proteins, transcription factors, proteases, small GTPases, GPCR related proteins, nanobody fusion constructs and nanobodies, bacterial T3SS effectors, bacterial T4SS effectors and viral proteins. Particular preferably the heterologous protein is selected from the group consisting of proteins involved in apoptosis or apoptosis regulation, cell cycle regulators, ankyrin repeat proteins, reporter proteins, small GTPases, GPCR related proteins, nanobody fusion constructs, bacterial T3SS effectors, bacterial T4SS effectors and viral proteins. Even more particular preferred are heterologous proteins selected from the group consisting of proteins involved in apoptosis or apoptosis regulation, cell cycle regulators, and ankyrin repeat proteins. Most preferred are proteins involved in apoptosis or apoptosis regulation, like animal, preferably human heterologous proteins involved in apoptosis or apoptosis regulation In some embodiments the vector of the Gram-neagtive bacterial strain of the present invention comprises two second DNA sequences encoding the identical or two different heterologous proteins fused independently from each other in frame to the 3'end of said first DNA sequence.

In some embodiments the vector of the Gram-neagtive bacterial strain of the present invention comprises three second DNA sequences encoding the identical or three different heterologous proteins fused independently from each other in frame to the 3'end of said first DNA sequence.

The heterologous protein expressed by the recombinant Gram-negative bacterial strain has usually a molecular weight of between 1 and 150lW, preferably between 1 and 120 kD, more preferably between land 100 kDa, most preferably between 15 and 100 kDa.

According to the present invention "proteins involved in apoptosis or apoptosis regulation" include, but are not limited to, Bad, Bcl2, Bak, Bmt, Bax, Puma, Noxa, Bim, Bcl-xL, Apafl, Caspase 9, Caspase 3, Caspase 6, Caspase 7, Caspase 10, DFFA, DFFB, ROCK1, APP, CAD, ICAD, CAD, EndoG, AIF, HtrA2, Smac/Diablo, Arts, ATM, ATR, Bok/Mtd, Bmf, Mcl-1(S), IAP family, LC8, PP2B, 14-3-3 proteins, PKA, PKC, PI3K, Erkl/2, p9ORSK, TRAF2, TRADD, FADD, Daxx, Caspase8, Caspase2, RIP, RAIDD, MKK7, JNK, FLIPS, FKHR, GSK3, CDKs and their inhibitors like the INK4-family (p16(Ink4a), p15(Ink4b), p18 (Ink4c), p19(Ink4d)), and the Cipl/Wafl/Kipl-2-family (p21 (Cipl/Wafl), p27(Kipl), p57(Kip2). Preferably Bad, Bmt, Bcl2, Bak, Bax, Puma, Noxa, Bim, Bcl-xL, Caspase9, Caspase3, Caspase6, Caspase7, Smac/Diablo, Bok/Mtd, Bmf, Mcl-1(S), LC8, PP2B, TRADD, Daxx, Caspase8, Caspase2, RIP, RAIDD, FKHR, CDKs and their inhibitors like the INK4-family (p16(Ink4a), p15(Ink4b), p18(Ink4c), p19(Ink4d)), most preferably BIM, Bid, truncated Bid, FADD, Caspase 3 (and subunits thereof), Bax, Bad, Akt, CDKs and their inhibitors like the INK4-family (p16(Ink4a), p15(Ink4b), p18(Ink4c), p19(Ink4d)) are used [32-34]. Additionally proteins involved in apoptosis or apoptosis regulation include DIVA, Bcl-Xs, Nbk/Bik, Hrk/Dp5, Bid and tBid, Egl-1, Bcl-Gs, Cytochrome C, Beclin, CED-13, BNIP1, BNIP3, Bch B, Bcl-W, Ced-9, Al, NR13, Bfl-1, Caspase 1, Caspase 2, Caspase 4, Caspase 5, Caspase 8. Proteins involved in apoptosis or apoptosis regulation are selected from the group consisting of pro-apoptotic proteins, anti-apoptotic proteins, inhibitors of apoptosis-prevention pathways and inhibitors of pro-survival signalling or pathways. Pro-apoptotic proteins comprise proteins selected form the group consisting of Bax, Bak, Diva, Bcl-Xs, Nbk/Bik, Hrk/Dp5, Bmf, Noxa, Puma, Bim, Bad, Bid and tBid, Bok, Apafl, Smac/Diablo, BNIP1, BNIP3, Bcl-Gs, Beclin 1, Egl-1 and CED-13, Cytochrome C, FADD, the Caspase family, and CDKs and their inhibitors like the INK4-family (p16(Ink4a), p15(Ink4b), p18(Ink4c), p19 (Ink4d)) or selected from the group consisting of Bax, Bak, Diva, Bcl-Xs, Nbk/Bik, Hrk/Dp5, Bmf, Noxa, Puma, Bim, Bad, Bid and tBid, Bok, Egl-1, Apafl, Smac/Diablo, BNIP1, BNIP3, Bcl-Gs, Beclin 1, Egl-1 and CED-13, Cytochrome C, FADD, and the Caspase family. Preferred are Bax, Bak, Diva, Bch Xs, Nbk/Bik, Hrk/Dp5, Bmf, Noxa, Puma, Bim, Bad, Bid and tBid, Bok, Egl-1, Apafl, BNIP1, BNIP3, Bcl-Gs, Beclin 1, Egl-1 and CED-13, Smac/Diablo, FADD, the Caspase family, CDKs and their inhibitors like the INK4-family (p 16(Ink4a), p 15(Ink4b), p 18(Ink4c), p19 (Ink4d)). Equally preferred are Bax, Bak, Diva, Bcl-Xs, Nbk/Bik, Hrk/Dp5, Bmf, Noxa, Puma, Bim, Bad, Bid and tBid, Bok, Apafl, BNIP1, BNIP3, Bcl-Gs, Beclin 1, Egl-1 and CED-13, Smac/Diablo, FADD, the Caspase family.

Anti-apoptotic proteins comprise proteins selected form the group consisting of Bcl-2, Bcl-Xl, Bcl-B, Bcl-W, Mcl-1, Ced-9, Al, NR13, IAP family and Bfi-1. Preferred are Bcl-2, Bcl-Xl, Bcl-B, Bcl-W, Mcl-1, Ced-9, Al, NR13 and Bfl-1.

Inhibitors of apoptosis-prevention pathways comprise proteins selected form the group consisting of Bad, Noxa and Cdc25A. Preferred are Bad and Noxa.

Inhibitors of pro-survival signalling or pathways comprise proteins selected form the group consisting of PTEN, ROCK, PP2A, PHLPP, JNK, p38. Preferred are PTEN, ROCK, PP2A and PHLPP.

In some embodiments the heterologous proteins involved in apoptosis or apoptosis regulation are selected from the group consisting of BH3-only proteins, caspases and intracellular signalling proteins of death receptor control of apoptosis.

BH3-only proteins comprise proteins selected form the group consisting of Bad, BIM, Bid and tBid, Puma, Bik/Nbk, Bod, Hrk/Dp5, BNIP1, BNIP3, Bmf, Noxa, Mcl-1, Bcl-Gs, Beclin 1, Egl-1 and CED-13. Preferred are Bad, BIM, Bid and tBid.

Caspases comprise proteins selected form the group consisting of Caspase 1, Caspase 2, Caspase 3, Caspase 4, Caspase 5, Caspase 6, Caspase 7, Caspase 8, Caspase 9, Caspase 10.

Preferred are Caspase 3, Caspase 8 and Caspase9.

Intracellular signalling proteins of death receptor control of apoptosis comprise proteins selected form the group consisting of FADD, TRADD, ASC, BAP31, GULP1/CED-6, CIDEA, MFG-E8, CIDEC, RIPK1/RIP1, CRADD, RIPK3/RIP3, Crk, SHB, CrkL, DAXX, the 14-3-3 family, FLIP, DFF40 and 45, PEA-15, SODD. Preferred are FADD and TRADD.

In some embodiments two heterologous proteins involved in apoptosis or apoptosis regulation are comprised by the vector of the Gram-negative bacterial strain of the present invention, wherein one protein is a pro-apoptotic protein and the other protein is an inhibitor of apoptosis-prevention pathways or wherein one protein is a pro-apoptotic protein and the other protein is an inhibitor of pro-survival signalling or pathways.

Pro-apoptotic proteins encompassed by the present invention have usually an alpha helical structure, preferably a hydrophobic helix surrounded by amphipathic helices and usually comprise at least one of BH1, BH2, BH3 or BH4 domains, preferably comprise at least one BH3 domain. Usually pro-apoptotic proteins encompassed by the present invention have no enzymatic activity.

The term "protease cleavage site" as used herein refers to a specific amino acid motif within an amino acid sequence e.g. within an amino acid sequence of a protein or a fusion protein, which is cleaved by a specific protease, which recognizes the amino acid motif. For review see [35]. Examples of protease cleavage sites are amino acid motifs, which are cleaved by a protease selected from the group consisting of enterokinase (light chain), enteropeptidase, prescission protease, human rhinovirus protease (HRV 3C), TEV protease, TVMV protease, FactorXa protease and thrombin.

The following amino acid motif is recognized by the respective protease:
 Asp-Asp-Asp-Asp-Lys: Enterokinase (light chain)/Enteropeptidase
 Leu-Glu-Val-Leu-Phe-Gln/Gly-Pro: PreScission Protease/human Rhinovirus protease (HRV 3C)
 Glu-Asn-Leu-Tyr-Phe-Gln-Ser and modified motifs based on the Glu-X-X-Tyr-X-Gln-Gly/Ser (where X is any amino acid) recognized by TEV protease (tobacco etch virus)
 Glu-Thr-Val-Arg-Phe-Gln-Ser: TVMV protease
 Ile-(Glu or Asp)-Gly-Arg: FactorXa protease
 Leu-Val-Pro-Arg/Gly-Ser: Thrombin.

Encompassed by the protease cleavage sites as used herein is ubiquitin. Thus in some preferred embodiments ubiquitin is used as protease cleavage site, i.e. the third DNA sequence encodes ubiquitin as protease cleavage site, which can be cleaved by a specific ubiquitin processing proteases at the N-terminal site, e.g. which can be cleaved by a specific ubiquitin processing proteases called Deubiquitinating enzymes at the N-terminal site endogeneously in the cell where the fusion protein has been delivered to. Ubiquitin is processed at its C-terminus by a group of endogenous Ubiquitin-specific C-terminal proteases (Deubiquitinating enzymes, DUBs). The cleavage of Ubiquitin by DUBs is supposed to happen at the very C-terminus of Ubiquitin (after G76).

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

The term "mutation" is used herein as a general term and includes changes of both single base pair and multiple base pairs. Such mutations may include substitutions, frame-shift mutations, deletions, insertions and truncations.

The term "labelling molecule or an acceptor site for a labelling molecule" as used herein refers to a small chemical compound binding to a specific amino acid sequence resulting in fluorescence of the bound chemical compound, preferably coumarin ligase/coumarine acceptor site (and derivates thereof), resorufin ligase/resorufin acceptor site (and derivates thereof) and the tetra-Cysteine motif (as Cys-Cys-Pro-Gly-Cys-Cys and derivates thereof) in use with FlAsH/ReAsH dye (life technologies) or a fluorescent protein as Enhanced Green Fluorescent Protein (EGFP).

The term "nuclear localization signal" as used herein refers to an amino acid sequence that marks a protein for import into the nucleus of a eukaryotic cell and includes preferably a viral nuclear localization signal such as the SV40 large T-antigen derived NLS (PPKKKRKV).

The term "multiple cloning site" as used herein refers to a short DNA sequence containing several restriction sites for cleavage by restriction endonucleases such as AclI, HindIII, SspI, MluCI, Tsp509I, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, SeaI, ClaI, BspDI, PI-SceI, NsiI, AseI, SwaI, CspCI, MfeI, BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BcII, NcoI, BseYI, FauI, SmaI, XmaI, TspMI, Nt.CviPII, LpnPI, AciI, SacII, BsrBI, MspI, HpaII, ScrFI, BssKI, StyD4I, BsaJI, BsII, BtgI, NciI, AvrII, MnlI, BbvCI, Nb.BbvCI, Nt.BbvCI, SbfI, BpuIOI, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI, EarI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I PflFI, PshAI, AhdI, DrdI, Eco53kI, SacI, BseRI, PleI, Nt.BstNBI, MlyI, HinfI, EcoRV, MboI, Sau3AI, DpnII BfuCI, DpnI, BsaBI, TfiI, BsrDI, Nb.BsrDI, BbvI, BtsI, Nb.BtsI, BstAPI, SfaNI, SphI, NmeAIII, NaeI, NgoMIV, BglI, AsiSI, BtgZI, HinP1I, HhaI, BssHII, NotI, Fnu4HI, Cac8I, MwoI, NheI, BmtI, SapI, BspQI, Nt.BspQI, BlpI, TseI, ApeKI, Bsp 12861, AlwI, Nt.AlwI, BamHI, FokI, BtsCI, HaeIII, PhoI, FseI, SfiI, NarI, KasI, SfoI, PluTI, AscI, EciI, BsmFI, ApaI, PspOMI, Sau96I, Nla1V, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI, BcoDI, ApaLI, BsgI, AccI, Hpy166II, Tsp45I, HpaI, PmeI, HindI, BsiHKAI, ApoI, NspI, BsrFI, BstYI, HaeII, CviKI-1, EcoO109I, PpuMI, I-CeuI, SnaBI, I-SceI, BspHI, BspEI, MmeI, TaqaI, NruI, Hpy 881, Hpy188III, XbaI, BclI, HpyCH4V, FspI, PI-PspI, MscI, BsrGI, MseI, PadI, PsiI, BstBI, DraI, PspXI, BsaWI, BsaAI, EaeI, preferably XhoI, XbaI, HindIII, NcoI, NotI, EcoRI, EcoRV, BamHI, NheI, SacI, SalI, BstBI. The term "multiple cloning site" as used herein further refers to a short DNA sequence used for recombination events as e.g in Gateway cloning strategy or for methods such as Gibbson assembly or topo cloning.

The term "*Yersinia* wild type strain" as used herein refers to a naturally occurring variant (as *Y. enterocolitica* E40) or a naturally occurring variant containing genetic modifications allowing the use of vectors, such as deletion mutations in restriction endonucleases or antibiotic resistance genes (as *Y. enterocolitica* MRS40, the Ampicillin sensitive derivate of *Y. enterocolitica* E40) These strains contain chromosomal DNA as well as an unmodified virulence plasmid (called pYV).

The term "comprise" is generally used in the sense of include, that is to say permitting the presence of one or more features or components.

In one embodiment the present invention provides a recombinant Gram-negative bacterial strain, wherein the Gram-negative bacterial strain is selected from the group consisting of the genera *Yersinia, Escherichia, Salmonella* and *Pseudomonas*. In one embodiment the present invention provides a recombinant Gram-negative bacterial strain, wherein the Gram-negative bacterial strain is selected from the group consisting of the genera *Yersinia* and *Salmonella*.

Preferably the Gram-negative bacterial strain is a *Yersinia* strain, more preferably a *Yersinia enterocolitica* strain. Most preferred is *Yersinia enterocolitica* E40 [13] or Ampicilline sensitive derivates thereof as *Y. enterocolitica* MRS40 as described in [36]. Also preferably the Gram-negative bacterial strain is a *Salmonella* strain, more preferably a *Salmonella enterica* strain. Most preferred is *Salmonella enterica* Serovar *Typhimurium* SL1344 as described by the Public health England culture collection (NCTC 13347).

In one embodiment of the present invention the delivery signal from a bacterial T3SS effector protein comprises a bacterial T3SS effector protein or a N-terminal fragment thereof wherein the T3SS effector protein or a N-terminal fragment thereof may comprise a chaperone binding site. A T3SS effector protein or a N-terminal fragment thereof which comprises a chaperone binding site is particular useful as delivery signal in the present invention. Preferred T3SS effector proteins or N-terminal fragments thereof are selected from the group consisting of SopE, SopE2, SptP, YopE, ExoS, SipA, SipB, SipD, SopA, SopB, SopD, IpgBl, IpgD, SipC, SifA, SseJ, Sse, SrfH, YopJ, AvrA, AvrBsT, YopT, YopH, YpkA, Tir, EspF, TccP2, IpgB2, OspF, Map, OspG, Ospl, IpaH, SspHl, VopF, ExoS, ExoT, HopAB2, XopD, AvrRpt2, HopAOl, HopPtoD2, HopUl, GALA family of proteins, AvrBs2, AvrDl, AvrBS3, YopO, YopP, YopE, YopM, YopT, EspG, EspH, EspZ, IpaA, IpaB, IpaC, VirA, IcsB, OspCl, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpml, HopPtoE, HopPtoF, HopPtoN, PopB, PopP2, AvrBs3, XopD, and AvrXv3. More preferred T3SS effector proteins or N-terminal fragments thereof are selected from the group consisting of SopE, SptP, YopE, ExoS, SopB, IpgBl, IpgD, YopJ, YopH, EspF, OspF, ExoS, YopO, YopP, YopE, YopM, YopT, whereof most preferred T3SS effector proteins or N-terminal fragments thereof are selected from the group consisting of IpgBl, SopE, SopB, SptP, OspF, IpgD, YopH, YopO, YopP, YopE, YopM, YopT, in particular YopE or an N-terminal fragment thereof.

Equally preferred T3SS effector proteins or N-terminal fragments thereof are selected from the group consisting of SopE, SopE2, SptP, SteA, SipA, SipB, SipD, SopA, SopB, SopD, IpgBl, IpgD, SipC, SifA, SifB, SseJ, Sse, SrfH, YopJ, AvrA, AvrBsT, YopH, YpkA, Tir, EspF, TccP2, IpgB2, OspF, Map, OspG, Ospl, IpaH, VopF, ExoS, ExoT, HopAB2, AvrRpt2, HopAOl, HopUl, GALA family of proteins, AvrBs2, AvrDl, YopO, YopP, YopE, YopT, EspG, EspH, EspZ, IpaA, IpaB, IpaC, VirA, IcsB, OspCl, OspE2, IpaH9.8, IpaH7.8, AvrB, AvrD, AvrPphB, AvrPphC, AvrPphEPto, AvrPpiBPto, AvrPto, AvrPtoB, VirPphA, AvrRpml, HopPtoD2, HopPtoE, HopPtoF, HopPtoN, PopB, PopP2, AvrBs3, XopD, and AvrXv3. Equally more preferred T3SS effector proteins or N-terminal fragments thereof are selected from the group consisting of SopE, SptP, SteA, SifB, SopB, IpgBl, IpgD, YopJ, YopH, EspF, OspF, ExoS, YopO, YopP, YopE, YopT, whereof equally most preferred T3SS effector proteins or N-terminal fragments thereof are selected from the group consisting of IpgBl, SopE, SopB, SptP, SteA, SifB, OspF, IpgD, YopH, YopO, YopP, YopE, and YopT, in particular SopE, SteA, or YopE or an N-terminal fragment thereof, more particular SteA or YopE or an N-terminal fragment thereof, most particular YopE or an N-terminal fragment thereof.

In some embodiments the delivery signal from the bacterial T3SS effector protein encoded by the first DNA sequence comprises the bacterial T3SS effector protein or an N-terminal fragment thereof, wherein the N-terminal fragment thereof includes at least the first 10, preferably at least the first 20, more preferably at least the first 100 amino acids of the bacterial T3SS effector protein.

In some embodiments the delivery signal from the bacterial T3SS effector protein encoded by the first DNA sequence comprises the bacterial T3SS effector protein or an N-terminal fragment thereof, wherein the bacterial T3SS effector protein or the N-terminal fragment thereof comprises a chaperone binding site.

Preferred T3SS effector proteins or a N-terminal fragment thereof, which comprise a chaperone binding site comprise the following combinations of chaperone binding site and T3SS effector protein or N-terminal fragment thereof: SycE-YopE, InvB-SopE, SicP-SptP, SycT-YopT, SycO-YopO, SycN/YscB-YopN, SycH-YopH, SpcS-ExoS, CesF-EspF, SycD-YopB, SycD-YopD. More preferred are SycE-YopE, InvB-SopE, SycT-YopT, SycO-YopO, SycN/YscB-YopN, SycH-YopH, SpcS-ExoS, CesF-EspF. Most preferred is a YopE or an N-terminal fragment thereof comprising the SycE chaperone binding site such as an N-terminal fragment of a YopE effector protein containing the N-terminal 138 amino acids of the YopE effector protein designated herein as YopEi_$i_{3_8}$ and as shown in SEQ ID NO. 2 or a SopE or an N-terminal fragment thereof comprising the InvB chaperone binding site s as uch an N-terminal fragment of a SopE effector protein containing the N-terminal 81 or 105 amino acids of the SopE effector protein designated herein as SopEi_$_{s^i}$ or SopEi_$i_{0^5}$ respectively, and as shown in SEQ ID NO. 142 or 143.

In one embodiment of the present invention the recombinant Gram-negative bacterial strain is a *Yersinia* strain and the delivery signal from the bacterial T3SS effector protein encoded by the first DNA sequence comprises a YopE effector protein or an N-terminal part, preferably the *Y. enterocolitica* YopE effector protein or an N-terminal part thereof. Preferably the SycE binding site is comprised within the N-terminal part of the YopE effector protein. In this connection an N-terminal fragment of a YopE effector protein may comprise the N-terminal 12, 16, 18, 52, 53, 80 or 138 amino acids [10, 37, 38]. Most preferred is an N-terminal fragment of a YopE effector protein containing the N-terminal 138 amino acids of the YopE effector protein e.g. as described in Forsberg and Wolf-Watz [39] designated herein as YopEi_$_{138}$ and as shown in SEQ ID NO. 2.

In one embodiment of the present invention the recombinant Gram-negative bacterial strain is a *Salmonella* strain and the delivery signal from the bacterial T3SS effector protein encoded by the first DNA sequence comprises a SopE or SteA effector protein or an N-terminal part thereof, preferably the *Salmonella enterica* SopE or SteA effector protein or an N-terminal part thereof. Preferably the chaperon binding site is comprised within the N-terminal part of the SopE effector protein. In this connection an N-terminal fragment of a SopE effector protein protein may comprise the N-terminal 81 or 105 amino acids. Most preferred is the full length SteA and an N-terminal fragment of a SopE effector protein containing the N-terminal 105 amino acids of the effector protein e.g. as described in SEQ ID NO. 142 or 143.

One skilled in the art is familiar with methods for identifying the polypeptide sequences of an effector protein that are capable of delivering a protein. For example, one such method is described by Sory et al. [13]. Briefly, polypeptide sequences from e.g. various portions of the Yop proteins can be fused in-frame to a reporter enzyme such as the calmodulin-activated adenylate cyclase domain (or Cya) of the *Bordetella pertussis* cyclolysin. Delivery of a Yop-Cya hybrid protein into the cytosol of eukaryotic cells is indicated by the appearance of cyclase activity in the infected eukaryotic cells that leads to the accumulation of cAMP. By employing such an approach, one skilled in the art can determine, if desired, the minimal sequence requirement, i.e., a contiguous amino acid sequence of the shortest length, that is capable of delivering a protein, see, e.g. [13]. Accordingly, preferred delivery signals of the present invention consists of at least the minimal sequence of amino acids of a T3SS effector protein that is capable of delivering a protein.

In one embodiment the present invention provides mutant recombinant Gram-negative bacterial strains in particular recombinant Gram-negative bacterial strains which are deficient in producing at least one T3SS functional effector protein.

According to the present invention, such a mutant Gram-negative bacterial strain e.g. such a mutant *Yersinia* strain can be generated by introducing at least one mutation into at least one effector-encoding gene. Preferably, such effector-encoding genes include YopE, YopH, YopO/YpkA, YopM, YopP/Y opJ and YopT as far as a *Yersinia* strain is concerned.

Preferably, such effector-encoding genes include AvrA, CigR, GogB, GtgA, GtgE, PipB, SifB, SipA/SspA, SipB, SipC/SspC, SipD/SspD, SlrP, SopB/SigD, SopA, SpiC/SsaB, SseB, SseC, SseD, SseF, SseG, SseI/SrfH, SopD, SopE, SopE2, SspH1, SspH2, PipB2, SifA, SopD2, SseJ, SseK1, SseK2, SseK3, SseL, SteC, SteA, SteB, SteD, SteE, SpvB, SpvC, SpvD, SrfJ, SptP, as far as a *Salmonella* strain is concerned. Most preferably, all effector-encoding genes are deleted. The skilled artisan may employ any number of standard techniques to generate mutations in these T3SS effector genes. Sambrook et al. describe in general such techniques. See Sambrook et al. [40].

In accordance with the present invention, the mutation can be generated in the promoter region of an effector-encoding gene so that the expression of such effector gene is abolished. The mutation can also be generated in the coding region of an effector-encoding gene such that the catalytic activity of the encoded effector protein is abolished. The "catalytic activity" of an effector protein refers normally to the anti-target cell function of an effector protein, i.e., toxicity. Such activity is governed by the catalytic motifs in the catalytic domain of an effector protein. The approaches for identifying the catalytic domain and/or the catalytic motifs of an effector protein are well known by those skilled in the art. See, for example, [41, 42]. Accordingly, one preferred mutation of the present invention is a deletion of the entire catalytic domain. Another preferred mutation is a frameshift mutation in an effector-encoding gene such that the catalytic domain is not present in the protein product expressed from such "frameshifted" gene. A most preferred mutation is a mutation with the deletion of the entire coding region of the effector protein. Other mutations are also contemplated by the present invention, such as small deletions or base pair substitutions, which are generated in the catalytic motifs of an effector protein leading to destruction of the catalytic activity of a given effector protein.

The mutations that are generated in the genes of the T3SS functional effector proteins may be introduced into the particular strain by a number of methods. One such method involves cloning a mutated gene into a "suicide" vector which is capable of introducing the mutated sequence into the strain via allelic exchange. An example of such a "suicide" vector is described by [43].

In this manner, mutations generated in multiple genes may be introduced successively into a Gram-negative bacterial strain giving rise to polymutant, e.g a sixtuple mutant recombinant strain. The order in which these mutated sequences are introduced is not important. Under some circumstances, it may be desired to mutate only some but not all of the effector genes. Accordingly, the present invention further contemplates polymutant *Yersinia* other than sixtuple-mutant *Yersinia*, e.g., double-mutant, triple-mutant, quadruple-mutant and quintuple-mutant strains. For the purpose of delivering proteins, the secretion and translocation system of the instant mutant strain needs to be intact.

A preferred recombinant Gram-negative bacterial strain of the present invention is a sixtuple-mutant *Yersinia* strain in which all the effector-encoding genes are mutated such that the resulting *Yersinia* no longer produce any functional effector proteins. Such sixtuple-mutant *Yersinia* strain is designated as AyopH,0,P,E,M,T for *Y. enterocolitica*. As an example such a sixtuple-mutant can be produced from the *Y. enterocolitica* MRS40 strain giving rise to *Y. enterocolitica* MRS40 AyopH,0,P,E,M,T, which is preferred.

A further aspect of the present invention is directed to a vector for use in combination with the recombinant Gram-negative bacterial strains to deliver a desired protein into eukaryotic cells, wherein the vector comprises in the 5' to 3' direction:

- a promoter;
- a first DNA sequence encoding a delivery signal from a bacterial T3SS effector protein, operably linked to said promoter;
- a second DNA sequence encoding a heterologous protein fused in frame to the 3'end of said first DNA sequence; and alternatively
- a third DNA sequence encoding a protease cleavage site, wherein the third DNA sequence is located between the 3'end of said first DNA sequence and the 5'end of said second DNA sequence.

Promoter, heterologous protein and protease cleavage site as described supra can be used for the vector of the Gram-negative bacterial strain.

Vectors which can be used according to the invention depend on the Gram-negative bacterial strains used as known to the skilled person. Vectors which can be used according to the invention include expression vectors, vectors for chromosomal or virulence plasmid insertion and DNA fragments for chromosomal or virulence plasmid insertion. Expression vectors which are useful in e.g. *Yersinia, Escherichia, Salmonella* or *Pseudomonas* strain are e.g pUC, pBad, pACYC, pUCP20 and pET plasmids. Vectors for chromosomal or virulence plasmid insertion which are useful in e.g. *Yersinia, Escherichia, Salmonella* or *Pseudomonas* strain are e.g pKNGlO1. DNA fragments for chromosomal or virulence plasmid insertion refer to methods used in e.g. *Yersinia, Escherichia, Salmonella* or *Pseudomonas* strain as e.g. lambda-red genetic engineering. Vectors for chromosomal or virulence plasmid insertion or DNA fragments for chromosomal or virulence plasmid insertion may insert the first, second and/or third DNA sequence of the present invention so that the first, second and/or third DNA sequence is operably linked to an endogenous promoter of the recombinant Gram-negative bacterial strain. Thus if a vector for chromosomal or virulence plasmid insertion or a DNA fragment for chromosomal or virulence plasmid insertion is used, an endogenous promoter can be encoded on the endogenous bacterial DNA (chromosomal or plasmid DNA) and only the first and second DNA sequence will be provided by the engineered vector for chromosomal or virulence plasmid insertion or DNA fragment for chromosomal or virulence plasmid insertion. Thus a promoter is not necessarily needed to be comprised by the vector used for transformation of the recombinant Gram-negative bacterial strains i.e. the recombinant Gram-negative bacterial strains of the present invention may be transformed with a vector which dose not comprise a promoter. Preferably an expression vector is used. The vector of the present invention is normally used for delivery of the heterologous proteins by the bacterial T3SS into eukaryotic cells in vitro and in vivo.

A preferred expression vector for *Yersinia* is selected from the group consisting of pBad_Si_1 and pBad_Si_2. pBad_Si2 was constructed by cloning of the SycE-YopEi_$i_{3_8}$ fragment containing endogenous promoters for YopE and SycE from purified pYV40 into Kpnl/Hindlll site of pBad-MycHisA (Invitrogen). Additional modifications include removal of the Ncol/BgUI fragment of pBad-MycHisA by digest, Klenow fragment treatment and religation. Further at the 3' end of YopEi_i$_{3_8}$ the following cleavage sites were added: Xbal-Xhol-BstBI-(Hindlll). pBad_Sil is equal to pBad_Si2 but encodes EGFP amplified from pEGFP-Cl (Clontech) in the Ncol/BgUI site under the Arabinose inducible promoter.

A preferred expression vector for *Salmonella* is selected from the group consisting of pSi_266, pSi_267, pSi_268 and pSi_269. Plasmids pSi_266, pSi_267, pSi_268 and pSi_269 containing the corresponding endogenous promoter and the SteAi_$_2$ofragment (pSi_266), the full length SteA sequence (pSi_267), the SopEi_$_8{}^i$ fragment (pSi_268) or the SopEi_i$_0{}^5$ fragment (pSi_269) were amplified from *S. enterica* SL1344 genomic DNA and cloned into Ncol/Kpnl site of pBad-MycHisA (Invitrogen).

The vectors of the instant invention may include other sequence elements such as a 3' termination sequence (including a stop codon and a poly A sequence), or a gene conferring a drug resistance which allows the selection of transformants having received the instant vector. The vectors of the present invention may be transformed by a number of known methods into the recombinant Gram-negative bacterial strains. For the purpose of the present invention, the methods of transformation for introducing a vector include, but are not limited to, electroporation, calcium phosphate mediated transformation, conjugation, or combinations thereof. For example, a vector can be transformed into a first bacteria strain by a standard electroporation procedure. Subsequently, such a vector can be transferred from the first bacteria strain into the desired strain by conjugation, a process also called "mobilization". Transformant (i.e., Gram-negative bacterial strains having taken up the vector) may be selected, e.g., with antibiotics. These techniques are well known in the art. See, for example, [13].

In accordance with the present invention, the promoter of the expression vector of the recombinant Gram-negative bacterial strain of the invention can be a native promoter of a T3SS effector protein of the respective strain or a compatible bacterial strain or a promoter used in expression vectors which are useful in e.g. *Yersinia, Escherichia, Salmonella* or *Pseudomonas* strain e.g pUC and pBad. Such promoters are the T7 promoter, Plac promoter or Ara-bad promoter.

If the recombinant Gram-negative bacterial strain is a *Yersinia* strain the promoter can be from a *Yersinia* virulon gene. A "*Yersinia* virulon gene" refers to genes on the *Yersinia* pYV plasmid, the expression of which is controlled both by temperature and by contact with a target cell. Such genes include genes coding for elements of the secretion machinery (the Ysc genes), genes coding for translocators (YopB, YopD, and LcrV), genes coding for the control elements (YopN, TyeA and LcrG), genes coding for T3SS effector chaperones (SycD, SycE, SycH, SycN, SycO and SycT), and genes coding for effectors (YopE, YopH, YopO/YpkA, YopM, YopT and YopP/Y opJ) as well as other pYV encoded proteins as VirF and YadA. In a preferred embodiment of the present invention, the promoter is the native promoter of a T3SS functional effector encoding gene. If the recombinant Gram-negative bacterial strain is a *Yersinia* strain the promoter is selected from any one of YopE, YopH, YopO/Y pkA, YopM and YopP/Y opJ. More preferably, the promoter is from YopE or SycE.

If the recombinant Gram-negative bacterial strain is a *Salmonella* strain the promoter can be from Spil or Spill pathogenicity island or from an effector protein elsewhere encoded. Such genes include genes coding for elements of the secretion machinery, genes coding for translocators, genes coding for the control elements, genes coding for T3SS effector chaperones, and genes coding for effectors as well as other proteins encoded by SPI-1 or SPI-2. In a preferred embodiment of the present invention, the promoter is the native promoter of a T3SS functional effector encoding gene. If the recombinant Gram-negative bacterial strain is a *Salmonella* strain the promoter is selected from any one of the effector proteins. More preferably, the promoter is from SopE, InvB or SteA.

In a preferred embodiment the expression vector comprises a DNA sequence encoding a protease cleavage site. Generation of a functional and generally applicable cleavage site allows cleaving off the delivery signal after translocation. As the delivery signal can interfere with correct localization and/or function of the translocated protein within the target cells the introduction of a protease cleavage site between the delivery signal and the protein of interest provides for the first time delivery of almost native proteins into eukaryotic cells. Preferably the protease cleavage site is an amino acid motif which is cleaved by a protease or the catalytic domains thereof selected from the group consisting of enterokinase (light chain), enteropeptidase, prescission protease, human rhinovirus protease 3C, TEV protease, TVMV protease, FactorXa protease and thrombin, more preferably an amino acid motif which is cleaved by TEV protease. Equally preferable the protease cleavage site is an amino acid motif which is cleaved by a protease or the catalytic domains thereof selected from the group consisting of enterokinase (light chain), enteropeptidase, prescission protease, human rhino virus protease 3C, TEV protease, TVMV protease, FactorXa protease, ubiquitin processing protease, called Deubiquitinating enzymes, and thrombin. Most preferred is an amino acid motif which is cleaved by TEV protease or by an ubiquitin processing protease. Thus in a further embodiment of the present invention, the heterologous protein is cleaved from the delivery signal from a bacterial T3SS effector protein by a protease. Preferred methods of cleavage are methods wherein:

a) the protease is translocated into the eukaryotic cell by a recombinant Gram-negative bacterial strain as described herein which expresses a fusion protein which comprises the delivery signal from the bacterial T3SS effector protein and the protease as heterologous protein; or
b) the protease is expressed constitutively or transiently in the eukaryotic cell.

Usually the recombinant Gram-negative bacterial strain used to deliver a desired protein into a eukaryotic cell and the recombinant Gram-negative bacterial strain translocating the protease into the eukaryotic cell are different.

In one embodiment of the present invention the vector comprises a further DNA sequence encoding a labelling molecule or an acceptor site for a labelling molecule. The further DNA sequence encoding a labelling molecule or an acceptor site for a labelling molecule is usually fused to the 5' end or to the 3' end of the second DNA sequence. A preferred labelling molecule or an acceptor site for a labelling molecule is selected from the group consisting of enhanced green fluorescent protein (EGFP), coumarin, coumarin ligase acceptor site, resorufin, resurofm ligase acceptor site, the tetra-Cysteine motif in use with FlAsH/ReAsH dye (life technologies). Most preferred is resorufin and a resurofm ligase acceptor site or EGFP. The use of a labelling molecule or an acceptor site for a labelling molecule will lead to the attachment of a labelling molecule to the heterologous protein of interest, which will then be delivered as such into the eukaryotic cell and enables tracking of the protein by e.g. live cell microscopy.

In one embodiment of the present invention the vector comprises a further DNA sequence encoding a peptide tag. The further DNA sequence encoding a peptide tag is usually fused to the 5' end or to the 3' end of the second DNA sequence. A preferred peptide tag is selected from the group consisting of Myc-tag, His-tag, Flag-tag, HA tag, Strep tag or V5 tag or a combination of two or more tags out of these groups. Most preferred is Myc-tag, Flag-tag, His-tag and combined Myc- and His-tags. The use of a peptide tag will lead to traceability of the tagged protein e.g by immunofluorescence or Western blotting using anti-tag antibodies. Further, the use of a peptide tag allows affinity purification of the desired protein either after secretion into the culture supernatant or after translocation into eukaryotic cells, in both cases using a purification method suiting the corresponding tag (e.g. metal-chelate affinity purification in use with a His-tag or anti-Flag antibody based purification in use with the Flag-tag).

In one embodiment of the present invention the vector comprises a further DNA sequence encoding a nuclear localization signal (NLS). The further DNA sequence encoding a nuclear localization signal (NLS) is usually fused to the 5'end or to the 3'end of the second DNA sequence wherein said further DNA sequence encodes a nuclear localization signal (NLS). A preferred NLS is selected from the group consisting of SV40 large T-antigen NLS and derivates thereof [44] as well as other viral NLS. Most preferred is SV40 large T-antigen NLS and derivates thereof.

In one embodiment of the present invention the vector comprises a multiple cloning site. The multiple cloning site is usually located at the 3'end of the first DNA sequence and/or at the 5'end or 3'end of the second DNA sequence. One or more than one multiple cloning sites can be comprised by the vector. A preferred multiple cloning site is selected from the group of restriction enzymes consisting of Xhol, Xbal, Hindlll, Ncol, Notl, EcoRI, EcoRV, BamHI, Nhel, Sad, Sail, BstBI. Most preferred is Xbal, Xhol, BstBI and Hindlll.

The protein expressed from the fused first and second and optional third DNA sequences of the vector is also termed as a "fusion protein" or a "hybrid protein", i.e., a fused protein or hybrid of delivery signal and a heterologous protein. The fusion protein can also comprise e.g. a delivery signal and two or more different heterologous proteins.

The present invention contemplates a method for delivering heterologous proteins as hereinabove described into eukaryotic cells in cell culture as well as in-vivo.

Thus in one embodiment the method for delivering heterologous proteins comprises i) culturing the Gram-negative bacterial strain as described herein;
ii) contacting a eukaryotic cell with the Gram-negative bacterial strain of i) wherein a fusion protein which comprises a delivery signal from a bacterial T3SS effector protein and the heterologous protein is expressed by the Gram-negative bacterial strain and is translocated into the eukaryotic cell; and optionally
iii) cleaving the fusion protein so that the heterologous protein is cleaved from the delivery signal from the bacterial T3SS effector protein.

In some embodiments at least two fusion proteins which comprises each a delivery signal from a bacterial T3SS effector protein and a heterologous protein are expressed by the Gram-negative bacterial strain and are translocated into the eukaryotic cell by the methods of the present inventions.

The recombinant Gram-negative bacterial strain can be cultured so that a fusion protein is expressed which comprises the delivery signal from the bacterial T3SS effector protein and the heterologous protein according to methods known in the art (e.g. FDA, Bacteriological Analytical Manual (BAM), chapter 8: *Yersinia enterocolitica*). Preferably the recombinant Gram-negative bacterial strain can be cultured in Brain Heart infusion broth e.g. at 28° C. For induction of expression of T3SS and e.g. YopE/SycE promoter dependent genes, bacteria can be grown at 37° C.

In a preferred embodiment, the eukaryotic cell is contacted with two Gram-negative bacterial strains of i), wherein the first Gram-negative bacterial strain expresses a first fusion protein which comprises the delivery signal from the bacterial T3SS effector protein and a first heterologous protein and the second Gram-negative bacterial strain expresses a second fusion protein which comprises the delivery signal from the bacterial T3SS effector protein and a second heterologous protein, so that the first and the second fusion protein are translocated into the eukaryotic cell. This embodiment provided for co-infection of e.g eukaryotic cells with two bacterial strains as a valid method to deliver e.g. two different hybrid proteins into single cells to address their functional interaction.

The present invention contemplates a wide range of eukaryotic cells that may be targeted by the instant recombinant Gram-negative bacterial strain e.g. Hi-5 (BTI-TN-5B1-4; life technologies B855-02), HeLa cells, e.g. HeLa Cc12 (as ATCC No. CCL-2), fibroblast cells, e.g. 3T3 fibroblast cells (as ATCC No. CCL-92) or Mef (as ATCC No. SCRC-1040), Hek (as ATCC No. CRL-1573), HUVECs (as ATCC No. PCS-100-0 13), CHO (as ATCC No. CCL-61), Jurkat (as ATCC No. TIB-152), Sf-9 (as ATCC No. CRL-171 1), HepG2 (as ATCC No. HB-8065), Vera (as ATCC No. CCL-81), MDCK (as ATCC No. CCL-34), THP-1 (as ATCC No. TIB-202), J774 (as ATCC No. TIB-67), RAW (as ATCC No. TIB-71), Caco2 (as ATCC No. HTB-37), NCI cell lines (as ATCC No. HTB-182), DU145 (as ATCC No. HTB-81), Lncap (as ATCC No. CRL-1740), MCF-7 (as ATCC No. HTB-22), MDA-MB cell lines (as ATCC No. HTB-128), PC3 (as ATCC No. CRL-1435), T47D (as ATCC No. CRL-2865), A549 (as ATCC No. CCL-185), U87 (as ATCC No. HTB-14), SHSY5Y (as ATCC No. CRL-2266s), Ea.Hy926 (as ATCC No. CRL-2922), Saos-2 (as ATCC No. HTBH-85), 4T1 (as ATCC No. CRL-2539), B 16F10 (as ATCC No. CRL-6475), or primary human hepatocytes (as life technologies HMCPIS), preferably HeLa, Hek, HUVECs, 3T3, CHO, Jurkat, Sf-9, HepG2 Vera, THP-1, Caco2, Mef, A549, 4T1, B16F10 and primary human hepatocytes and most preferably HeLa, Hek, HUVECs, 3T3, CHO, Jurkat, THP-1, A549 and Mef. By "target", is meant the extracellular adhesion of the recombinant Gram-negative bacterial strain to a eukaryotic cell.

In accordance with the present invention, the delivery of a protein can be achieved by contacting a eukaryotic cell with a recombinant Gram-negative bacterial strain under appropriate conditions. Various references and techniques are conventionally available for those skilled in the art regarding the conditions for inducing the expression and translocation of virulon genes, including the desired temperature, $Ca^{++}$ concentration, addition of inducers as Congo Red, manners in which the recombinant Gram-negative bacterial strain and target cells are mixed, and the like. See, for example, [45]. The conditions may vary depending on the type of eukaryotic cells to be targeted and the recombinant bacterial strain to be used. Such variations can be addressed by those skilled in the art using conventional techniques.

Those skilled in the art can also use a number of assays to determine whether the delivery of a fusion protein is successful. For example, the fusion protein may be detected via immunofluorescence using antibodies recognizing a fused tag (like Myc-tag). The determination can also be based on the enzymatic activity of the protein being delivered, e.g., the assay described by [13].

In one embodiment the present invention provides a method of purifying a heterologous protein comprising culturing the Gram-negative bacterial strain as described herein so that a fusion protein which comprises a delivery signal from a bacterial T3SS effector protein and the heterologous protein is expressed and secreted into the supernatant of the culture. The fusion protein expressed may further comprise a protease cleavage site between the delivery signal from the bacterial T3SS effector protein and the heterologous protein and/or may further comprise a peptide tag.

Thus in a particular embodiment the method of purifying a heterologous protein comprises
  i) culturing the Gram-negative bacterial strain as described herein so that a fusion protein which comprises a delivery signal from a bacterial T3SS effector protein, the heterologous protein and a protease cleavage site between the delivery signal from the bacterial T3SS effector protein and the heterologous protein is expressed and secreted into the supernatant of the culture;
  ii) adding a protease to the supernatant of the culture wherein the protease cleaves the fusion protein so that the heterologous protein is cleaved from the delivery signal from the bacterial T3SS effector protein;
  iii) optionally isolating the heterologous protein from the supernatant of the culture Thus in another particular embodiment the method of purifying a heterologous protein comprises
  i) culturing the Gram-negative bacterial strain as described herein so that a fusion protein which comprises a delivery signal from a bacterial T3SS effector protein, the heterologous protein and a peptide tag is expressed and secreted into the supernatant of the culture;
  ii) targeting the peptide tag e.g. by affinity column purification of the supernatant.

Thus in another particular embodiment the method of purifying a heterologous protein comprises
  i) culturing the Gram-negative bacterial strain as described herein so that a fusion protein which comprises a delivery signal from a bacterial T3SS effector protein, the heterologous protein, a protease cleavage site between the delivery signal from the bacterial T3SS effector protein and the heterologous protein and a peptide tag is expressed and secreted into the supernatant of the culture;
  ii) adding a protease to the supernatant of the culture wherein the protease cleaves the fusion protein so that the heterologous protein is cleaved from the delivery signal from the bacterial T3SS effector protein;
  ii) targeting the peptide tag e.g. by affinity column purification of the supernatant.

In the above described particular embodiments the protease can be added to the supernatant of the culture in the form of e.g a purified protease protein or by adding a bacterial strain expressing and secreting a protease to the supernatant of the culture. Further steps may include removal of the protease e.g. via affinity column purification.

In one embodiment the present invention provides the recombinant Gram-negative bacterial strain as described herein for use in medicine.

In one embodiment the present invention provides the recombinant Gram-negative bacterial strain as described herein for use in the delivery of a heterologous protein as a medicament or as a vaccine to a subject. The heterologous protein can be delivered to a subject as a vaccine by contacting the Gram-negative bacterial strain with eukaryotic cells, e.g. with a living animal in vivo so that the heterologous protein is translocated into the living animal which then produces antibodies against the heterologous protein. The antibodies produced can be directly used or be isolated and purified and used in diagnosis, in research use as well as in therapy. The B-cells producing the antibodies or the therein contained DNA sequence can be used for further production of specific antibodies for use in diagnosis, in research use as well as in therapy In one embodiment the present invention provides a method for delivering a heterologous protein, wherein the heterologous protein is delivered in vitro into a eukaryotic cell.

In a further embodiment the present invention provides a method for delivering a heterologous protein, wherein the eukaryotic cell is a living animal wherein the living animal is contacted with the Gram-negative bacterial strain in vivo so that a fusion protein is translocated into the living animal. The preferred animal is a mammal, more preferably a human being.

In a further embodiment the present invention provides the use of the recombinant Gram-negative bacterial strain as described supre for High Throughput Screenings of inhibitors for a cellular pathway or event triggered by the translocated heterologous protein(s).

In a further embodiment the present invention provides a library of Gram-negative bacterial strains, wherein the heterologous protein encoded by the second DNA sequence of the expression vector of the Gram-negative bacterial strains is a human or murine protein, preferably a human protein and, wherein each human or murein protein expressed by a Gram-negative bacterial strain is different in amino acid sequence. A possible library could e.g.

contain the 560 protein containing Addgene human kinase Orf collection (Addgene No. 1000000014). As cloning vector for expression the above described expression vectors can be used.

In a further embodiment the present invention provides a kit comprising a vector as described herein and a bacterial strain expressing and secreting a protease capable of cleaving the protease cleavage site comprised by the vector. A particular useful vector is a vector for use in combination with the bacterial strain to deliver a desired protein into eukaryotic cells as described above, wherein the vector comprises in the 5' to 3' direction:
- a promoter;
- a first DNA sequence encoding a delivery signal from a bacterial T3SS effector protein, operably linked to said promoter;
- a second DNA sequence encoding a heterologous protein fused in frame to the 3'end of said first DNA sequence; and alternatively
- a third DNA sequence encoding a protease cleavage site, wherein the third DNA sequence is located between the 3'end of said first DNA sequence and the 5'end of said second DNA sequence.

EXAMPLES

Example 1

A) Materials and Methods

Bacterial strains and growth conditions. The strains used in this study are listed in FIGS. 15A to M. *E. coli* Top 10, used for plasmid purification and cloning, and *E. coli* SmlO λ pir, used for conjugation, as well as *E. coli* BW19610 [46], used to propagate pKNGlOl, were routinely grown on LB agar plates and in LB broth at 37° C. AmpiciUin was used at a concentration of 200 μg/ml {*Yersinia*) or 100 μg/ml (*E. coli*) to select for expression vectors. Streptomycin was used at a concentration of 100 μg/ml to select for suicide vectors. *Y. enterocolitica* MRS40 [36] a non AmpiciUin resistant E40-derivate [13] and strains derived thereof were routinely grown on Brain Heart Infusion (BHI; Difco) at RT. To all *Y. enterocolitica* strains Nalidixic acid was added (35 μg/ml) and all *Y. enterocolitica* asd strains were additionally supplemented with 100 μg/ml meso-2,6-Diaminopimelic acid (mDAP, Sigma Aldrich). *S. enterica* SL1344 were routinely grown on LB agar plates and in LB broth at 37° C. AmpiciUin was used at a concentration of 100 μg/ml to select for expression vectors in *S. enterica*.

Genetic Manipulations of *Y. enterocolitica*.

Genetic manipulations of *Y. enterocolitica* has been described [47, 48]. Briefly, mutators for modification or deletion of genes in the pYV plasmids or on the chromosome were constructed by 2-fragment overlapping PCR using purified pYV40 plasmid or genomic DNA as template, leading to 200-250 bp of flanking sequences on both sides of the deleted or modified part of the respective gene. Resulting fragments were cloned in pKNGl 01 [43] in *E. coli* BW19610 [46]. Sequence verified plasmids were transformed into *E. coli* SmlO λ pir, from where plasmids were mobilized into the corresponding *Y. enterocolitica* strain. Mutants carrying the integrated vector were propagated for several generations without selection pressure. Then sucrose was used to select for clones that have lost the vector. Finally mutants were identified by colony PCR.

Construction of Plasmids.

Plasmid pBad_Si2 or pBad_Sil (FIG. 10) were used for cloning of fusion proteins with the N-terminal 138 amino acids of YopE (SEQ ID No. 2). pBad_Si2 was constructed by cloning of the SycE-YopEi_$i_{3_8}$ fragment containing endogenous promoters for YopE and SycE from purified pYV40 into Kpnl/HindIII site of pBad-MycHisA (Invitrogen).

Additional modifications include removal of the NcoI/BgUI fragment of pBad-MycHisA by digestion, Klenow fragment treatment and religation. A bidirectional transcriptional terminator (BBa_B1006; iGEM foundation) was cloned into Kpnl cut and Klenow treated (pBad_Si2) or Bglll cut site (pBad_Sil). Further at the 3' end of YopEi_$i_{3_8}$ the following cleavage sites were added: XbaI-XhoI-BstBI-(HindIII) (FIG. 10 B). pBad_Sil is equal to pBad_Si2 but encodes EGFP amplified from pEGFP-Cl (Clontech) in the NcoI/BgUI site under the Arabinose inducible promoter. Plasmids pSi_266, pSi_267, pSi_268 and pSi_269 containing the corresponding endogenous promoter and the SteAL_2ofragment (pSi_266), the full length SteA sequence (pSi_267), the SopEi_$_{s^j}$ fragment (pSi_268) or the SopEi_$i_0^5$ fragment (pSi_269) were amplified from *S. enterica* SL1344 genomic DNA and cloned into NcoI/Kpnl site of pBad-MycHisA (Invitrogen).

Full length genes or fragments thereof were amplified with the specific primers listed in Table I below and cloned as fusions to YopEi_$i_3$, into plasmid pBad_Si2 or in case of z-BIM (SEQ ID No. 21) into pBad_Sil (see Table II below). For fusion to SteA or SopE, synthetic DNA constructs were cleaved by KpnI/HindII and cloned into pSi_266, pSi_267, pSi_268 or pSi_269 respectively. In case of genes of bacterial species, purified genomic DNA was used as template (*S. flexneri* M90T, *Salmonella enterica* subsp. *enterica* serovar *Typhimurium* SL1344, *Bartonella henselae* ATCC 49882). For human genes a universal cDNA library (Clontech) was used if not otherwise stated (FIGS. 15A to M), zebrafish genes were amplified from a cDNA library (a kind gift of M. Affolter). Ligated plasmids were cloned in *E. coli* Top 10. Sequenced plasmids were electroporated into the desired *Y. enterocolitica* or *S. enterica* strain using settings as for standard *E. coli* electroporation.

TABLE I

| (Primer Nr. Si_:Sequence) |
|---|
| 285: CATACCATGGGAGTGAGCAAGGGCGAG |
| 286: GGAAGATCTttACTTGTACAGCTCGTCCAT |
| 287: CGGGGTACCTCAACTAAATGACCGTGGTG |
| 288: GTTAAAGCTTttcgaatctagactcgagCGTGGCGAACTGGTC |
| 292: CAGTctcgagCAAATTCTAAACAAAATACTTCCAC |
| 293: cagtTTCGAATTAATTTGTATTGCTTTGACGG |
| 296: CAGTctcgagACTAACATAACACTATCCACCCAG |
| 297: GTTAAAGCTTTCAGGAGGCATTCTGAAG |
| 299: CAGTctcgagCAGGCCATCAAGTGTGTG |
| 300: cagtTTCGAATCATTTTCTCTTCCTCTTCTTCA |
| 301: CAGTctcgagGCTGCCATCCGGAA |
| 302: cagtTTCGAATCACAAGACAAGGCACCC |
| 306: GTTAAAGCTTGGAGGCATTCTGAAGatacttatt |
| 307: CAGTctcgagCAAATACAGAGCTTCTATCACTCAG |
| 308: GTTAAAGCTTTCAAGATGTGATTAATGAAGAAATG |
| 317: cagtTTCGAACCCATAAAAAAGCCCTGTC |
| 318: GTTAAAGCTTCTACTCTATCATCAAACGATAAATGg |
| 324: CAGTctcgagTTCACTCAAGAAACGCAAA |
| 339: cagtTTCGAATTTTCTCTTCCTCTTCTTCAcg |

TABLE I-continued (Primer Nr. Si_:Sequence)

341: cgtaTCTAGAAAAATGATGAAAATGGAGACTG

342: GTTAAAGCTTttaGCTGGAGACGGTGAC

346: CAGTctcgagTTCCAGATCCCAGAGTTTG

347: GTTAAAGCTTTCACTGGGAGGGGG

351: CAGTctcgagctcgagTTATCTACTCATAGAAACTACTTTTGCAG

352: cgcGGATCCtcagtgtctctgcggcatta

353: CATTTATTCCTCCTAGTTAGTCAcagcaactgctgctcctttc

354: gaaaggagcagcagttgctgTGACTAACTAGGAGGAATAAATG

355: cgattcacggattgctttctCATTATTCCCTCCAGGTACTA

356: TAGTACCTGGAGGGAATAATGagaaagcaatccgtgaatcg

357: cgtaTCTAGAcggctttaagtgcgacattc

364: cgtaTCTAGACTAAAGTATGAGGAGAGAAAATTGAA

365: GTTAAAGCTTTCAGCTTGCCGTCGT

367: CGTAtctagaGACCCGTTCCTGGTGC

369: cgtaTCTAGAccccccaagaagaagc

373: GTTAAAGCTTGCTGGAGACGGTGACC

386: CGTAtctagaTCAGGACGCTTCGGAGGTAG

387: CGTAtctagaATGGACTGTGAGGTCAACAA

389: CGTAtctagaGGCAACCGCAGCA

391: GTTAAAGCTTTCAGTCCATCCCATTTCTg

403: CGTAtctagatctggaatatccctggaca

406: GTTAAAGCTTgtctgtctcaatgccacagt

410: CAGTctcgagATGTCCGGGGTGGTg

413: cagtTTCGAATCACTGCAGCATGATGTC

417: CAGTctcgagAGTGGTGTTGATGATGACATG

420: cagtTTCGAATTAGTGATAAAAATAGAGTTCTTTTGTGAG

423: CAGTctcgagATGCACATAACTAATTTGGGATT

424: cagtTTCGAATTATACAAATGACGAATACCCTTT

425: GTTAAAGCTTttacaccttgcgcttcttcttgggcggGCTGGAGACGGTGAC

428: CGTAtctagaATGGACTTCAACAGGAACTTT

429: CGTAtctagaGGACATAGTCCACCAGCG

430: GTTAAAGCTTTCAGTTGGATCCGAAAAAC

433: CGTAtctagaGAATTAAAAAAAACACTCATCCCA

434: CGTAtctagaCCAAAGGCAAAAGCAAAAA

435: GTTAAAGCTTTTAGCTAGCCATGGCAAGC

436: CGTAtctagaATGCCCCGCCCC

437: GTTAAAGCTTCTACCCACCGTACTCGTCAAT

438: CGTAtctagaATGTCTGACACGTCCAGAGAG

439: GTTAAAGCTTTCATCTTCTTCGCAGGAAAAG

445: cgcGGATCCttatgggttctcacagcaaaa

446: CATTTATTCCTCCTAGTTAGTCAaggcaacagccaatcaagag

447: ctcttgattggctgttgcctTGACTAACTAGGAGGAATAAATG

448: ttgattgcagtgacatggtgCATTATTCCCTCCAGGTACTA

449: TAGTACCTGGAGGGAATAATGcaccatgtcactgcaatcaa

450: cgtaTCTAGAtagccgcagatgttggtatg

451: CGTAtctagaGATCAAGTCCAACTGGTGG

463: CAGTctcgaggaaagcttgtttaagggggc

464: cagtTTCGAAttagcgacggcgacg

476: GTTAAAGCTTttACTTGTACAGCTCGTCCAT

477: CGTAtctagaGTGAGCAAGGGCGAG

478: CAGTctcgagATGGAAGATTATACCAAAATAGAGAAA

479: GTTAAAGCTTCTACATCTTCTTAATCTGATTGTCCa

482: CGTAtctagaATGGCGCTGCAGCt

483: GTTAAAGCTTTCAGTCATTGACAGGAATTTTg

486: CGTAtctagaATGGAGCCGGCGGCG

487: GTTAAAGCTTTCAATCGGGGATGTCTg

492: CGTAtctagaATGCGCGAGGAGAACAAGGG

493: GTTAAAGCTTTCAGTCCCTGTGGCTGTGc

494: CGTAtctagaATGGCCGAGCCTTG

495: GTTAAAGCTTttaTTGAAGATTTGTGGCTCC

504: CGTAtctagaGAAAATCTGTATTTTCAAAGTGAAAATCTGTATTTCAAAGTATGCCCCGCCCC

505: GTTAAAGCTTCCCACCGTACTCGTCAATtc

508: CGTAtctagaGAAAATCTGTATTTTCAAAGTGAAAATCTGTATTTTCAAAGTATGGCCGAGCCTTG

509: GTTAAAGCTTTTGAAGATTTGTGGCTCCc

511: CGTAtctagaGAAAATCTGTATTTTCAAAGTGAAAATCTGTATTTTCAAAGTGTGAGCAAGGGCGAG

512: CGTAtctagaGAAAATCTGTATTTTCAAAGTGAAAATCTGTATTTTCAAAGTCCGCCGAAAAAAAACGTAAAGTTGTGAGCAAGGGCGAG 513: GTTAAAGCTTttAAACTTTACGTTTTTTTTCGGCGGCTTGTACAGCTCGTCCAT 515: CGTAtctagaGAAAATCTGTATTTTCAAAGTGAAAATCTGTATTTTCAAAGTGATTATAAAGATGATGATGATAAAATGGCCGAGCCTTG

558: CGTATCTAGAATGACCAGTTTTGAAGATGC

559: GTTAAAGCTTTCATGACTCATTTTCATCCAT

561: CGTATCTAGAATGAGTCTCTTAAACTGTGAGAACAG

562: GTTAAAGCTTCTACACCCCCGCATCA

580: catgccatggATTTATGGTCATAGATATGACCTC

585: CAGTctcgagATGCAGATCTTCGTCAAGAC

586: GTTAAAGCTTgctagatcgaaACCACCACGTAGACGTAAGAC

TABLE I-continued (Primer Nr. Si_:Sequence)

588: cagtTTCGAAGATTATAAAGATGATGATGATAAAATGGCCGAGCCTTG

612: CGGGGTACCatgaggtagatatttcctgataaag

613: CGGGGTACCataattgtccaaatagttatggtagc

614: catgccatggCGGCAAGGCTCCTC

615: cggggtaccTTTATTTGTCAACACTGCCC

616: cggggtaccTGCGGGGTCTTTACTCG

677: TTACTATTCGAAGAAATTATTCATAAATATTGCCCGCCATCTGGCCCAAATTGGTGATGAAATGGATCATTAAGCTTGGAGTA

678: TACTCCAAGCTTAATGATCCATTTCATCACCAATTTGGGCCAGATGGCGGGCAATATTATGAATAATTTCTTCGAATAGTAA

682: TTACTACTGAGAAAAACTGAGCGAATGTCTGCGCCGCATTGGTGATGAACTGGATAGCTAAGCTTGGAGTA

683: TACTCCAAGCTTAGCTATCCAGTTCATCACCAATGCGGCGCAGACATTCGCTCAGTTTTTCTCGAGTAGTAA

TABLE II

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| YopEl-138-MycHis | 3 | pBad-MycHisA (Invitrogen) | pBad_Si_1 | 285/286 (EGFP), 287/288 (sycE-YopEl-138) | 44/45 and 46/47 |
| YopEl-138-MycHis | 3 | pBad-MycHisA (Invitrogen) | pBad_Si_2 | 287/288 (sycE-YopEl-138) | 46/47 |
| YopEl-138-IpgBl | 4 | pBad_Si_2 | pSi_16 | 292/293 | 48/49 |
| YopEl-138-SopE | 5 | pBad_Si_2 | pSi_20 | 296/297 | 50/51 |
| YopEl-138-Racl Q61L | 26 | pBad_Si_2 | pSi_22 | 299/300 | 52/53 |
| YopEl-138-RhoA Q61E | 27 | pBad_Si_2 | pSi_24 | 301/302 | 54/55 |
| YopEl-138-SopE-MycHis | 135 | pBad_Si_2 | pSi_28 | 296/306 | 50/56 |
| YopEl-138-SopB | 6 | pBad_Si_2 | pSi_30 | 307/308 | 57/58 |
| YopEl-138-FADD | 28 | pBad_Si_2 | pSi_37 | 367/386 | 76/79 |
| YopEl-138-OspF | 7 | pBad_Si_2 | pSi_38 | 317/318 | 59/60 |
| YopEl-138-BepG 715-end | 136 | pBad_Si_2 | pSi_43 | 324/351 | 61/67 |
| YopEl-138-Racl Q61L-MycHis | 137 | pBad_Si_2 | pSi_51 | 299/339 | 52/62 |
| YopEl-138-Slmbl-VhH4 | 32 | pBad_Si_2 | pSi_53 | 341/342 | 63/64 |
| YopEl-138-Bad | 29 | pBad_Si_2 | pSi_57 | 346/347 | 65/66 |
| YopEl-138-SptP | 8 | pBad_Si_2 | pSi_64 | 364/365 | 74/75 |
| YopEl-138-NLS-Slmbl-VhH4 | 33 | pBad_Si_2 | pSi_70 | 369/342 | 77/64 |
| YopEl-138-Bid | 24 | pBad_Si_2 | pSi_85 | 387/391 | 80/82 |
| YopEl-138-t-Bid | 25 | pBad_Si_2 | pSi_87 | 389/391 | 81/82 |
| YopEl-138-Caspase3 pl7 | 22 | pBad_Si_2 | pSi_97 | 403/406 | 83/84 |
| YopEl-138-GPCR GNA12 | 30 | pBad_Si_2 | pSi_103 | 410/413 | 85/86 |
| YopEl-138-Caspase3 plO/12 | 23 | pBad_Si_2 | pSi_106 | 417/420 | 87/88 |
| YopEl-138-IpgD | 9 | pBad_Si_2 | pSi_111 | 423/424 | 89/90 |
| YopEl-138-Slmbl-VhH4-NLS | 34 | pBad_Si_2 | pSi_112 | 341/425 | 63/91 |
| YopEl-138-z-Bid | 19 | pBad_Si_2 | pSi_116 | 428/430 | 92/94 |
| YopEl-138-z-t-Bid | 20 | pBad_Si_2 | pSi_117 | 429/430 | 93/94 |
| YopEl-138-BepA E305-end | 11 | pBad_Si_2 | pSi_118 | 433/435 | 95/97 |
| YopEl-138-BepA | 10 | pBad_Si_2 | pSi_119 | 434/435 | 96/97 |
| YopEl-138-ET1 | 36 | pBad_Si_2 | pSi_120 | 436/437 | 98/99 |
| YopEl-138-z-BIM | 21 | pbad_Si_1 | pSi_121 | 438/439 | 100/101 |
| YopEl-138-VhH4 nanobody recognizing EGFP | 31 | pBad_Si_2 | pSi_124 | 451/373 | 108/78 |
| YopEl-138-TEV protease S219V | 42 | pBad_Si_2 | pSi_132 | 463/464 | 109/1 10 |
| YopEl-138-EGFP | 37 | pBad_Si_2 | pSi_140 | 477/476 | 112/1 11 |
| YopEl-138-Cdkl | 14 | pBad_Si_2 | pSi_143 | 478/479 | 113/1 14 |
| YopEl-138-Mad2 | 15 | pBad_Si_2 | pSi_145 | 482/483 | 115/1 16 |
| YopEl-138-Ink4A | 16 | pBad_Si_2 | pSi_147 | 486/487 | 117/1 18 |
| YopEl-138-Ink4B | 17 | pBad_Si_2 | pSi_150 | 492/493 | 119/120 |
| YopEl-138-Ink4C | 18 | pBad_Si_2 | pSi_151 | 494/495 | 121/122 |
| YopEl-138-TIFA | 13 | pBad_Si_2 | pSi_153 | 558/559 | 131/132 |
| YopEl-138-2x TEVsite-ET1 | 41 | pBad_Si_2 | pSi_156 | 504/505 | 123/124 |
| YopEl-138-2xTEVsite-EGFP-NLS | 39 | pBad_Si_2 | pSi_159 | 511/513 | 127/129 |
| YopEl-138-2xTEVsite-NLS-EGFP | 38 | pBad_Si_2 | pSi_160 | 512/476 | 128/1 11 |
| YopEl-138-2x TEVsite-INK4C | 40 | pBad_Si_2 | pSi_161 | 508/509 | 125/126 |
| YopEl-138-2x TEVsite-Flag-INK4C | 43 | pBad_Si_2 | pSi_164 | 515/509 | 130/126 |
| YopEl-138-murine Traf6 | 12 | pBad_Si_2 | pSi_166 | 561/562 | 133/134 |
| YopEl-138-Y. enterocolitica codon optimized murine tBid BH3 part | 138 | pBad_Si_2 | pSi_318 | 677/678 | 148/149 |
| YopEl-138-Y. enterocolitica codon optimized | 139 | pBad_Si_2 | pSi_322 | 682/683 | 150/151 |

TABLE II-continued

Cloned fusion proteins

| Protein to be delivred by T3SS | Protein Seq. ID. No. | Backbone plasmid | Resulting plasmid name | Primers. Si_Nr.: | Primer Seq. ID No. |
|---|---|---|---|---|---|
| murine Bax BH3 part SteAl-20 | 140 | pBad-MycHisA (Invitrogen) | pSi_266 | 580/612 | 152/153 |
| SteA | 141 | pBad-MycHisA (Invitrogen) | pSi_267 | 580/613 | 152/154 |
| SopEl-81 | 142 | pBad-MycHisA (Invitrogen) | pSi_268 | 614/615 | 155/156 |
| SopEl-105 | 143 | pBad-MycHisA (Invitrogen) | pSi_269 | 614/616 | 155/157 |
| SteAl-20-S. enterica codon optimized murine tBid | 144 | pSi_266 | pSi_270 | synthetic construct | / |
| SteA-S. enterica codon optimized murine tBid | 145 | pSi_267 | pSi_271 | synthetic construct | / |
| SopEl-81-S. enterica codon optimized murine tBid | 146 | pSi_268 | pSi_272 | synthetic construct | / |
| SopEl-105-S. enterica codon optimized murine tBid | 147 | pSi_269 | pSi_273 | synthetic construct | / |
| YopEl-138-Y. enterocolitica codon optimized Ink4A 84-103 | 158 | pBad_Si_2 | pSi_362 | 745/746 | 172/173 |
| YopEl-138-Y. enterocolitica codon optimized pl07/RBLl 657-662 (AAA02489.1) | 159 | pBad_Si_2 | pSi_363 | 747/748 | 174/175 |
| YopEl-138-Y. enterocolitica codon optimized p21 141-160 (AAH13967.1) | 160 | pBad_Si_2 | pSi_364 | 749/750 | 176/177 |
| YopEl-138-Y. enterocolitica codon optimized p21 145-160 (AAH13967.1) | 161 | pBad_Si_2 | pSi_366 | 753/754 | 178/179 |
| YopEl-138-Y. enterocolitica codon optimized p21 17-33 (AAH13967.1) | 162 | pBad_Si_2 | pSi_367 | 755/756 | 180/181 |
| YopEl-138-Y. enterocolitica codon optimized cyclin D2 139-147 (CAA48493.1) | 163 | pBad_Si_2 | pSi_368 | 757/758 | 182/183 |
| SteA-Ink4a-MycHis | 164 | pSi_267 | pSi_333 | 703/704 | 184/185 |
| SopEl-105-Ink4a-MycHis | 165 | pSi_269 | pSi_334 | 703/704 | 184/185 |
| SteA-Ink4c-MycHis | 166 | pSi-267 | pSi_335 | PCR1: 705/706 PCR2: 707/708 overlapping PCR: 705/708 | 186/187, 188/189 |
| SopEl-105 Ink4c-MycHis | 167 | pSi_269 | pSi_336 | PCR1: 705/706; PCR2: 707/708; overlapping PCR: 705/708 | 186/187; 188/189 |
| SteA-Mad2-MycHis | 168 | pSi_267 | pSi_337 | 709/710 | 190/191 |
| SopEl-105-Mad2-MycHis | 169 | pSi_269 | pSi_338 | 709/710 | 190/191 |
| SteA-Cdkl-MycHis | 170 | pSi_267 | pSi_339 | 711/712 | 192/193 |
| SopEl-105-Cdkl-MycHis | 171 | pSi_269 | pSi_340 | 711/712 | 192/193 |
| YopEl-138-Y. enterocolitica codon optimized murine tBid | 194 | pBad_Si_2 | pSi_315 | synthetic construct | / |
| YopEl-138-Ubiquitin | 195 | pBad_Si_2 | pSi_236 | 585/586 | 197/198 |
| YopEl-138-Ubiquitin-Flag-INK4C-MycHis | 196 | pSi_236 | pSi_237_II | 588/509 | 199/126 |

Yop Secretion.

Induction of the yop regulon was performed by shifting the culture to 37° C. in BHI-Ox (secretion-permissive conditions) [49]. As carbon source glucose was added (4 mg/ml).

Total cell and supernatant fractions were separated by centrifugation at 20 800 g for 10 min at 4° C. The cell pellet was taken as total cell fraction. Proteins in the supernatant were precipitated with trichloroacetic acid 10% (w/v) final for 1 h at 4° C. After centrifugation (20 800 g for 15 min) and removal of the supernatant, the resulting pellet was washed in ice-cold Acetone over-night. The samples were centrifuged again, the supernatant was discarded and the pellet was air-dried and resuspened in 1×SDS loading dye.

Secreted proteins were analysed by SDS-PAGE; in each case, proteins secreted by $3\times10^8$ bacteria were loaded per lane. Detection of specific secreted proteins by immunoblotting was performed using 12.5% SDS-PAGE gels. For detection of proteins in total cells, $2\times10^8$ bacteria were loaded per lane, if not stated otherwise, and proteins were separated on 12.5% SDS-PAGE gels before detection by immunoblotting.

Immunoblotting was carried out using rat monoclonal antibodies against YopE (MIPA193-13A9; 1:1000, [50]). The antiserum was preabsorbed twice overnight against Y. enterocolitica ΔHOPEMT asd to reduce background staining. Detection was performed with secondary antibodies directed against rat antibodies and conjugated to horseradish peroxidase (1:5000; Southern biotech), before development with ECL chemiluminescent substrate (LumiGlo, KPM).

Cell Culture and Infections.

HeLa Cc12, swiss 3T3 fibroblast cells, 4T1, B16F10 and D2A1 were cultured in Dulbecco's modified Eagle's medium (DMEM) supplemented with 10%>FCS and 2 mM L-Glutamine (cDMEM). HUVECs were isolated and cultivated as described [51]. Jurkat and 4T1 cells were cultured in RPMI 1640 supplemented with 10% FCS and 2 mM L-Glutamine. *Y. enterocolitica* were grown in BHI with additives overnight at RT, diluted in fresh BHI to an $OD_{600}$ of 0.2 and grown for 2 h at RT before a temperature shift to a 37° C. waterbath shaker for further 30 min or for 1 h in case of delivery of EGFP. Finally, the bacteria were collected by centrifugation (6000 rcf, 30 sec) and washed once with DMEM supplemented with 10 mM HEPES and 2 mM L-glutamine. *S. enterica* were grown in LB with additives overnight at 37° C. and either diluted 1:40 in fresh LB and grown for 2.5 h at 37° C. (Spil T3SS inducing conditions) or the overnight culture was further incubated at 37° C. (SpiII T3SS inducing conditions). Finally, the bacteria were collected by centrifugation (6000 rcf, 30 sec) and washed once with DMEM supplemented with 10 mM HEPES and 2 mM L-glutamine. Cells seeded in 96-well (for Immunofluorescence) or 6-well (for Western blotting) plates were infected at indicated MOIs in DMEM supplemented with 10 mM HEPES and 2 mM L-glutamine. After adding bacteria, plates were centrifuged for 1 min at 1750 rpm and placed at 37° C. for indicated time periods. Extracellular bacteria were killed by gentamicin (100 mg/ml) if indicated. In case of immunofluorescence analysis, infection assays were stopped by 4% PFA fixation. For Western blot analysis cells were washed twice with ice-cold PBS and Phospho-safe lysis buffer (Novagen) was added to lyse the cells. After incubation on ice, the cells were centrifuged (16 000 rcf, 25 min, 4° C.). Supernatants were collected and analyzed for total protein content by Bradford BCA assay (Pierce) before SDS PAGE and Western blotting using anti-Phospho-Akt (Ser473 and T308, both Cell Signaling), anti-Actin (Millipore), Anti-Bid (Cell Signaling), anti-Myc (Santa Cruz), anti-p38 (Cell Signaling), anti-phospho-p-38 (Thr180/Tyr182; Cell Signaling), anti-Caspase-3 p17 (Cell Signaling) and anti-Ink4C (Cell Signaling) antibody.

Secretion Analysis with *S. enterica*.

For induction of protein secretion by *S. enterica*, *S. enterica* were cultivated overnight in LB containing 0.3 M NaCl on an orbital shaker (set to 150 rpm). *S. enterica* were then diluted 1:50 in fresh LB containing 0.3 M NaCl and grown for 4 h at 37° C. without shaking.

Total cell and supernatant fractions were separated by centrifugation at 20 800 g for 20 min at 4° C. The cell pellet was taken as total cell fraction. Proteins in the supernatant were precipitated with trichloroacetic acid 10% (w/v) final for 1 h at 4° C. After centrifugation (20 800 g for 15 min) and removal of the supernatant, the resulting pellet was washed in ice-cold Acetone over-night. The samples were centrifuged again, the supernatant was discarded and the pellet was air-dried and resuspended in 1×SDS loading dye.

Secreted proteins were analysed by SDS-PAGE; in each case, proteins secreted by 3×10⁸ bacteria were loaded per lane. Detection of specific secreted proteins by immunoblotting was performed using 12.5% SDS-PAGE gels. For detection of proteins in total cells, 2×10⁸ bacteria were loaded per lane, if not stated otherwise, and proteins were separated on 12.5% SDS-PAGE gels before detection by immunoblotting. Immunoblotting was carried out using anti-Myc (Santa Cruz) antibody.

Western Blotting of T3SS Translocated Proteins from Infected Cells.

HeLa cells in 6-well plates were infected at an MOI of 100 as described above. In case of coinfection with the TEV protease translocating *Y. enterocolitica* strain, the $OD_{600}$ of the strains was set and the two bacterial suspensions were mixed in a tube at a ratio of 1:1 (if not otherwise indicated) before addition to the cells. At the end of the infection, the cells were washed twice with ice-cold PBS and collected by scraping in a small volume of ice-cold PBS. After centrifugation (16 000 rcf, 5 min, 4° C.) the pellet was dissolved in 0.002% digitonin supplemented with a protease inhibitor cocktail (Roche complete, Roche). The dissolved pellets were incubated for 5 minutes on ice and then centrifuged (16 000 rcf, 25 min, 4° C.). Supernatants were collected and analyzed for total protein content by Bradford BCA assay (Pierce) before SDS PAGE and Western blotting using an anti-Myc (Santa Cruz, 9E1 1) or anti-Ink4C (Cell Signaling) antibody.

Immunofluorescence.

Cell seeded in 96-well plates (Corning) were infected as described above and after fixation with 4% PFA the cells were washed three times with PBS. The wells were then blocked using 5% goat serum in PBS 0.3% Triton X-100 for 1 h at RT. The primary antibody (anti-Myc, Santa Cruz, 1:100) was diluted in PBS with 1% BSA and 0.3% Triton X-100 and cells were incubated overnight at 4° C. Cells were washed 4 times with PBS before the secondary antibody (AF 488 anti-mouse, life technologies, 1:250) diluted in PBS with 1% BSA and 0.3%>Triton X-100 was added. If needed Hoechst DNA staining (life technologies, 1:2500) and/or actin staining (Dy647-Phalloidin, DyeOmics) were included. In some cases only the DNA and/or actin stain was applied directly after washing the PFA off. Cells were incubated for 1 h at RT, washed three times with PBS and analyzed by automated image analysis as described below.

Automated Microscopy and Image Analysis.

Images were automatically acquired with an ImageXpress Micro (Molecular devices, Sunnyvale, USA). Quantification of anti-Myc staining intensities was performed using MetaXpress (Molecular devices, Sunnyvale, USA). Regions within cells excluding nuclear regions and regions containing bacteria were manually chosen (circles with an area of 40 pixels) and average intensity was recorded.

TNFa Stimulation and Western Blotting of Phospho-p38.

HeLa cells seeded in 6-well plates were infected with an MOI of 100 as described above. 30 min p.i Gentamicin was added and 45 min p.i. TNFa was added (10 ng/ml). 1 h 15 min p.i. cells were washed twice with ice-cold PBS and Phospho-safe lysis buffer (Novagen) was added to lyse the cells. After incubation on ice, the cells were centrifuged (16 000 rcf, 25 min, 4° C.). Supernatants were collected and analyzed for total protein content by Bradford BCA assay (Pierce) before SDS PAGE and Western blotting using an anti-Phospho-p38, total p38 antibodies (Cell Signaling) and anti-Actin antibody (Millipore).

cAMP Level Determination of Infected HeLa Cells.

HeLa cells seeded in 96-well plates were infected as described above. 30 min before the infection cDMEM was changed to DMEM supplemented with 10 mM HEPES and 2 mM L-glutamine and 100 uM 3-Isobutyl-1-methylxanthin (IBMX, Sigma Aldrich). 60 min p.i. Gentamicin was added and cells were further incubated at 37° C. for another 90 min. Determination of cAMP was performed using a competitive ELISA according to the manufacturers instructions (Amersham, cAMP Biotrak, RPN225). As a positive control indicated amount of cholera toxin (C8052, Sigma Aldrich) was added for 1 h to cells in DMEM supplemented with 10 mM HEPES and 2 mM L-glutamine and 100 uM IBMX.

Zebrafish Embryo Infections, Imaging and Automated Image Quantification.

All animal experiments were performed according to approved guidelines. Zebrafish were maintained at standard conditions [52]. Embryos were staged by hours postfertilization (hpf) at 28.5° C. [53]. The following zebrafish lines were used in this study: wild type fish (AB/EK and EK/TL).

Infection protocol followed guidelines given in [54]. 12 hpf embryos were maintained in E3 medium containing 0.2 mM N-phenylthiourea (PTU) to prevent pigment formation. 2 days postfertilization (dpi) embryos were anesthetized by 0.2 mg/ml Tricaine and aligned on 1% agar plates in E3 using a hair loop tool [54]. *Y. enterocolitica* were grown in BHI supplemented with 0.4% Arabinose and antibiotics and mDap overnight at RT, diluted in fresh BHI with 0.5% Arabinose and other additives to an $OD_{600}$ of 0.2 and grown for 2 h at RT before a temperature shift to a 37° C. waterbath shaker for further 45 min. Finally, the bacteria were collected by centrifugation (6000 rcf, 30 sec) and washed once with PBS. The $OD_{600}$ was set to 2 in PBS containing mDAP. 1-2 nL of this suspension were injected into the hindbrain of aligned zebrafish embryos using an Femtojet Microinjector (Eppendorf) using Femtotips II (Eppendorf), where the tip of the needle had been broken off with fine tweezers. The injection time was set to 0.2 s and the compensation pressure to 15 hPa (Eppendorf, Femtojet) and the injection pressure was adjusted between 600 and 800 hPa. Drop size and thus the inoculum was checked by microscopy and by control plating. Following microinjection the fish were collected in E3 containing Tricaine and PTU and incubated for 30 min at 37° C. and incubated for further 5 h at 28° C. A fluorescence binocular (Leica) was used to observe bacterial EGFP fluorescence 1 h post infection in zebrafish hindbrains, and embryos that are not properly injected were discarded. At the end of the infection, fish were fixed with 2% ice-cold PFA for 1 h on ice and further with fresh ice-cold PFA overnight at 4° C. Antibody staining was performed as described previously [55, 56]. Briefly, embryos were washed 4 times with PBS 0.1% Tween for 5 min each wash and permeabilized with PBS-T+0.5% Triton X-100 for 30 min at RT. Embryos were blocked in blocking solution (PBS 0.1% Tween 0.1% TritonX-100 5%>goat serum and 1% BSA) at 4° C. overnight. Antibody (Cleaved Caspase-3 (Asp 175), Cell Signaling) was diluted 1:100 in blocking solution and incubated under shaking at 4° C. in the dark. Fish were washed 7 times with PBS 0.1% Tween for 30 min before the secondary antibody (goat anti-rabbit AF647, Invitrogen, 1:500) diluted in blocking solution was added and incubated at 4° C. overnight. Larvae were washed with PBS 0.1% Tween four times 30 min at 4° C. and once overnight and further washed 3-4 times. Images were taken with Leica TCS SP5 confocal microscope using a 40× water immersion objective. Images were analyzed using Imaris (Bitplane) and Image J software (http://imagej.nih.gov/ij/).

Image analysis (on n=14 for pBad_Si2 or n=19 for z-BIM) was performed via CellProfiler [57] on maximum intensity z projections of recorded z-stack images. Briefly, bacteria were detected via the GFP channel. Around each area of a bacterial spot a circle with a radius of 10 pixels was created. Overlapping regions were separated equally among the connecting members. In those areas closely surrounding bacteria, the Caspase 3 pl7 staining intensity was measured.

Sample Preparation for Phosphoproteomics.

For each condition, two 6-well plates of HeLa CCL-2 cells were grown to confluency. Cells were infected for 30 min as described above. At the indicated time-points, the plates were put on ice and washed twice with ice-cold PBS. Samples were then collected in urea solution [8 M Urea (AppliChem), 0.1 M Ammoniumbicarbonate (Sigma), 0.1%) RapiGest (Waters), 1×PhosSTOP (Roche)]. The samples were briefly vortexed, sonicated at 4° C. (Hielscher), shaked for 5 min on a thermomixer (Eppendorf) and centrifuged for 20 min at 4° C. and 16000 g. Supernatants were collected and stored at −80° C. for further processing. BCA Protein Assay (Pierce) was used to measure protein concentration.

Phosphopeptide Enrichment.

Disulfide bonds were reduced with tris(2-carboxyethyl) phosphine at a final concentration of 10 mM at 37° C. for 1 h. Free thiols were alkylated with 20 mM iodoacetamide (Sigma) at room temperature for 30 min in the dark. The excess of iodoacetamide was quenched with N-acetyl cysteine at a final concentration of 25 mM for 10 min at room temperature. Lys-C endopeptidase (Wako) was added to a final enzyme/protein ratio of 1:200 (w/w) and incubated for 4 h at 37° C. The solution was subsequently diluted with 0.1 M ammoniumbicarbonate (Sigma) to a final concentration below 2 M urea and digested overnight at 37° C. with sequencing-grade modified trypsin (Promega) at a protein-to-enzyme ratio of 50:1. Peptides were desalted on a C18 Sep-Pak cartridge (Waters) and dried under vacuum.

Phosphopeptides were isolated from 2 mg of total peptide mass with $TiO_2$ as described previously [58]. Briefly, dried peptides were dissolved in an 80% acetonitrile (ACN)-2.5% trifluoroacetic acid (TFA) solution saturated with phthalic acid. Peptides were added to the same amount of equilibrated $TiO_2$ (5-μm bead size, GL Sciences) in a blocked Mobicol spin column (MoBiTec) that was incubated for 30 min with end-over-end rotation. The column was washed twice with the saturated phthalic acid solution, twice with 80% ACN and 0.1% TFA, and finally twice with 0.1% TFA. The peptides were eluted with a 0.3 M $NH_4OH$ solution. The pH of the eluates was adjusted to be below 2.5 with 5%>TFA solution and 2 M HCl. Phosphopeptides were again desalted with microspin C18 cartridges (Harvard Apparatus).

LC-MS/MS Analysis.

Chromatographic separation of peptides was carried out using an EASY nano-LC system (Thermo Fisher Scientific), equipped with a heated RP-HPLC column (75μm×45 cm) packed in-house with 1.9μm Cl8 resin (Reprosil-AQ Pur, Dr. Maisch). Aliquots of 1 μg total phosphopeptide sample were analyzed per LC-MS/MS run using a linear gradient ranging from 98% solvent A (0. 15% formic acid) and 2% solvent B (98% acetonitrile, 2% water, 0.15% formic acid) to 30% solvent B over 120 minutes at a flow rate of 200 nl/min. Mass spectrometry analysis was performed on a dual pressure LTQ-Orbitrap mass spectrometer equipped with a nanoelectrospray ion source (both Thermo Fisher Scientific) . Each MSI scan (acquired in the Orbitrap) was followed by collision-induced dissociation (CID, acquired in the LTQ) of the 20 most abundant precursor ions with dynamic exclusion for 30 seconds. For phosphopeptide analysis the 10 most abundant precursor ions were subjected to CID with enabled multistage activation. Total cycle time was approximately 2 s. For MSI, $10^6$ ions were accumulated in the Orbitrap cell over a maximum time of 300 ms and scanned at a resolution of 60,000 FWHM (at 400 m/z). MS2 scans were acquired using the normal scan mode, a target setting of $10^4$ ions, and accumulation time of 25 ms. Singly charged ions and ions with unassigned charge state were excluded from triggering MS2 events. The normalized collision energy was set to 32%>, and one microscan was acquired for each spectrum.

Label-Free Quantification and Database Searching.

The acquired raw-files were imported into the Progenesis software tool (Nonlinear Dynamics, Version 4.0) for label-free quantification using the default parameters. MS2 spectra were exported directly from Progenesis in mgf format and searched using the MASCOT algorithm (Matrix Science, Version 2.4) against a decoy database [59] containing normal and reverse sequences of the predicted SwissProt entries of *Homo sapiens* (www.ebi.ac.uk, release date 16 May 2012) and commonly observed contaminants (in total 41,250 sequences) generated using the SequenceReverser tool from the MaxQuant software (Version 1.0.13.13). To identify proteins originating from *Y. enterocolitica*, non phosphopeptide enriched samples were searched against the same database above including predicted SwissProt entries of *Y. enterocolitica* (www.ebi.ac.uk, release date 15 Aug. 2013) The precursor ion tolerance was set to 10 ppm and fragment ion tolerance was set to 0.6 Da. The search criteria were set as follows: full tryptic specificity was required (cleavage after lysine or arginine residues unless followed by proline), 2 missed cleavages were allowed, carbamidomethylation (C) was set as fixed modification and phosphorylation (S,T,Y) or oxidation (M) as a variable modification for TiO2 enriched or not enriched samples, respectively. Finally, the database search results were exported as an xml-file and imported back to the Progenesis software for MSI feature assignment. For phosphopeptide quantification, a csv-file containing the MSI peak abundances of all detected features was exported and for not enriched samples, a csv-file containing all protein measurements based on the summed feature intensities of all identified peptides per protein was created Importantly, the Progenesis software was set that proteins identified by similar sets of peptides are grouped together and that only non-conflicting peptides with specific sequences for single proteins in the database were employed for protein quantification. Both files were further processed using the in-house developed SafeQuant v1.O R script (unpublished data, available at https://github.com/eahrne/SafeQuant/). In brief, the software sets the identification level False Discovery Rate to 1% (based on the number of decoy protein sequence database hits) and normalizes the identified MS1 peak abundances (Extracted Ion Chromatogram, XIC) across all samples, i.e. the summed XIC of all confidently identified peptide features is scaled to be equal for all LC-MS runs. Next, all quantified phosphopeptides/proteins are assigned an abundance ratio for each time point, based on the median XIC per time point. The statistical significance of each ratio is given by its q-value (False Discovery Rate adjusted p-values), obtained by calculating modified t-statistic p-values [60] and adjusting for multiple testing [61].

The location of the phosphorylated residues was automatically assigned by MASCOT (score>10). All annotated spectra together with the MS raw files and search parameters employed, will be deposited to the ProteomeXchange Consortium (http://proteomecentral.proteomexchange.org) via the PRIDE partner repository [62]. Sequence alignment was performed using EMBL-EBI web based ClustalW2 multiple sequence alignment tool at http://www.ebi.ac.uk/Tools/msa/clustalw2/.

B) Results

A Protein Delivery System Based on Type 3 Secretion of YopE Fusion Proteins

While the very N-terminus of the *Y. enterocolitica* T3SS effector YopE (SEQ ID No. 1) contains the secretion signal sufficient to translocate heterologous proteins [10], the chaperone-binding site (CBS) for its chaperone (SycE) is not included [63]. We selected the N-terminal 138 amino acids of YopE (SEQ ID No. 2) to be fused to proteins to be delivered, as this had been shown to give best results for translocation of other heterologous T3S substrates [38]. As these N-terminal 138 amino acids of YopE contain the CBS, we further decided to coexpress SycE. The SycE-YopEi_$i_{3_8}$ fragment cloned from purified *Y. enterocolitica* pYV40 virulence plasmid contains the endogenous promoters of YopE and of its chaperone SycE (FIG. 10). Therefore, SycE and any YopEi_$i_{3_8}$ fusion protein are induced by a rapid temperature shift from growth at RT to 37° C. Culture time at 37° C. will affect fusion protein amount present in bacteria. A multiple cloning site (MCS) was added at the 3' end of YopEi_$i_{3_8}$ (FIG. 10 B) followed by a Myc and a 6×His tag and a Stop codon.

The background strain was carefully selected. First, to limit the translocation of endogenous effectors, we used a *Y. enterocolitica* strain that was deleted for all known effectors, Yop H, O, P, E, M and T (named ΔHOPEMT) [64]. In addition, we used an auxotroph mutant that cannot grow in absence of exogenous meso-2,6-diaminopimelic acid [65]. This strain was deleted for the aspartate-beta-semialdehyde dehydrogenase gene (Aasd), and classified as biosafety level 1 by the Swiss safety agency (amendment to A O10088/2). In addition, we deleted the adhesion proteins YadA and/or InvA to offer a larger choice of background strains. While the use of the yadA or yadA/invA strains reduce the background signalling induced [66], the delivered protein amount is affected as well [67].

Characterization of YopE Fusion Protein Delivery into Eukaryotic Cells

In an in-vitro secretion assay (see FIG. 1 A), protein secretion into the surrounding liquid is artificially induced. After TCA based protein precipitation, Western blot analysis with anti-YopE antibody was used to determine protein amounts secreted (FIG. 1 B). While a wt strain secreted full length YopE, the ΔHOPEMT asd strains did not. Upon presence of YopEi_$i_{38}$-Myc-His (further termed YopEi_$i_{3_8}$-Myc; SEQ_ID_No._3) a smaller YopE band became visible (FIG. 1 B). Hence, the YopEi_$i_{3_8}$ fragment is well secreted in the set up described here. To analyze homogeneity of protein translocation into eukaryotic cells, we infected HeLa cells with the YopEi_i38-Myc encoding strain and stained the Myc tag by IF (FIGS. 2 A and B). While in the beginning only the bacteria were stained, at 30 min post infection (p.i.) cell outlines start to be visible, which is enhanced upon increased infection time (FIG. 2 B). This trend is well reflected by the Myc tag staining intensity inside HeLa cells (FIGS. 2 A and B). The YopEi_$i_{38}$-Myc can be detected everywhere in the cells (FIG. 2 A), except in the nuclei [68]. Remarkably, most if not all cells were reached by this approach in a comparable way. As *Y. enterocolitica* is known to infect many different cell types [69], we followed YopEi_$i_{38}$-Myc delivery into various cell lines. The same homogenous anti-Myc IF staining was observed in infected murine fibroblasts, Jurkat cells and HUVECs (FIG. 11). Even more, tuning the MOI up or down allows modulating the protein amount delivered (FIG. 2 C), while still most of the cells remain targeted. A low bacterial number will not result in few cells with lots of delivered protein but rather with most cells containing a low amount of delivered protein (FIG. 2 C).

Redirection of T3SS Delivered Proteins to the Nucleus

As YopE itself localized to the cytoplasm (FIG. 2 A), it is of special interest to test if the YopEi_$i_{38}$ fragment hampers localization of nuclear fusion proteins. We therefore added the SV40 NLS to the C-terminus (and N-terminus, similar results) of YopEi_$i_{38}$-EGFP (SEQ ID No. 39 and SEQ ID No. 38, respectively). While YopEi_$i_{38}$-EGFP (SEQ ID No. 37) led to a weak cytoplasmic staining, YopEi_$i_{38}$-EGFP-NLS gave rise to a stronger nuclear EGFP signal in HeLa cells infected (FIG. 3). This indicates that the YopEi_$i_{38}$ fragment is compatible with the use of an NLS. While mCherry had already been used in plant pathogens [70], this represents a successful delivery of a GFP-like protein via human or animal pathogenic bacteria encoding a T3SS. This validates the SycE and YopEi_i$_{38}$ dependent strategy to be very promising for delivery of many proteins of choice.

Figure 4:
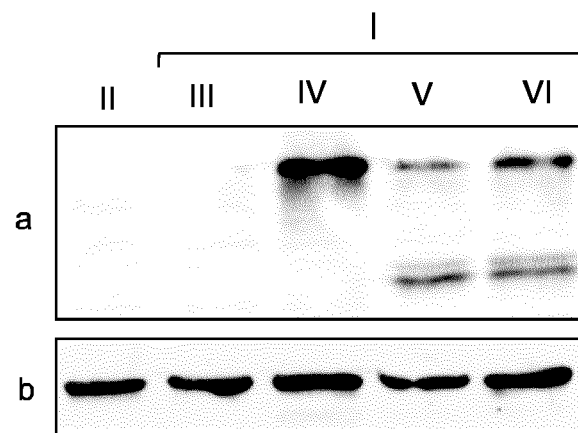
Figure 4:
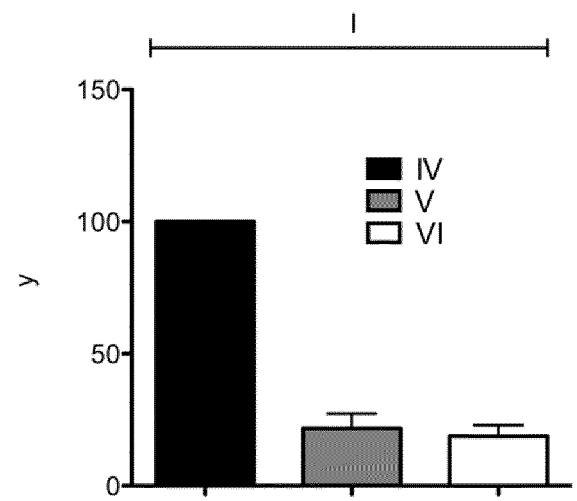
Figure 4:
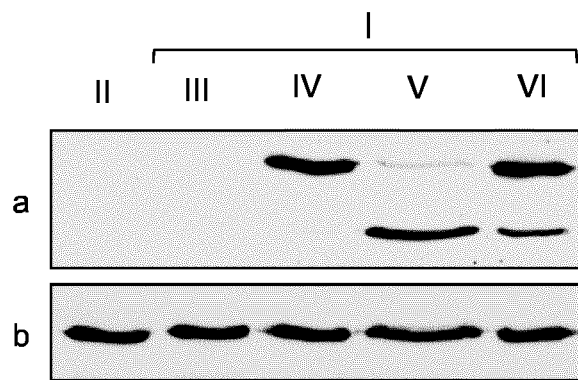

Removal of the YopEi.i$_{38}$ Appendage after Translocation of the Fusion Protein to the Eukaryotic Cell While for bacterial delivery the YopEi_i$_3$, fragment is of great benefit, it might hamper the fusion proteins function and/or localization. Therefore, its removal after protein delivery would be optimal. To this end, we introduced two TEV cleavage sites (ENLYFQS) [71-73] in between YopEi_i$_{3_8}$ and a fusion partner (the transcriptional regulator ET1-Myc (SEQ ID No. 36 and 41) [74] and human INK4C (SEQ ID No. 40 and SEQ ID No. 43)). To keep the advantages of the presented method, we further fused the TEV protease (S219V variant; [75]) to YopEi_i38 (SEQ ID No. 42) in another *Y. enterocolitica* strain. HeLa cells were infected with both strains at once. To allow analysis of the translocated fraction of proteins only, infected HeLa cells were lysed at 2 h p.i. (FIG. 4) with Digitonin, which is known not to lyse the bacteria ([76]; see FIG. 12 for control). Western blot analysis revealed the presence of the YopEi_i3$_8$-2xTEV-cleavage-site-ET1-Myc or YopEi_i$_{38}$-2xTEV-cleavage-site-Flag-INK4C-Myc only when cells had been infected with the corresponding strain (FIGS. 4 A and C). Upon overnight digestion of this cell-lysate with purified TEV protease, a shifted band could be observed (FIGS. 4 A and C). This band corresponds to ET1-Myc (FIG. 4 C) or Flag-INK4C (FIG. 4 A) with the N-terminal remnants of the TEV cleavage site, most likely only one Serine. Upon coinfection of cells with the strain delivering the TEV protease, the same cleaved ET1-Myc or Flag-INK4C fragment became visible, indicating that the TEV protease delivered via T3SS is functional and that single cells had been infected by both bacterial strains (FIGS. 4 A and C). While cleavage is not complete, the majority of translocated protein is cleaved already 2 h post infection and even over-night digestion with purified TEV protease did not yield better cleavage rates (FIG. 4 B). As reported, TEV protease dependent cleavage might need optimization dependent on the fusion protein [77, 78]. TEV protease dependent removal of the YopEi_i38 appendage after translocation hence provides for the first time a T3SS protein delivery of almost native heterologous proteins, changing the amino acid composition by only one N-terminal amino acid.

An alternative approach to the TEV protease dependent cleavage of the YopE fragment consisted in incorporating Ubiquitin into the fusion protein of interest. Indeed, Ubiquitin is processed at its C-terminus by a group of endogenous Ubiquitin-specific C-terminal proteases (Deubiquitinating enzymes, DUBs). As the cleavage is supposed to happen at the very C-terminus of Ubiquitin (after G76), the protein of interest should be free of additional amino acid sequence. This method was tested on the YopEl-138-Ubiquitin-Flag-INK4C-MycHis fusion protein. In control cells infected by YopEl-138-Flag-INK4C-MycHis-expressing bacteria, a band corresponding to YopEl-138-Flag-INK4C-MycHis was found, indicative of efficient translocation of the fusion protein (FIG. 24). When cells were infected for 1 h with YopEl-138-Ubiquitin-Flag-INK4C-MycHis-expressing bacteria, an additional band corresponding to the size of Flag-INK4C-MycHis was visible, indicating that part of the fusion protein was cleaved. This result shows that the introduction of Ubiquitin into the fusion protein enables to cleave off the YopEl-138 fragment without a need for an exogenous protease.

Translocation of Type III and Type IV Bacterial Effectors

SopE from *Salmonella enterica* is a well-characterized guanine nucleotide exchange factor (GEF) that interacts with Cdc42, promoting actin cytoskeletal remodeling [79]. Whereas the translocation of YopEi_i$_3$,-Myc into HeLa cells has no effect, translocated YopEi_i$_{3_8}$-SopE (SEQ ID No. 5 and 135) induced dramatic changes in the actin network (FIG. 5 A). Similar results were obtained with another GEF effector protein, IpgB1 from *Shigella flexneri* (SEQ ID No. 4). Remarkably, first changes in the actin cytoskeleton were observed as fast as 2 min p.i. (FIG. 5 A). Therefore, one can conclude that T3SS dependent protein delivery happens immediately after infection is initiated by centrifugation. To proof strict T3SS dependent transport, one of the T3SS proteins forming the translocation pore into the eukaryotic cell membrane was deleted (YopB, see [80]) (FIG. 12).

During *Salmonella* infection, SopE translocation is followed by translocation of SptP, which functions as a GTPase activating protein (GAP) for Cdc42 [81]. Whereas the translocation of YopEi_i38-SopE-Myc (SEQ ID No. 135) alone triggered massive F-actin rearrangements, the co-infection with YopEi_i$_{3_8}$-SptP (SEQ ID No. 8) expressing bacteria abolished this effect in a dose dependent manner (FIG. 5 B). An anti-Myc staining indicated that this inhibition was not due to a reduced level of YopEi_i$_{3_8}$-SopE-Myc translocation (FIG. 5 B). Together these results showed that the co-infection of cells with two bacterial strains is a valid method to deliver two different effectors into single cells to address their functional interaction.

The *S. flexneri* type III effector OspF functions as a phosphothreonine lyase that dephosphorylates MAP kinases p38 and ERK [82]. To test the functionality of translocated YopEi_i38-OspF (SEQ ID No. 7), we monitored the phosphorylation of p38 after stimulation with TNFa. In uninfected cells or in cells infected with YopEi_i$_{3_8}$-Myc expressing bacteria, TNFaDinduced p38 phosphorylation. In contrast, after translocation of YopEi_i$_{3_8}$-OspF, TNFa-induced phosphorylation was abolished, showing that the delivered OspF is active towards p38 (FIG. 6 A).

During *Salmonella* infection, the type III effector SopB protects epithelial cells from apoptosis by sustained activation of Akt [83]. Whereas the translocation of YopEi_i$_{3_8}$-Myc or YopEi_i$_{38}$-SopE had no effect on Akt, the translocation of YopEi_i$_{38}$-SopB (SEQ ID No. 6) induced a strong phosphorylation of Akt at T308 and S473, reflecting the active form (FIG. 6 B). Similar results were obtained with the SopB-homolog from *S. flexneri* (IpgD, SEQ ID No. 9). Altogether, our results show that the YopEi_i$_{38}$-based delivery system functions for all T3S effectors tested so far, and that it allows investigating proteins involved in the control of central cellular functions including the cytoskeleton, inflammation and cell survival.

A number of bacteria, including *Agrobacterium tumefaciens, Legionella pneumophila* and *Bartonella henselae*, use type IV secretion to inject effectors into cells. We tested whether the type IV effector BepA from *B. henselae* could be translocated into HeLa cells using our tool. Full length BepA (SEQ ID No. 10) and BepA$_{E305-end}$ (SEQ ID No. 11) containing the C-terminal Bid domain, were cloned and cells were infected with the respective strains. As BepA was shown to induce the production of cyclic AMP (cAMP) [84], the level of cAMP in HeLa cells was measured after infection. Whereas the translocation of the Bid domain of the *B. henselae* effector BepG (SEQ ID No. 136) failed to induce cAMP, full length BepA and BepA$_{E30\ 5-end}$ triggered cAMP production in expected amounts [84] (FIG. 6 C). This result shows, that type IV effectors can also be effectively delivered by the YopEi_$i_{38}$-based delivery system into host cell targets and that they are functional.

Translocation of Eukaryotic Proteins into Epithelial Cells

To show that human proteins can translocate via type III secretion we fused human apoptosis inducers for delivery by *Y. enterocolitica* to YopEi_$i_{38}$ or for delivery by *S. enterica* to SteAi_$_2$o, SteA, SopEi_$_8$j or SopEi_$i_0$5. We then monitored the translocation of the human BH3 interacting-domain death agonist (BID, SEQ ID No. 24), which is a pro-apoptotic member of the Bcl-2 protein family. It is a mediator of mitochondrial damage induced by caspase-8 (CASP8). CASP8 cleaves BID, and the truncated BID (tBID, SEQ ID No. 25) translocates to mitochondria where it triggers cytochrome c release. The latter leads to the intrinsic mode of caspase 3 (CASP3) activation during which it is cleaved into 17 and 12 kDa subunits [85]. Whereas infection for 1 h with YopEi_i$_{3_8}$-Myc or YopEi_i$_{3_8}$-BID expressing *Y. enterocolitica* failed to induce apoptosis, the translocation of human tBID triggered cell death in larger extend than the well-characterized apoptosis inducer staurosporin (FIGS. 7 A and C). As expected, the translocation of tBID lead to the production of CASP3 pl7 subunit, even in larger amounts as with staurosporin (FIG. 7 A). To be able to compare translocated protein amounts to endogenous Bid, HeLa cells were lysed with Digitonin and analyzed by Western blotting using an anti Bid antibody (FIG. 7 B). T3SS delivered YopEi_i$_{3_8}$-tBID reached about endogenous Bid levels in HeLa cells, while delivered YopEi_i$_{3_8}$-BID was present in even higher quantities (2.5 fold) (FIG. 7 B). A deep proteome and transcriptome mapping of HeLa cells estimated 4.4 fold $10^5$ copies of BID per single cell [86]. Therefore, one can conclude that T3SS dependent human protein delivery reaches $10^5$ to $10^6$ proteins per cell. These numbers fit the copies per cell of nanobodies translocated via *E. coli* T3SS [19]. Assuming a levelling of a factor of 10 for the MOI and for the duration of the infection, a factor of 3.2 for the time-point of antibiotic addition and for the culture time at 37° C. before infection, the delivered protein copies/cell can be tuned from some 1000 copies/cell up to some $10^6$ copies/cell Altogether, these results indicated that translocated tBID was functional and delivered at relevant levels. This validated the translocation tool to study the role of proteins in the regulation of apoptosis, a central aspect of cell biology.

We further fused murine tBID (codon optimized for *Y. enterocolitica*; SEQ ID No. 194) or the BH3 domains of murine tBID or murine BAX (in both cases codon optimized for *Y. enterocolitica*; SEQ ID No. 138 and 139) to YopEi_i$_{38}$ for delivery by *Y. enterocolitica*. Whereas infection for 2.5 h with *Y. enterocolitica* ΔHOPEMT asd delivering no protein or YopEi_i$_{38}$-Myc failed to induce apoptosis, the translocation of murine tBID (codon optimized to *Y. enterocolitica*, SEQ ID No. 194) triggered cell death in B16F10 (FIG. 16), D2A1 (FIG. 17), HeLa (FIG. 18) and 4T1 (FIG. 19) cells. The translocation of the BH3 domain of murine BID codon optimized for *Y. enterocolitica* (SEQ ID 138) or murine BAX codon optimized for *Y. enterocolitica* (SEQ ID 139) were as well found to induce massive cell death in B16F10 (FIG. 16), D2A1 (FIG. 17), HeLa (FIG. 18) and 4T1 (FIG. 19) cells.

Whereas infection for 4 h with *S. enterica* aroA bacteria failed to induce apoptosis, the translocation of murine tBID triggered apoptosis, as the translocation of murine tBID lead to the production of CASP3 pl7 subunit (FIGS. 20 and 21). The extent of apoptosis induction for SopE fusion proteins was larger when using Spil T3SS inducing conditions (FIG. 20), which reflects the transport of SopE exclusively by Spil T3SS. SteAi_$_2$o fused murine tBID failed to induce apoptosis, very likely because the secretion signal within the 20 N-terminal amino acids of SteA is not sufficient to allow delivery of a fusion protein (FIGS. 20 and 21). Murine tBID fused to full length SteA lead to apoptosis induction in HeLa cells (FIGS. 20 and 21), both in Spil and Spill T3SS inducing conditions, reflecting the ability of SteA to be transported by both T3SS. It has to be noted that even under Spill T3SS inducing conditions, a partial activity of the Spil T3SS is expected as seen by the activity of SopE fusion proteins in Spill T3SS inducing conditions (FIG. 21).

Besides the here functionally elaborated translocated eukaryotic proteins, several other eukaryotic proteins have been secreted using the here-described tool. This includes for delivery by *Y. enterocolitica* (FIGS. 13, 14 and 23) proteins from cell cycle regulation (Mad2 (SEQ ID No. 15), CDK1 (SEQ ID No. 14), INK4A (SEQ ID No. 16), INK4B (SEQ ID No. 17) and INK4C (SEQ ID No. 18)) as well as parts thereof (INK4A 84-103 (SEQ ID No. 158), p107 657-662 (SEQ ID No. 159), p21 141-160 (SEQ ID No. 160), p21 145-160 (SEQ ID No. 161), p21 17-33 (SEQ ID No. 162) and cyclin D2 139-147 (SEQ ID No 163)), apoptosis related proteins (Bad (SEQ ID No. 29), FADD (SEQ ID No. 28), and Caspase 3 pl7 (SEQ ID No. 22) and p12 (SEQ ID No. 23), zebrafish Bid (SEQ ID No. 19) and t-Bid (SEQ ID No. 20)) as well as parts thereof (tBid BH3 (SEQ ID No. 138), Bax BH3 (SEQ ID No. 139)), signalling proteins (murine TRAF6 (SEQ ID No. 12), TIFA (SEQ ID No. 13)), GPCR Ga subunit (GNA12, shortest isoform, (SEQ ID No. 30)), nanobody (vhhGFP4, (SEQ ID No. 31)) and nanobody fusion constructs for targeted protein degradation (Slmb-vhhGFP4; (SEQ ID Nos. 32, 33, 34) [87]) (FIGS. 13 and 14) as well as small GTPases (Racl Q61E (SEQ ID No. 26 and 137) and RhoA Q63L (SEQ ID No. 27) and Pleckstrin homology domain from human Akt (SEQ ID No. 35). Besides the functionally elaborated apoptosis related proteins (murine tBid, SEQ ID No. 144-147), this further includes for delivery by *S. enterica* (FIG. 22) proteins from cell cycle regulation (Mad2 (SEQ ID No. 168-169), CDK1 (SEQ ID No. 170-171), INK4A (SEQ ID No. 164-165) and INK4C (SEQ ID No. 166-167)). While those proteins have not been functionally validated, the possibility of T3SS dependent secretion of diverse eukaryotic proteins in combination with the possible removal of the YopE appendage opens up new vistas on the broad applicability of T3SS in cell biology.

In Vivo Translocation of Truncated Bid in Zebrafish Embryos Induces Apoptosis

An interesting feature of this bacterial tool is the potential use in living animals. Zebrafish in their embryonic state can be kept transparent allowing fluorescent staining and microscopy [54, 88, 89]. Few zebrafish apoptosis inducers have been described in detail, whereof z-BIM is the most potent [90]. Therefore, we decided to clone z-BIM into our system. Even if weakly homolgous to human BIM, we assayed the potency of apoptosis induction of YopEi_i$_{3_8}$-z-BIM (SEQ ID No. 21) in human epithelial cells. HeLa cells infected for 1 h with the strain translocating YopEi_i$_{3_8}$-z-BIM showed clear signs of cell death. We then performed in-vivo experiments with 2 days post fertilization (dpf) zebrafish embryos, using a localized infection model via microinjection of bacteria into the hindbrain [54]. After infection for 5.5 h the fish were fixed, permeabilized and stained for presence of CASP3 p i 7. Upon infection with the YopEi_i38-Myc expressing strain, bacteria were visible in the hindbrain region (staining "b", FIG. 8 A I) but no induction of apoptosis around the bacteria was detected (staining "c", FIG. 8 A I). In contrast, upon infection with the strain delivering YopEi_i$_{3_8}$-z-BIM a strong increase in presence of cleaved CASP3 was observed in regions surrounding the bacteria (FIG. 8 A II). Automated image analysis on maximum intensity z projections confirms that YopEi_i$_{3_8}$-z-BIM translocating bacteria induce apoptosis in nearby cells by far more than control bacteria do (FIG. 8 B). This indicates that z-BIM is functional in zebrafish upon bacterial translocation. These results further validate the use of T3SS for eukaryotic protein delivery in living animals.

Phosphoproteomics Reveal the Global Impact of Translocated Proteins on Protein Phosphorylation Phosphorylation is a wide-spread post-translational modification which can either activate or inactivate biological processes and is therefore a suitable target to study signaling events [91, 92]. Despite this, no systems-level analysis of phosphorylation in apoptosis is available today. To analyze the impact of human tBid delivered into HeLa cells, we used a label-free phosphoproteomic approach by LC-MS/MS. In three independent experiments, cells were either left untreated, infected with ΔHOPEMT asd+YopEi_i$_{38}$-Myc or with ΔHOPEMT asd+YopEi_i$_{38}$-tBid for 30 minutes. Cells were lysed, followed by enzymatic digestion, phosphopetide enrichment and quantification and identification of individual phosphpeptides. We compared cells infected with ΔHOPEMT asd+YopEi$_{i3_8}$-Myc to cells infected with ΔHOPEMT asd+YopE$_{-i3_8}$-tBid, allowing us to identify 363 tBid dependent phosphorylation events. 286 phosphopeptides showed an increase in phosphorylation whereas 77 were less phosphorylated upon tBid delivery, corresponding to 243 different proteins, which we defined as the tBid phosphoproteome. The STRING database was used to create a protein-protein interaction network of the tBid phosphoproteome [93] (FIG. 9 A). Additionally 27 proteins known to be related to mitochondrial apoptosis were added to the network, building a central cluster. Interestingly, only few proteins from the tBid phosphoproteome are connected to this central cluster indicating that many proteins undergo a change in phosphorylation that were so far not directly linked to apoptotic proteins. To characterize the biological functions covered by the tBid phosphoproteome, we performed a gene ontology analysis using the functional annotation tool of the Database for Annotation, Visualization, and Integrated Discovery (DAVID, http://david.abcc.ncifcrf.gov/) [94, 95]. Identified biological functions show that diverse cellular processes are affected by tBid. Many proteins involved in chromatin rearrangement and the regulation of transcription undergo a change in phosphorylation (i.e. CBX3, CBX5, TRIM28, HDAC1). HDAC1 for example is a histone deacetylase playing a role in regulation of transcription. It has been shown that HDAC1 can modulate transcriptional activity of NF-kB, a protein also participating in apoptosis. We additionally identified a cluster of proteins involved in RNA processing which has previously been shown to play an important role in the regulation of apoptosis [96]. FINRPK for instance mediates a p53/TP53 response to DNA damage and is necessary for the induction of apoptosis [97]. Furthermore, the phosphorylation of proteins involved in protein translation is also affected. Several eukaryotic initiation factors (i.e. EIF4E2, EIF4B, EIF3A, EIF4G2) undergo a change in phosphorylation, which is in line with the observation that overall protein synthesis is decreased in apoptotic cells. Interestingly, the phosphorylation of many proteins involved in cytoskeleton remodeling (e.g. PXN, MAP1B9 are altered upon tBid delivery. This is in concordance with the observation that the morphology of cells changes dramatically upon tBid delivery (FIG. 9 B). Cells shrinkage and loss of contact is reflected by the fact that we observe phosphorylation of adhesion related proteins like ZO2 and Paxillin. Similarly, shrinkage of the nuclei is accompanied by phosphorylation of laminar proteins like LaminA/C and Lamin Bl. Altogether, tBID delivery induces a rapid apoptotic response also indicated by rupture of the mitochondrial integrity (FIG. 9 B). We showed that tBid induced apoptosis affects hundreds of phosphorylation events participating in diverse cellular processes. While many identified proteins have been related to apoptosis, only few were known to be phosphorylated upon apoptosis induction. The phosphoproteomic approach thus provides a useful resource for further studies on apoptosis.

LIST OF REFERENCES

1. Gibson, T. J., M. Seiler, and R. A. Veitia (2013) The transience of transient overexpression. Nat Methods. 10: 715-21.
2. Inoue, T., W. D. Heo, J. S. Grimley, T. J. Wandless, and T. Meyer (2005) An inducible translocation strategy to rapidly activate and inhibit small GTPase signaling pathways. Nat Methods. 2: 415-8.
3. Pust, S., H. Hochmann, E. Kaiser, G. von Figura, K. Heine, et al. (2007) A cell-permeable fusion toxin as a tool to study the consequences of actin-ADP-ribosylation caused by the *Salmonella enterica* virulence factor SpvB in intact cells. J Biol Chem. 282: 10272-82.
4. Hayes, C. S., S. K. Aoki, and D. A. Low (2010) Bacterial contact-dependent delivery systems. Annu Rev Genet. 44: 71-90.
5. Cornelis, G. R. (2006) The type III secretion injectisome. Nat Rev Microbiol. 4: 811-25.
6. Michiels, T., P. Wattiau, R. Brasseur, J. M. Ruysschaert, and G. Cornelis (1990) Secretion of Yop proteins by Yersiniae. Infect Immun. 58: 2840-9.
7. Letzelter, M., I. Sorg, L. J. Mota, S. Meyer, J. Stalder, et al. (2006) The discovery of SycO highlights a new function for type III secretion effector chaperones. EMBO J. 25: 3223-33.
8. Gauthier, A., and B. B. Finlay (2003) Translocated intimin receptor and its chaperone interact with ATPase of the type III secretion apparatus of enteropathogenic *Escherichia coli*. J Bacteriol. 185: 6747-55.
9. Wattiau, P., and G. R. Cornelis (1993) SycE, a chaperone-like protein of *Yersinia enterocolitica* involved in the secretion of YopE. Mol Microbiol. 8: 123-3 1.
10. Feldman, M. F., S. Muller, E. Wuest, and G. R. Cornelis (2002) SycE allows secretion of YopE-DHFR hybrids by the *Yersinia enterocolitica* type III Ysc system. Mol Microbiol. 46: 1183-97.
11. Akeda, Y., and J. E. Galan (2005) Chaperone release and unfolding of substrates in type III secretion. Nature. 437: 9 11-5.
12. Pais, S. V., C. Milho, F. Almeida, and L. J. Mota (2013) Identification of novel type III secretion chaperone-substrate complexes of *Chlamydia trachomatis*. PLoS One. 8: e56292.
13. Sory, M. P., and G. R. Cornelis (1994) Translocation of a hybrid YopE-adenylate cyclase from *Yersinia enterocolitica* into HeLa cells. Mol Microbiol. 14: 583-94.
14. Garcia, J. T., F. Ferracci, M. W. Jackson, S. S. Joseph, I. Pattis, et al. (2006) Measurement of effector protein injection by type III and type IV secretion systems by using a 13-residue phosphorylatable glycogen synthase kinase tag. Infect Immun. 74: 5645-57.

15. Chen, L. M., G. Briones, R. O. Donis, and J. E. Galan (2006) Optimization of the delivery of heterologous proteins by the *Salmonella enterica* serovar *Typhimurium* type III secretion system for vaccine development. Infect Immun. 74: 5826-33.
16. Russmann, H., H. Shams, F. Poblete, Y. Fu, J. E. Galan, et al. (1998) Delivery of epitopes by the *Salmonella* type III secretion system for vaccine development. Science. 281: 565-8.
17. Russmann, H., U. Gerdemann, E. I. Igwe, K. Panthel, J. Heesemann, et al. (2003) Attenuated *Yersinia pseudotuberculosis* carrier vaccine for simultaneous antigen-specific CD4 and CD8 T-cell induction. Infect Immun. 71: 3463-72.
18. Chaux, P., R. Luiten, N. Demotte, V. Vantomme, V. Stroobant, et al. (1999) Identification of five MAGE-Al epitopes recognized by cytolytic T lymphocytes obtained by in vitro stimulation with dendritic cells transduced with MAGE-Al. J Immunol. 163: 2928-36.
19. Blanco-Toribio, A., S. Muyldermans, G. Frankel, and L. A. Fernandez (2010) Direct injection of functional single-domain antibodies from *E. coli* into human cells. PLoS One. 5: e15227.
20. Bichsel, C, D. Neeld, T. Hamazaki, L. J. Chang, L. J. Yang, et al. (2013) Direct reprogramming of fibroblasts to myocytes via bacterial injection of MyoD protein. Cell Reprogram. 15: 117-25.
21. Bichsel, C, D. K. Neeld, T. Hamazaki, D. Wu, L. J. Chang, et al. (201 1) Bacterial delivery of nuclear proteins into pluripotent and differentiated cells. PLoS One. 6: e16465.
22. Chamekh, M., A. Phalipon, R. Quertainmont, I. Salmon, P. Sansonetti, et al. (2008) Delivery of biologically active anti-inflammatory cytokines IL-10 and IL-lra in vivo by the *Shigella* type III secretion apparatus. J Immunol. 180: 4292-8.
23. Hoffman, R. M. (201 1) Tumor-seeking *Salmonella* amino acid auxotrophs. Curr Opin Biotechnol. 22: 917-23.
24. Hoang, T. T., S. Williams, H. P. Schweizer, and J. S. Lam (1997) Molecular genetic analysis of the region containing the essential *Pseudomonas aeruginosa* asd gene encoding aspartate-beta-semialdehyde dehydrogenase. Microbiology. 143 (Pt 3): 899-907.
25. Skurnik, M., and H. Wolf-Watz (1989) Analysis of the yopA gene encoding the Yopl virulence determinants of *Yersinia* spp. Mol Microbiol. 3: 517-29.
26. Tertti, R., M. Skurnik, T. Vartio, and P. Kuusela (1992) Adhesion protein YadA of *Yersinia* species mediates binding of bacteria to fibronectin. Infect Immun. 60: 3021-4.
27. Isberg, R. R., and J. M. Leong (1990) Multiple beta 1 chain integrins are receptors for invasin, a protein that promotes bacterial penetration into mammalian cells. Cell. 60: 861-71.
28. Isberg, R. R., D. L. Voorhis, and S. Falkow (1987) Identification of invasin: a protein that allows enteric bacteria to penetrate cultured mammalian cells. Cell. 50: 769-78.
29. Leong, J. M., R. S. Fournier, and R. R. Isberg (1990) Identification of the integrin binding domain of the *Yersinia pseudotuberculosis* invasin protein. EMBO J. 9: 1979-89.
30. Mota, L. J., and G. R. Cornells (2005) The bacterial injection kit: type III secretion systems. Ann Med. 37: 234-49.
31. Trosky, J. E., A. D. Liverman, and K. Orth (2008) *Yersinia* outer proteins: Yops. Cell Microbiol. 10: 557-65.
32. Brenner, D., and T. W. Mak (2009) Mitochondrial cell death effectors. Curr Opin Cell Biol. 21: 871-7.
33. Chalah, A., and R. Khosravi-Far (2008) The mitochondrial death pathway. Adv Exp Med Biol. 615: 25-45.
34. Fuchs, Y., and H. Steller (201 1) Programmed cell death in animal development and disease. Cell. 147: 742-58.
35. Waugh, D. S. (201 1) An overview of enzymatic reagents for the removal of affinity tags. Protein Expr Purif. 80: 283-93.
36. Sarker, M. R., C. Neyt, I. Stainier, and G. R. Cornelis (1998) The *Yersinia* Yop virulon: LcrV is required for extrusion of the translocators YopB and YopD. J Bacteriol. 180: 1207-14.
37. Ramamurthi, K. S., and O. Schneewind (2005) A synonymous mutation in *Yersinia enterocolitica* yopE affects the function of the YopE type III secretion signal. J Bacteriol. 187: 707-15.
38. Wolke, S., N. Ackermann, and J. Heesemann (201 1) The *Yersinia enterocolitica* type 3 secretion system (T3SS) as toolbox for studying the cell biological effects of bacterial Rho GTPase modulating T3SS effector proteins. Cell Microbiol. 13: 1339-57.
39. Forsberg, A., and H. Wolf-Watz (1990) Genetic analysis of the yopE region of *Yersinia* spp.: identification of a novel conserved locus, yerA, regulating yopE expression. J Bacteriol. 172: 1547-55.
40. Sambrook, J. 2001. Molecular cloning: a laboratory manual. D. W. Russell, editor. Cold Spring Harbor Laboratory Press, Cold Spring Harbor, N.Y.
41. Alto, N. M., and J. E. Dixon (2008) Analysis of Rho-GTPase mimicry by a family of bacterial type III effector proteins. Methods Enzymol. 439: 131-43.
42. Alto, N. M., F. Shao, C. S. Lazar, R. L. Brost, G. Chua, et al. (2006) Identification of a bacterial type III effector family with G protein mimicry functions. Cell. 124: 133-45.
43. Kaniga, K., I. Delor, and G. R. Cornelis (1991) A wide-host-range suicide vector for improving reverse genetics in gram-negative bacteria: inactivation of the blaA gene of *Yersinia enterocolitica*. Gene. 109: 137-41.
44. Yoneda, Y., T. Semba, Y. Kaneda, R. L. Noble, Y. Matsuoka, et al. (1992) A long synthetic peptide containing a nuclear localization signal and its flanking sequences of SV40 T-antigen directs the transport of IgM into the nucleus efficiently. Exp Cell Res. 201: 313-20.
45. Cornelis, G. R. 1997. Cross talk between *Yersinia* and eukaryotic cells. In Molecular aspects of host-pathoge interactions. S. MoCRAE, SMYTH, STOW, editor. Cambridge University Press.
46. Metcalf, W. W., W. Jiang, and B. L. Wanner (1994) Use of the rep technique for allele replacement to construct new *Escherichia coli* hosts for maintenance of R6K gamma origin plasmids at different copy numbers. Gene. 138: 1-7.
47. Diepold, A., M. Amstutz, S. Abel, I. Sorg, U. Jenal, et al. (2010) Deciphering the assembly of the *Yersinia* type III secretion injectisome. EMBO J. 29: 1928-40.
48. Iriarte, M., I. Stainier, and G. R. Cornelis (1995) The rpoS gene from *Yersinia enterocolitica* and its influence on expression of virulence factors. Infect Immun. 63: 1840-7.
49. Cornelis, G., J. C. Vanootegem, and C. Sluiters (1987) Transcription of the yop regulon from *Y. enterocolitica* requires trans acting pYV and chromosomal genes. Microb Pathog. 2: 367-79.

50. Grosdent, N., I. Maridonneau-Parini, M. P. Sory, and G. R. Cornelis (2002) Role of Yops and adhesins in resistance of *Yersinia enterocolitica* to phagocytosis. Infect Immun. 70: 4165-76.

51. Dehio, C, M. Meyer, J. Berger, H. Schwarz, and C. Lanz (1997) Interaction of *Bartonella henselae* with endothelial cells results in bacterial aggregation on the cell surface and the subsequent engulfment and internalisation of the bacterial aggregate by a unique structure, the invasome. J Cell Sci. 110 (Pt 18): 2141-54.

52. Westerfield, M. (2000) The Zebrafish Book: A Guide for the Laboratory Use of Zebrafish Danio rerio University of Oregon Press, Eugene, OR p.

53. Kimmel, C. B., W. W. Ballard, S. R. Kimmel, B. Ullmann, and T. F. Schilling (1995) Stages of embryonic development of the zebrafish. Dev Dyn. 203: 253-310.

54. Benard, EX., A. M. van der Sar, F. Ellett, G. J. Lieschke, H. P. Spaink, et al. (2012) Infection of zebrafish embryos with intracellular bacterial pathogens. J Vis Exp.

55. Blum, Y., H. G. Belting, E. EUertsdottir, L. Herwig, F. Luders, et al. (2008) Complex cell rearrangements during intersegmental vessel sprouting and vessel fusion in the zebrafish embryo. Dev Biol. 316: 312-22.

56. Herwig, L., Y. Blum, A. Krudewig, E. EUertsdottir, A. Lenard, et al. (201 1) Distinct cellular mechanisms of blood vessel fusion in the zebrafish embryo. Curr Biol. 21: 1942-8.

57. Carpenter, A. E., T. R. Jones, M. R. Lamprecht, C. Clarke, I. H. Kang, et al. (2006) CellProfiler: image analysis software for identifying and quantifying cell phenotypes. Genome Biol. 7:R100.

58. Bensimon, A., A. Schmidt, Y. Ziv, R. Elkon, S. Y. Wang, et al. (2010) ATM-dependent and -independent dynamics of the nuclear phosphoproteome after DNA damage. Sci Signal. 3: rs3.

59. Perkins, D. N., D. J. Pappin, D. M. Creasy, and J. S. Cottrell (1999) Probability-based protein identification by searching sequence databases using mass spectrometry data. Electrophoresis. 20: 3551-67.

60. Smyth, G. K. (2004) Linear models and empirical bayes methods for assessing differential expression in microarray experiments. Stat Appl Genet Mol Biol. 3: Article3.

61. Ting, L., M. J. Cowley, S. L. Hoon, M. Guilhaus, M. J. Raftery, et al. (2009) Normalization and statistical analysis of quantitative proteomics data generated by metabolic labeling. Mol Cell Proteomics. 8: 2227-42.

62. Vizcaino, J. A., R. G. Cote, A. Csordas, J. A. Dianes, A. Fabregat, et al. (2013) The PRoteomics IDEntifications (PRIDE) database and associated tools: status in 2013. Nucleic Acids Res. 41: D1063-9.

63. Boyd, A. P., I. Lambermont, and G. R. Cornells (2000) Competition between the Yops of *Yersinia enterocolitica* for delivery into eukaryotic cells: role of the SycE chaperone binding domain of YopE. J Bacteriol. 182: 481 1-21.

64. Iriarte, M., and G. R. Cornells (1998) YopT, a new *Yersinia* Yop effector protein, affects the cytoskeleton of host cells. Mol Microbiol. 29: 915-29.

65. Kudryashev, M., M. Stenta, S. Schmelz, M. Amstutz, U. Wiesand, et al. (2013) In situ structural analysis of the *Yersinia enterocolitica* injectisome. Elife. 2: e00792.

66. Schulte, R., G. A. Grassl, S. Preger, S. Fessele, C. A. Jacobi, et al. (2000) *Yersinia enterocolitica* invasin protein triggers IL-8 production in epithelial cells via activation of Rel p65-p65 homodimers. FASEB J. 14: 1471-84.

67. Mota, L. J., L. Journet, I. Sorg, C. Agrain, and G. R. Cornells (2005) Bacterial injectisomes: needle length does matter. Science. 307: 1278.

68. Isaksson, EX., M. Aili, A. Fahlgren, S. E. Carlsson, R. Rosqvist, et al. (2009) The membrane localization domain is required for intracellular localization and autoregulation of YopE in *Yersinia pseudotuberculosis*. Infect Immun. 77: 4740-9.

69. Denecker, G., S. Totemeyer, L. J. Mota, P. Troisfontaines, I. Lambermont, et al. (2002) Effect of low- and high-virulence *Yersinia enterocolitica* strains on the inflammatory response of human umbilical vein endothelial cells. Infect Immun. 70: 3510-20.

70. Sharma, S., A. Hirabuchi, K. Yoshida, K. Fujisaki, A. Ito, et al. (2013) Deployment of the *Burkholderia glumae* type III secretion system as an efficient tool for translocating pathogen effectors to monocot cells. Plant J. 74: 701-12.

71. Carrington, J. C., and W. G. Dougherty (1988) A viral cleavage site cassette: identification of amino acid sequences required for tobacco etch virus polyprotein processing. Proc Natl Acad Sci USA. 85: 3391-5.

72. Kapust, R. B., J. Tozser, T. D. Copeland, and D. S. Waugh (2002) The PF specificity of tobacco etch virus protease. Biochem Biophys Res Commun. 294: 949-55.

73. Liang, H., H. Gao, C. A. Maynard, and W. A. Powell (2005) Expression of a self-processing, pathogen resistance-enhancing gene construct in *Arabidopsis*. Biotechnol Lett. 27: 435-42.

74. Weber, W., C. Fux, M. Daoud-el Baba, B. Keller, C. C. Weber, et al. (2002) Macrolide-based transgene control in mammalian cells and mice. Nat Biotechnol. 20: 901-7.

75. Kapust, R. B., J. Tozser, J. D. Fox, D. E. Anderson, S. Cherry, et al. (2001) Tobacco etch virus protease: mechanism of autolysis and rational design of stable mutants with wild-type catalytic proficiency. Protein Eng. 14: 993-1000.

76. Lee, V. T., D. M. Anderson, and O. Schneewind (1998) Targeting of *Yersinia* Yop proteins into the cytosol of HeLa cells: one-step translocation of YopE across bacterial and eukaryotic membranes is dependent on SycE chaperone. Mol Microbiol. 28: 593-601.

77. Gray, D. C., S. Mahrus, and J. A. Wells (2010) Activation of specific apoptotic caspases with an engineered small-molecule-activated protease. Cell. 142: 637-46.

78. Henrichs, T., N. Mikhaleva, C. Conz, E. Deuerling, D. Boyd, et al. (2005) Target-directed proteolysis at the ribosome. Proc Natl Acad Sci USA. 102: 4246-51.

79. Hardt, W. D., L. M. Chen, K. E. Schuebel, X. R. Bustelo, and J. E. Galan (1998) *S. typhimurium* encodes an activator of Rho GTPases that induces membrane ruffling and nuclear responses in host cells. Cell. 93: 815-26.

80. Hakansson, S., K. Schesser, C. Persson, E. E. Galyov, R. Rosqvist, et al. (1996) The YopB protein of *Yersinia pseudotuberculosis* is essential for the translocation of Yop effector proteins across the target cell plasma membrane and displays a contact-dependent membrane disrupting activity. EMBO J. 15: 5812-23.

81. Stebbins, C. E., and J. E. Galan (2001) Structural mimicry in bacterial virulence. Nature. 412: 701-5.

82. Li, FL, H. Xu, Y. Zhou, J. Zhang, C. Long, et al. (2007) The phosphothreonine lyase activity of a bacterial type III effector family. Science. 315: 1000-3.

83. Norris, F. A., M. P. Wilson, T. S. Wallis, E. E. Galyov, and P. W. Majerus (1998) SopB, a protein required for virulence of *Salmonella* dublin, is an inositol phosphate phosphatase. Proc Natl Acad Sci USA. 95: 14057-9.

84. Pulliainen, A. T., K. Pieles, C. S. Brand, B. Hauert, A. Bohm, et al. (2012) Bacterial effector binds host cell adenylyl cyclase to potentiate Galphas-dependent cAMP production. Proc Natl Acad Sci USA. 109: 9581-6.
85. Li, FL, H. Zhu, C. J. Xu, and J. Yuan (1998) Cleavage of BID by caspase 8 mediates the mitochondrial damage in the Fas pathway of apoptosis. Cell. 94: 491-501.
86. Nagaraj, N., J. R. Wisniewski, T. Geiger, J. Cox, M. Kircher, et al. (201 1) Deep proteome and transcriptome mapping of a human cancer cell line. Mol Syst Biol. 7: 548.
87. Caussinus, E., O. Kanca, and M. Affolter (201 1) Fluorescent fusion protein knockout mediated by anti-GFP nanobody. Nat Struct Mol Biol. 19: 117-21.
88. Cosma, C. L., L. E. Swaim, H. Volkman, L. Ramakrishnan, and J. M. Davis (2006) Zebrafish and frog models of *Mycobacterium marinum* infection. Curr Protoc Microbiol. Chapter 10: Unit 10B 2.
89. Mathias, J. R., M. E. Dodd, K. B. Walters, S. K. Yoo, E. A. Ranheim, et al. (2009) Characterization of zebrafish larval inflammatory macrophages. Dev Comp Immunol. 33: 1212-7.
90. Jette, C. A., A. M. Flanagan, J. Ryan, U. J. Pyati, S. Carbonneau, et al. (2008) BIM and other BCL-2 family proteins exhibit cross-species conservation of function between zebrafish and mammals. Cell Death Differ. 15: 1063-72.
91. Olsen, J. V., B. Blagoev, F. Gnad, B. Macek, C. Kumar, et al. (2006) Global, in vivo, and site-specific phosphorylation dynamics in signaling networks. Cell. 127: 635-48.
92. Schmutz, C, E. Ahrne, C. A. Kasper, T. Tschon, I. Sorg, et al. (2013) Systems-Level Overview of Host Protein Phosphorylation During *Shigella flexneri* Infection Revealed by Phosphoproteomics. Mol Cell Proteomics. 12: 2952-68.
93. Szklarczyk, D., A. Franceschini, M. Kuhn, M. Simonovic, A. Roth, et al. (201 1) The STRING database in 201 1: functional interaction networks of proteins, globally integrated and scored. Nucleic Acids Res. 39: D561-8.
94. Huang da, W., B. T. Sherman, and R. A. Lempicki (2009) Bioinformatics enrichment tools: paths toward the comprehensive functional analysis of large gene lists. Nucleic Acids Res. 37: 1-13.
95. Huang da, W., B. T. Sherman, R. Stephens, M. W. Baseler, H. C. Lane, et al. (2008) DAVID gene ID conversion tool. Bioinformation. 2: 428-30.
96. Schwerk, C, and K. Schulze-Osthoff (2005) Regulation of apoptosis by alternative pre-mRNA splicing. Mol Cell. 19: 1-13.
97. Papagiannakopoulos, T., A. Shapiro, and K. S. Kosik (2008) MicroRNA-21 targets a network of key tumor-suppressive pathways in glioblastoma cells. Cancer Res. 68: 8164-72.
98. Hoiseth, S. K., B. A. Stocker (1981) Aromatic-dependent *Salmonella typhimurium* are non-virulent and effective as live vaccines. Nature 291:238-239.

The invention claimed is:

1. A recombinant Gram-negative bacterial strain transformed with a vector which comprises in the 5' to 3' direction:

a promoter;

a first DNA sequence encoding a delivery signal from a bacterial T3SS effector protein, operably linked to said promoter; and a second DNA sequence encoding a heterologous protein fused in frame to the 3'end of said first DNA sequence, wherein the heterologous protein is involved in apoptosis or apoptosis regulation and is selected from the group consisting of BH3-only proteins, caspases and intracellular signalling proteins of death receptor control of apoptosis, wherein the recombinant Gram-negative bacterial strain is a *Yersinia* strain and the delivery signal from the bacterial T3SS effector protein encoded by the first DNA sequence comprises the YopE effector protein or an N-terminal fragment thereof.

2. The recombinant Gram-negative bacterial strain of claim 1, wherein the vector comprises a third DNA sequence encoding a protease cleavage site, wherein the third DNA sequence is located between the 3'end of said first DNA sequence and the 5'end of said second DNA sequence.

3. The recombinant Gram-negative bacterial strain of claim 1, wherein the recombinant Gram-negative bacterial strain is a *Yersinia* strain and wherein said *Yersinia* strain is wild type or deficient in the production of at least one T3SS effector protein and wherein the delivery signal from the bacterial T3SS effector protein comprises the N-terminal 138 amino acids of the *Y. enterocolitica* YopE effector protein.

4. The recombinant Gram-negative bacterial strain of claim 1, wherein the Gram-negative bacterial strain is deficient to produce adhesion proteins binding to a eukaryotic cell surface or extracellular matrix.

5. A vector which comprises in the 5' to 3' direction:

a promoter;

a first DNA sequence encoding a delivery signal from a bacterial T3SS effector protein, operably linked to said promoter;

a second DNA sequence encoding a heterologous protein fused in frame to the 3'end of said first DNA sequence, wherein the heterologous protein is involved in apoptosis or apoptosis regulation and is selected from the group consisting of BH3-only proteins, caspases and intracellular signalling proteins of death receptor control of apoptosis.

6. A recombinant Gram-negative bacterial strain transformed with a vector which comprises in the 5' to 3' direction:

a promoter;

a first DNA sequence encoding a delivery signal from a bacterial T3SS effector protein, operably linked to said promoter; and two second DNA sequences fused in frame to the 3'end of said first DNA sequence, wherein the two second DNA sequences encode two identical heterologous proteins or two different heterologous proteins, wherein both heterologous proteins are proteins involved in apoptosis or apoptosis regulation and wherein one protein is a pro-apoptotic protein and the other protein is an inhibitor of apoptosis-prevention pathways or wherein one protein is a pro-apoptotic protein and the other protein is an inhibitor of pro-survival signalling or pathways, wherein the recombinant Gram-negative bacterial strain is a *Yersinia* strain and the delivery signal from the bacterial T3SS effector protein encoded by the first DNA sequence comprises the YopE effector protein or an N-terminal fragment thereof.

7. The recombinant Gram-negative bacterial strain of claim 1, wherein the delivery signal from the bacterial T3SS effector protein encoded by the first DNA sequence comprises the bacterial T3SS effector protein or an N-terminal fragment thereof, wherein the N-terminal fragment thereof includes at least the first 10 amino acids of the bacterial T3SS effector protein.

8. A method for delivering a heterologous protein into a eukaryotic cell comprising the following steps:

i) culturing the Gram-negative bacterial strain of claim 1; and ii) contacting a eukaryotic cell with the Gram-negative bacterial strain of i), wherein a fusion protein which comprises a delivery signal from a bacterial T3SS effector protein and the heterologous protein is expressed by the Gram-negative bacterial strain and is translocated into the eukaryotic cell.

9. A method of purifying a heterologous protein comprising:

culturing the Gram-negative bacterial strain of claim 1 so that a fusion protein which comprises a delivery signal from a bacterial T3SS effector protein and the heterologous protein is expressed and secreted into the supernatant of the culture.

10. The recombinant Gram-negative bacterial strain of claim 1 for use in the delivery of a heterologous protein as a medicament or as a vaccine to a subject.

11. The vector of claim 5, further comprising a third DNA sequence encoding a protease cleavage site, wherein the third DNA sequence is located between the 3'end of said first DNA sequence and the 5'end of said second DNA sequence.

* * * * *

```
                        SEQUENCE LISTING

<160> NUMBER OF SEQ ID NOS: 199

<210> SEQ ID NO 1
<211> LENGTH: 219
<212> TYPE: PRT
<213> ORGANISM: Yersinia enterocolitica

<400> SEQUENCE: 1

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Gly Ser Gly Pro Leu Arg
        130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175
```

```
Pro Phe Ser Gln Trp Gly Thr Val Gly Gly Ala Ala Ser Ala Tyr Val
                180                 185                 190

Ala Ser Gly Val Asp Leu Thr Gln Ala Ala Asn Glu Ile Lys Gly Leu
            195                 200                 205

Gly Gln Gln Met Gln Gln Leu Leu Ser Leu Met
        210                 215

<210> SEQ ID NO 2
<211> LENGTH: 138
<212> TYPE: PRT
<213> ORGANISM: Yersinia enterocolitica

<400> SEQUENCE: 2

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Ph

Leu Gln Lys Asn His Asp Gln Phe Ala Thr Leu Glu Ser Arg Phe Glu
130                 135                 140

Lys Leu Gly Pro Glu Gln Lys Leu Ile Ser Glu Glu Asp Leu Asn Ser
145                 150                 155                 160

Ala Val Asp His His His His His His
                165

<210> SEQ ID NO 4
<211> LENGTH: 348
<212> TYPE: PRT
<213> ORGANISM: Artificial Sequence
<220> FEATURE:
<223> OTHER INFORMATION: YopE1-138 - IpgB1

<400> SEQUENCE: 4

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
                35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
                115                 120                 125

Leu Gln Lys Asn His Asp Gln Phe Ala Thr Leu Glu Met Gln Ile Leu
130                 135                 140

Asn Lys Ile Leu Pro Gln Val Glu Phe Ala Ile Pro Arg Pro Ser Phe
145                 150                 155                 160

Asp Ser Leu Ser Arg Asn Lys Leu Val Lys Ile Leu Ser Val Phe
                165                 170                 175

Asn Leu Lys Gln Arg Phe Pro Gln Lys Asn Phe Gly Cys Pro Val Asn
                180                 185                 190

Ile Asn Lys Ile Arg Asp Ser Val Ile Asp Lys Ile Lys Asp Ser Asn
                195                 200                 205

Ser Gly Asn Gln Leu Phe Cys Trp Met Ser Gln Glu Arg Thr Thr Tyr
    210                 215                 220

Val Ser Ser Met Ile Asn Arg Ser Ile Asp Glu Met Ala Ile His Asn
225                 230                 235                 240

Gly Val Val Leu Thr Ser Asp Asn Lys Arg Asn Ile Phe Ala Ala Ile
                245                 250                 255

Glu Lys Lys Phe Pro Asp Ile Lys Leu Asp Glu Lys Ser Ala Gln Thr
                260                 265                 270

Ser Ile Ser His Thr Ala Leu Asn Glu Ile Ala Ser Ser Gly Leu Arg
                275                 280                 285

Ala Lys Ile Leu Lys Arg Tyr Ser Ser Asp Met Asp Leu Phe Asn Thr
                290                 295                 300

Gln Met Lys Asp Leu Thr Asn Leu Val Ser Ser Val Tyr Asp Lys
305                 310                 315                 320

```
Ile Phe Asn Glu Ser Thr Lys Val Leu Gln Ile Glu Ile Ser Ala Glu
            325                 330                 335

Val Leu Lys Ala Val Tyr Arg Gln Ser Asn Thr Asn
            340                 345

<210> SEQ ID NO 5
<211> LENGTH: 380
<212> TYPE: PRT
<213> ORGANISM: Artificial Sequence
<220> FEATURE:
<223> OTHER INFORMATION: YopE1-138 - SopE

<400> SEQUENCE: 5

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Val Thr Asn Ile
    130                 135                 140

Thr Leu Ser Thr Gln His Tyr Arg Ile His Arg Ser Asp Val Glu Pro
145                 150                 155                 160

Val Lys Glu Lys Thr Thr Glu Lys Asp Ile Phe Ala Lys Ser Ile Thr
                165                 170                 175

Ala Val Arg Asn Ser Phe Ile Ser Leu Ser Thr Ser Leu Ser Asp Arg
            180                 185                 190

Phe Ser Leu His Gln Gln Thr Asp Ile Pro Thr Thr His Phe His Arg
        195                 200                 205

Gly Asn Ala Ser Glu Gly Arg Ala Val Leu Thr Ser Lys Thr Val Lys
    210                 215                 220

Asp Phe Met Leu Gln Lys Leu Asn Ser Leu Asp Ile Lys Gly Asn Ala
225                 230                 235                 240

Ser Lys Asp Pro Ala Tyr Ala Arg Gln Thr Cys Glu Ala Ile Leu Ser
                245                 250                 255

Ala Val Tyr Ser Asn Asn Lys Asp Gln Cys Cys Lys Leu Leu Ile Ser
            260                 265                 270

Lys Gly Val Ser Ile Thr Pro Phe Leu Lys Glu Ile Gly Glu Ala Ala
        275                 280                 285

Gln Asn Ala Gly Leu Pro Gly Glu Ile Lys Asn Gly Val Phe Thr Pro
    290                 295                 300

Gly Gly Ala Gly Ala Asn Pro Phe Val Val Pro Leu Ile Ala Ser Ala
305                 310                 315                 320

Ser Ile Lys Tyr Pro His Met Phe Ile Asn His Asn Gln Gln Val Ser
                325                 330                 335
```

Phe Lys Ala Tyr Ala Glu Lys Ile Val Met Lys Glu Val Thr Pro Leu
                340                 345                 350

Phe Asn Lys Gly Thr Met Pro Thr Pro Gln Gln Phe Gln Leu Thr Ile
                355                 360                 365

Glu Asn Ile Ala Asn Lys Tyr Leu Gln Asn Ala Ser
            370                 375                 380

<210> SEQ ID NO 6
<211> LENGTH: 701
<212> TYPE: PRT
<213> ORGANISM: Artificial Sequence
<220> FEATURE:
<223> OTHER INFORMATION: YopE1-138 - SopB

<400> SEQUENCE: 6

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
                35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
                115                 120                 125

Leu Gln Lys Asn His Asp Gln Phe Ala Thr Leu Glu Met Gln Ile Gln
        130                 135                 140

Ser Phe Tyr His Ser Ala Ser Leu Lys Thr Gln Glu Ala Phe Lys Ser
145                 150                 155                 160

Leu Gln Lys Thr Leu Tyr Asn Gly Met Gln Ile Leu Ser Gly Gln Gly
                165                 170                 175

Lys Ala Pro Ala Lys Ala Pro Asp Ala Arg Pro Glu Ile Ile Val Leu
                180                 185                 190

Arg Glu Pro Gly Ala Thr Trp Gly Asn Tyr Leu Gln His Gln Lys Ala
                195                 200                 205

Ser Asn His Ser Leu His Asn Leu Tyr Asn Leu Gln Arg Asp Leu Leu
        210                 215                 220

Thr Val Ala Ala Thr Val Leu Gly Lys Gln Asp Pro Val Leu Thr Ser
225                 230                 235                 240

Met Ala Asn Gln Met Glu Leu Ala Lys Val Lys Ala Asp Arg Pro Ala
                245                 250                 255

Thr Lys Gln Glu Glu Ala Ala Lys Ala Leu Lys Lys Asn Leu Ile
                260                 265                 270

Glu Leu Ile Ala Ala Arg Thr Gln Gln Asp Gly Leu Pro Ala Lys
        275                 280                 285

Glu Ala His Arg Phe Ala Ala Val Ala Phe Arg Asp Ala Gln Val Lys
        290                 295                 300

Gln Leu Asn Asn Gln Pro Trp Gln Thr Ile Lys Asn Thr Leu Thr His
305                 310                 315                 320

```
Asn Gly His His Tyr Thr Asn Thr Gln Leu Pro Ala Ala Glu Met Lys
            325                 330                 335

Ile Gly Ala Lys Asp Ile Phe Pro Ser Ala Tyr Glu Gly Lys Gly Val
        340                 345                 350

Cys Ser Trp Asp Thr Lys Asn Ile His His Ala Asn Asn Leu Trp Met
            355                 360                 365

Ser Thr Val Ser Val His Glu Asp Gly Lys Asp Lys Thr Leu Phe Cys
370                 375                 380

Gly Ile Arg His Gly Val Leu Ser Pro Tyr His Glu Lys Asp Pro Leu
385                 390                 395                 400

Leu Arg His Val Gly Ala Glu Asn Lys Ala Lys Glu Val Leu Thr Ala
            405                 410                 415

Ala Leu Phe Ser Lys Pro Glu Leu Leu Asn Lys Ala Leu Ala Gly Glu
        420                 425                 430

Ala Val Ser Leu Lys Leu Val Ser Val Gly Leu Leu Thr Ala Ser Asn
            435                 440                 445

Ile Phe Gly Lys Glu Gly Thr Met Val Glu Asp Gln Met Arg Ala Trp
        450                 455                 460

Gln Ser Leu Thr Gln Pro Gly Lys Met Ile His Leu Lys Ile Arg Asn
465                 470                 475                 480

Lys Asp Gly Asp Leu Gln Thr Val Lys Ile Lys Pro Asp Val Ala Ala
            485                 490                 495

Phe Asn Val Gly Val Asn Glu Leu Ala Leu Lys Leu Gly Phe Gly Leu
        500                 505                 510

Lys Ala Ser Asp Ser Tyr Asn Ala Glu Ala Leu His Gln Leu Leu Gly
            515                 520                 525

Asn Asp Leu Arg Pro Glu Ala Arg Pro Gly Gly Trp Val Gly Glu Trp
530                 535                 540

Leu Ala Gln Tyr Pro Asp Asn Tyr Glu Val Val Asn Thr Leu Ala Arg
545                 550                 555                 560

Gln Ile Lys Asp Ile Trp Lys Asn Asn Gln His His Lys Asp Gly Gly
            565                 570                 575

Glu Pro Tyr Lys Leu Ala Gln Arg Leu Ala Met Leu Ala His Glu Ile
        580                 585                 590

Asp Ala Val Pro Ala Trp Asn Cys Lys Ser Gly Lys Asp Arg Thr Gly
            595                 600                 605

Met Met Asp Ser Glu Ile Lys Arg Glu Ile Ile Ser Leu His Gln Thr
        610                 615                 620

His Met Leu Ser Ala Pro Gly Ser Leu Pro Asp Ser Gly Gly Gln Lys
625                 630                 635                 640

Ile Phe Gln Lys Val Leu Leu Asn Ser Gly Asn Leu Glu Ile Gln Lys
            645                 650                 655

Gln Asn Thr Gly Gly Ala Gly Asn Lys Val Met Lys Asn Leu Ser Pro
        660                 665                 670

Glu Val Leu Asn Leu Ser Tyr Gln Lys Arg Val Gly Asp Glu Asn Ile
            675                 680                 685

Trp Gln Ser Val Lys Gly Ile Ser Ser Leu Ile Thr Ser
        690                 695                 700

<210> SEQ ID NO 7
<211> LENGTH: 383
<212> TYPE: PRT
<213> ORGANISM: Artificial Sequence
<220> FEATURE:
<223> OTHER INFORMATION: YopE1-138 - OspF
```

<400> SEQUENCE: 7

```
Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Glu Arg Leu Ser
    50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Ser Arg Phe Glu
    130                 135                 140

Met Pro Ile Lys Lys Pro Cys Leu Lys Leu Asn Leu Asp Ser Leu Asn
145             150                 155                 160

Val Val Arg Ser Glu Ile Pro Gln Met Leu Ser Ala Asn Glu Arg Leu
                165                 170                 175

Lys Asn Asn Phe Asn Ile Leu Tyr Asn Gln Ile Arg Gln Tyr Pro Ala
            180                 185                 190

Tyr Tyr Phe Lys Val Ala Ser Asn Val Pro Thr Tyr Ser Asp Ile Cys
        195                 200                 205

Gln Ser Phe Ser Val Met Tyr Gln Gly Phe Gln Ile Val Asn His Ser
    210                 215                 220

Gly Asp Val Phe Ile His Ala Cys Arg Glu Asn Pro Gln Ser Lys Gly
225                 230                 235                 240

Asp Phe Val Gly Asp Lys Phe His Ile Ser Ile Ala Arg Glu Gln Val
            245                 250                 255

Pro Leu Ala Phe Gln Ile Leu Ser Gly Leu Leu Phe Ser Glu Asp Ser
            260                 265                 270

Pro Ile Asp Lys Trp Lys Ile Thr Asp Met Asn Arg Val Ser Gln Gln
            275                 280                 285

Ser Arg Val Gly Ile Gly Ala Gln Phe Thr Leu Tyr Val Lys Ser Asp
    290                 295                 300

Gln Glu Cys Ser Gln Tyr Ser Ala Leu Leu Leu His Lys Ile Arg Gln
305                 310                 315                 320

Phe Ile Met Cys Leu Glu Ser Asn Leu Leu Arg Ser Lys Ile Ala Pro
                325                 330                 335

Gly Glu Tyr Pro Ala Ser Asp Val Arg Pro Glu Asp Trp Lys Tyr Val
            340                 345                 350

Ser Tyr Arg Asn Glu Leu Arg Ser Asp Arg Asp Gly Ser Glu Arg Gln
    355                 360                 365

Glu Gln Met Leu Arg Glu Glu Pro Phe Tyr Arg Leu Met Ile Glu
370                 375                 380
```

<210> SEQ ID NO 8
<211> LENGTH: 685
<212> TYPE: PRT

<210> ORGANISM: Artificial Sequence
<220> FEATURE:
<223> OTHER INFORMATION: YopE1-138 - SptP

<400> SEQUENCE: 8

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Leu
    130                 135                 140

Lys Tyr Glu Glu Arg Lys Leu Asn Asn Leu Thr Leu Ser Ser Phe Ser
145                 150                 155                 160

Lys Val Gly Val Ser Asn Asp Ala Arg Leu Tyr Ile Ala Lys Glu Asn
                165                 170                 175

Thr Asp Lys Ala Tyr Val Ala Pro Glu Lys Phe Ser Ser Lys Val Leu
            180                 185                 190

Thr Trp Leu Gly Lys Met Pro Leu Phe Lys Asn Thr Glu Val Val Gln
        195                 200                 205

Lys His Thr Glu Asn Ile Arg Val Gln Asp Gln Lys Ile Leu Gln Thr
    210                 215                 220

Phe Leu His Ala Leu Thr Glu Lys Tyr Gly Glu Thr Ala Val Asn Asp
225                 230                 235                 240

Ala Leu Leu Met Ser Arg Ile Asn Met Asn Lys Pro Leu Thr Gln Arg
                245                 250                 255

Leu Ala Val Gln Ile Thr Glu Cys Val Lys Ala Ala Asp Glu Gly Phe
            260                 265                 270

Ile Asn Leu Ile Lys Ser Lys Asp Asn Val Gly Val Arg Asn Ala Ala
        275                 280                 285

Leu Val Ile Lys Gly Gly Asp Thr Lys Val Ala Glu Lys Asn Asn Asp
    290                 295                 300

Val Gly Ala Glu Ser Lys Gln Pro Leu Leu Asp Ile Ala Leu Lys Gly
305                 310                 315                 320

Leu Lys Arg Thr Leu Pro Gln Leu Glu Gln Met Asp Gly Asn Ser Leu
                325                 330                 335

Arg Glu Asn Phe Gln Glu Met Ala Ser Gly Asn Gly Pro Leu Arg Ser
            340                 345                 350

Leu Met Thr Asn Leu Gln Asn Leu Asn Lys Ile Pro Glu Ala Lys Gln
        355                 360                 365

Leu Asn Asp Tyr Val Thr Thr Leu Thr Asn Ile Gln Val Gly Val Ala
    370                 375                 380

Arg Phe Ser Gln Trp Gly Thr Cys Gly Gly Glu Val Glu Arg Trp Val
```

```
            385                 390                 395                 400
Asp Lys Ala Ser Thr His Glu Leu Thr Gln Ala Val Lys Lys Ile His
                    405                 410                 415

Val Ile Ala Lys Glu Leu Lys Asn Val Thr Ala Glu Leu Glu Lys Ile
                420                 425                 430

Glu Ala Gly Ala Pro Met Pro Gln Thr Met Ser Gly Pro Thr Leu Gly
            435                 440                 445

Leu Ala Arg Phe Ala Val Ser Ser Ile Pro Ile Asn Gln Gln Thr Gln
        450                 455                 460

Val Lys Leu Ser Asp Gly Met Pro Val Pro Val Asn Thr Leu Thr Phe
465                 470                 475                 480

Asp Gly Lys Pro Val Ala Leu Ala Gly Ser Tyr Pro Lys Asn Thr Pro
                485                 490                 495

Asp Ala Leu Glu Ala His Met Lys Met Leu Leu Glu Lys Glu Cys Ser
            500                 505                 510

Cys Leu Val Val Leu Thr Ser Glu Asp Gln Met Gln Ala Lys Gln Leu
        515                 520                 525

Pro Pro Tyr Phe Arg Gly Ser Tyr Thr Phe Gly Glu Val His Thr Asn
    530                 535                 540

Ser Gln Lys Val Ser Ser Ala Ser Gln Gly Glu Ala Ile Asp Gln Tyr
545                 550                 555                 560

Asn Met Gln Leu Ser Cys Gly Glu Lys Arg Tyr Thr Ile Pro Val Leu
                565                 570                 575

His Val Lys Asn Trp Pro Asp His Gln Pro Leu Pro Ser Thr Asp Gln
            580                 585                 590

Leu Glu Tyr Leu Ala Asp Arg Val Lys Asn Ser Asn Gln Asn Gly Ala
        595                 600                 605

Pro Gly Arg Ser Ser Asp Lys His Leu Pro Met Ile His Cys Leu
    610                 615                 620

Gly Gly Val Gly Arg Thr Gly Thr Met Ala Ala Ala Leu Val Leu Lys
625                 630                 635                 640

Asp Asn Pro His Ser Asn Leu Glu Gln Val Arg Ala Asp Phe Arg Asp
                645                 650                 655

Ser Arg Asn Asn Arg Met Leu Glu Asp Ala Ser Gln Phe Val Gln Leu
            660                 665                 670

Lys Ala Met Gln Ala Gln Leu Leu Met Thr Thr Ala Ser
        675                 680                 685

<210> SEQ ID NO 9
<211> LENGTH: 678
<212> TYPE: PRT
<213> ORGANISM: Artificial Sequence
<220> FEATURE:
<223> OTHER INFORMATION: YopE1-138 - IpgD

<400> SEQUENCE: 9

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
```

```
                65                  70                  75                  80
Gly Ser His Lys Pro Val Val Thr Pro Ala Leu Thr Pro Ala Gln Met
                        85                  90                  95
Pro Ser Pro Thr Ser Phe Ser Asp Ser Ile Lys Gln Leu Ala Ala Glu
                100                 105                 110
Thr Leu Pro Lys Tyr Met Gln Gln Leu Ser Ser Leu Asp Ala Glu Thr
                115                 120                 125
Leu Gln Lys Asn His Asp Gln Phe Ala Thr Leu Glu Met His Ile Thr
        130                 135                 140
Asn Leu Gly Leu His Gln Val Ser Phe Gln Ser Gly Asp Ser Tyr Lys
145                 150                 155                 160
Gly Ala Glu Glu Thr Gly Lys His Lys Gly Val Ser Val Ile Ser Tyr
                    165                 170                 175
Gln Arg Val Lys Asn Gly Glu Arg Asn Lys Gly Ile Glu Ala Leu Asn
                180                 185                 190
Arg Leu Tyr Leu Gln Asn Gln Thr Ser Leu Thr Gly Lys Ser Leu Leu
            195                 200                 205
Phe Ala Arg Asp Lys Ala Glu Val Phe Cys Glu Ala Ile Lys Leu Ala
        210                 215                 220
Gly Gly Asp Thr Ser Lys Ile Lys Ala Met Met Glu Arg Leu Asp Thr
225                 230                 235                 240
Tyr Lys Leu Gly Glu Val Asn Lys Arg His Ile Asn Glu Leu Asn Lys
                    245                 250                 255
Val Ile Ser Glu Glu Ile Arg Ala Gln Leu Gly Ile Lys Asn Lys Lys
                260                 265                 270
Glu Leu Gln Thr Lys Ile Lys Gln Ile Phe Thr Asp Tyr Leu Asn Asn
            275                 280                 285
Lys Asn Trp Gly Pro Val Asn Lys Asn Ile Ser His His Gly Lys Asn
        290                 295                 300
Tyr Ser Phe Gln Leu Thr Pro Ala Ser His Met Lys Ile Gly Asn Lys
305                 310                 315                 320
Asn Ile Phe Val Lys Glu Tyr Asn Gly Lys Gly Ile Cys Cys Ala Ser
                    325                 330                 335
Thr Arg Glu Arg Asp His Ile Ala Asn Met Trp Leu Ser Lys Val Val
                340                 345                 350
Asp Asp Glu Gly Lys Glu Ile Phe Ser Gly Ile Arg His Gly Val Ile
            355                 360                 365
Ser Ala Tyr Gly Leu Lys Lys Asn Ser Ser Glu Arg Ala Val Ala Ala
        370                 375                 380
Arg Asn Lys Ala Glu Glu Leu Val Ser Ala Ala Leu Tyr Ser Arg Pro
385                 390                 395                 400
Glu Leu Leu Ser Gln Ala Leu Ser Gly Lys Thr Val Asp Leu Lys Ile
                    405                 410                 415
Val Ser Thr Ser Leu Leu Thr Pro Thr Ser Leu Thr Gly Gly Glu Glu
                420                 425                 430
Ser Met Leu Lys Asp Gln Val Ser Ala Leu Lys Gly Leu Asn Ser Lys
            435                 440                 445
Arg Gly Gly Pro Thr Lys Leu Leu Ile Arg Asn Ser Asp Gly Leu Leu
        450                 455                 460
Lys Glu Val Ser Val Asn Leu Lys Val Val Thr Phe Asn Phe Gly Val
465                 470                 475                 480
Asn Glu Leu Ala Leu Lys Met Gly Leu Gly Trp Arg Asn Val Asp Lys
                    485                 490                 495
```

```
Leu Asn Asp Glu Ser Ile Cys Ser Leu Leu Gly Asp Asn Phe Leu Lys
            500                 505                 510

Asn Gly Val Ile Gly Gly Trp Ala Glu Ala Ile Glu Lys Asn Pro
        515                 520                 525

Pro Cys Lys Asn Asp Val Ile Tyr Leu Ala Asn Gln Ile Lys Glu Ile
        530                 535                 540

Val Asn Asn Lys Leu Gln Lys Asn Asp Asn Gly Glu Pro Tyr Lys Leu
545                 550                 555                 560

Ser Gln Arg Val Thr Leu Leu Ala Tyr Thr Ile Gly Ala Val Pro Cys
                565                 570                 575

Trp Asn Cys Lys Ser Gly Lys Asp Arg Thr Gly Met Gln Asp Ala Glu
            580                 585                 590

Ile Lys Arg Glu Ile Ile Arg Lys His Glu Thr Gly Gln Phe Ser Gln
            595                 600                 605

Leu Asn Ser Lys Leu Ser Ser Glu Glu Lys Arg Leu Phe Ser Thr Ile
            610                 615                 620

Leu Met Asn Ser Gly Asn Met Glu Ile Gln Glu Met Asn Thr Gly Val
625                 630                 635                 640

Pro Gly Asn Lys Val Met Lys Lys Leu Pro Leu Ser Ser Leu Glu Leu
                645                 650                 655

Ser Tyr Ser Glu Arg Ile Gly Asp Pro Lys Ile Trp Asn Met Val Lys
                660                 665                 670

Gly Tyr Ser Ser Phe Val
            675

<210> SEQ ID NO 10
<211> LENGTH: 446
<212> TYPE: PRT
<213> ORGANISM: Artificial Sequence
<220> FEATURE:
<223> OTHER INFORMATION: YopE1-138 - BepA

<400> SEQUENCE: 10

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Pro
    130                 135                 140

Lys Ala Lys Ala Lys Thr Lys Asn Thr Glu Ile Ile Ser Pro His His
145                 150                 155                 160

Tyr Val Tyr Pro Asn Thr Thr Thr Leu Lys Asn Lys Tyr Gly Ile Lys
                165                 170                 175
```

Asn Leu Asn Ala Phe Leu Glu Lys Cys Ser His Asp Thr Ala Lys Ala
            180                 185                 190

Met Ile Asn Leu Arg Glu Glu Ser Leu Pro Glu Tyr Phe Asp Thr Ala
        195                 200                 205

Tyr Leu Cys His Ile His Gln Gln Leu Phe Lys Asn Thr Phe Glu Trp
    210                 215                 220

Ala Gly Tyr Leu Arg His Ile Pro Phe Thr Phe Ala Asp Gly Thr Thr
225                 230                 235                 240

Ala Ala Met Pro Glu Met Lys Arg Thr Gly Trp Lys Asn Ala Phe Ala
                245                 250                 255

Ile Gly Asp Glu Ile Gln Glu Gly Leu Gln Arg Leu Asp Gln Thr Leu
            260                 265                 270

Ala Glu Lys Asn Asn Leu Gln Gly Leu Thr Arg Glu Glu Phe Asn Ser
        275                 280                 285

Glu Ala Ile Glu Leu Phe Asn Ser Leu Asn Gln Leu His Pro Phe Arg
    290                 295                 300

Glu Gly Asn Gly Arg Thr Gln Arg Leu Phe Phe Glu Asn Leu Ala Lys
305                 310                 315                 320

Ala Ala Gly His Gln Leu Asn Phe Ser Leu Ile Thr Lys Glu Arg Met
                325                 330                 335

Met Val Ala Ser Val Ala Val Ala Glu Asn Gly Asp Leu Glu Pro Met
            340                 345                 350

Gln His Leu Phe Glu Asp Ile Ser Asn Pro Glu Lys Ile Arg Leu Leu
        355                 360                 365

Lys Glu Phe Met His Thr Met Lys Asn Thr Gly Arg Asn Val Asn Asp
    370                 375                 380

Arg Pro Val Met Val Ala Lys Glu Gly Glu Thr Tyr Thr Gly Thr Tyr
385                 390                 395                 400

Arg Gly Ala Gly Leu Glu Gly Phe Ala Leu Asn Val Lys Gly Ala Tyr
                405                 410                 415

Ile Ile Gly Asn Ile Asp His Leu Pro Pro Glu Gln Leu Lys Ile Leu
            420                 425                 430

Lys Pro Gly Asp Lys Ile Thr Phe Thr Ala Pro Lys Ala Glu
        435                 440                 445

<210> SEQ ID NO 11
<211> LENGTH: 284
<212> TYPE: PRT
<213> ORGANISM: Artificial Sequence
<220> FEATURE:
<223> OTHER INFORMATION: YopE1-138 - BepA E305-end

<400> SEQUENCE: 11

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

-continued

```
Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Ser Arg Glu Gly
        130                 135                 140

Asn Gly Arg Thr Gln Arg Leu Phe Phe Glu Asn Leu Ala Lys Ala Ala
145                 150                 155                 160

Gly His Gln Leu Asn Phe Ser Leu Ile Thr Lys Glu Arg Met Met Val
                165                 170                 175

Ala Ser Val Ala Val Ala Glu Asn Gly Asp Leu Glu Pro Met Gln His
            180                 185                 190

Leu Phe Glu Asp Ile Ser Asn Pro Glu Lys Ile Arg Leu Leu Lys Glu
        195                 200                 205

Phe Met His Thr Met Lys Asn Thr Gly Arg Asn Val Asn Asp Arg Pro
    210                 215                 220

Val Met Val Ala Lys Glu Gly Glu Thr Tyr Thr Gly Thr Tyr Arg Gly
225                 230                 235                 240

Ala Gly Leu Glu Gly Phe Ala Leu Asn Val Lys Gly Ala Tyr Ile Ile
                245                 250                 255

Gly Asn Ile Asp His Leu Pro Pro Glu Gln Leu Lys Ile Leu Lys Pro
            260                 265                 270

Gly Asp Lys Ile Thr Phe Thr Ala Pro Lys Ala Glu
        275                 280

<210> SEQ ID NO 12
<211> LENGTH: 672
<212> TYPE: PRT
<213> ORGANISM: Artificial Sequence
<220> FEATURE:
<223> OTHER INFORMATION: YopE1-138 - murine Traf6

<400> SEQUENCE: 12

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Ser Arg Met Ser
        130                 135                 140

Leu Leu Asn Cys Glu Asn Ser Cys Gly Ser Ser Gln Ser Ser Ser Asp
145                 150                 155                 160

Cys Cys Ala Ala Met Ala Ala Ser Cys Ser Ala Ala Val Lys Asp Asp
                165                 170                 175
```

```
Ser Val Ser Gly Ser Ala Ser Thr Gly Asn Leu Ser Ser Ser Phe Met
            180                 185                 190

Glu Glu Ile Gln Gly Tyr Asp Val Glu Phe Asp Pro Pro Leu Glu Ser
            195                 200             205

Lys Tyr Glu Cys Pro Ile Cys Leu Met Ala Leu Arg Glu Ala Val Gln
        210                 215                 220

Thr Pro Cys Gly His Arg Phe Cys Lys Ala Cys Ile Ile Lys Ser Ile
225                 230                 235                 240

Arg Asp Ala Gly His Lys Cys Pro Val Asp Asn Glu Ile Leu Leu Glu
                245                 250                 255

Asn Gln Leu Phe Pro Asp Asn Phe Ala Lys Arg Glu Ile Leu Ser Leu
            260                 265                 270

Thr Val Lys Cys Pro Asn Lys Gly Cys Leu Gln Lys Met Glu Leu Arg
        275                 280                 285

His Leu Glu Asp His Gln Val His Cys Glu Phe Ala Leu Val Asn Cys
        290                 295                 300

Pro Gln Cys Gln Arg Pro Phe Gln Lys Cys Gln Val Asn Thr His Ile
305                 310                 315                 320

Ile Glu Asp Cys Pro Arg Arg Gln Val Ser Cys Val Asn Cys Ala Val
                325                 330                 335

Ser Met Ala Tyr Glu Glu Lys Glu Ile His Asp Gln Ser Cys Pro Leu
            340                 345                 350

Ala Asn Ile Ile Cys Glu Tyr Cys Gly Thr Ile Leu Ile Arg Glu Gln
        355                 360                 365

Met Pro Asn His Tyr Asp Leu Asp Cys Pro Thr Ala Pro Ile Pro Cys
        370                 375                 380

Thr Phe Ser Val Phe Gly Cys His Gln Lys Met Gln Arg Asn His Leu
385                 390                 395                 400

Ala Arg His Leu Gln Glu Asn Thr Gln Leu His Met Arg Leu Leu Ala
                405                 410                 415

Gln Ala Val His Asn Val Asn Leu Ala Leu Arg Pro Cys Asp Ala Ala
            420                 425                 430

Ser Pro Ser Arg Gly Cys Arg Pro Glu Asp Pro Asn Tyr Glu Glu Thr
        435                 440                 445

Ile Lys Gln Leu Glu Ser Arg Leu Val Arg Gln Asp His Gln Ile Arg
        450                 455                 460

Glu Leu Thr Ala Lys Met Glu Thr Gln Ser Met Tyr Val Gly Glu Leu
465                 470                 475                 480

Lys Arg Thr Ile Arg Thr Leu Glu Asp Lys Val Ala Glu Met Glu Ala
                485                 490                 495

Gln Gln Cys Asn Gly Ile Tyr Ile Trp Lys Ile Gly Lys Phe Gly Met
            500                 505                 510

His Leu Lys Ser Gln Glu Glu Arg Pro Val Val Ile His Ser Pro
        515                 520                 525

Gly Phe Tyr Thr Gly Arg Pro Gly Tyr Lys Leu Cys Met Arg Leu His
        530                 535                 540

Leu Gln Leu Pro Thr Ala Gln Arg Cys Ala Asn Tyr Ile Ser Leu Phe
545                 550                 555                 560

Val His Thr Met Gln Gly Glu Tyr Asp Ser His Leu Pro Trp Pro Phe
                565                 570                 575

Gln Gly Thr Ile Arg Leu Thr Ile Leu Asp Gln Ser Glu Ala Leu Ile
            580                 585                 590
```

```
Arg Gln Asn His Glu Glu Val Met Asp Ala Lys Pro Glu Leu Leu Ala
            595                 600                 605

Phe Gln Arg Pro Thr Ile Pro Arg Asn Pro Lys Gly Phe Gly Tyr Val
    610                 615                 620

Thr Phe Met His Leu Glu Ala Leu Arg Gln Gly Thr Phe Ile Lys Asp
625                 630                 635                 640

Asp Thr Leu Leu Val Arg Cys Glu Val Ser Thr Arg Phe Asp Met Gly
                645                 650                 655

Gly Leu Arg Lys Glu Gly Phe Gln Pro Arg Ser Thr Asp Ala Gly Val
            660                 665                 670
```

<210> SEQ ID NO 13
<211> LENGTH: 326
<212> TYPE: PRT
<213> ORGANISM: Artificial Sequence
<220> FEATURE:
<223> OTHER INFORMATION: YopE1-138 - TIFA

<400> SEQUENCE: 13

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Thr
    130                 135                 140

Ser Phe Glu Asp Ala Asp Thr Glu Glu Thr Val Thr Cys Leu Gln Met
145                 150                 155                 160

Thr Val Tyr His Pro Gly Gln Leu Gln Cys Gly Ile Phe Gln Ser Ile
                165                 170                 175

Ser Phe Asn Arg Glu Lys Leu Pro Ser Ser Glu Val Val Lys Phe Gly
            180                 185                 190

Arg Asn Ser Asn Ile Cys His Tyr Thr Phe Gln Asp Lys Gln Val Ser
        195                 200                 205

Arg Val Gln Phe Ser Leu Gln Leu Phe Lys Lys Phe Asn Ser Ser Val
    210                 215                 220

Leu Ser Phe Glu Ile Lys Asn Met Ser Lys Lys Thr Asn Leu Ile Val
225                 230                 235                 240

Asp Ser Arg Glu Leu Gly Tyr Leu Asn Lys Met Asp Leu Pro Tyr Arg
                245                 250                 255

Cys Met Val Arg Phe Gly Glu Tyr Gln Phe Leu Met Glu Lys Glu Asp
            260                 265                 270

Gly Glu Ser Leu Glu Phe Glu Thr Gln Phe Ile Leu Ser Pro Arg
        275                 280                 285
```

```
Ser Leu Leu Gln Glu Asn Asn Trp Pro Pro His Arg Pro Ile Pro Glu
        290                 295                 300

Tyr Gly Thr Tyr Ser Leu Cys Ser Ser Gln Ser Ser Pro Thr Glu
305                 310                 315                 320

Met Asp Glu Asn Glu Ser
                325

<210> SEQ ID NO 14
<211> LENGTH: 437
<212> TYPE: PRT
<213> ORGANISM: Artificial Sequence
<220> FEATURE:
<223> OTHER INFORMATION: YopE1-138 - Cdk1

<400> SEQUENCE: 14

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Met Glu Asp Tyr
    130                 135                 140

Thr Lys Ile Glu Lys Ile Gly Glu Gly Thr Tyr Gly Val Val Tyr Lys
145                 150                 155                 160

Gly Arg His Lys Thr Thr Gly Gln Val Val Ala Met Lys Lys Ile Arg
                165                 170                 175

Leu Glu Ser Glu Glu Glu Gly Val Pro Ser Thr Ala Ile Arg Glu Ile
            180                 185                 190

Ser Leu Leu Lys Glu Leu Arg His Pro Asn Ile Val Ser Leu Gln Asp
        195                 200                 205

Val Leu Met Gln Asp Ser Arg Leu Tyr Leu Ile Phe Glu Phe Leu Ser
    210                 215                 220

Met Asp Leu Lys Lys Tyr Leu Asp Ser Ile Pro Pro Gly Gln Tyr Met
225                 230                 235                 240

Asp Ser Ser Leu Val Lys Ser Tyr Leu Tyr Gln Ile Leu Gln Gly Ile
                245                 250                 255

Val Phe Cys His Ser Arg Arg Val Leu His Arg Asp Leu Lys Pro Gln
            260                 265                 270

Asn Leu Leu Ile Asp Asp Lys Gly Thr Ile Lys Leu Ala Asp Phe Gly
        275                 280                 285

Leu Ala Arg Ala Phe Gly Ile Pro Ile Arg Val Tyr Thr His Glu Val
    290                 295                 300

Val Thr Leu Trp Tyr Arg Ser Pro Glu Val Leu Leu Gly Ser Ala Arg
305                 310                 315                 320
```

```
Tyr Ser Thr Pro Val Asp Ile Trp Ser Ile Gly Thr Ile Phe Ala Glu
                325                 330                 335

Leu Ala Thr Lys Lys Pro Leu Phe His Gly Asp Ser Glu Ile Asp Gln
            340                 345                 350

Leu Phe Arg Ile Phe Arg Ala Leu Gly Thr Pro Asn Asn Glu Val Trp
        355                 360                 365

Pro Glu Val Glu Ser Leu Gln Asp Tyr Lys Asn Thr Phe Pro Lys Trp
    370                 375                 380

Lys Pro Gly Ser Leu Ala Ser His Val Lys Asn Leu Asp Glu Asn Gly
385                 390                 395                 400

Leu Asp Leu Leu Ser Lys Met Leu Ile Tyr Asp Pro Ala Lys Arg Ile
            405                 410                 415

Ser Gly Lys Met Ala Leu Asn His Pro Tyr Phe Asn Asp Leu Asp Asn
        420                 425                 430

Gln Ile Lys Lys Met
            435

<210> SEQ ID NO 15
<211> LENGTH: 347
<212> TYPE: PRT
<213> ORGANISM: Artificial Sequence
<220> FEATURE:
<223> OTHER INFORMATION: YopE1-138 - Mad2

<400> SEQUENCE: 15

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
        100                 105                 110

Thr Leu Pro Lys Tyr Met Gln Gln Leu Ser Ser Leu Asp Ala Glu Thr
    115                 120                 125

Leu Gln Lys Asn His Asp Gln Phe Ala Thr Leu Glu Ser Arg Met Ala
130                 135                 140

Leu Gln Leu Ser Arg Glu Gln Gly Ile Thr Leu Arg Gly Ser Ala Glu
145                 150                 155                 160

Ile Val Ala Glu Phe Phe Ser Phe Gly Ile Asn Ser Ile Leu Tyr Gln
            165                 170                 175

Arg Gly Ile Tyr Pro Ser Glu Thr Phe Thr Arg Val Gln Lys Tyr Gly
        180                 185                 190

Leu Thr Leu Leu Val Thr Thr Asp Leu Glu Leu Ile Lys Tyr Leu Asn
    195                 200                 205

Asn Val Val Glu Gln Leu Lys Asp Trp Leu Tyr Lys Cys Ser Val Gln
210                 215                 220

Lys Leu Val Val Val Ile Ser Asn Ile Glu Ser Gly Glu Val Leu Glu
225                 230                 235                 240
```

```
Arg Trp Gln Phe Asp Ile Glu Cys Asp Lys Thr Ala Lys Asp Asp Ser
                245                 250                 255

Ala Pro Arg Glu Lys Ser Gln Lys Ala Ile Gln Asp Glu Ile Arg Ser
        260                 265                 270

Val Ile Arg Gln Ile Thr Ala Thr Val Thr Phe Leu Pro Leu Leu Glu
    275                 280                 285

Val Ser Cys Ser Phe Asp Leu Leu Ile Tyr Thr Asp Lys Asp Leu Val
290                 295                 300

Val Pro Glu Lys Trp Glu Ser Gly Pro Gln Phe Ile Thr Asn Ser
305                 310                 315                 320

Glu Glu Val Arg Leu Arg Ser Phe Thr Thr Thr Ile His Lys Val Asn
                325                 330                 335

Ser Met Val Ala Tyr Lys Ile Pro Val Asn Asp
                340                 345

<210> SEQ ID NO 16
<211> LENGTH: 298
<212> TYPE: PRT
<213> ORGANISM: Artificial Sequence
<220> FEATURE:
<223> OTHER INFORMATION: YopE1-138 - Ink4A

<400> SEQUENCE: 16

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Glu
    130                 135                 140

Pro Ala Ala Gly Ser Ser Met Glu Pro Ser Ala Asp Trp Leu Ala Thr
145                 150                 155                 160

Ala Ala Ala Arg Gly Arg Val Glu Glu Val Arg Ala Leu Leu Glu Ala
                165                 170                 175

Gly Ala Leu Pro Asn Ala Pro Asn Ser Tyr Gly Arg Arg Pro Ile Gln
            180                 185                 190

Val Met Met Met Gly Ser Ala Arg Val Ala Glu Leu Leu Leu Leu His
        195                 200                 205

Gly Ala Glu Pro Asn Cys Ala Asp Pro Ala Thr Leu Thr Arg Pro Val
    210                 215                 220

His Asp Ala Ala Arg Glu Gly Phe Leu Asp Thr Leu Val Val Leu His
225                 230                 235                 240

Arg Ala Gly Ala Arg Leu Asp Val Arg Asp Ala Trp Gly Arg Leu Pro
                245                 250                 255
```

Val Asp Leu Ala Glu Leu Gly His Arg Asp Val Ala Arg Tyr Leu
            260                 265                 270

Arg Ala Ala Gly Gly Thr Arg Gly Ser Asn His Ala Arg Ile Asp
            275                 280                 285

Ala Ala Glu Gly Pro Ser Asp Ile Pro Asp
        290                 295

<210> SEQ ID NO 17
<211> LENGTH: 280
<212> TYPE: PRT
<213> ORGANISM: Artificial Sequence
<220> FEATURE:
<223> OTHER INFORMATION: YopE1-138 - Ink4B

<400> SEQUENCE: 17

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Arg
    130                 135                 140

Glu Glu Asn Lys Gly Met Pro Ser Gly Gly Gly Ser Asp Glu Gly Leu
145                 150                 155                 160

Ala Ser Ala Ala Ala Arg Gly Leu Val Glu Lys Val Arg Gln Leu Leu
                165                 170                 175

Glu Ala Gly Ala Asp Pro Asn Gly Val Asn Arg Phe Gly Arg Arg Ala
            180                 185                 190

Ile Gln Val Met Met Met Gly Ser Ala Arg Val Ala Glu Leu Leu Leu
        195                 200                 205

Leu His Gly Ala Glu Pro Asn Cys Ala Asp Pro Ala Thr Leu Thr Arg
    210                 215                 220

Pro Val His Asp Ala Ala Arg Glu Gly Phe Leu Asp Thr Leu Val Val
225                 230                 235                 240

Leu His Arg Ala Gly Ala Arg Leu Asp Val Arg Asp Ala Trp Gly Arg
                245                 250                 255

Leu Pro Val Asp Leu Ala Glu Glu Gly His Arg Asp Val Ala Gly
            260                 265                 270

Tyr Leu Arg Thr Ala Thr Gly Asp
        275                 280

<210> SEQ ID NO 18
<211> LENGTH: 310
<212> TYPE: PRT
<213> ORGANISM: Artificial Sequence
<220> FEATURE:

<223> OTHER INFORMATION: YopE1-138 - Ink4C

<400> SEQUENCE: 18

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Ala
    130                 135                 140

Glu Pro Trp Gly Asn Glu Leu Ala Ser Ala Ala Arg Gly Asp Leu
145                 150                 155                 160

Glu Gln Leu Thr Ser Leu Leu Gln Asn Asn Val Asn Val Asn Ala Gln
                165                 170                 175

Asn Gly Phe Gly Arg Thr Ala Leu Gln Val Met Lys Leu Gly Asn Pro
            180                 185                 190

Glu Ile Ala Arg Arg Leu Leu Leu Arg Gly Ala Asn Pro Asp Leu Lys
        195                 200                 205

Asp Arg Thr Gly Phe Ala Val Ile His Asp Ala Ala Arg Ala Gly Phe
    210                 215                 220

Leu Asp Thr Leu Gln Ala Leu Pro Glu Phe Gln Ala Asp Val Asn Ile
225                 230                 235                 240

Glu Asp Asn Glu Gly Asn Leu Pro Leu His Leu Ala Ala Lys Glu Gly
                245                 250                 255

His Leu Arg Val Val Glu Phe Leu Val Lys His Thr Ala Ser Asn Val
            260                 265                 270

Gly His Arg Asn His Lys Gly Asp Thr Ala Cys Asp Leu Ala Arg Leu
        275                 280                 285

Tyr Gly Arg Asn Glu Val Val Ser Leu Met Gln Ala Asn Gly Ala Gly
    290                 295                 300

Gly Ala Thr Asn Leu Gln
305                 310

<210> SEQ ID NO 19
<211> LENGTH: 329
<212> TYPE: PRT
<213> ORGANISM: Artificial Sequence
<220> FEATURE:
<223> OTHER INFORMATION: YopE1-138 - z-Bid

<400> SEQUENCE: 19

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Asp
130                 135                 140

Phe Asn Arg Asn Phe Asp His Ile Pro His Thr Ser Leu Val Leu Leu
145                 150                 155                 160

Ser Phe Leu Asn Gln Lys Asp Cys Gln Asn Gly Glu Ser Gly Arg Val
                165                 170                 175

Phe Asp Tyr Arg Glu Asp Asn Leu Ser Thr Asn His Ile Asp Ser Asp
            180                 185                 190

Gly Asp Ile Glu Thr Asp Gly His Ser Pro Pro Ala Thr Tyr Arg Asp
        195                 200                 205

Leu Leu His Glu Leu Gln His Glu Val Gln Pro Gly Leu Ser Val Asn
210                 215                 220

Ala Glu Glu Ala Arg Ala Arg Glu Met Ala Ala Glu Leu Ile Arg
225                 230                 235                 240

Ile Ala Asp Leu Leu Glu Gln Ser Val Leu Ser Gln Ala Ala Glu Ser
                245                 250                 255

Leu Thr Lys Lys Leu Arg Ser Phe Gly Glu Gln Val Trp Ala Ser His
            260                 265                 270

Leu Ser Lys Gly Val Gln Thr Leu Leu Gln His Val Ala Ala Ala Lys
        275                 280                 285

Glu Phe Lys Lys Glu Leu Val Glu Met Ala Phe Thr Phe Met Leu Met
290                 295                 300

Lys Thr Val Cys Glu Arg Thr Pro Asp Phe Leu Phe Gly Leu Tyr Gly
305                 310                 315                 320

Thr Val Val Gln Phe Phe Gly Ser Asn
                325

<210> SEQ ID NO 20
<211> LENGTH: 273
<212> TYPE: PRT
<213> ORGANISM: Artificial Sequence
<220> FEATURE:
<223> OTHER INFORMATION: YopE1-138 - z-t-Bid

<400> SEQUENCE: 20

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

```
Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95

Pro Ser Pro Thr Ser Phe Ser Asp Ser Ile Lys Gln Leu Ala Ala Glu
             100                 105                 110

Thr Leu Pro Lys Tyr Met Gln Gln Leu Ser Ser Leu Asp Ala Glu Thr
             115                 120                 125

Leu Gln Lys Asn His Asp Gln Phe Ala Thr Leu Glu Ser Arg Gly His
    130                 135                 140

Ser Pro Pro Ala Thr Tyr Arg Asp Leu Leu His Glu Leu Gln His Glu
145                 150                 155                 160

Val Gln Pro Gly Leu Ser Val Asn Ala Glu Glu Ala Arg Ala Ala Arg
                165                 170                 175

Glu Met Ala Ala Glu Leu Ile Arg Ile Ala Asp Leu Leu Glu Gln Ser
                180                 185                 190

Val Leu Ser Gln Ala Ala Glu Ser Leu Thr Lys Lys Leu Arg Ser Phe
            195                 200                 205

Gln Glu Gln Val Trp Ala Ser His Leu Ser Lys Gly Val Gln Thr Leu
        210                 215                 220

Leu Gln His Val Ala Ala Ala Lys Glu Phe Lys Lys Glu Leu Val Glu
225                 230                 235                 240

Met Ala Phe Thr Phe Met Leu Met Lys Thr Val Cys Glu Arg Thr Pro
                245                 250                 255

Asp Phe Leu Phe Gly Leu Tyr Gly Thr Val Val Gln Phe Phe Gly Ser
                260                 265                 270

Asn

<210> SEQ ID NO 21
<211> LENGTH: 318
<212> TYPE: PRT
<213> ORGANISM: Artificial Sequence
<220> FEATURE:
<223> OTHER INFORMATION: YopE1-138 - z-BIM

<400> SEQUENCE: 21

Met Lys Ile Ser Ser Phe Ile Ser Thr Ser Leu Pro Leu Pro Ala Ser
 1               5                  10                  15

Val Ser Gly Ser Ser Val Gly Glu Met Ser Gly Arg Ser Val Ser
                 20                  25                  30

Gln Gln Lys Ser Asp Gln Tyr Ala Asn Asn Leu Ala Gly Arg Thr Glu
         35                  40                  45

Ser Pro Gln Gly Ser Ser Leu Ala Ser Arg Ile Ile Glu Arg Leu Ser
     50                  55                  60

Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95

Pro Ser Pro Thr Ser Phe Ser Asp Ser Ile Lys Gln Leu Ala Ala Glu
             100                 105                 110

Thr Leu Pro Lys Tyr Met Gln Gln Leu Ser Ser Leu Asp Ala Glu Thr
             115                 120                 125

Leu Gln Lys Asn His Asp Gln Phe Ala Thr Leu Glu Ser Arg Met Ser
    130                 135                 140
```

```
Asp Thr Ser Arg Glu Gln Thr Leu Ala Asn Gly Pro Ala Ser Gln Gly
145                 150                 155                 160

Ser Gly Glu Ser Thr Gly Gly Val Val Leu Pro Ala Gly His Phe
            165                 170                 175

Asp Phe Pro Gln Pro Gly Glu Gly Asp Pro Leu Arg Gly Gly Ile Ser
            180                 185                 190

Met Ser Asn Asn Gln Ser Arg Ser Pro Met Asn Arg Thr Phe Ser Arg
            195                 200                 205

Ser Ser Ser Gly Tyr Phe Ser Val Asp Ser Asp Ser Val Pro Gly Ser
            210                 215                 220

Pro Leu Met Pro Asn Ile Ser Glu Ala Gln Asp Gly Gln Asn Asp Glu
225                 230                 235                 240

Val Trp Leu Ser Glu His Ser His Gln His Leu Gln Met Ala Ala Pro
                245                 250                 255

Val Ala Ala Leu Pro Pro Glu Met Val Val Ala Arg Glu Leu Arg Arg
                260                 265                 270

Ile Gly Asp Glu Phe Asn Arg Leu Tyr Cys Glu Ala Gly Ala Gly Val
            275                 280                 285

Asn Gln Leu Arg Ala Pro Asn Glu His Ala Ile Val Leu Trp Met Asn
290                 295                 300

Val Ile Ile Gly Arg Leu Val His Phe Phe Leu Arg Arg Arg
305                 310                 315

<210> SEQ ID NO 22
<211> LENGTH: 289
<212> TYPE: PRT
<213> ORGANISM: Artificial Sequence
<220> FEATURE:
<223> OTHER INFORMATION: YopE1-138 - Caspase3 p17

<400> SEQUENCE: 22

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
    115                 120                 125

Leu Gln Lys Asn His Asp Gln Phe Ala Thr Leu Glu Ser Arg Ser Gly
130                 135                 140

Ile Ser Leu Asp Asn Ser Tyr Lys Met Asp Tyr Pro Glu Met Gly Leu
145                 150                 155                 160

Cys Ile Ile Ile Asn Asn Lys Asn Phe His Lys Ser Thr Gly Met Thr
                165                 170                 175

Ser Arg Ser Gly Thr Asp Val Asp Ala Ala Asn Leu Arg Glu Thr Phe
            180                 185                 190
```

```
Arg Asn Leu Lys Tyr Glu Val Arg Asn Lys Asn Asp Leu Thr Arg Glu
            195                 200                 205

Glu Ile Val Glu Leu Met Arg Asp Val Ser Lys Glu Asp His Ser Lys
210                 215                 220

Arg Ser Ser Phe Val Cys Val Leu Leu Ser His Gly Glu Glu Gly Ile
225                 230                 235                 240

Ile Phe Gly Thr Asn Gly Pro Val Asp Leu Lys Lys Ile Thr Asn Phe
            245                 250                 255

Phe Arg Gly Asp Arg Cys Arg Ser Leu Thr Gly Lys Pro Lys Leu Phe
                260                 265                 270

Ile Ile Gln Ala Cys Arg Gly Thr Glu Leu Asp Cys Gly Ile Glu Thr
            275                 280                 285

Asp
```

```
<210> SEQ ID NO 23
<211> LENGTH: 242
<212> TYPE: PRT
<213> ORGANISM: Artificial Sequence
<220> FEATURE:
<223> OTHER INFORMATION: YopE1-138 - Caspase3 p10/12

<400> SEQUENCE: 23

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Gly Val Asp
    130                 135                 140

Asp Asp Met Ala Cys His Lys Ile Pro Val Glu Ala Asp Phe Leu Tyr
145                 150                 155                 160

Ala Tyr Ser Thr Ala Pro Gly Tyr Tyr Ser Trp Arg Asn Ser Lys Asp
                165                 170                 175

Gly Ser Trp Phe Ile Gln Ser Leu Cys Ala Met Leu Lys Gln Tyr Ala
            180                 185                 190

Asp Lys Leu Glu Phe Met His Ile Leu Thr Arg Val Asn Arg Lys Val
        195                 200                 205

Ala Thr Glu Phe Glu Ser Phe Ser Phe Asp Ala Thr Phe His Ala Lys
210                 215                 220

Lys Gln Ile Pro Cys Ile Val Ser Met Leu Thr Lys Glu Leu Tyr Phe
225                 230                 235                 240

Tyr His
```

```
<210> SEQ ID NO 24
```

<211> LENGTH: 337
<212> TYPE: PRT
<213> ORGANISM: Artificial Sequence
<220> FEATURE:
<223> OTHER INFORMATION: YopE1-138 - human Bid

<400> SEQUENCE: 24

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Asp
    130                 135                 140

Cys Glu Val Asn Asn Gly Ser Ser Leu Arg Asp Glu Cys Ile Thr Asn
145                 150                 155                 160

Leu Leu Val Phe Gly Phe Leu Gln Ser Cys Ser Asp Asn Ser Phe Arg
                165                 170                 175

Arg Glu Leu Asp Ala Leu Gly His Glu Leu Pro Val Leu Ala Pro Gln
            180                 185                 190

Trp Glu Gly Tyr Asp Glu Leu Gln Thr Asp Gly Asn Arg Ser Ser His
        195                 200                 205

Ser Arg Leu Gly Arg Ile Glu Ala Asp Ser Glu Ser Gln Glu Asp Ile
    210                 215                 220

Ile Arg Asn Ile Ala Arg His Leu Ala Gln Val Gly Asp Ser Met Asp
225                 230                 235                 240

Arg Ser Ile Pro Pro Gly Leu Val Asn Gly Leu Ala Leu Gln Leu Arg
                245                 250                 255

Asn Thr Ser Arg Ser Glu Glu Asp Arg Asn Arg Asp Leu Ala Thr Ala
            260                 265                 270

Leu Glu Gln Leu Leu Gln Ala Tyr Pro Arg Asp Met Glu Lys Glu Lys
        275                 280                 285

Thr Met Leu Val Leu Ala Leu Leu Ala Lys Lys Val Ala Ser His
    290                 295                 300

Thr Pro Ser Leu Leu Arg Asp Val Phe His Thr Thr Val Asn Phe Ile
305                 310                 315                 320

Asn Gln Asn Leu Arg Thr Tyr Val Arg Ser Leu Ala Arg Asn Gly Met
                325                 330                 335

Asp
```

<210> SEQ ID NO 25
<211> LENGTH: 277
<212> TYPE: PRT
<213> ORGANISM: Artificial Sequence
<220> FEATURE:

<223> OTHER INFORMATION: YopE1-138 - human t-Bid

<400> SEQUENCE: 25

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Gly Asn
    130                 135                 140

Arg Ser Ser His Ser Arg Leu Gly Arg Ile Glu Ala Asp Ser Glu Ser
145                 150                 155                 160

Gln Glu Asp Ile Ile Arg Asn Ile Ala Arg His Leu Ala Gln Val Gly
                165                 170                 175

Asp Ser Met Asp Arg Ser Ile Pro Pro Gly Leu Val Asn Gly Leu Ala
            180                 185                 190

Leu Gln Leu Arg Asn Thr Ser Arg Ser Glu Glu Asp Arg Asn Arg Asp
        195                 200                 205

Leu Ala Thr Ala Leu Glu Gln Leu Leu Gln Ala Tyr Pro Arg Asp Met
    210                 215                 220

Glu Lys Glu Lys Thr Met Leu Val Leu Ala Leu Leu Leu Ala Lys Lys
225                 230                 235                 240

Val Ala Ser His Thr Pro Ser Leu Leu Arg Asp Val Phe His Thr Thr
                245                 250                 255

Val Asn Phe Ile Asn Gln Asn Leu Arg Thr Tyr Val Arg Ser Leu Ala
            260                 265                 270

Arg Asn Gly Met Asp
        275

<210> SEQ ID NO 26
<211> LENGTH: 327
<212> TYPE: PRT
<213> ORGANISM: Artificial Sequence
<220> FEATURE:
<223> OTHER INFORMATION: YopE1-138 - Rac1 Q61E

<400> SEQUENCE: 26

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

```
Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Gln Ala Ile Lys
        130                 135                 140

Cys Val Val Val Gly Asp Gly Ala Val Gly Lys Thr Cys Leu Leu Ile
145                 150                 155                 160

Ser Tyr Thr Thr Asn Ala Phe Pro Gly Glu Tyr Ile Pro Thr Val Phe
                165                 170                 175

Asp Asn Tyr Ser Ala Asn Val Met Val Asp Gly Lys Pro Val Asn Leu
            180                 185                 190

Gly Leu Trp Asp Thr Ala Gly Glu Glu Asp Tyr Asp Arg Leu Arg Pro
            195                 200                 205

Leu Ser Tyr Pro Gln Thr Asp Val Phe Leu Ile Cys Phe Ser Leu Val
        210                 215                 220

Ser Pro Ala Ser Phe Glu Asn Val Arg Ala Lys Trp Tyr Pro Glu Val
225                 230                 235                 240

Arg His His Cys Pro Asn Thr Pro Ile Ile Leu Val Gly Thr Lys Leu
                245                 250                 255

Asp Leu Arg Asp Asp Lys Asp Thr Ile Glu Lys Leu Lys Glu Lys Lys
            260                 265                 270

Leu Thr Pro Ile Thr Tyr Pro Gln Gly Leu Ala Met Ala Lys Glu Ile
            275                 280                 285

Gly Ala Val Lys Tyr Leu Glu Cys Ser Ala Leu Thr Gln Arg Gly Leu
        290                 295                 300

Lys Thr Val Phe Asp Glu Ala Ile Arg Ala Val Leu Cys Pro Pro Pro
305                 310                 315                 320

Val Lys Lys Arg Lys Arg Lys
                325
```

<210> SEQ ID NO 27
<211> LENGTH: 333
<212> TYPE: PRT
<213> ORGANISM: Artificial Sequence
<220> FEATURE:
<223> OTHER INFORMATION: YopE1-138 - RhoA Q63L

<400> SEQUENCE: 27

```
Met Lys Ile Ser Ser Phe Ile Ser Thr Ser Leu Pro Leu Pro Ala Ser
 1               5                  10                  15

Val Ser Gly Ser Ser Ser Val Gly Glu Met Ser Gly Arg Ser Val Ser
                 20                  25                  30

Gln Gln Lys Ser Asp Gln Tyr Ala Asn Asn Leu Ala Gly Arg Thr Glu
             35                  40                  45

Ser Pro Gln Gly Ser Ser Leu Ala Ser Arg Ile Ile Glu Arg Leu Ser
         50                  55                  60

Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95
```

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Met Ala Ala Ile
130                 135                 140

Arg Lys Lys Leu Val Ile Val Gly Asp Gly Ala Cys Gly Lys Thr Cys
145                 150                 155                 160

Leu Leu Ile Val Phe Ser Lys Asp Gln Phe Pro Glu Val Tyr Val Pro
                165                 170                 175

Thr Val Phe Glu Asn Tyr Val Ala Asp Ile Glu Val Asp Gly Lys Gln
            180                 185                 190

Val Glu Leu Ala Leu Trp Asp Thr Ala Gly Leu Glu Asp Tyr Asp Arg
        195                 200                 205

Leu Arg Pro Leu Ser Tyr Pro Asp Thr Asp Val Ile Leu Met Cys Phe
210                 215                 220

Ser Ile Asp Ser Pro Asp Ser Leu Glu Asn Ile Pro Glu Lys Trp Thr
225                 230                 235                 240

Pro Glu Val Lys His Phe Cys Pro Asn Val Pro Ile Ile Leu Val Gly
                245                 250                 255

Asn Lys Lys Asp Leu Arg Asn Asp Glu His Thr Arg Arg Glu Leu Ala
            260                 265                 270

Lys Met Lys Gln Glu Pro Val Lys Pro Glu Glu Gly Arg Asp Met Ala
        275                 280                 285

Asn Arg Ile Gly Ala Phe Gly Tyr Met Glu Cys Ser Ala Lys Thr Lys
290                 295                 300

Asp Gly Val Arg Glu Val Phe Glu Met Ala Thr Arg Ala Ala Leu Gln
305                 310                 315                 320

Ala Arg Arg Gly Lys Lys Lys Ser Gly Cys Leu Val Leu
                325                 330

<210> SEQ ID NO 28
<211> LENGTH: 350
<212> TYPE: PRT
<213> ORGANISM: Artificial Sequence
<220> FEATURE:
<223> OTHER INFORMATION: YopE1-138 - FADD

<400> SEQUENCE: 28

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Ser Arg Met Asp
            130                 135                 140

Pro Phe Leu Val Leu Leu His Ser Val Ser Ser Leu Ser Ser Ser
145                 150                 155                 160

Glu Leu Thr Glu Leu Lys Phe Leu Cys Leu Gly Arg Val Gly Lys Arg
                165                 170                 175

Lys Leu Glu Arg Val Gln Ser Gly Leu Asp Leu Phe Ser Met Leu Leu
            180                 185                 190

Glu Gln Asn Asp Leu Glu Pro Gly His Thr Glu Leu Leu Arg Glu Leu
            195                 200                 205

Leu Ala Ser Leu Arg Arg His Asp Leu Leu Arg Arg Val Asp Asp Phe
210                 215                 220

Glu Ala Gly Ala Ala Gly Ala Ala Pro Gly Glu Glu Asp Leu Cys
225                 230                 235                 240

Ala Ala Phe Asn Val Ile Cys Asp Asn Val Gly Lys Asp Trp Arg Arg
                245                 250                 255

Leu Ala Arg Gln Leu Lys Val Ser Asp Thr Lys Ile Asp Ser Ile Glu
            260                 265                 270

Asp Arg Tyr Pro Arg Asn Leu Thr Glu Arg Val Arg Glu Ser Leu Arg
            275                 280                 285

Ile Trp Lys Asn Thr Glu Lys Glu Asn Ala Thr Val Ala His Leu Val
290                 295                 300

Gly Ala Leu Arg Ser Cys Gln Met Asn Leu Val Ala Asp Leu Val Gln
305                 310                 315                 320

Glu Val Gln Gln Ala Arg Asp Leu Gln Asn Arg Ser Gly Ala Met Ser
                325                 330                 335

Pro Met Ser Trp Asn Ser Asp Ala Ser Thr Ser Glu Ala Ser
            340                 345                 350

<210> SEQ ID NO 29
<211> LENGTH: 308
<212> TYPE: PRT
<213> ORGANISM: Artificial Sequence
<220> FEATURE:
<223> OTHER INFORMATION: YopE1-138 - Bad

<400> SEQUENCE: 29

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Met Phe Gln Ile
    130                 135                 140

-continued

```
Pro Glu Phe Glu Pro Ser Gln Glu Asp Ser Ser Ala Glu Arg
145                 150                 155                 160

Gly Leu Gly Pro Ser Pro Ala Gly Asp Gly Pro Ser Gly Ser Gly Lys
                165                 170                 175

His His Arg Gln Ala Pro Gly Leu Leu Trp Asp Ala Ser His Gln Gln
            180                 185                 190

Glu Gln Pro Thr Ser Ser His His Gly Gly Ala Gly Ala Val Glu
        195                 200                 205

Ile Arg Ser Arg His Ser Ser Tyr Pro Ala Gly Thr Glu Asp Asp Glu
    210                 215                 220

Gly Met Gly Glu Glu Pro Ser Pro Phe Arg Gly Arg Ser Arg Ser Ala
225                 230                 235                 240

Pro Pro Asn Leu Trp Ala Ala Gln Arg Tyr Gly Arg Glu Leu Arg Arg
                245                 250                 255

Met Ser Asp Glu Phe Val Asp Ser Phe Lys Lys Gly Leu Pro Arg Pro
                260                 265                 270

Lys Ser Ala Gly Thr Ala Thr Gln Met Arg Gln Ser Ser Ser Trp Thr
            275                 280                 285

Arg Val Phe Gln Ser Trp Asp Arg Asn Leu Gly Arg Gly Ser Thr
290                 295                 300

Ala Pro Ser Gln
305

<210> SEQ ID NO 30
<211> LENGTH: 309
<212> TYPE: PRT
<213> ORGANISM: Artificial Sequence
<220> FEATURE:
<223> OTHER INFORMATION: YopE1-138 - GPCR GNA12

<400> SEQUENCE: 30

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Met Ser Gly Val
        130                 135                 140

Val Gly Pro Met Gln Glu Pro Gly Ala Leu Asp Val Gly Gly Leu Arg
145                 150                 155                 160

Ser Gln Arg Gln Lys Trp Phe Gln Cys Phe Asp Gly Ile Thr Ser Ile
                165                 170                 175

Leu Phe Met Val Ser Ser Ser Glu Tyr Asp Gln Val Leu Met Glu Asp
                180                 185                 190
```

```
Arg Arg Thr Asn Arg Leu Val Glu Ser Met Asn Ile Phe Glu Thr Ile
        195                 200                 205

Val Asn Asn Lys Leu Phe Phe Asn Val Ser Ile Ile Leu Phe Leu Asn
    210                 215                 220

Lys Met Asp Leu Leu Val Glu Lys Val Lys Thr Val Ser Ile Lys Lys
225                 230                 235                 240

His Phe Pro Asp Phe Arg Gly Asp Pro His Arg Leu Glu Asp Val Gln
                245                 250                 255

Arg Tyr Leu Val Gln Cys Phe Asp Arg Lys Arg Asn Arg Ser Lys
            260                 265                 270

Pro Leu Phe His His Phe Thr Thr Ala Ile Asp Thr Glu Asn Val Arg
                275                 280                 285

Phe Val Phe His Ala Val Lys Asp Thr Ile Leu Gln Glu Asn Leu Lys
        290                 295                 300

Asp Ile Met Leu Gln
305

<210> SEQ ID NO 31
<211> LENGTH: 259
<212> TYPE: PRT
<213> ORGANISM: Artificial Sequence
<220> FEATURE:
<223> OTHER INFORMATION: YopE1-138 - VhH4 nanobody recognizing EGFP

<400> SEQUENCE: 31

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Ser Arg Met Asp
        130                 135                 140

Gln Val Gln Leu Val Glu Ser Gly Gly Ala Leu Val Gln Pro Gly Gly
145                 150                 155                 160

Ser Leu Arg Leu Ser Cys Ala Ala Ser Gly Phe Pro Val Asn Arg Tyr
                165                 170                 175

Ser Met Arg Trp Tyr Arg Gln Ala Pro Gly Lys Glu Arg Glu Trp Val
                180                 185                 190

Ala Gly Met Ser Ser Ala Gly Asp Arg Ser Ser Tyr Glu Asp Ser Val
                195                 200                 205

Lys Gly Arg Phe Thr Ile Ser Arg Asp Asp Ala Arg Asn Thr Val Tyr
        210                 215                 220

Leu Gln Met Asn Ser Leu Lys Pro Glu Asp Thr Ala Val Tyr Tyr Cys
225                 230                 235                 240
```

```
Asn Val Asn Val Gly Phe Glu Tyr Trp Gly Gln Gly Thr Gln Val Thr
                245                 250                 255

Val Ser Ser

<210> SEQ ID NO 32
<211> LENGTH: 458
<212> TYPE: PRT
<213> ORGANISM: Artificial Sequence
<220> FEATURE:
<223> OTHER INFORMATION: YopE1-138 - Slmb1-VhH4

<400> SEQUENCE: 32

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Lys Met
    130                 135                 140

Met Lys Met Glu Thr Asp Lys Ile Met Asp Glu Thr Asn Ser Asn Ala
145                 150                 155                 160

Gln Ala Phe Thr Thr Thr Met Leu Tyr Asp Pro Val Arg Lys Lys Asp
                165                 170                 175

Ser Ser Pro Thr Tyr Gln Thr Glu Arg Glu Leu Cys Phe Gln Tyr Phe
            180                 185                 190

Thr Gln Trp Ser Glu Ser Gly Gln Val Asp Phe Val Glu His Leu Leu
        195                 200                 205

Ser Arg Met Cys His Tyr Gln His Gly Gln Ile Asn Ala Tyr Leu Lys
    210                 215                 220

Pro Met Leu Gln Arg Asp Phe Ile Thr Leu Leu Pro Ile Lys Gly Leu
225                 230                 235                 240

Asp His Ile Ala Glu Asn Ile Leu Ser Tyr Leu Asp Ala Glu Ser Leu
                245                 250                 255

Lys Ser Ser Glu Leu Val Cys Lys Glu Trp Leu Arg Val Ile Ser Glu
            260                 265                 270

Gly Met Leu Trp Lys Lys Leu Ile Glu Arg Lys Val Arg Thr Asp Ser
        275                 280                 285

Leu Trp Arg Gly Leu Ala Glu Arg Arg Asn Trp Met Gln Tyr Leu Phe
    290                 295                 300

Lys Pro Arg Pro Gly Gln Thr Gln Arg Pro His Ser Phe His Arg Glu
305                 310                 315                 320

Leu Phe Pro Lys Ile Met Asn Asp Ile Asp Ser Ile Glu Asn Asn Trp
                325                 330                 335
```

Arg Thr Gly Arg His Met Asp Gln Val Gln Leu Val Glu Ser Gly Gly
                340                 345                 350

Ala Leu Val Gln Pro Gly Gly Ser Leu Arg Leu Ser Cys Ala Ala Ser
            355                 360                 365

Gly Phe Pro Val Asn Arg Tyr Ser Met Arg Trp Tyr Arg Gln Ala Pro
        370                 375                 380

Gly Lys Glu Arg Glu Trp Val Ala Gly Met Ser Ser Ala Gly Asp Arg
385                 390                 395                 400

Ser Ser Tyr Glu Asp Ser Val Lys Gly Arg Phe Thr Ile Ser Arg Asp
                405                 410                 415

Asp Ala Arg Asn Thr Val Tyr Leu Gln Met Asn Ser Leu Lys Pro Glu
            420                 425                 430

Asp Thr Ala Val Tyr Tyr Cys Asn Val Asn Val Gly Phe Glu Tyr Trp
        435                 440                 445

Gly Gln Gly Thr Gln Val Thr Val Ser Ser
    450                 455

<210> SEQ ID NO 33
<211> LENGTH: 470
<212> TYPE: PRT
<213> ORGANISM: Artificial Sequence
<220> FEATURE:
<223> OTHER INFORMATION: YopE1-138 - NLS-Slmb1-VhH4

<400> SEQUENCE: 33

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Pro Pro
    130                 135                 140

Lys Lys Lys Arg Lys Val Gln Phe Lys Met Met Lys Met Glu Thr Asp
145                 150                 155                 160

Lys Ile Met Asp Glu Thr Asn Ser Asn Ala Gln Ala Phe Thr Thr Thr
                165                 170                 175

Met Leu Tyr Asp Pro Val Arg Lys Lys Asp Ser Ser Pro Thr Tyr Gln
            180                 185                 190

Thr Glu Arg Glu Leu Cys Phe Gln Tyr Phe Thr Gln Trp Ser Glu Ser
        195                 200                 205

Gly Gln Val Asp Phe Val Glu His Leu Leu Ser Arg Met Cys His Tyr
    210                 215                 220

Gln His Gly Gln Ile Asn Ala Tyr Leu Lys Pro Met Leu Gln Arg Asp
225                 230                 235                 240

```
Phe Ile Thr Leu Leu Pro Ile Lys Gly Leu Asp His Ile Ala Glu Asn
                245                 250                 255

Ile Leu Ser Tyr Leu Asp Ala Glu Ser Leu Lys Ser Ser Glu Leu Val
            260                 265                 270

Cys Lys Glu Trp Leu Arg Val Ile Ser Glu Gly Met Leu Trp Lys Lys
        275                 280                 285

Leu Ile Glu Arg Lys Val Arg Thr Asp Ser Leu Trp Arg Gly Leu Ala
    290                 295                 300

Glu Arg Arg Asn Trp Met Gln Tyr Leu Phe Lys Pro Arg Pro Gly Gln
305                 310                 315                 320

Thr Gln Arg Pro His Ser Phe His Arg Glu Leu Phe Pro Lys Ile Met
                325                 330                 335

Asn Asp Ile Asp Ser Ile Glu Asn Asn Trp Arg Thr Gly Arg His Leu
            340                 345                 350

Glu Met Asp Gln Val Gln Leu Val Glu Ser Gly Gly Ala Leu Val Gln
        355                 360                 365

Pro Gly Gly Ser Leu Arg Leu Ser Cys Ala Ala Ser Gly Phe Pro Val
    370                 375                 380

Asn Arg Tyr Ser Met Arg Trp Tyr Arg Gln Ala Pro Gly Lys Glu Arg
385                 390                 395                 400

Glu Trp Val Ala Gly Met Ser Ser Ala Gly Asp Arg Ser Ser Tyr Glu
                405                 410                 415

Asp Ser Val Lys Gly Arg Phe Thr Ile Ser Arg Asp Asp Ala Arg Asn
            420                 425                 430

Thr Val Tyr Leu Gln Met Asn Ser Leu Lys Pro Glu Asp Thr Ala Val
        435                 440                 445

Tyr Tyr Cys Asn Val Asn Val Gly Phe Glu Tyr Trp Gly Gln Gly Thr
    450                 455                 460

Gln Val Thr Val Ser Ser
465                 470

<210> SEQ ID NO 34
<211> LENGTH: 466
<212> TYPE: PRT
<213> ORGANISM: Artificial Sequence
<220> FEATURE:
<223> OTHER INFORMATION: YopE1-138 - Slmb1-VhH4-NLS

<400> SEQUENCE: 34

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125
```

Leu Gln Lys Asn His Asp Gln Phe Ala Thr Leu Glu Ser Arg Lys Met
130                 135                 140

Met Lys Met Glu Thr Asp Lys Ile Met Asp Glu Thr Asn Ser Asn Ala
145                 150                 155                 160

Gln Ala Phe Thr Thr Thr Met Leu Tyr Asp Pro Val Arg Lys Lys Asp
                165                 170                 175

Ser Ser Pro Thr Tyr Gln Thr Glu Arg Glu Leu Cys Phe Gln Tyr Phe
            180                 185                 190

Thr Gln Trp Ser Glu Ser Gly Gln Val Asp Phe Val Glu His Leu Leu
        195                 200                 205

Ser Arg Met Cys His Tyr Gln His Gly Gln Ile Asn Ala Tyr Leu Lys
210                 215                 220

Pro Met Leu Gln Arg Asp Phe Ile Thr Leu Leu Pro Ile Lys Gly Leu
225                 230                 235                 240

Asp His Ile Ala Glu Asn Ile Leu Ser Tyr Leu Asp Ala Glu Ser Leu
                245                 250                 255

Lys Ser Ser Glu Leu Val Cys Lys Glu Trp Leu Arg Val Ile Ser Glu
            260                 265                 270

Gly Met Leu Trp Lys Lys Leu Ile Glu Arg Lys Val Arg Thr Asp Ser
        275                 280                 285

Leu Trp Arg Gly Leu Ala Glu Arg Asn Trp Met Gln Tyr Leu Phe
290                 295                 300

Lys Pro Arg Pro Gly Gln Thr Gln Arg Pro His Ser Phe His Arg Glu
305                 310                 315                 320

Leu Phe Pro Lys Ile Met Asn Asp Ile Asp Ser Ile Glu Asn Asn Trp
                325                 330                 335

Arg Thr Gly Arg His Met Asp Gln Val Gln Leu Val Glu Ser Gly Gly
            340                 345                 350

Ala Leu Val Gln Pro Gly Gly Ser Leu Arg Leu Ser Cys Ala Ala Ser
        355                 360                 365

Gly Phe Pro Val Asn Arg Tyr Ser Met Arg Trp Tyr Arg Gln Ala Pro
370                 375                 380

Gly Lys Glu Arg Glu Trp Val Ala Gly Met Ser Ser Ala Gly Asp Arg
385                 390                 395                 400

Ser Ser Tyr Glu Asp Ser Val Lys Gly Arg Phe Thr Ile Ser Arg Asp
                405                 410                 415

Asp Ala Arg Asn Thr Val Tyr Leu Gln Met Asn Ser Leu Lys Pro Glu
            420                 425                 430

Asp Thr Ala Val Tyr Tyr Cys Asn Val Asn Val Gly Phe Glu Tyr Trp
        435                 440                 445

Gly Gln Gly Thr Gln Val Thr Val Ser Ser Pro Pro Lys Lys Lys Arg
450                 455                 460

Lys Val
465

<210> SEQ ID NO 35
<211> LENGTH: 246
<212> TYPE: PRT
<213> ORGANISM: Artificial Sequence
<220> FEATURE:
<223> OTHER INFORMATION: YopE1-138 - Akt PH-domain

<400> SEQUENCE: 35

Met Lys Ile Ser Ser Phe Ile Ser Thr Ser Leu Pro Leu Pro Ala Ser
1               5                   10                  15

```
Val Ser Gly Ser Ser Val Gly Glu Met Ser Gly Arg Ser Val Ser
            20              25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Ala Ile
    130                 135                 140

Val Lys Glu Gly Trp Leu His Lys Arg Gly Glu Tyr Ile Lys Thr Trp
145                 150                 155                 160

Arg Pro Arg Tyr Phe Leu Leu Lys Asn Asp Gly Thr Phe Ile Gly Tyr
                165                 170                 175

Lys Glu Arg Pro Gln Asp Val Asp Gln Arg Glu Ala Pro Leu Asn Asn
            180                 185                 190

Phe Ser Val Ala Gln Cys Gln Leu Met Lys Thr Glu Arg Pro Arg Pro
        195                 200                 205

Asn Thr Phe Ile Ile Arg Cys Leu Gln Trp Thr Thr Val Ile Glu Arg
    210                 215                 220

Thr Phe His Val Glu Thr Pro Glu Glu Arg Glu Glu Trp Thr Thr Ala
225                 230                 235                 240

Ile Gln Thr Val Ala Asp
                245

<210> SEQ ID NO 36
<211> LENGTH: 465
<212> TYPE: PRT
<213> ORGANISM: Artificial Sequence
<220> FEATURE:
<223> OTHER INFORMATION: YopE1-138 - ET1

<400> SEQUENCE: 36

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20              25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125
```

Leu Gln Lys Asn His Asp Gln Phe Ala Thr Leu Glu Ser Arg Met Pro
    130                 135                 140

Arg Pro Lys Leu Lys Ser Asp Asp Glu Val Leu Glu Ala Ala Thr Val
145                 150                 155                 160

Val Leu Lys Arg Cys Gly Pro Ile Glu Phe Thr Leu Ser Gly Val Ala
                165                 170                 175

Lys Glu Val Gly Leu Ser Arg Ala Ala Leu Ile Gln Arg Phe Thr Asn
            180                 185                 190

Arg Asp Thr Leu Leu Val Arg Met Met Glu Arg Gly Val Glu Gln Val
        195                 200                 205

Arg His Tyr Leu Asn Ala Ile Pro Ile Gly Ala Gly Pro Gln Gly Leu
    210                 215                 220

Trp Glu Phe Leu Gln Val Leu Val Arg Ser Met Asn Thr Arg Asn Asp
225                 230                 235                 240

Phe Ser Val Asn Tyr Leu Ile Ser Trp Tyr Glu Leu Gln Val Pro Glu
                245                 250                 255

Leu Arg Thr Leu Ala Ile Gln Arg Asn Arg Ala Val Val Glu Gly Ile
            260                 265                 270

Arg Lys Arg Leu Pro Pro Gly Ala Pro Ala Ala Glu Leu Leu Leu
        275                 280                 285

His Ser Val Ile Ala Gly Ala Thr Met Gln Trp Ala Val Asp Pro Asp
    290                 295                 300

Gly Glu Leu Ala Asp His Val Leu Ala Gln Ile Ala Ala Ile Leu Cys
305                 310                 315                 320

Leu Met Phe Pro Glu His Asp Asp Phe Gln Leu Leu Gln Ala His Ala
                325                 330                 335

Ser Ala Tyr Ser Arg Ala Arg Thr Lys Asn Asn Tyr Gly Ser Thr Ile
            340                 345                 350

Glu Gly Leu Leu Asp Leu Pro Asp Asp Ala Pro Glu Glu Ala Gly
        355                 360                 365

Leu Ala Ala Pro Arg Leu Ser Phe Leu Pro Ala Gly His Thr Arg Arg
    370                 375                 380

Leu Ser Thr Ala Pro Pro Thr Asp Val Ser Leu Gly Asp Glu Leu His
385                 390                 395                 400

Leu Asp Gly Glu Asp Val Ala Met Ala His Ala Asp Ala Leu Asp Asp
                405                 410                 415

Phe Asp Leu Asp Met Leu Gly Asp Gly Asp Ser Pro Gly Pro Gly Phe
            420                 425                 430

Thr Pro His Asp Ser Ala Pro Tyr Gly Ala Leu Asp Met Ala Asp Phe
        435                 440                 445

Glu Phe Glu Gln Met Phe Thr Asp Ala Leu Gly Ile Asp Glu Tyr Gly
    450                 455                 460

Gly
465

<210> SEQ ID NO 37
<211> LENGTH: 381
<212> TYPE: PRT
<213> ORGANISM: Artificial Sequence
<220> FEATURE:
<223> OTHER INFORMATION: YopE1-138 - EGFP

<400> SEQUENCE: 37

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Met Val
    130                 135                 140

Ser Lys Gly Glu Glu Leu Phe Thr Gly Val Val Pro Ile Leu Val Glu
145                 150                 155                 160

Leu Asp Gly Asp Val Asn Gly His Lys Phe Ser Val Ser Gly Glu Gly
                165                 170                 175

Glu Gly Asp Ala Thr Tyr Gly Lys Leu Thr Leu Lys Phe Ile Cys Thr
            180                 185                 190

Thr Gly Lys Leu Pro Val Pro Trp Pro Thr Leu Val Thr Thr Leu Thr
        195                 200                 205

Tyr Gly Val Gln Cys Phe Ser Arg Tyr Pro Asp His Met Lys Gln His
    210                 215                 220

Asp Phe Phe Lys Ser Ala Met Pro Glu Gly Tyr Val Gln Glu Arg Thr
225                 230                 235                 240

Ile Phe Phe Lys Asp Asp Gly Asn Tyr Lys Thr Arg Ala Glu Val Lys
                245                 250                 255

Phe Glu Gly Asp Thr Leu Val Asn Arg Ile Glu Leu Lys Gly Ile Asp
            260                 265                 270

Phe Lys Glu Asp Gly Asn Ile Leu Gly His Lys Leu Glu Tyr Asn Tyr
        275                 280                 285

Asn Ser His Asn Val Tyr Ile Met Ala Asp Lys Gln Lys Asn Gly Ile
    290                 295                 300

Lys Val Asn Phe Lys Ile Arg His Asn Ile Glu Asp Gly Ser Val Gln
305                 310                 315                 320

Leu Ala Asp His Tyr Gln Gln Asn Thr Pro Ile Gly Asp Gly Pro Val
                325                 330                 335

Leu Leu Pro Asp Asn His Tyr Leu Ser Thr Gln Ser Ala Leu Ser Lys
            340                 345                 350

Asp Pro Asn Glu Lys Arg Asp His Met Val Leu Leu Glu Phe Val Thr
        355                 360                 365

Ala Ala Gly Ile Thr Leu Gly Met Asp Glu Leu Tyr Lys
    370                 375                 380

<210> SEQ ID NO 38
<211> LENGTH: 402
<212> TYPE: PRT
<213> ORGANISM: Artificial Sequence
<220> FEATURE:
<223> OTHER INFORMATION: YopE1-138 - 2xTEVsite - NLS - EGFP

<400> SEQUENCE: 38

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Pro Pro Lys Lys
145                 150                 155                 160

Lys Arg Lys Val Val Ser Lys Gly Glu Glu Leu Phe Thr Gly Val Val
                165                 170                 175

Pro Ile Leu Val Glu Leu Asp Gly Asp Val Asn Gly His Lys Phe Ser
            180                 185                 190

Val Ser Gly Glu Gly Glu Gly Asp Ala Thr Tyr Gly Lys Leu Thr Leu
        195                 200                 205

Lys Phe Ile Cys Thr Thr Gly Lys Leu Pro Val Pro Trp Pro Thr Leu
210                 215                 220

Val Thr Thr Leu Thr Tyr Gly Val Gln Cys Phe Ser Arg Tyr Pro Asp
225                 230                 235                 240

His Met Lys Gln His Asp Phe Phe Lys Ser Ala Met Pro Glu Gly Tyr
                245                 250                 255

Val Gln Glu Arg Thr Ile Phe Phe Lys Asp Asp Gly Asn Tyr Lys Thr
            260                 265                 270

Arg Ala Glu Val Lys Phe Glu Gly Asp Thr Leu Val Asn Arg Ile Glu
        275                 280                 285

Leu Lys Gly Ile Asp Phe Lys Glu Asp Gly Asn Ile Leu Gly His Lys
    290                 295                 300

Leu Glu Tyr Asn Tyr Asn Ser His Asn Val Tyr Ile Met Ala Asp Lys
305                 310                 315                 320

Gln Lys Asn Gly Ile Lys Val Asn Phe Lys Ile Arg His Asn Ile Glu
                325                 330                 335

Asp Gly Ser Val Gln Leu Ala Asp His Tyr Gln Gln Asn Thr Pro Ile
            340                 345                 350

Gly Asp Gly Pro Val Leu Leu Pro Asp Asn His Tyr Leu Ser Thr Gln
        355                 360                 365

Ser Ala Leu Ser Lys Asp Pro Asn Glu Lys Arg Asp His Met Val Leu
    370                 375                 380

Leu Glu Phe Val Thr Ala Ala Gly Ile Thr Leu Gly Met Asp Glu Leu
385                 390                 395                 400

Tyr Lys

<210> SEQ ID NO 39
```

<211> LENGTH: 402
<212> TYPE: PRT
<213> ORGANISM: Artificial Sequence
<220> FEATURE:
<223> OTHER INFORMATION: YopE1-138 - 2xTEVsite - EGFP - NLS

<400> SEQUENCE: 39

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Val Ser Lys Gly
145                 150                 155                 160

Glu Glu Leu Phe Thr Gly Val Val Pro Ile Leu Val Glu Leu Asp Gly
                165                 170                 175

Asp Val Asn Gly His Lys Phe Ser Val Ser Gly Glu Gly Glu Gly Asp
            180                 185                 190

Ala Thr Tyr Gly Lys Leu Thr Leu Lys Phe Ile Cys Thr Thr Gly Lys
        195                 200                 205

Leu Pro Val Pro Trp Pro Thr Leu Val Thr Thr Leu Thr Tyr Gly Val
    210                 215                 220

Gln Cys Phe Ser Arg Tyr Pro Asp His Met Lys Gln His Asp Phe Phe
225                 230                 235                 240

Lys Ser Ala Met Pro Glu Gly Tyr Val Gln Glu Arg Thr Ile Phe Phe
                245                 250                 255

Lys Asp Asp Gly Asn Tyr Lys Thr Arg Ala Glu Val Lys Phe Glu Gly
            260                 265                 270

Asp Thr Leu Val Asn Arg Ile Glu Leu Lys Gly Ile Asp Phe Lys Glu
        275                 280                 285

Asp Gly Asn Ile Leu Gly His Lys Leu Glu Tyr Asn Tyr Asn Ser His
    290                 295                 300

Asn Val Tyr Ile Met Ala Asp Lys Gln Lys Asn Gly Ile Lys Val Asn
305                 310                 315                 320

Phe Lys Ile Arg His Asn Ile Glu Asp Gly Ser Val Gln Leu Ala Asp
                325                 330                 335

His Tyr Gln Gln Asn Thr Pro Ile Gly Asp Gly Pro Val Leu Leu Pro
            340                 345                 350

Asp Asn His Tyr Leu Ser Thr Gln Ser Ala Leu Ser Lys Asp Pro Asn
        355                 360                 365

Glu Lys Arg Asp His Met Val Leu Leu Glu Phe Val Thr Ala Ala Gly
    370                 375                 380
```

```
Ile Thr Leu Gly Met Asp Glu Leu Tyr Lys Pro Pro Lys Lys Arg
385                 390                 395                 400

Lys Val

<210> SEQ ID NO 40
<211> LENGTH: 324
<212> TYPE: PRT
<213> ORGANISM: Artificial Sequence
<220> FEATURE:
<223> OTHER INFORMATION: YopE1-138 - 2x TEVsite - INK4C

<400> SEQUENCE: 40

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
130                 135                 140

Leu Tyr Phe Gln Ser Glu Asn Leu Tyr Phe Gln Ser Met Ala Glu Pro
145                 150                 155                 160

Trp Gly Asn Glu Leu Ala Ser Ala Ala Ala Arg Gly Asp Leu Glu Gln
                165                 170                 175

Leu Thr Ser Leu Leu Gln Asn Asn Val Asn Val Asn Ala Gln Asn Gly
            180                 185                 190

Phe Gly Arg Thr Ala Leu Gln Val Met Lys Leu Gly Asn Pro Glu Ile
        195                 200                 205

Ala Arg Arg Leu Leu Leu Arg Gly Ala Asn Pro Asp Leu Lys Asp Arg
210                 215                 220

Thr Gly Phe Ala Val Ile His Asp Ala Ala Arg Ala Gly Phe Leu Asp
225                 230                 235                 240

Thr Leu Gln Ala Leu Pro Glu Phe Gln Ala Asp Val Asn Ile Glu Asp
                245                 250                 255

Asn Glu Gly Asn Leu Pro Leu His Leu Ala Ala Lys Glu Gly His Leu
            260                 265                 270

Arg Val Val Glu Phe Leu Val Lys His Thr Ala Ser Asn Val Gly His
        275                 280                 285

Arg Asn His Lys Gly Asp Thr Ala Cys Asp Leu Ala Arg Leu Tyr Gly
290                 295                 300

Arg Asn Glu Val Val Ser Leu Met Gln Ala Asn Gly Ala Gly Gly Ala
305                 310                 315                 320

Thr Asn Leu Gln
```

<210> SEQ ID NO 41
<211> LENGTH: 479
<212> TYPE: PRT
<213> ORGANISM: Artificial Sequence
<220> FEATURE:
<223> OTHER INFORMATION: YopE1-138 - 2x TEVsite - ET1

<400> SEQUENCE: 41

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

```
                370                 375                 380
Ala Pro Arg Leu Ser Phe Leu Pro Ala Gly His Thr Arg Arg Leu Ser
385                 390                 395                 400

Thr Ala Pro Pro Thr Asp Val Ser Leu Gly Asp Glu Leu His Leu Asp
                405                 410                 415

Gly Glu Asp Val Ala Met Ala His Ala Asp Ala Leu Asp Asp Phe Asp
                420                 425                 430

Leu Asp Met Leu Gly Asp Gly Asp Ser Pro Gly Pro Gly Phe Thr Pro
                435                 440                 445

His Asp Ser Ala Pro Tyr Gly Ala Leu Asp Met Ala Asp Phe Glu Phe
                450                 455                 460

Glu Gln Met Phe Thr Asp Ala Leu Gly Ile Asp Glu Tyr Gly Gly
465                 470                 475
```

<210> SEQ ID NO 42
<211> LENGTH: 380
<212> TYPE: PRT
<213> ORGANISM: Artificial Sequence
<220> FEATURE:
<223> OTHER INFORMATION: YopE1-138 - TEV protease S219V

<400> SEQUENCE: 42

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
                20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Glu Ser Leu Phe
        130                 135                 140

Lys Gly Pro Arg Asp Tyr Asn Pro Ile Ser Ser Thr Ile Cys His Leu
145                 150                 155                 160

Thr Asn Glu Ser Asp Gly His Thr Thr Ser Leu Tyr Gly Ile Gly Phe
                165                 170                 175

Gly Pro Phe Ile Ile Thr Asn Lys His Leu Phe Arg Arg Asn Asn Gly
                180                 185                 190

Thr Leu Leu Val Gln Ser Leu His Gly Val Phe Lys Val Lys Asn Thr
            195                 200                 205

Thr Thr Leu Gln Gln His Leu Ile Asp Gly Arg Asp Met Ile Ile Ile
        210                 215                 220

Arg Met Pro Lys Asp Phe Pro Pro Phe Pro Gln Lys Leu Lys Phe Arg
225                 230                 235                 240

Glu Pro Gln Arg Glu Glu Arg Ile Cys Leu Val Thr Thr Asn Phe Gln
                245                 250                 255

Thr Lys Ser Met Ser Ser Met Val Ser Asp Thr Ser Cys Thr Phe Pro
```

-continued

```
                260                 265                 270
Ser Ser Asp Gly Ile Phe Trp Lys His Trp Ile Gln Thr Lys Asp Gly
                275                 280                 285

Gln Cys Gly Ser Pro Leu Val Ser Thr Arg Asp Gly Phe Ile Val Gly
            290                 295                 300

Ile His Ser Ala Ser Asn Phe Thr Asn Thr Asn Tyr Phe Thr Ser
305                 310                 315                 320

Val Pro Lys Asn Phe Met Glu Leu Leu Thr Asn Gln Glu Ala Gln Gln
                325                 330                 335

Trp Val Ser Gly Trp Arg Leu Asn Ala Asp Ser Val Leu Trp Gly Gly
            340                 345                 350

His Lys Val Phe Met Val Lys Pro Glu Glu Pro Phe Gln Pro Val Lys
                355                 360                 365

Glu Ala Thr Gln Leu Met Asn Arg Arg Arg Arg
            370                 375                 380

<210> SEQ ID NO 43
<211> LENGTH: 332
<212> TYPE: PRT
<213> ORGANISM: Artificial Sequence
<220> FEATURE:
<223> OTHER INFORMATION: YopE1-138 - 2x TEVsite - Flag - INK4C

<400> SEQUENCE: 43

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Ser Arg Glu Asn
    130                 135                 140

Leu Tyr Phe Gln Ser Glu Asn Leu Tyr Phe Gln Ser Asp Tyr Lys Asp
145                 150                 155                 160

Asp Asp Asp Lys Met Ala Glu Pro Trp Gly Asn Glu Leu Ala Ser Ala
                165                 170                 175

Ala Ala Arg Gly Asp Leu Glu Gln Leu Thr Ser Leu Leu Gln Asn Asn
            180                 185                 190

Val Asn Val Asn Ala Gln Asn Gly Phe Gly Arg Thr Ala Leu Gln Val
        195                 200                 205

Met Lys Leu Gly Asn Pro Glu Ile Ala Arg Arg Leu Leu Arg Gly
    210                 215                 220

Ala Asn Pro Asp Leu Lys Asp Arg Thr Gly Phe Ala Val Ile His Asp
225                 230                 235                 240

Ala Ala Arg Ala Gly Phe Leu Asp Thr Leu Gln Ala Leu Pro Glu Phe
```

```
                        245                 250                 255
Gln Ala Asp Val Asn Ile Glu Asp Asn Glu Gly Asn Leu Pro Leu His
        260                 265                 270

Leu Ala Ala Lys Glu Gly His Leu Arg Val Val Glu Phe Leu Val Lys
        275                 280                 285

His Thr Ala Ser Asn Val Gly His Arg Asn His Lys Gly Asp Thr Ala
        290                 295                 300

Cys Asp Leu Ala Arg Leu Tyr Gly Arg Asn Glu Val Val Ser Leu Met
305                 310                 315                 320

Gln Ala Asn Gly Ala Gly Gly Ala Thr Asn Leu Gln
            325                 330

<210> SEQ ID NO 44
<211> LENGTH: 27
<212> TYPE: DNA
<213> ORGANISM: Artificial Sequence
<220> FEATURE:
<223> OTHER INFORMATION: Primer No. : Si_285

<400> SEQUENCE: 44
cataccatgg gagtgagcaa gggcgag                                        27

<210> SEQ ID NO 45
<211> LENGTH: 30
<212> TYPE: DNA
<213> ORGANISM: Artificial Sequence
<220> FEATURE:
<223> OTHER INFORMATION: Primer No. : Si_286

<400> SEQUENCE: 45
ggaagatctt tacttgtaca gctcgtccat                                     30

<210> SEQ ID NO 46
<211> LENGTH: 29
<212> TYPE: DNA
<213> ORGANISM: Artificial Sequence
<220> FEATURE:
<223> OTHER INFORMATION: Primer No. : Si_287

<400> SEQUENCE: 46
cggggtacct caactaaatg accgtggtg                                      29

<210> SEQ ID NO 47
<211> LENGTH: 43
<212> TYPE: DNA
<213> ORGANISM: Artificial Sequence
<220> FEATURE:
<223> OTHER INFORMATION: Primer No. : Si_288

<400> SEQUENCE: 47
gttaaagctt ttcgaatcta gactcgagcg tggcgaactg gtc                      43

<210> SEQ ID NO 48
<211> LENGTH: 35
<212> TYPE: DNA
<213> ORGANISM: Artificial Sequence
<220> FEATURE:
<223> OTHER INFORMATION: Primer No. : Si_292

<400> SEQUENCE: 48
cagtctcgag caaattctaa acaaaatact tccac                               35

<210> SEQ ID NO 49
```

```
<211> LENGTH: 32
<212> TYPE: DNA
<213> ORGANISM: Artificial Sequence
<220> FEATURE:
<223> OTHER INFORMATION: Primer No.: Si_293

<400> SEQUENCE: 49
cagtttcgaa ttaatttgta ttgctttgac gg                              32

<210> SEQ ID NO 50
<211> LENGTH: 34
<212> TYPE: DNA
<213> ORGANISM: Artificial Sequence
<220> FEATURE:
<223> OTHER INFORMATION: Primer No.: Si_296

<400> SEQUENCE: 50
cagtctcgag actaacataa cactatccac ccag                            34

<210> SEQ ID NO 51
<211> LENGTH: 28
<212> TYPE: DNA
<213> ORGANISM: Artificial Sequence
<220> FEATURE:
<223> OTHER INFORMATION: Primer No.: Si_297

<400> SEQUENCE: 51
gttaaagctt tcaggaggca ttctgaag                                   28

<210> SEQ ID NO 52
<211> LENGTH: 28
<212> TYPE: DNA
<213> ORGANISM: Artificial Sequence
<220> FEATURE:
<223> OTHER INFORMATION: Primer No.: Si_299

<400> SEQUENCE: 52
cagtctcgag caggccatca agtgtgtg                                   28

<210> SEQ ID NO 53
<211> LENGTH: 33
<212> TYPE: DNA
<213> ORGANISM: Artificial Sequence
<220> FEATURE:
<223> OTHER INFORMATION: Primer No.: Si_300

<400> SEQUENCE: 53
cagtttcgaa tcattttctc ttcctcttct tca                             33

<210> SEQ ID NO 54
<211> LENGTH: 24
<212> TYPE: DNA
<213> ORGANISM: Artificial Sequence
<220> FEATURE:
<223> OTHER INFORMATION: Primer No.: Si_301

<400> SEQUENCE: 54
cagtctcgag gctgccatcc ggaa                                       24

<210> SEQ ID NO 55
<211> LENGTH: 28
<212> TYPE: DNA
<213> ORGANISM: Artificial Sequence
<220> FEATURE:
<223> OTHER INFORMATION: Primer No.: Si_302

<400> SEQUENCE: 55
```
cagtttcgaa tcacaagaca aggcaccc                                          28

<210> SEQ ID NO 56
<211> LENGTH: 34
<212> TYPE: DNA
<213> ORGANISM: Artificial Sequence
<220> FEATURE:
<223> OTHER INFORMATION: Primer No. : Si_306

<400> SEQUENCE: 56
gttaaagctt ggaggcattc tgaagatact tatt                                   34

<210> SEQ ID NO 57
<211> LENGTH: 35
<212> TYPE: DNA
<213> ORGANISM: Artificial Sequence
<220> FEATURE:
<223> OTHER INFORMATION: Primer No. : Si_307

<400> SEQUENCE: 57
cagtctcgag caaatacaga gcttctatca ctcag                                  35

<210> SEQ ID NO 58
<211> LENGTH: 35
<212> TYPE: DNA
<213> ORGANISM: Artificial Sequence
<220> FEATURE:
<223> OTHER INFORMATION: Primer No. : Si_308

<400> SEQUENCE: 58
gttaaagctt tcaagatgtg attaatgaag aaatg                                  35

<210> SEQ ID NO 59
<211> LENGTH: 29
<212> TYPE: DNA
<213> ORGANISM: Artificial Sequence
<220> FEATURE:
<223> OTHER INFORMATION: Primer No. : Si_317

<400> SEQUENCE: 59
cagtttcgaa cccataaaaa agccctgtc                                         29

<210> SEQ ID NO 60
<211> LENGTH: 37
<212> TYPE: DNA
<213> ORGANISM: Artificial Sequence
<220> FEATURE:
<223> OTHER INFORMATION: Primer No. : Si_318

<400> SEQUENCE: 60
gttaaagctt ctactctatc atcaaacgat aaaatgg                                37

<210> SEQ ID NO 61
<211> LENGTH: 29
<212> TYPE: DNA
<213> ORGANISM: Artificial Sequence
<220> FEATURE:
<223> OTHER INFORMATION: Primer No. : Si_324

<400> SEQUENCE: 61
cagtctcgag ttcactcaag aaacgcaaa                                         29

<210> SEQ ID NO 62
<211> LENGTH: 32
<212> TYPE: DNA

```
<213> ORGANISM: Artificial Sequence
<220> FEATURE:
<223> OTHER INFORMATION: Primer No. : Si_339

<400> SEQUENCE: 62
cagtttcgaa ttttctcttc ctcttcttca cg                              32

<210> SEQ ID NO 63
<211> LENGTH: 32
<212> TYPE: DNA
<213> ORGANISM: Artificial Sequence
<220> FEATURE:
<223> OTHER INFORMATION: Primer No. : Si_341

<400> SEQUENCE: 63
cgtatctaga aaatgatga aaatggagac tg                               32

<210> SEQ ID NO 64
<211> LENGTH: 28
<212> TYPE: DNA
<213> ORGANISM: Artificial Sequence
<220> FEATURE:
<223> OTHER INFORMATION: Primer No. : Si_342

<400> SEQUENCE: 64
gttaaagctt ttagctggag acggtgac                                   28

<210> SEQ ID NO 65
<211> LENGTH: 29
<212> TYPE: DNA
<213> ORGANISM: Artificial Sequence
<220> FEATURE:
<223> OTHER INFORMATION: Primer No. : Si_346

<400> SEQUENCE: 65
cagtctcgag ttccagatcc cagagtttg                                  29

<210> SEQ ID NO 66
<211> LENGTH: 24
<212> TYPE: DNA
<213> ORGANISM: Artificial Sequence
<220> FEATURE:
<223> OTHER INFORMATION: Primer No. : Si_347

<400> SEQUENCE: 66
gttaaagctt tcactgggag gggg                                       24

<210> SEQ ID NO 67
<211> LENGTH: 45
<212> TYPE: DNA
<213> ORGANISM: Artificial Sequence
<220> FEATURE:
<223> OTHER INFORMATION: Primer No. : Si_351

<400> SEQUENCE: 67
cagtctcgag ctcgagttat ctactcatag aaactacttt tgcag                45

<210> SEQ ID NO 68
<211> LENGTH: 29
<212> TYPE: DNA
<213> ORGANISM: Artificial Sequence
<220> FEATURE:
<223> OTHER INFORMATION: Primer No. : Si_352

<400> SEQUENCE: 68
cgcggatcct cagtgtctct gcggcatta                                  29
```

<210> SEQ ID NO 69
<211> LENGTH: 43
<212> TYPE: DNA
<213> ORGANISM: Artificial Sequence
<220> FEATURE:
<223> OTHER INFORMATION: Primer No. : Si_353

<400> SEQUENCE: 69
catttattcc tcctagttag tcacagcaac tgctgctcct ttc        43

<210> SEQ ID NO 70
<211> LENGTH: 43
<212> TYPE: DNA
<213> ORGANISM: Artificial Sequence
<220> FEATURE:
<223> OTHER INFORMATION: Primer No. : Si_354

<400> SEQUENCE: 70
gaaaggagca gcagttgctg tgactaacta ggaggaataa atg        43

<210> SEQ ID NO 71
<211> LENGTH: 41
<212> TYPE: DNA
<213> ORGANISM: Artificial Sequence
<220> FEATURE:
<223> OTHER INFORMATION: Primer No. : Si_355

<400> SEQUENCE: 71
cgattcacgg attgctttct cattattccc tccaggtact a          41

<210> SEQ ID NO 72
<211> LENGTH: 41
<212> TYPE: DNA
<213> ORGANISM: Artificial Sequence
<220> FEATURE:
<223> OTHER INFORMATION: Primer No. : Si_356

<400> SEQUENCE: 72
tagtacctgg agggaataat gagaaagcaa tccgtgaatc g          41

<210> SEQ ID NO 73
<211> LENGTH: 30
<212> TYPE: DNA
<213> ORGANISM: Artificial Sequence
<220> FEATURE:
<223> OTHER INFORMATION: Primer No. : Si_357

<400> SEQUENCE: 73
cgtatctaga cggctttaag tgcgacattc                       30

<210> SEQ ID NO 74
<211> LENGTH: 36
<212> TYPE: DNA
<213> ORGANISM: Artificial Sequence
<220> FEATURE:
<223> OTHER INFORMATION: Primer No. : Si_364

<400> SEQUENCE: 74
cgtatctaga ctaaagtatg aggagagaaa attgaa                36

<210> SEQ ID NO 75
<211> LENGTH: 25
<212> TYPE: DNA
<213> ORGANISM: Artificial Sequence
<220> FEATURE:

<223> OTHER INFORMATION: Primer No. : Si_365

<400> SEQUENCE: 75
gttaaagctt tcagcttgcc gtcgt                                     25

<210> SEQ ID NO 76
<211> LENGTH: 26
<212> TYPE: DNA
<213> ORGANISM: Artificial Sequence
<220> FEATURE:
<223> OTHER INFORMATION: Primer No. : Si_367

<400> SEQUENCE: 76
cgtatctaga gacccgttcc tggtgc                                    26

<210> SEQ ID NO 77
<211> LENGTH: 26
<212> TYPE: DNA
<213> ORGANISM: Artificial Sequence
<220> FEATURE:
<223> OTHER INFORMATION: Primer No. : Si_369

<400> SEQUENCE: 77
cgtatctaga cccccaaga agaagc                                     26

<210> SEQ ID NO 78
<211> LENGTH: 26
<212> TYPE: DNA
<213> ORGANISM: Artificial Sequence
<220> FEATURE:
<223> OTHER INFORMATION: Primer No. : Si_373

<400> SEQUENCE: 78
gttaaagctt gctggagacg gtgacc                                    26

<210> SEQ ID NO 79
<211> LENGTH: 30
<212> TYPE: DNA
<213> ORGANISM: Artificial Sequence
<220> FEATURE:
<223> OTHER INFORMATION: Primer No. : Si_386

<400> SEQUENCE: 79
cgtatctaga tcaggacgct tcggaggtag                                30

<210> SEQ ID NO 80
<211> LENGTH: 30
<212> TYPE: DNA
<213> ORGANISM: Artificial Sequence
<220> FEATURE:
<223> OTHER INFORMATION: Primer No. : Si_387

<400> SEQUENCE: 80
cgtatctaga atggactgtg aggtcaacaa                                30

<210> SEQ ID NO 81
<211> LENGTH: 23
<212> TYPE: DNA
<213> ORGANISM: Artificial Sequence
<220> FEATURE:
<223> OTHER INFORMATION: Primer No. : Si_389

<400> SEQUENCE: 81
cgtatctaga ggcaaccgca gca                                       23

```
<210> SEQ ID NO 82
<211> LENGTH: 29
<212> TYPE: DNA
<213> ORGANISM: Artificial Sequence
<220> FEATURE:
<223> OTHER INFORMATION: Primer No. : Si_391

<400> SEQUENCE: 82
gttaaagctt tcagtccatc ccatttctg                                    29

<210> SEQ ID NO 83
<211> LENGTH: 29
<212> TYPE: DNA
<213> ORGANISM: Artificial Sequence
<220> FEATURE:
<223> OTHER INFORMATION: Primer No. : Si_403

<400> SEQUENCE: 83
cgtatctaga tctggaatat ccctggaca                                    29

<210> SEQ ID NO 84
<211> LENGTH: 30
<212> TYPE: DNA
<213> ORGANISM: Artificial Sequence
<220> FEATURE:
<223> OTHER INFORMATION: Primer No. : Si_406

<400> SEQUENCE: 84
gttaaagctt gtctgtctca atgccacagt                                   30

<210> SEQ ID NO 85
<211> LENGTH: 25
<212> TYPE: DNA
<213> ORGANISM: Artificial Sequence
<220> FEATURE:
<223> OTHER INFORMATION: Primer No. : Si_410

<400> SEQUENCE: 85
cagtctcgag atgtccgggg tggtg                                        25

<210> SEQ ID NO 86
<211> LENGTH: 28
<212> TYPE: DNA
<213> ORGANISM: Artificial Sequence
<220> FEATURE:
<223> OTHER INFORMATION: Primer No. : Si_413

<400> SEQUENCE: 86
cagtttcgaa tcactgcagc atgatgtc                                     28

<210> SEQ ID NO 87
<211> LENGTH: 31
<212> TYPE: DNA
<213> ORGANISM: Artificial Sequence
<220> FEATURE:
<223> OTHER INFORMATION: Primer No. : Si_417

<400> SEQUENCE: 87
cagtctcgag agtggtgttg atgatgacat g                                 31

<210> SEQ ID NO 88
<211> LENGTH: 40
<212> TYPE: DNA
<213> ORGANISM: Artificial Sequence
<220> FEATURE:
<223> OTHER INFORMATION: Primer No. : Si_420
```

-continued

<400> SEQUENCE: 88
cagtttcgaa ttagtgataa aaatagagtt cttttgtgag                                40

<210> SEQ ID NO 89
<211> LENGTH: 33
<212> TYPE: DNA
<213> ORGANISM: Artificial Sequence
<220> FEATURE:
<223> OTHER INFORMATION: Primer No. : Si_423

<400> SEQUENCE: 89
cagtctcgag atgcacataa ctaatttggg att                                       33

<210> SEQ ID NO 90
<211> LENGTH: 34
<212> TYPE: DNA
<213> ORGANISM: Artificial Sequence
<220> FEATURE:
<223> OTHER INFORMATION: Primer No. : Si_424

<400> SEQUENCE: 90
cagtttcgaa ttatacaaat gacgaatacc cttt                                      34

<210> SEQ ID NO 91
<211> LENGTH: 52
<212> TYPE: DNA
<213> ORGANISM: Artificial Sequence
<220> FEATURE:
<223> OTHER INFORMATION: Primer No. : Si_425

<400> SEQUENCE: 91
gttaaagctt ttcacccttg cgcttcttct tgggcgggct ggagacggtg ac                  52

<210> SEQ ID NO 92
<211> LENGTH: 31
<212> TYPE: DNA
<213> ORGANISM: Artificial Sequence
<220> FEATURE:
<223> OTHER INFORMATION: Primer No. : Si_428

<400> SEQUENCE: 92
cgtatctaga atggacttca acaggaactt t                                         31

<210> SEQ ID NO 93
<211> LENGTH: 28
<212> TYPE: DNA
<213> ORGANISM: Artificial Sequence
<220> FEATURE:
<223> OTHER INFORMATION: Primer No. : Si_429

<400> SEQUENCE: 93
cgtatctaga ggacatagtc caccagcg                                             28

<210> SEQ ID NO 94
<211> LENGTH: 29
<212> TYPE: DNA
<213> ORGANISM: Artificial Sequence
<220> FEATURE:
<223> OTHER INFORMATION: Primer No. : Si_430

<400> SEQUENCE: 94
gttaaagctt tcagttggat ccgaaaaac                                            29

<210> SEQ ID NO 95
<211> LENGTH: 34

```
<212> TYPE: DNA
<213> ORGANISM: Artificial Sequence
<220> FEATURE:
<223> OTHER INFORMATION: Primer No. : Si_433

<400> SEQUENCE: 95
cgtatctaga gaattaaaaa aaacactcat ccca                                34

<210> SEQ ID NO 96
<211> LENGTH: 29
<212> TYPE: DNA
<213> ORGANISM: Artificial Sequence
<220> FEATURE:
<223> OTHER INFORMATION: Primer No. : Si_434

<400> SEQUENCE: 96
cgtatctaga ccaaaggcaa aagcaaaaa                                     29

<210> SEQ ID NO 97
<211> LENGTH: 29
<212> TYPE: DNA
<213> ORGANISM: Artificial Sequence
<220> FEATURE:
<223> OTHER INFORMATION: Primer No. : Si_435

<400> SEQUENCE: 97
gttaaagctt ttagctagcc atggcaagc                                     29

<210> SEQ ID NO 98
<211> LENGTH: 22
<212> TYPE: DNA
<213> ORGANISM: Artificial Sequence
<220> FEATURE:
<223> OTHER INFORMATION: Primer No. : Si_436

<400> SEQUENCE: 98
cgtatctaga atgccccgcc cc                                            22

<210> SEQ ID NO 99
<211> LENGTH: 31
<212> TYPE: DNA
<213> ORGANISM: Artificial Sequence
<220> FEATURE:
<223> OTHER INFORMATION: Primer No. : Si_437

<400> SEQUENCE: 99
gttaaagctt ctacccaccg tactcgtcaa t                                  31

<210> SEQ ID NO 100
<211> LENGTH: 31
<212> TYPE: DNA
<213> ORGANISM: Artificial Sequence
<220> FEATURE:
<223> OTHER INFORMATION: Primer No. : Si_438

<400> SEQUENCE: 100
cgtatctaga atgtctgaca cgtccagaga g                                  31

<210> SEQ ID NO 101
<211> LENGTH: 32
<212> TYPE: DNA
<213> ORGANISM: Artificial Sequence
<220> FEATURE:
<223> OTHER INFORMATION: Primer No. : Si_439

<400> SEQUENCE: 101
```
gttaaagctt tcatcttctt cgcaggaaaa ag                                    32

<210> SEQ ID NO 102
<211> LENGTH: 30
<212> TYPE: DNA
<213> ORGANISM: Artificial Sequence
<220> FEATURE:
<223> OTHER INFORMATION: Primer No. : Si_445

<400> SEQUENCE: 102
cgcggatcct tatgggttct cacagcaaaa                                        30

<210> SEQ ID NO 103
<211> LENGTH: 43
<212> TYPE: DNA
<213> ORGANISM: Artificial Sequence
<220> FEATURE:
<223> OTHER INFORMATION: Primer No. : Si_446

<400> SEQUENCE: 103
catttattcc tcctagttag tcaaggcaac agccaatcaa gag                         43

<210> SEQ ID NO 104
<211> LENGTH: 43
<212> TYPE: DNA
<213> ORGANISM: Artificial Sequence
<220> FEATURE:
<223> OTHER INFORMATION: Primer No. : Si_447

<400> SEQUENCE: 104
ctcttgattg gctgttgcct tgactaacta ggaggaataa atg                         43

<210> SEQ ID NO 105
<211> LENGTH: 41
<212> TYPE: DNA
<213> ORGANISM: Artificial Sequence
<220> FEATURE:
<223> OTHER INFORMATION: Primer No. : Si_448

<400> SEQUENCE: 105
ttgattgcag tgacatggtg cattattccc tccaggtact a                           41

<210> SEQ ID NO 106
<211> LENGTH: 41
<212> TYPE: DNA
<213> ORGANISM: Artificial Sequence
<220> FEATURE:
<223> OTHER INFORMATION: Primer No. : Si_449

<400> SEQUENCE: 106
tagtacctgg agggaataat gcaccatgtc actgcaatca a                           41

<210> SEQ ID NO 107
<211> LENGTH: 30
<212> TYPE: DNA
<213> ORGANISM: Artificial Sequence
<220> FEATURE:
<223> OTHER INFORMATION: Primer No. : Si_450

<400> SEQUENCE: 107
cgtatctaga tagccgcaga tgttggtatg                                        30

<210> SEQ ID NO 108
<211> LENGTH: 29
<212> TYPE: DNA
<213> ORGANISM: Artificial Sequence
<220> FEATURE:
<223> OTHER INFORMATION: Primer No. : Si_451

<400> SEQUENCE: 108
cgtatctaga gatcaagtcc aactggtgg                                29

<210> SEQ ID NO 109
<211> LENGTH: 29
<212> TYPE: DNA
<213> ORGANISM: Artificial Sequence
<220> FEATURE:
<223> OTHER INFORMATION: Primer No. : Si_463

<400> SEQUENCE: 109
cagtctcgag gaaagcttgt ttaaggggc                                29

<210> SEQ ID NO 110
<211> LENGTH: 25
<212> TYPE: DNA
<213> ORGANISM: Artificial Sequence
<220> FEATURE:
<223> OTHER INFORMATION: Primer No. : Si_464

<400> SEQUENCE: 110
cagtttcgaa ttagcgacgg cgacg                                    25

<210> SEQ ID NO 111
<211> LENGTH: 31
<212> TYPE: DNA
<213> ORGANISM: Artificial Sequence
<220> FEATURE:
<223> OTHER INFORMATION: Primer No. : Si_476

<400> SEQUENCE: 111
gttaaagctt ttacttgtac agctcgtcca t                             31

<210> SEQ ID NO 112
<211> LENGTH: 25
<212> TYPE: DNA
<213> ORGANISM: Artificial Sequence
<220> FEATURE:
<223> OTHER INFORMATION: Primer No. : Si_477

<400> SEQUENCE: 112
cgtatctaga gtgagcaagg gcgag                                    25

<210> SEQ ID NO 113
<211> LENGTH: 37
<212> TYPE: DNA
<213> ORGANISM: Artificial Sequence
<220> FEATURE:
<223> OTHER INFORMATION: Primer No. : Si_478

<400> SEQUENCE: 113
cagtctcgag atggaagatt ataccaaaat agagaaa                       37

<210> SEQ ID NO 114
<211> LENGTH: 36
<212> TYPE: DNA
<213> ORGANISM: Artificial Sequence
<220> FEATURE:
<223> OTHER INFORMATION: Primer No. : Si_479

<400> SEQUENCE: 114
gttaaagctt ctacatcttc ttaatctgat tgtcca                        36

```
<210> SEQ ID NO 115
<211> LENGTH: 24
<212> TYPE: DNA
<213> ORGANISM: Artificial Sequence
<220> FEATURE:
<223> OTHER INFORMATION: Primer No. : Si_482

<400> SEQUENCE: 115
cgtatctaga atggcgctgc agct                                          24

<210> SEQ ID NO 116
<211> LENGTH: 32
<212> TYPE: DNA
<213> ORGANISM: Artificial Sequence
<220> FEATURE:
<223> OTHER INFORMATION: Primer No. : Si_483

<400> SEQUENCE: 116
gttaaagctt tcagtcattg acaggaattt tg                                 32

<210> SEQ ID NO 117
<211> LENGTH: 25
<212> TYPE: DNA
<213> ORGANISM: Artificial Sequence
<220> FEATURE:
<223> OTHER INFORMATION: Primer No. : Si_486

<400> SEQUENCE: 117
cgtatctaga atggagccgg cggcg                                         25

<210> SEQ ID NO 118
<211> LENGTH: 27
<212> TYPE: DNA
<213> ORGANISM: Artificial Sequence
<220> FEATURE:
<223> OTHER INFORMATION: Primer No. : Si_487

<400> SEQUENCE: 118
gttaaagctt tcaatcgggg atgtctg                                       27

<210> SEQ ID NO 119
<211> LENGTH: 30
<212> TYPE: DNA
<213> ORGANISM: Artificial Sequence
<220> FEATURE:
<223> OTHER INFORMATION: Primer No. : Si_492

<400> SEQUENCE: 119
cgtatctaga atgcgcgagg agaacaaggg                                    30

<210> SEQ ID NO 120
<211> LENGTH: 30
<212> TYPE: DNA
<213> ORGANISM: Artificial Sequence
<220> FEATURE:
<223> OTHER INFORMATION: Primer No. : Si_493

<400> SEQUENCE: 120
gttaaagctt tcagtcccct gtggctgtgc                                    30

<210> SEQ ID NO 121
<211> LENGTH: 24
<212> TYPE: DNA
<213> ORGANISM: Artificial Sequence
<220> FEATURE:
<223> OTHER INFORMATION: Primer No. : Si_494
```

-continued

<400> SEQUENCE: 121
cgtatctaga atggccgagc cttg                                          24

<210> SEQ ID NO 122
<211> LENGTH: 31
<212> TYPE: DNA
<213> ORGANISM: Artificial Sequence
<220> FEATURE:
<223> OTHER INFORMATION: Primer No. : Si_495

<400> SEQUENCE: 122
gttaaagctt ttattgaaga tttgtggctc c                                  31

<210> SEQ ID NO 123
<211> LENGTH: 64
<212> TYPE: DNA
<213> ORGANISM: Artificial Sequence
<220> FEATURE:
<223> OTHER INFORMATION: Primer No. : Si_504

<400> SEQUENCE: 123
cgtatctaga gaaaatctgt attttcaaag tgaaaatctg tattttcaaa gtatgccccg    60
cccc                                                                64

<210> SEQ ID NO 124
<211> LENGTH: 30
<212> TYPE: DNA
<213> ORGANISM: Artificial Sequence
<220> FEATURE:
<223> OTHER INFORMATION: Primer No. : Si_505

<400> SEQUENCE: 124
gttaaagctt cccaccgtac tcgtcaattc                                    30

<210> SEQ ID NO 125
<211> LENGTH: 66
<212> TYPE: DNA
<213> ORGANISM: Artificial Sequence
<220> FEATURE:
<223> OTHER INFORMATION: Primer No. : Si_508

<400> SEQUENCE: 125
cgtatctaga gaaaatctgt attttcaaag tgaaaatctg tattttcaaa gtatggccga    60
gccttg                                                              66

<210> SEQ ID NO 126
<211> LENGTH: 29
<212> TYPE: DNA
<213> ORGANISM: Artificial Sequence
<220> FEATURE:
<223> OTHER INFORMATION: Primer No. : Si_509

<400> SEQUENCE: 126
gttaaagctt ttgaagattt gtggctccc                                     29

<210> SEQ ID NO 127
<211> LENGTH: 67
<212> TYPE: DNA
<213> ORGANISM: Artificial Sequence
<220> FEATURE:
<223> OTHER INFORMATION: Primer No. : Si_511

<400> SEQUENCE: 127
cgtatctaga gaaaatctgt attttcaaag tgaaaatctg tattttcaaa gtgtgagcaa    60
gggcgag                                                              67

<210> SEQ ID NO 128
<211> LENGTH: 91
<212> TYPE: DNA
<213> ORGANISM: Artificial Sequence
<220> FEATURE:
<223> OTHER INFORMATION: Primer No. : Si_512

<400> SEQUENCE: 128
cgtatctaga gaaaatctgt attttcaaag tgaaaatctg tattttcaaa gtccgccgaa    60
aaaaaaacgt aaagttgtga gcaagggcga g                                   91

<210> SEQ ID NO 129
<211> LENGTH: 55
<212> TYPE: DNA
<213> ORGANISM: Artificial Sequence
<220> FEATURE:
<223> OTHER INFORMATION: Primer No. : Si_513

<400> SEQUENCE: 129
gttaaagctt ttaaacttta cgttttttttt cggcggctt gtacagctcg tccat          55

<210> SEQ ID NO 130
<211> LENGTH: 90
<212> TYPE: DNA
<213> ORGANISM: Artificial Sequence
<220> FEATURE:
<223> OTHER INFORMATION: Primer No. : Si_515

<400> SEQUENCE: 130
cgtatctaga gaaaatctgt attttcaaag tgaaaatctg tattttcaaa gtgattataa    60
agatgatgat gataaaatgg ccgagccttg                                     90

<210> SEQ ID NO 131
<211> LENGTH: 30
<212> TYPE: DNA
<213> ORGANISM: Artificial Sequence
<220> FEATURE:
<223> OTHER INFORMATION: Primer No. : Si_558

<400> SEQUENCE: 131
cgtatctaga atgaccagtt ttgaagatgc                                     30

<210> SEQ ID NO 132
<211> LENGTH: 31
<212> TYPE: DNA
<213> ORGANISM: Artificial Sequence
<220> FEATURE:
<223> OTHER INFORMATION: Primer No. : Si_559

<400> SEQUENCE: 132
gttaaagctt tcatgactca ttttcatcca t                                   31

<210> SEQ ID NO 133
<211> LENGTH: 36
<212> TYPE: DNA
<213> ORGANISM: Artificial Sequence
<220> FEATURE:
<223> OTHER INFORMATION: Primer No. : Si_561

<400> SEQUENCE: 133
cgtatctaga atgagtctct taaactgtga gaacag                              36

<210> SEQ ID NO 134
<211> LENGTH: 26
<212> TYPE: DNA
<213> ORGANISM: Artificial Sequence
<220> FEATURE:
<223> OTHER INFORMATION: Primer No. : Si_562

<400> SEQUENCE: 134
gttaaagctt ctacaccccc gcatca                                          26

<210> SEQ ID NO 135
<211> LENGTH: 405
<212> TYPE: PRT
<213> ORGANISM: Artificial Sequence
<220> FEATURE:
<223> OTHER INFORMATION: YopE1-138 - SopE - MycHis

<400> SEQUENCE: 135

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Val Thr Asn Ile
    130                 135                 140

Thr Leu Ser Thr Gln His Tyr Arg Ile His Arg Ser Asp Val Glu Pro
145                 150                 155                 160

Val Lys Glu Lys Thr Thr Glu Lys Asp Ile Phe Ala Lys Ser Ile Thr
                165                 170                 175

Ala Val Arg Asn Ser Phe Ile Ser Leu Ser Thr Ser Leu Ser Asp Arg
            180                 185                 190

Phe Ser Leu His Gln Gln Thr Asp Ile Pro Thr Thr His Phe His Arg
        195                 200                 205

Gly Asn Ala Ser Glu Gly Arg Ala Val Leu Thr Ser Lys Thr Val Lys
    210                 215                 220

Asp Phe Met Leu Gln Lys Leu Asn Ser Leu Asp Ile Lys Gly Asn Ala
225                 230                 235                 240

Ser Lys Asp Pro Ala Tyr Ala Arg Gln Thr Cys Glu Ala Ile Leu Ser
                245                 250                 255

Ala Val Tyr Ser Asn Asn Lys Asp Gln Cys Cys Lys Leu Leu Ile Ser
            260                 265                 270

Lys Gly Val Ser Ile Thr Pro Phe Leu Lys Glu Ile Gly Glu Ala Ala
        275                 280                 285

Gln Asn Ala Gly Leu Pro Gly Glu Ile Lys Asn Gly Val Phe Thr Pro
    290                 295                 300

```
Gly Gly Ala Gly Ala Asn Pro Phe Val Val Pro Leu Ile Ala Ser Ala
305                 310                 315                 320

Ser Ile Lys Tyr Pro His Met Phe Ile Asn His Gln Gln Val Ser
                325                 330                 335

Phe Lys Ala Tyr Ala Glu Lys Ile Val Met Lys Glu Val Thr Pro Leu
            340                 345                 350

Phe Asn Lys Gly Thr Met Pro Thr Pro Gln Gln Phe Gln Leu Thr Ile
            355                 360                 365

Glu Asn Ile Ala Asn Lys Tyr Leu Gln Asn Ala Ser Lys Leu Gly Pro
            370                 375                 380

Glu Gln Lys Leu Ile Ser Glu Glu Asp Leu Asn Ser Ala Val Asp His
385                 390                 395                 400

His His His His His
                405

<210> SEQ ID NO 136
<211> LENGTH: 435
<212> TYPE: PRT
<213> ORGANISM: Artificial Sequence
<220> FEATURE:
<223> OTHER INFORMATION: YopE1-138 - BepG 715-end

<400> SEQUENCE: 136

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Phe Thr Gln Glu
    130                 135                 140

Thr Gln Lys Met Leu Ile Glu Lys Glu Ile Ile Pro Pro Leu Ser Tyr
145                 150                 155                 160

Val Asp Val Ala Ser Lys Ile Arg Glu Ser Glu Val Val Lys Ser Ser
                165                 170                 175

Met Gln Lys Ile Lys Thr Leu Cys Gly Val Val Tyr Gly Asn Pro Asp
            180                 185                 190

Ile Leu Glu Gly Lys Met Pro Lys Met Gly Ile Pro Val Thr Asn Lys
        195                 200                 205

Asn Val Glu Glu Leu Glu Lys Phe Ala Arg Gln Val Gly Asn Phe Pro
    210                 215                 220

Ser Ser Cys Gly Lys Ile Val Gly Phe Ser Phe Leu Gly Ile Lys Ser
225                 230                 235                 240

Glu Ala Arg Ala His Ala Glu Glu Asn Phe Leu Pro Leu Ser His Ala
                245                 250                 255
```

-continued

```
Ile Phe Ser Tyr Ala His Asn Val Lys Gln Ala Glu Lys Asp Ile Leu
            260                 265                 270

Glu Ala Tyr Phe Lys Glu Gln Glu Arg Cys Ala Gln Ser Val Glu Thr
            275                 280                 285

Pro Ser Glu Glu Ile Thr Asn Leu Leu Ser Phe Thr Gln Glu Gln Gln
            290                 295                 300

Lys Glu Ile Leu Ser Asn Ser Pro Lys Leu Arg Thr Gln Val Lys Ala
305                 310                 315                 320

Tyr Ser Gln Lys Leu His Asn Arg Leu Ser Pro Asn Asp Leu Gln Ala
            325                 330                 335

Ile Ser Glu Arg Ser His Thr Lys Leu Ala Glu Ser Leu Gly Thr Ser
            340                 345                 350

Val Asn Gln Ala Glu Lys Ile Ala Gln Ile Leu Thr Gln Thr Lys Asp
            355                 360                 365

Val Val Gln Ile Leu Gln Gln Gln Lys Leu Gly Leu Tyr Gln Ser
            370                 375                 380

Ile Met Lys Gly Asp Gly Arg Glu Thr Ala Lys Val Asn Met Ser Ala
385                 390                 395                 400

Ile Lys Ala Thr Gln Met Thr Thr Lys Val Thr Ser Leu Lys Ala Val
            405                 410                 415

Glu Gln Ile Val Arg Pro Pro Lys Val Glu Thr Ala Lys Val Val Ser
            420                 425                 430

Met Ser Arg
        435

<210> SEQ ID NO 137
<211> LENGTH: 354
<212> TYPE: PRT
<213> ORGANISM: Artificial Sequence
<220> FEATURE:
<223> OTHER INFORMATION: YopE1-138 - Rac1 Q61E - MycHis

<400> SEQUENCE: 137

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Gln Ala Ile Lys
            130                 135                 140

Cys Val Val Val Gly Asp Gly Ala Val Gly Lys Thr Cys Leu Leu Ile
145                 150                 155                 160

Ser Tyr Thr Thr Asn Ala Phe Pro Gly Glu Tyr Ile Pro Thr Val Phe
            165                 170                 175
```

```
Asp Asn Tyr Ser Ala Asn Val Met Val Asp Gly Lys Pro Val Asn Leu
            180                 185                 190

Gly Leu Trp Asp Thr Ala Gly Glu Glu Asp Tyr Asp Arg Leu Arg Pro
            195                 200                 205

Leu Ser Tyr Pro Gln Thr Asp Val Phe Leu Ile Cys Phe Ser Leu Val
            210                 215                 220

Ser Pro Ala Ser Phe Glu Asn Val Arg Ala Lys Trp Tyr Pro Glu Val
225                 230                 235                 240

Arg His His Cys Pro Asn Thr Pro Ile Ile Leu Val Gly Thr Lys Leu
                245                 250                 255

Asp Leu Arg Asp Asp Lys Asp Thr Ile Glu Lys Leu Lys Glu Lys Lys
            260                 265                 270

Leu Thr Pro Ile Thr Tyr Pro Gln Gly Leu Ala Met Ala Lys Glu Ile
            275                 280                 285

Gly Ala Val Lys Tyr Leu Glu Cys Ser Ala Leu Thr Gln Arg Gly Leu
            290                 295                 300

Lys Thr Val Phe Asp Glu Ala Ile Arg Ala Val Leu Cys Pro Pro Pro
305                 310                 315                 320

Val Lys Lys Arg Lys Arg Lys Phe Glu Lys Leu Gly Pro Glu Gln Lys
            325                 330                 335

Leu Ile Ser Glu Glu Asp Leu Asn Ser Ala Val Asp His His His His
            340                 345                 350

His His

<210> SEQ ID NO 138
<211> LENGTH: 163
<212> TYPE: PRT
<213> ORGANISM: Artificial Sequence
<220> FEATURE:
<223> OTHER INFORMATION: YopE1-138 - Y. enterocolitica codon optimized
      murine BID BH3 part

<400> SEQUENCE: 138

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala As

```
<210> SEQ ID NO 139
<211> LENGTH: 156
<212> TYPE: PRT
<213> ORGANISM: Artificial Sequence
<220> FEATURE:
<223> OTHER INFORMATION: YopE1-138 - Y. enterocolitica codon optimized
      murine Bax BH3 part

<400> SEQUENCE: 139
```

Met Lys Ile

```
                85                  90                  95
Arg Met Leu Thr Phe Glu Gln Leu Ser Leu Ile Ala Glu Gly Lys Pro
            100                 105                 110

Ile Val Arg Ile Ser Asp Gly Glu His Thr Val Glu Val Glu Gly Thr
        115                 120                 125

Phe Glu Glu Ile Cys Met Arg Leu Glu Glu Gly Phe Phe Glu Ala Pro
    130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
        195                 200                 205

Asn Tyr
    210

<210> SEQ ID NO 142
<211> LENGTH: 81
<212> TYPE: PRT
<213> ORGANISM: Salmonella enterica

<400> SEQUENCE: 142

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys

<210> SEQ ID NO 143
<211> LENGTH: 105
<212> TYPE: PRT
<213> ORGANISM: Salmonella enterica

<400> SEQUENCE: 143

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala
            100                 105
```

<210> SEQ ID NO 144
<211> LENGTH: 158
<212> TYPE: PRT
<213> ORGANISM: Artificial Sequence
<220> FEATURE:
<223> OTHER INFORMATION: SteA1-20 - S. enterica codon optimized murine t-BID

<400> SEQUENCE: 144

```
Met Pro Tyr Thr Ser Val Ser Thr Tyr Ala Arg Ala Leu Ser Gly Asn
1               5                   10                  15

Lys Leu Pro His Gly Thr Gly Ser Gln Ala Ser Arg Ser Phe Asn Gln
            20                  25                  30

Gly Arg Ile Glu Pro Asp Ser Glu Ser Gln Glu Glu Ile Ile His Asn
        35                  40                  45

Ile Ala Arg His Leu Ala Gln Ile Gly Asp Glu Met Asp His Asn Ile
    50                  55                  60

Gln Pro Thr Leu Val Arg Gln Leu Ala Ala Gln Phe Met Asn Gly Ser
65                  70                  75                  80

Leu Ser Glu Glu Asp Lys Arg Asn Cys Leu Ala Lys Ala Leu Asp Glu
                85                  90                  95

Val Lys Thr Ala Phe Pro Arg Asp Met Glu Asn Asp Lys Ala Met Leu
            100                 105                 110

Ile Met Thr Met Leu Leu Ala Lys Lys Val Ala Ser His Ala Pro Ser
        115                 120                 125

Leu Leu Arg Asp Val Phe His Thr Thr Val Asn Phe Ile Asn Gln Asn
    130                 135                 140

Leu Phe Ser Tyr Val Arg Asn Leu Val Arg Asn Glu Met Asp
145                 150                 155
```

<210> SEQ ID NO 145
<211> LENGTH: 348
<212> TYPE: PRT
<213> ORGANISM: Artificial Sequence
<220> FEATURE:
<223> OTHER INFORMATION: SteA - S. enterica codon optimized murine t-BID

<400> SEQUENCE: 145

```
Met Pro Tyr Thr Ser Val Ser Thr Tyr Ala Arg Ala Leu Ser Gly Asn
1               5                   10                  15

Lys Leu Pro His Val Ala Ala Gly Asp T

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
            165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
            195                 200                 205

Asn Tyr Gly Thr Gly Ser Gln Ala Ser Arg Ser Phe Asn Gln Gly Arg
        210                 215                 220

Ile Glu Pro Asp Ser Glu Ser Gln Glu Glu Ile Ile His Asn Ile Ala
225                 230                 235                 240

Arg His Leu Ala Gln Ile Gly Asp Glu Met Asp His Asn Ile Gln Pro
                245                 250                 255

Thr Leu Val Arg Gln Leu Ala Ala Gln Phe Met Asn Gly Ser Leu Ser
            260                 265                 270

Glu Glu Asp Lys Arg Asn Cys Leu Ala Lys Ala Leu Asp Glu Val Lys
        275                 280                 285

Thr Ala Phe Pro Arg Asp Met Glu Asn Asp Lys Ala Met Leu Ile Met
290                 295                 300

Thr Met Leu Leu Ala Lys Lys Val Ala Ser His Ala Pro Ser Leu Leu
305                 310                 315                 320

Arg Asp Val Phe His Thr Thr Val Asn Phe Ile Asn Gln Asn Leu Phe
                325                 330                 335

Ser Tyr Val Arg Asn Leu Val Arg Asn Glu Met Asp
            340                 345

<210> SEQ ID NO 146
<211> LENGTH: 219
<212> TYPE: PRT
<213> ORGANISM: Artificial Sequence
<220> FEATURE:
<223> OTHER INFORMATION: SopE1-81 - S. enterica codon optimized murine
      t-BID

<400> SEQUENCE: 146

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Gly Thr Gly Ser Gln Ala Ser Arg Ser Phe Asn Gln Gly Arg Ile
            85                  90                  95

Glu Pro Asp Ser Glu Ser Gln Glu Glu Ile Ile His Asn Ile Ala Arg
        100                 105                 110

His Leu Ala Gln Ile Gly Asp Glu Met Asp His Asn Ile Gln Pro Thr
    115                 120                 125

Leu Val Arg Gln Leu Ala Ala Gln Phe Met Asn Gly Ser Leu Ser Glu
130                 135                 140

Glu Asp Lys Arg Asn Cys Leu Ala Lys Ala Leu Asp Glu Val Lys Thr
145                 150                 155                 160

Ala Phe Pro Arg Asp Met Glu Asn Asp Lys Ala Met Leu Ile Met Thr
            165                 170                 175

Met Leu Leu Ala Lys Lys Val Ala Ser His Ala Pro Ser Leu Leu Arg
        180                 185                 190

Asp Val Phe His Thr Thr Val Asn Phe Ile Asn Gln Asn Leu Phe Ser
    195                 200                 205

Tyr Val Arg Asn Leu Val Arg Asn Glu Met Asp
    210                 215

<210> SEQ ID NO 147
<211> LENGTH: 243
<212> TYPE: PRT
<213> ORGANISM: Artificial Sequence
<220> FEATURE:
<223> OTHER INFORMATION: SopE1-105 - S. enterica codon optimized murine
      t-BID

<400> SEQUENCE: 147

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala Gly Thr Gly Ser Gln Ala Ser
            100                 105                 110

Arg Ser Phe Asn Gln Gly Arg Ile Glu Pro Asp Ser Glu Ser Gln Glu
        115                 120                 125

Glu Ile Ile His Asn Ile Ala Arg His Leu Ala Gln Ile Gly Asp Glu
    130                 135                 140

Met Asp His Asn Ile Gln Pro Thr Leu Val Arg Gln Leu Ala Ala Gln
145                 150                 155                 160

Phe Met Asn Gly Ser Leu Ser Glu Glu Asp Lys Arg Asn Cys Leu Ala
                165                 170                 175

Lys Ala Leu Asp Glu Val Lys Thr Ala Phe Pro Arg Asp Met Glu Asn
            180                 185                 190

Asp Lys Ala Met Leu Ile Met Thr Met Leu Leu Ala Lys Lys Val Ala
        195                 200                 205

Ser His Ala Pro Ser Leu Leu Arg Asp Val Phe His Thr Thr Val Asn
    210                 215                 220

Phe Ile Asn Gln Asn Leu Phe Ser Tyr Val Arg Asn Leu Val Arg Asn
225                 230                 235                 240

Glu Met Asp

<210> SEQ ID NO 148
<211> LENGTH: 82
<212> TYPE: DNA
<213> ORGANISM: Artificial Sequence
<220> FEATURE:
<223> OTHER INFORMATION: Primer No. : Si_677

-continued

<400> SEQUENCE: 148
ttactattcg aagaaattat tcataatatt gcccgccatc tggcccaaat tggtgatgaa    60
atggatcatt aagcttggag ta    82

<210> SEQ ID NO 149
<211> LENGTH: 82
<212> TYPE: DNA
<213> ORGANISM: Artificial Sequence
<220> FEATURE:
<223> OTHER INFORMATION: Primer No. : Si_678

<400> SEQUENCE: 149
tactccaagc ttaatgatcc atttcatcac caatttgggc cagatggcgg gcaatattat    60
gaataatttc ttcgaatagt aa    82

<210> SEQ ID NO 150
<211> LENGTH: 73
<212> TYPE: DNA
<213> ORGANISM: Artificial Sequence
<220> FEATURE:
<223> OTHER INFORMATION: Primer No. : Si_682

<400> SEQUENCE: 150
ttactactcg agaaaaaact gagcgaatgt ctgcgccgca ttggtgatga actggatagc    60
taagcttgga gta    73

<210> SEQ ID NO 151
<211> LENGTH: 73
<212> TYPE: DNA
<213> ORGANISM: Artificial Sequence
<220> FEATURE:
<223> OTHER INFORMATION: Primer No. : Si_683

<400> SEQUENCE: 151
tactccaagc ttagctatcc agttcatcac caatgcggcg cagacattcg ctcagttttt    60
tctcgagtag taa    73

<210> SEQ ID NO 152
<211> LENGTH: 34
<212> TYPE: DNA
<213> ORGANISM: Artificial Sequence
<220> FEATURE:
<223> OTHER INFORMATION: Primer No. : Si_580

<400> SEQUENCE: 152
catgccatgg atttatggtc atagatatga cctc    34

<210> SEQ ID NO 153
<211> LENGTH: 35
<212> TYPE: DNA
<213> ORGANISM: Artificial Sequence
<220> FEATURE:
<223> OTHER INFORMATION: Primer No. : Si_612

<400> SEQUENCE: 153
cggggtacca tgaggtagct tatttcctga taaag    35

<210> SEQ ID NO 154
<211> LENGTH: 35
<212> TYPE: DNA
<213> ORGANISM: Artificial Sequence
<220> FEATURE:
<223> OTHER INFORMATION: Primer No. : Si_613

-continued

<400> SEQUENCE: 154
cggggtacca taattgtcca aatagttatg gtagc								35

<210> SEQ ID NO 155
<211> LENGTH: 24
<212> TYPE: DNA
<213> ORGANISM: Artificial Sequence
<220> FEATURE:
<223> OTHER INFORMATION: Primer No. : Si_614

<400> SEQUENCE: 155
catgccatgg cggcaaggct cctc								24

<210> SEQ ID NO 156
<211> LENGTH: 29
<212> TYPE: DNA
<213> ORGANISM: Artificial Sequence
<220> FEATURE:
<223> OTHER INFORMATION: Primer No. : Si_615

<400> SEQUENCE: 156
cggggtacct ttatttgtca acactgccc								29

<210> SEQ ID NO 157
<211> LENGTH: 26
<212> TYPE: DNA
<213> ORGANISM: Artificial Sequence
<220> FEATURE:
<223> OTHER INFORMATION: Primer No. : Si_616

<400> SEQUENCE: 157
cggggtacct gcggggtctt tactcg								26

<210> SEQ ID NO 158
<211> LENGTH: 164
<212> TYPE: PRT
<213> ORGANISM: Artificial Sequence
<220> FEATURE:
<223> OTHER INFORMATION: YopE1-138-Y. enterocolitica codon optimized
      Ink4A 84-103

<400> SEQUENCE: 158

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

```
Asp Ala Ala Arg Glu Gly Phe Leu Asp Thr Leu Val Val Leu His Arg
145                 150                 155                 160

Ala Gly Ala Arg

<210> SEQ ID NO 159
<211> LENGTH: 164
<212> TYPE: PRT
<213> ORGANISM: Artificial Sequence
<220> FEATURE:
<223> OTHER INFORMATION: YopE1-138-Y. enterocolitica codon optimized
      p107/RBL1 657-662 (AAA02489.1)

<400> SEQUENCE: 159

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

Tyr Gly Arg Lys Lys Arg Arg Gln Arg Arg Gly Pro Val Lys Arg
145                 150                 155                 160

Arg Leu Phe Gly

<210> SEQ ID NO 160
<211> LENGTH: 164
<212> TYPE: PRT
<213> ORGANISM: Artificial Sequence
<220> FEATURE:
<223> OTHER INFORMATION: YopE1-138-Y. enterocolitica codon optimized p21
      141-160 (AAH13967.1)

<400> SEQUENCE: 160

Met Lys Ile Ser Ser Phe Ile Ser Thr Ser Leu Pro Leu Pro Ala Ser
1               5                   10                  15

Val Ser Gly Ser Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
                85                  90                  95

Pro Ser Pro Thr Ser Phe Ser Asp Ser Ile Lys Gln Leu Ala Ala Glu
            100                 105                 110
```

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

Lys Arg Arg Gln Thr Ser Met Thr Ala Phe Tyr His Ser Lys Arg Arg
145                 150                 155                 160

Leu Ile Phe Ser

<210> SEQ ID NO 161
<211> LENGTH: 160
<212> TYPE: PRT
<213> ORGANISM: Artificial Sequence
<220> FEATURE:
<223> OTHER INFORMATION: YopE1-138-Y. enterocolitica codon optimized p21
      145-160 (AAH13967.1)

<400> SEQUENCE: 161

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
        100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Leu Glu Gly Ala Ile Asp
    130                 135                 140

Thr Ser Met Thr Ala Phe Tyr His Ser Lys Arg Arg Leu Ile Phe Ser
145                 150                 155                 160

<210> SEQ ID NO 162
<211> LENGTH: 161
<212> TYPE: PRT
<213> ORGANISM: Artificial Sequence
<220> FEATURE:
<223> OTHER INFORMATION: YopE1-138-Y. enterocolitica codon optimized p21
      17-33 (AAH13967.1)

<400> SEQUENCE: 162

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65              70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
        100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Gly Ala Ile Asp
    130                 135                 140

Ala Cys Arg Arg Leu Phe Gly Pro Val Asp Ser Glu Gln Leu Ser Arg
145                 150                 155                 160

Asp

<210> SEQ ID NO 163
<211> LENGTH: 153
<212> TYPE: PRT
<213> ORGANISM: Artificial Sequence
<220> FEATURE:
<223> OTHER INFORMATION: YopE1-138-Y. enterocolitica codon optimized
      cyclin D2 139-147 (CAA48493.1)

<400> SEQUENCE: 163

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
        100                 105                 110

Thr Leu Pro Lys Tyr Met Gln Gln Leu Ser Ser Leu Asp Ala Glu Thr
            115                 120                 125

Leu Gln Lys Asn His Asp Gln Phe Ala Thr Leu Glu Gly Ala Ile Asp
    130                 135                 140

Trp Glu Leu Val Val Leu Gly Lys Leu
145                 150

<210> SEQ ID NO 164
<211> LENGTH: 397
<212> TYPE: PRT
<213> ORGANISM: Artificial Sequence
<220> FEATURE:
<223> OTHER INFORMATION: SteA-Ink4a-MycHis

<400> SEQUENCE: 164

Met Pro Tyr Thr Ser Val Ser Thr Tyr Ala Arg Ala Leu Ser Gly Asn
1               5                   10                  15

Lys Leu Pro His Val Ala Ala Gly Asp Tyr Glu Asn Lys Leu Ser Thr
            20                  25                  30

Lys Ile Met Lys Gly Ile Leu Tyr Val Leu Thr Ala Gly Leu Ala Tyr
        35                  40                  45

Gly Phe Thr Arg Val Ile Glu His Tyr Cys Asn Val Thr Pro Lys Val
    50                  55                  60

Ala Glu Phe Cys Ala Asn Ala Gly Asn Ile His Asn His Leu Ala Asp
65                  70                  75                  80

Ala Val Arg Asp Gly Leu Phe Thr Ile Asp Val Glu Leu Ser Asp Gly
            85                  90                  95

Arg Met Leu Thr Phe Glu Gln Leu Ser Leu Ile Ala Glu Gly Lys Pro
        100                 105                 110

Ile Val Arg Ile Ser Asp Gly Glu His Thr Val Glu Val Glu Gly Thr
    115                 120                 125

Phe Glu Glu Ile Cys Met Arg Leu Glu Glu Gly Phe Phe Glu Ala Pro
130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
        195                 200                 205

Asn Tyr Gly Thr Ile Trp Glu Phe Met Glu Pro Ala Ala Gly Ser Ser
210                 215                 220

Met Glu Pro Ser Ala Asp Trp Leu Ala Thr Ala Ala Arg Gly Arg
225                 230                 235                 240

Val Glu Glu Val Arg Ala Leu Leu Glu Ala Gly Ala Leu Pro Asn Ala
                245                 250                 255

Pro Asn Ser Tyr Gly Arg Arg Pro Ile Gln Val Met Met Met Gly Ser
            260                 265                 270

Ala Arg Val Ala Glu Leu Leu Leu Leu His Gly Ala Glu Pro Asn Cys
        275                 280                 285

Ala Asp Pro Ala Thr Leu Thr Arg Pro Val His Asp Ala Ala Arg Glu
290                 295                 300

Gly Phe Leu Asp Thr Leu Val Val Leu His Arg Ala Gly Ala Arg Leu
305                 310                 315                 320

Asp Val Arg Asp Ala Trp Gly Arg Leu Pro Val Asp Leu Ala Glu Glu
                325                 330                 335

Leu Gly His Arg Asp Val Ala Arg Tyr Leu Arg Ala Ala Ala Gly Gly
            340                 345                 350

Thr Arg Gly Ser Asn His Ala Arg Ile Asp Ala Ala Glu Gly Pro Ser
        355                 360                 365

Asp Ile Pro Asp Lys Leu Gly Pro Glu Gln Lys Leu Ile Ser Glu Glu
370                 375                 380

Asp Leu Asn Ser Ala Val Asp His His His His His His
385                 390                 395

<210> SEQ ID NO 165
<211> LENGTH: 292
<212> TYPE: PRT
<213> ORGANISM: Artificial Sequence
<220> FEATURE:
<223> OTHER INFORMATION: SopE1-105-Ink4a-MycHis

<400> SEQUENCE: 165

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

-continued

```
Lys Ser Ile Leu Ala Val Lys Asn His Phe Ile Glu Leu Arg Ser Lys
            35                  40                  45

Leu Ser Glu Arg Phe Ile Ser His Lys Asn Thr Glu Ser Ser Ala Thr
 50                  55                  60

His Phe His Arg Gly Ser Ala Ser Glu Gly Arg Ala Val Leu Thr Asn
 65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala Gly Thr Ile Trp Glu Phe Met
            100                 105                 110

Glu Pro Ala Ala Gly Ser Ser Met Glu Pro Ser Ala Asp Trp Leu Ala
            115                 120                 125

Thr Ala Ala Ala Arg Gly Arg Val Glu Val Arg Ala Leu Leu Glu
130                 135                 140

Ala Gly Ala Leu Pro Asn Ala Pro Asn Ser Tyr Gly Arg Arg Pro Ile
145                 150                 155                 160

Gln Val Met Met Met Gly Ser Ala Arg Val Ala Glu Leu Leu Leu Leu
                165                 170                 175

His Gly Ala Glu Pro Asn Cys Ala Asp Pro Ala Thr Leu Thr Arg Pro
            180                 185                 190

Val His Asp Ala Ala Arg Glu Gly Phe Leu Asp Thr Leu Val Val Leu
            195                 200                 205

His Arg Ala Gly Ala Arg Leu Asp Val Arg Asp Ala Trp Gly Arg Leu
            210                 215                 220

Pro Val Asp Leu Ala Glu Leu Gly His Arg Asp Val Ala Arg Tyr
225                 230                 235                 240

Leu Arg Ala Ala Ala Gly Gly Thr Arg Gly Ser Asn His Ala Arg Ile
                245                 250                 255

Asp Ala Ala Glu Gly Pro Ser Asp Ile Pro Asp Lys Leu Gly Pro Glu
            260                 265                 270

Gln Lys Leu Ile Ser Glu Glu Asp Leu Asn Ser Ala Val Asp His His
            275                 280                 285

His His His His
    290

<210> SEQ ID NO 166
<211> LENGTH: 409
<212> TYPE: PRT
<213> ORGANISM: Artificial Sequence
<220> FEATURE:
<223> OTHER INFORMATION: SteA-Ink4c-MycHis

<400> SEQUENCE: 166

Met Pro Tyr Thr Ser Val Ser Thr Tyr Ala Arg Ala Leu Ser Gly Asn
1               5                   10                  15

Lys Leu Pro His Val Ala Ala Gly Asp Tyr Glu Asn Lys Leu Ser Thr
            20                  25                  30

Lys Ile Met Lys Gly Ile Leu Tyr Val Leu Thr Ala Gly Leu Ala Tyr
        35                  40                  45

Gly Phe Thr Arg Val Ile Glu His Tyr Cys Asn Val Thr Pro Lys Val
    50                  55                  60

Ala Glu Phe Cys Ala Asn Ala Gly Asn Ile His Asn His Leu Ala Asp
65                  70                  75                  80

Ala Val Arg Asp Gly Leu Phe Thr Ile Asp Val Glu Leu Ser Asp Gly
                85                  90                  95
```

Arg Met Leu Thr Phe Glu Gln Leu Ser Leu Ile Ala Glu Gly Lys Pro
                100                 105                 110

Ile Val Arg Ile Ser Asp Gly Glu His Thr Val Glu Glu Gly Thr
            115                 120                 125

Phe Glu Glu Ile Cys Met Arg Leu Glu Glu Gly Phe Phe Glu Ala Pro
130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
        195                 200                 205

Asn Tyr Gly Thr Ile Trp Glu Phe Met Ala Glu Pro Trp Gly Asn Glu
210                 215                 220

Leu Ala Ser Ala Ala Ala Arg Gly Asp Leu Glu Gln Leu Thr Ser Leu
225                 230                 235                 240

Leu Gln Asn Asn Val Asn Val Asn Ala Gln Asn Gly Phe Gly Arg Thr
                245                 250                 255

Ala Leu Gln Val Met Lys Leu Gly Asn Pro Glu Ile Ala Arg Arg Leu
            260                 265                 270

Leu Leu Arg Gly Ala Asn Pro Asp Leu Lys Asp Arg Thr Gly Phe Ala
        275                 280                 285

Val Ile His Asp Ala Ala Arg Ala Gly Phe Leu Asp Thr Leu Gln Thr
290                 295                 300

Leu Leu Glu Phe Gln Ala Asp Val Asn Ile Glu Asp Asn Glu Gly Asn
305                 310                 315                 320

Leu Pro Leu His Leu Ala Ala Lys Glu Gly His Leu Arg Val Val Glu
                325                 330                 335

Phe Leu Val Lys His Thr Ala Ser Asn Val Gly His Arg Asn His Lys
            340                 345                 350

Gly Asp Thr Ala Cys Asp Leu Ala Arg Leu Tyr Gly Arg Asn Glu Val
        355                 360                 365

Val Ser Leu Met Gln Ala Asn Gly Ala Gly Ala Thr Asn Leu Gln
370                 375                 380

Lys Leu Gly Pro Glu Gln Lys Leu Ile Ser Glu Glu Asp Leu Asn Ser
385                 390                 395                 400

Ala Val Asp His His His His His His
                405

<210> SEQ ID NO 167
<211> LENGTH: 304
<212> TYPE: PRT
<213> ORGANISM: Artificial Sequence
<220> FEATURE:
<223> OTHER INFORMATION: SopE1-105-Ink4c-MycHis

<400> SEQUENCE: 167

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

```
Leu Ser Glu Arg Phe Ile Ser His Lys Asn Thr Glu Ser Ala Thr
 50                  55                  60

His Phe His Arg Gly Ser Ala Ser Glu Gly Arg Ala Val Leu Thr Asn
 65                  70                  75                  80

Lys Val Val Lys Asp Phe Met Leu Gln Thr Leu Asn Asp Ile Asp Ile
                 85                  90                  95

Arg Gly Ser Ala Ser Lys Asp Pro Ala Gly Thr Ile Trp Glu Phe Met
            100                 105                 110

Ala Glu Pro Trp Gly Asn Glu Leu Ala Ser Ala Ala Arg Gly Asp
        115                 120                 125

Leu Glu Gln Leu Thr Ser Leu Leu Gln Asn Asn Val Asn Val Asn Ala
    130                 135                 140

Gln Asn Gly Phe Gly Arg Thr Ala Leu Gln Val Met Lys Leu Gly Asn
145                 150                 155                 160

Pro Glu Ile Ala Arg Arg Leu Leu Leu Arg Gly Ala Asn Pro Asp Leu
                165                 170                 175

Lys Asp Arg Thr Gly Phe Ala Val Ile His Asp Ala Ala Arg Ala Gly
            180                 185                 190

Phe Leu Asp Thr Leu Gln Thr Leu Leu Glu Phe Gln Ala Asp Val Asn
        195                 200                 205

Ile Glu Asp Asn Glu Gly Asn Leu Pro Leu His Leu Ala Ala Lys Glu
    210                 215                 220

Gly His Leu Arg Val Val Glu Phe Leu Val Lys His Thr Ala Ser Asn
225                 230                 235                 240

Val Gly His Arg Asn His Lys Gly Asp Thr Ala Cys Asp Leu Ala Arg
                245                 250                 255

Leu Tyr Gly Arg Asn Glu Val Val Ser Leu Met Gln Ala Asn Gly Ala
            260                 265                 270

Gly Gly Ala Thr Asn Leu Gln Lys Leu Gly Pro Glu Gln Lys Leu Ile
        275                 280                 285

Ser Glu Glu Asp Leu Asn Ser Ala Val Asp His His His His His
    290                 295                 300
```

<210> SEQ ID NO 168
<211> LENGTH: 446
<212> TYPE: PRT
<213> ORGANISM: Artificial Sequence
<220> FEATURE:
<223> OTHER INFORMATION: SteA-Mad2-MycHis

<400> SEQUENCE: 168

```
Met Pro Tyr Thr Ser Val Ser Thr Tyr Ala Arg Ala Leu Ser Gly Asn
 1                   5                  10                  15

Lys Leu Pro His Val Ala Ala Gly Asp Tyr Glu Asn Lys Leu Ser Thr
                 20                  25                  30

Lys Ile Met Lys Gly Ile Leu Tyr Val Leu Thr Ala Gly Leu Ala Tyr
            35                  40                  45

Gly Phe Thr Arg Val Ile Glu His Tyr Cys Asn Val Thr Pro Lys Val
 50                  55                  60

Ala Glu Phe Cys Ala Asn Ala Gly Asn Ile His Asn His Leu Ala Asp
 65                  70                  75                  80

Ala Val Arg Asp Gly Leu Phe Thr Ile Asp Val Glu Leu Ser Asp Gly
                 85                  90                  95

Arg Met Leu Thr Phe Glu Gln Leu Ser Leu Ile Ala Glu Gly Lys Pro
            100                 105                 110
```

```
Ile Val Arg Ile Ser Asp Gly Glu His Thr Val Glu Val Gly Thr
        115                 120                 125

Phe Glu Glu Ile Cys Met Arg Leu Glu Glu Gly Phe Phe Glu Ala Pro
            130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
            180                 185                 190

Ala Gln Trp Ala Ala Asp Ile Lys Ala Arg Tyr His Asn Tyr Leu Asp
        195                 200                 205

Asn Tyr Gly Thr Ile Trp Glu Phe Met Ala Leu Gln Leu Ser Arg Glu
    210                 215                 220

Gln Gly Ile Thr Leu Arg Gly Ser Ala Glu Ile Val Ala Glu Phe Phe
225                 230                 235                 240

Ser Phe Gly Ile Asn Ser Ile Leu Tyr Gln Arg Gly Ile Tyr Pro Ser
                245                 250                 255

Glu Thr Phe Thr Arg Val Gln Lys Tyr Gly Leu Thr Leu Leu Val Thr
            260                 265                 270

Thr Asp Leu Glu Leu Ile Lys Tyr Leu Asn Asn Val Val Glu Gln Leu
        275                 280                 285

Lys Asp Trp Leu Tyr Lys Cys Ser Val Gln Lys Leu Val Val Val Ile
    290                 295                 300

Ser Asn Ile Glu Ser Gly Glu Val Leu Glu Arg Trp Gln Phe Asp Ile
305                 310                 315                 320

Glu Cys Asp Lys Thr Ala Lys Asp Asp Ser Ala Pro Arg Glu Lys Ser
                325                 330                 335

Gln Lys Ala Ile Gln Asp Glu Ile Arg Ser Val Ile Arg Gln Ile Thr
            340                 345                 350

Ala Thr Val Thr Phe Leu Pro Leu Leu Glu Val Ser Cys Ser Phe Asp
        355                 360                 365

Leu Leu Ile Tyr Thr Asp Lys Asp Leu Val Val Pro Glu Lys Trp Glu
    370                 375                 380

Glu Ser Gly Pro Gln Phe Ile Thr Asn Ser Glu Glu Val Arg Leu Arg
385                 390                 395                 400

Ser Phe Thr Thr Thr Ile His Lys Val Asn Ser Met Val Ala Tyr Lys
                405                 410                 415

Ile Pro Val Asn Asp Lys Leu Gly Pro Glu Gln Lys Leu Ile Ser Glu
            420                 425                 430

Glu Asp Leu Asn Ser Ala Val Asp His His His His His
        435                 440                 445

<210> SEQ ID NO 169
<211> LENGTH: 341
<212> TYPE: PRT
<213> ORGANISM: Artificial Sequence
<220> FEATURE:
<223> OTHER INFORMATION: SopE1-105-Mad2-MycHis

<400> SEQUENCE: 169

Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30
```

```
Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
 50                  55                  60

His Phe His Arg Gly Ser Ala Ser Glu Gly Arg Ala Val Leu Thr Asn
 65                  70                  75                  80

Lys Val Val Lys Asp Phe Met Leu Gln Thr Leu Asn Asp Ile Asp Ile
                 85                  90                  95

Arg Gly Ser Ala Ser Lys Asp Pro Ala Gly Thr Ile Trp Glu Phe Met
                100                 105                 110

Ala Leu Gln Leu Ser Arg Glu Gln Gly Ile Thr Leu Arg Gly Ser Ala
                115                 120                 125

Glu Ile Val Ala Glu Phe Phe Ser Phe Gly Ile Asn Ser Ile Leu Tyr
        130                 135                 140

Gln Arg Gly Ile Tyr Pro Ser Glu Thr Phe Thr Arg Val Gln Lys Tyr
145                 150                 155                 160

Gly Leu Thr Leu Leu Val Thr Thr Asp Leu Glu Leu Ile Lys Tyr Leu
                165                 170                 175

Asn Asn Val Val Glu Gln Leu Lys Asp Trp Leu Tyr Lys Cys Ser Val
            180                 185                 190

Gln Lys Leu Val Val Ile Ser Asn Ile Glu Ser Gly Glu Val Leu
        195                 200                 205

Glu Arg Trp Gln Phe Asp Ile Glu Cys Asp Lys Thr Ala Lys Asp Asp
        210                 215                 220

Ser Ala Pro Arg Glu Lys Ser Gln Lys Ala Ile Gln Asp Glu Ile Arg
225                 230                 235                 240

Ser Val Ile Arg Gln Ile Thr Ala Thr Val Thr Phe Leu Pro Leu Leu
                245                 250                 255

Glu Val Ser Cys Ser Phe Asp Leu Leu Ile Tyr Thr Asp Lys Asp Leu
            260                 265                 270

Val Val Pro Glu Lys Trp Glu Glu Ser Gly Pro Gln Phe Ile Thr Asn
        275                 280                 285

Ser Glu Glu Val Arg Leu Arg Ser Phe Thr Thr Thr Ile His Lys Val
    290                 295                 300

Asn Ser Met Val Ala Tyr Lys Ile Pro Val Asn Asp Lys Leu Gly Pro
305                 310                 315                 320

Glu Gln Lys Leu Ile Ser Glu Glu Asp Leu Asn Ser Ala Val Asp His
                325                 330                 335

His His His His His
        340

<210> SEQ ID NO 170
<211> LENGTH: 538
<212> TYPE: PRT
<213> ORGANISM: Artificial Sequence
<220> FEATURE:
<223> OTHER INFORMATION: SteA-Cdk1-MycHis

<400> SEQUENCE: 170

Met Pro Tyr Thr Ser Val Ser Tyr Ala Arg Ala Leu Ser Gly Asn
1               5                   10                  15

Lys Leu Pro His Val Ala Ala Gly Asp Tyr Glu Asn Lys Leu Ser Thr
                20                  25                  30

Lys Ile Met Lys Gly Ile Leu Tyr Val Leu Thr Ala Gly Leu Ala Tyr
        35                  40                  45
```

```
Gly Phe Thr Arg Val Ile Glu His Tyr Cys Asn Val Thr Pro Lys Val
 50                  55                  60

Ala Glu Phe Cys Ala Asn Ala Gly Asn Ile His Asn His Leu Ala Asp
 65                  70                  75                  80

Ala Val Arg Asp Gly Leu Phe Thr Ile Asp Val Glu Leu Ser Asp Gly
                 85                  90                  95

Arg Met Leu Thr Phe Glu Gln Leu Ser Leu Ile Ala Glu Gly Lys Pro
                100                 105                 110

Ile Val Arg Ile Ser Asp Gly Glu His Thr Val Glu Val Glu Gly Thr
                115                 120                 125

Phe Glu Glu Ile Cys Met Arg Leu Glu Glu Gly Phe Phe Glu Ala Pro
130                 135                 140

Ala Tyr Tyr Asp Tyr Asp Ile Asp Glu Lys Tyr Lys Thr Val Arg Glu
145                 150                 155                 160

Arg Met Ala Ala Tyr Asn Ala Leu Pro Gln Ala Leu Gly Ala Ile Pro
                165                 170                 175

Cys Leu Glu Tyr Tyr Ile Ala Arg Ala Ser Asn Met Gln Glu Ala Lys
                180                 185                 190

Ala Gln Trp Ala Ala Asp Ile Lys Ala Arg Tyr His Asn Tyr Leu Asp
                195                 200                 205

Asn Tyr Gly Thr Ile Trp Glu Phe Met Glu Asp Tyr Thr Lys Ile Glu
210                 215                 220

Lys Ile Gly Glu Gly Thr Tyr Gly Val Val Tyr Lys Gly Arg His Lys
225                 230                 235                 240

Thr Thr Gly Gln Val Val Ala Met Lys Lys Ile Arg Leu Glu Ser Glu
                245                 250                 255

Glu Glu Gly Val Pro Ser Thr Ala Ile Arg Glu Ile Ser Leu Leu Lys
                260                 265                 270

Glu Leu Arg His Pro Asn Ile Val Ser Leu Gln Asp Val Leu Met Gln
                275                 280                 285

Asp Ser Arg Leu Tyr Leu Ile Phe Glu Phe Leu Ser Met Asp Leu Lys
290                 295                 300

Lys Tyr Leu Asp Ser Ile Pro Pro Gly Gln Tyr Met Asp Ser Ser Leu
305                 310                 315                 320

Val Lys Ser Tyr Leu Tyr Gln Ile Leu Gln Gly Ile Val Phe Cys His
                325                 330                 335

Ser Arg Arg Val Leu His Arg Asp Leu Lys Pro Gln Asn Leu Leu Ile
                340                 345                 350

Asp Asp Lys Gly Thr Ile Lys Leu Ala Asp Phe Gly Leu Ala Arg Ala
                355                 360                 365

Phe Gly Ile Pro Ile Arg Val Tyr Thr His Glu Val Val Thr Leu Trp
370                 375                 380

Tyr Arg Ser Pro Glu Val Leu Leu Gly Ser Ala Arg Tyr Ser Thr Pro
385                 390                 395                 400

Val Asp Ile Trp Ser Ile Gly Thr Ile Phe Ala Glu Leu Ala Thr Lys
                405                 410                 415

Lys Pro Leu Phe His Gly Asp Ser Glu Ile Asp Gln Leu Phe Arg Ile
                420                 425                 430

Phe Arg Ala Leu Gly Thr Pro Asn Asn Glu Val Trp Pro Glu Val Glu
                435                 440                 445

Ser Leu Gln Asp Tyr Lys Asn Thr Phe Pro Lys Trp Lys Pro Gly Ser
450                 455                 460
```

```
Leu Ala Ser His Val Lys Asn Leu Asp Glu Asn Gly Leu Asp Leu Leu
465                 470                 475                 480

Ser Lys Met Leu Ile Tyr Asp Pro Ala Lys Arg Ile Ser Gly Lys Met
            485                 490                 495

Ala Leu Asn His Pro Tyr Phe Asn Asp Leu Asp Asn Gln Ile Lys Lys
                500                 505                 510

Met Lys Leu Gly Pro Glu Gln Lys Leu Ile Ser Glu Glu Asp Leu Asn
            515                 520                 525

Ser Ala Val Asp His His His His His His
            530                 535
```

<210> SEQ ID NO 171
<211> LENGTH: 433
<212> TYPE: PRT
<213> ORGANISM: Artificial Sequence
<220> FEATURE:
<223> OTHER INFORMATION: SopE1-105-Cdk1-MycHis

<400> SEQUENCE: 171

```
Val Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala Gly Thr Ile Trp Glu Phe Met
            100                 105                 110

Glu Asp Tyr Thr Lys Ile Glu Lys Ile Gly Glu Gly Thr Tyr Gly Val
        115                 120                 125

Val Tyr Lys Gly Arg His Lys Thr Thr Gly Gln Val Val Ala Met Lys
    130                 135                 140

Lys Ile Arg Leu Glu Ser Glu Glu Gly Val Pro Ser Thr Ala Ile
145                 150                 155                 160

Arg Glu Ile Ser Leu Leu Lys Glu Leu Arg His Pro Asn Ile Val Ser
                165                 170                 175

Leu Gln Asp Val Leu Met Gln Asp Ser Arg Leu Tyr Leu Ile Phe Glu
            180                 185                 190

Phe Leu Ser Met Asp Leu Lys Lys Tyr Leu Asp Ser Ile Pro Pro Gly
        195                 200                 205

Gln Tyr Met Asp Ser Ser Leu Val Lys Ser Tyr Leu Tyr Gln Ile Leu
    210                 215                 220

Gln Gly Ile Val Phe Cys His Ser Arg Arg Val Leu His Arg Asp Leu
225                 230                 235                 240

Lys Pro Gln Asn Leu Leu Ile Asp Asp Lys Gly Thr Ile Lys Leu Ala
                245                 250                 255

Asp Phe Gly Leu Ala Arg Ala Phe Gly Ile Pro Ile Arg Val Tyr Thr
            260                 265                 270

His Glu Val Val Thr Leu Trp Tyr Arg Ser Pro Glu Val Leu Leu Gly
        275                 280                 285
```

```
Ser Ala Arg Tyr Ser Thr Pro Val Asp Ile Trp Ser Ile Gly Thr Ile
    290                 295                 300

Phe Ala Glu Leu Ala Thr Lys Lys Pro Leu Phe His Gly Asp Ser Glu
305                 310                 315                 320

Ile Asp Gln Leu Phe Arg Ile Phe Arg Ala Leu Gly Thr Pro Asn Asn
                325                 330                 335

Glu Val Trp Pro Glu Val Glu Ser Leu Gln Asp Tyr Lys Asn Thr Phe
                340                 345                 350

Pro Lys Trp Lys Pro Gly Ser Leu Ala Ser His Val Lys Asn Leu Asp
                355                 360                 365

Glu Asn Gly Leu Asp Leu Leu Ser Lys Met Leu Ile Tyr Asp Pro Ala
370                 375                 380

Lys Arg Ile Ser Gly Lys Met Ala Leu Asn His Pro Tyr Phe Asn Asp
385                 390                 395                 400

Leu Asp Asn Gln Ile Lys Lys Met Lys Leu Gly Pro Glu Gln Lys Leu
                405                 410                 415

Ile Ser Glu Glu Asp Leu Asn Ser Ala Val Asp His His His His
                420                 425                 430

His
```

```
<210> SEQ ID NO 172
<211> LENGTH: 95
<212> TYPE: DNA
<213> ORGANISM: Artificial Sequence
<220> FEATURE:
<223> OTHER INFORMATION: Primer No. : Si_745

<400> SEQUENCE: 172
catgctcgag ggtgccatcg atgatgccgc ccgcgaaggt tttctggata ccctggtggt    60
gctgcatcgc gccggtgccc gctaattcga acatg                              95

<210> SEQ ID NO 173
<211> LENGTH: 95
<212> TYPE: DNA
<213> ORGANISM: Artificial Sequence
<220> FEATURE:
<223> OTHER INFORMATION: Primer No. : Si_746

<400> SEQUENCE: 173
catgttcgaa ttagcgggca ccggcgcgat gcagcaccac cagggtatcc agaaaacctt    60
cgcgggcggc atcatcgatg gcaccctcga gcatg                              95

<210> SEQ ID NO 174
<211> LENGTH: 95
<212> TYPE: DNA
<213> ORGANISM: Artificial Sequence
<220> FEATURE:
<223> OTHER INFORMATION: Primer No. : Si_747

<400> SEQUENCE: 174
catgctcgag ggtgccatcg attatggtcg caaaaaacgc cgccaacgcc gccgcggtcc    60
ggtgaaacgc cgcctgtttg gttaattcga acatg                              95

<210> SEQ ID NO 175
<211> LENGTH: 95
<212> TYPE: DNA
<213> ORGANISM: Artificial Sequence
<220> FEATURE:
<223> OTHER INFORMATION: Primer No. : Si_748
```

<400> SEQUENCE: 175
catgttcgaa ttaaccaaac aggcggcgtt tcaccggacc gcggcggcgt tggcggcgtt    60
ttttgcgacc ataatcgatg gcaccctcga gcatg                              95

<210> SEQ ID NO 176
<211> LENGTH: 95
<212> TYPE: DNA
<213> ORGANISM: Artificial Sequence
<220> FEATURE:
<223> OTHER INFORMATION: Primer No. : Si_749

<400> SEQUENCE: 176
catgctcgag ggtgccatcg ataaacgccg ccaaaccagc atgaccgcct tttatcatag    60
caaacgccgc ctgatttta gctaattcga acatg                               95

<210> SEQ ID NO 177
<211> LENGTH: 95
<212> TYPE: DNA
<213> ORGANISM: Artificial Sequence
<220> FEATURE:
<223> OTHER INFORMATION: Primer No. : Si_750

<400> SEQUENCE: 177
catgttcgaa ttagctaaaa atcaggcggc gtttgctatg ataaaaggcg gtcatgctgg    60
tttggcggcg tttatcgatg gcaccctcga gcatg                              95

<210> SEQ ID NO 178
<211> LENGTH: 83
<212> TYPE: DNA
<213> ORGANISM: Artificial Sequence
<220> FEATURE:
<223> OTHER INFORMATION: Primer No. : Si_753

<400> SEQUENCE: 178
catgctcgag ggtgccatcg ataccagcat gaccgccttt tatcatagca aacgccgcct    60 gattttagc taattcgaac atg                                             83

<210> SEQ ID NO 179
<211> LENGTH: 83
<212> TYPE: DNA
<213> ORGANISM: Artificial Sequence
<220> FEATURE:
<223> OTHER INFORMATION: Primer No. : Si_754

<400> SEQUENCE: 179
catgttcgaa ttagctaaaa atcaggcggc gtttgctatg ataaaaggcg gtcatgctgg    60
tatcgatggc accctcgagc atg                                            83

<210> SEQ ID NO 180
<211> LENGTH: 86
<212> TYPE: DNA
<213> ORGANISM: Artificial Sequence
<220> FEATURE:
<223> OTHER INFORMATION: Primer No. : Si_755

<400> SEQUENCE: 180
catgctcgag ggtgccatcg atgcctgtcg ccgcctgttt ggtccggtgg atagcgaaca    60
actgagccgc gattaattcg aacatg                                         86

<210> SEQ ID NO 181
<211> LENGTH: 86

```
<212> TYPE: DNA
<213> ORGANISM: Artificial Sequence
<220> FEATURE:
<223> OTHER INFORMATION: Primer No. : Si_756

<400> SEQUENCE: 181
catgttcgaa ttaatcgcgg ctcagttgtt cgctatccac cggaccaaac aggcggcgac    60
aggcatcgat ggcaccctcg agcatg                                          86

<210> SEQ ID NO 182
<211> LENGTH: 62
<212> TYPE: DNA
<213> ORGANISM: Artificial Sequence
<220> FEATURE:
<223> OTHER INFORMATION: Primer No. : Si_757

<400> SEQUENCE: 182
catgctcgag ggtgccatcg attgggaact ggtggtgctg ggtaaactgt aattcgaaca    60
tg                                                                    62

<210> SEQ ID NO 183
<211> LENGTH: 62
<212> TYPE: DNA
<213> ORGANISM: Artificial Sequence
<220> FEATURE:
<223> OTHER INFORMATION: Primer No. : Si_758

<400> SEQUENCE: 183
catgttcgaa ttacagttta cccagcacca ccagttccca atcgatggca ccctcgagca    60
tg                                                                    62

<210> SEQ ID NO 184
<211> LENGTH: 27
<212> TYPE: DNA
<213> ORGANISM: Artificial Sequence
<220> FEATURE:
<223> OTHER INFORMATION: Primer No. : Si_703

<400> SEQUENCE: 184
gacatggaat tcatggagcc ggcggcg                                         27

<210> SEQ ID NO 185
<211> LENGTH: 28
<212> TYPE: DNA
<213> ORGANISM: Artificial Sequence
<220> FEATURE:
<223> OTHER INFORMATION: Primer No. : Si_704

<400> SEQUENCE: 185
catgaagctt atcggggatg tctgaggg                                        28

<210> SEQ ID NO 186
<211> LENGTH: 29
<212> TYPE: DNA
<213> ORGANISM: Artificial Sequence
<220> FEATURE:
<223> OTHER INFORMATION: Primer No. : Si_705

<400> SEQUENCE: 186
gacatggaat tcatggccga gccttgggg                                       29

<210> SEQ ID NO 187
<211> LENGTH: 51
<212> TYPE: DNA
```

```
<213> ORGANISM: Artificial Sequence
<220> FEATURE:
<223> OTHER INFORMATION: Primer No. : Si_706

<400> SEQUENCE: 187
gttaacatca gcttgaaact ccagcaaagt ctgtaaagtg tccaggaaac c            51

<210> SEQ ID NO 188
<211> LENGTH: 51
<212> TYPE: DNA
<213> ORGANISM: Artificial Sequence
<220> FEATURE:
<223> OTHER INFORMATION: Primer No. : Si_707

<400> SEQUENCE: 188
ggtttcctgg acactttaca gactttgctg gagtttcaag ctgatgttaa c            51

<210> SEQ ID NO 189
<211> LENGTH: 30
<212> TYPE: DNA
<213> ORGANISM: Artificial Sequence
<220> FEATURE:
<223> OTHER INFORMATION: Primer No. : Si_708

<400> SEQUENCE: 189
catgaagctt ttgaagattt gtggctcccc                                    30

<210> SEQ ID NO 190
<211> LENGTH: 30
<212> TYPE: DNA
<213> ORGANISM: Artificial Sequence
<220> FEATURE:
<223> OTHER INFORMATION: Primer No. : Si_709

<400> SEQUENCE: 190
gacatggaat tcatggcgct gcagctctcc                                    30

<210> SEQ ID NO 191
<211> LENGTH: 33
<212> TYPE: DNA
<213> ORGANISM: Artificial Sequence
<220> FEATURE:
<223> OTHER INFORMATION: Primer No. : Si_710

<400> SEQUENCE: 191
catgaagctt gtcattgaca ggaattttgt agg                                33

<210> SEQ ID NO 192
<211> LENGTH: 38
<212> TYPE: DNA
<213> ORGANISM: Artificial Sequence
<220> FEATURE:
<223> OTHER INFORMATION: Primer No. : Si_711

<400> SEQUENCE: 192
gacatggaat tcatggaaga ttataccaaa atagagaa                           38

<210> SEQ ID NO 193
<211> LENGTH: 34
<212> TYPE: DNA
<213> ORGANISM: Artificial Sequence
<220> FEATURE:
<223> OTHER INFORMATION: Primer No. : Si_712

<400> SEQUENCE: 193
catgaagctt catcttctta atctgattgt ccaa                               34
```

<210> SEQ ID NO 194
<211> LENGTH: 276
<212> TYPE: PRT
<213> ORGANISM: Artificial Sequence
<220> FEATURE:
<223> OTHER INFORMATION: YopE1-138-Y. enterocolitica codon optimized murine tBid

<400> SEQUENCE: 194

Met Lys Ile Ser Ser Phe Ile Ser Thr Ser Leu Pro Leu Pro Ala Ser
1 5 10 15

Val Ser Gly Ser Ser Ser Val Gly Glu Met Ser Gly Arg Ser Val Ser
20 25 30

Gln Gln Lys Ser Asp Gln Tyr Ala Asn Asn Leu Ala Gly Arg Thr Glu
35 40 45

Ser Pro Gln Gly Ser Ser Leu Ala Ser Arg Ile Ile Glu Arg Leu Ser
50 55 60

Ser Met Ala His Ser Val Ile Gly Phe Ile Gln Arg Met Phe Ser Glu
65 70 75 80

Gly Ser His Lys Pro Val Val Thr Pro Ala Leu Thr Pro Ala Gln Met
85 90 95

Pro Ser Pro Thr Ser Phe Ser Asp Ser Ile Lys Gln Leu Ala Ala Glu
100 105 110

Thr Leu Pro Lys Tyr Met Gln Gln Leu Ser Ser Leu Asp Ala Glu Thr
115 120 125

Leu Gln Lys Asn His Asp Gln Phe Ala Thr Leu Glu Gly Ser Gln Ala
130 135 140

Ser Arg Ser Phe Asn Gln Gly Arg Ile Glu Pro Asp Ser Glu Ser Gln
145 150 155 160

Glu Glu Ile Ile His Asn Ile Ala Arg His Leu Ala Gln Ile Gly Asp
165 170 175

Glu Met Asp His Asn Ile Gln Pro Thr Leu Val Arg Gln Leu Ala Ala
180 185 190

Gln Phe Met Asn Gly Ser Leu Ser Glu Glu Asp Lys Arg Asn Cys Leu
195 200 205

Ala Lys Ala Leu Asp Glu Val Lys Thr Ala Phe Pro Arg Asp Met Glu
210 215 220

Asn Asp Lys Ala Met Leu Ile Met Thr Met Leu Leu Ala Lys Lys Val
225 230 235 240

Ala Ser His Ala Pro Ser Leu Leu Arg Asp Val Phe His Thr Thr Val
245 250 255

Asn Phe Ile Asn Gln Asn Leu Phe Ser Tyr Val Arg Asn Leu Val Arg
260 265 270

Asn Glu Met Asp
275

<210> SEQ ID NO 195
<211> LENGTH: 245
<212> TYPE: PRT
<213> ORGANISM: Artificial Sequence
<220> FEATURE:
<223> OTHER INFORMATION: YopE1-138-Ubiquitin

<400> SEQUENCE: 195

Met Lys Ile Ser Ser Phe Ile Ser Thr Ser Leu Pro Leu Pro Ala Ser
1 5 10 15

```
Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
         35                  40                  45

Ser Pro Gln Gly Ser Ser Leu Ala Ser Arg Ile Ile Glu Arg Leu Ser
 50                  55                  60

Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95

Pro Ser Pro Thr Ser Phe Ser Asp Ser Ile Lys Gln Leu Ala Ala Glu
             100                 105                 110

Thr Leu Pro Lys Tyr Met Gln Gln Leu Ser Ser Leu Asp Ala Glu Thr
         115                 120                 125

Leu Gln Lys Asn His Asp Gln Phe Ala Thr Leu Glu Met Gln Ile Phe
130                 135                 140

Val Lys Thr Leu Thr Gly Lys Thr Ile Thr Leu Glu Val Glu Pro Ser
145                 150                 155                 160

Asp Thr Ile Glu Asn Val Lys Ala Lys Ile Gln Asp Lys Glu Gly Ile
                165                 170                 175

Pro Pro Asp Gln Gln Arg Leu Ile Phe Ala Gly Lys Gln Leu Glu Asp
            180                 185                 190

Gly Arg Thr Leu Ser Asp Tyr Asn Ile Gln Lys Glu Ser Thr Leu His
        195                 200                 205

Leu Val Leu Arg Leu Arg Gly Gly Phe Glu Ala Ser Lys Leu Gly Pro
210                 215                 220

Glu Gln Lys Leu Ile Ser Glu Glu Asp Leu Asn Ser Ala Val Asp His
225                 230                 235                 240

His His His His
            245

<210> SEQ ID NO 196
<211> LENGTH: 419
<212> TYPE: PRT
<213> ORGANISM: Artificial Sequence
<220> FEATURE:
<223> OTHER INFORMATION: YopE1-138-Ubiquitin-Flag-INK4C-MycHis

<400> SEQUENCE: 196

Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
         35                  40                  45

Ser Pro Gln Gly Ser Ser Leu Ala Ser Arg Ile Ile Glu Arg Leu Ser
 50                  55                  60

Ser Met Ala His Ser Val Ile Gly Phe Ile Gln Arg Met Phe Ser Glu
 65                  70                  75                  80

Gly Ser His Lys Pro Val Val Thr Pro Ala Leu Thr Pro Ala Gln Met
                 85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Ser Ser Leu Asp Ala Glu Thr
         115                 120                 125
```

Leu Gln Lys Asn His Asp Gln Phe Ala Thr Leu Glu Met Gln Ile Phe
    130                 135                 140

Val Lys Thr Leu Thr Gly Lys Thr Ile Thr Leu Glu Val Glu Pro Ser
145                 150                 155                 160

Asp Thr Ile Glu Asn Val Lys Ala Lys Ile Gln Asp Lys Glu Gly Ile
                165                 170                 175

Pro Pro Asp Gln Gln Arg Leu Ile Phe Ala Gly Lys Gln Leu Glu Asp
            180                 185                 190

Gly Arg Thr Leu Ser Asp Tyr Asn Ile Gln Lys Glu Ser Thr Leu His
        195                 200                 205

Leu Val Leu Arg Leu Arg Gly Gly Phe Glu Asp Tyr Lys Asp Asp Asp
    210                 215                 220

Asp Lys Met Ala Glu Pro Trp Gly Asn Glu Leu Ala Ser Ala Ala Ala
225                 230                 235                 240

Arg Gly Asp Leu Glu Gln Leu Thr Ser Leu Leu Gln Asn Asn Val Asn
                245                 250                 255

Val Asn Ala Gln Asn Gly Phe Gly Arg Thr Ala Leu Gln Val Met Lys
            260                 265                 270

Leu Gly Asn Pro Glu Ile Ala Arg Arg Leu Leu Leu Arg Gly Ala Asn
        275                 280                 285

Pro Asp Leu Lys Asp Arg Thr Gly Phe Ala Val Ile His Asp Ala Ala
    290                 295                 300

Arg Ala Gly Phe Leu Asp Thr Leu Gln Ala Leu Pro Glu Phe Gln Ala
305                 310                 315                 320

Asp Val Asn Ile Glu Asp Asn Glu Gly Asn Leu Pro Leu His Leu Ala
                325                 330                 335

Ala Lys Glu Gly His Leu Arg Val Val Glu Phe Leu Val Lys His Thr
            340                 345                 350

Ala Ser Asn Val Gly His Arg Asn His Lys Gly Asp Thr Ala Cys Asp
        355                 360                 365

Leu Ala Arg Leu Tyr Gly Arg Asn Glu Val Val Ser Leu Met Gln Ala
    370                 375                 380

Asn Gly Ala Gly Gly Ala Thr Asn Leu Gln Lys Leu Gly Pro Glu Gln
385                 390                 395                 400

Lys Leu Ile Ser Glu Glu Asp Leu Asn Ser Ala Val Asp His His His
                405                 410                 415

His His His

<210> SEQ ID NO 197
<211> LENGTH: 30
<212> TYPE: DNA
<213> ORGANISM: Artificial Sequence
<220> FEATURE:
<223> OTHER INFORMATION: Primer No. : Si_585

<400> SEQUENCE: 197
cagtctcgag atgcagatct tcgtcaagac                                      30

<210> SEQ ID NO 198
<211> LENGTH: 43
<212> TYPE: DNA
<213> ORGANISM: Artificial Sequence
<220> FEATURE:
<223> OTHER INFORMATION: Primer No. : Si_586

<400> SEQUENCE: 198
gttaaagctt gctagcttcg aaaccaccac gtagacgtaa gac                        43

-continued

```
<210> SEQ ID NO 199
<211> LENGTH: 48
<212> TYPE: DNA
<213> ORGANISM: Artificial Sequence
<220> FEATURE:
<223> OTHER INFORMATION: Primer No. : Si_588

<400> SEQUENCE: 199
cagtttcgaa gattataaag atgatgatga taaaatggcc gagccttg            48
```